(12) United States Patent
Harrop et al.

(10) Patent No.: US 8,147,838 B2
(45) Date of Patent: Apr. 3, 2012

(54) PEPTIDE

(75) Inventors: Richard Harrop, Oxford (GB); William Shingler, Oxford (GB); Susan Mary Kingsman, Oxford (GB)

(73) Assignee: Oxford Biomedica (UK) Limited, Oxfordshire (GB)

( * ) Notice: Subject to any disclaimer, the term of this patent is extended or adjusted under 35 U.S.C. 154(b) by 692 days.

(21) Appl. No.: 11/914,084

(22) PCT Filed: May 12, 2006

(86) PCT No.: PCT/GB2006/001769
§ 371 (c)(1),
(2), (4) Date: Oct. 14, 2008

(87) PCT Pub. No.: WO2006/120473
PCT Pub. Date: Nov. 16, 2006

(65) Prior Publication Data
US 2009/0280138 A1    Nov. 12, 2009

(30) Foreign Application Priority Data

May 13, 2005 (GB) .................................. 0509835.5
Aug. 8, 2005 (GB) .................................. 0516303.5

(51) Int. Cl.
*C07K 7/06* (2006.01)
(52) U.S. Cl. ..................... 424/185.1; 530/300; 530/328; 530/329
(58) Field of Classification Search ............... 424/185.1; 530/300, 328, 329
See application file for complete search history.

(56) References Cited

FOREIGN PATENT DOCUMENTS

| WO | WO-00/29428 | 5/2000 |
| WO | WO-03/068815 | 8/2003 |
| WO | WO-03/068816 | 8/2003 |

OTHER PUBLICATIONS

Southall et al. (Br.J.Can. 61:89-95 (1990)).*
Pancer et al. (Annual Review of Immunology vol. 24: 497-518 (Volume publication date Apr. 2006) First published online as a Review in Advance on Jan. 16, 2006; Abstract).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006).*
Talmadge et al. (Am. J. Pathol 170(3):793-804 (2007)).*
Myers et al., Isolation of a CDNA encoding 5T4 oncofetal trophoblast glycoprotein. *J. Biol. Chem.* 269: 9319-24 (1994).
Redchenko et al., Identification of the first CD8+ T cell epitope within tumor-associated antigen 5T4. *Proceedings of the Annual Meeting of the American Association for Cancer Research.* 44: 361, Abstract 1857 (2003).
Shaw et al., Glycosylation and epitope mapping of the 5T4 glycoprotein oncofoetal antigen. *Biochem. J.* 363: 137-45 (2002).
International Search Report, PCT/GB2006/001769, dated Jan. 16, 2008.
Written Opinion of the International Searching Authority, PCT/GB2006/001769, dated Jan. 16, 2008.
International Preliminary Report on Patentability, PCT/GB2006/001769, dated Jan. 29, 2008.

* cited by examiner

*Primary Examiner* — Lynn Bristol
(74) *Attorney, Agent, or Firm* — Marshall, Gerstein & Borun LLP

(57) ABSTRACT

The present invention relates to peptide epitopes of 5T4 antigen and their use in immunotherapy. In particular, the present invention relates to any one of the peptide epitopes as described herein as well as their used in diagnosis and therapy of cancer.

2 Claims, 14 Drawing Sheets

Figure 1: Method for identifying 5T4 CTL epitopes.
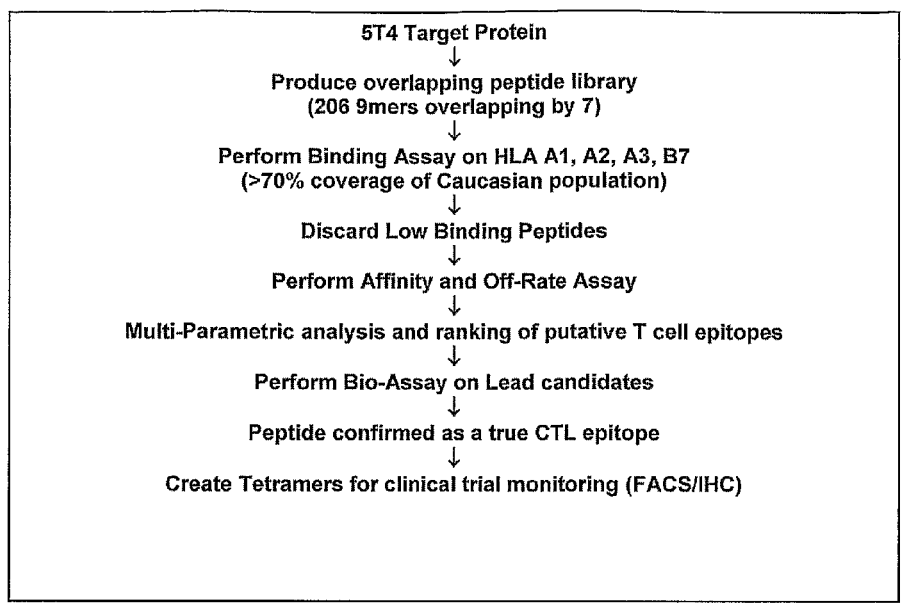
Figure 2: The basic iTopia binding assay.
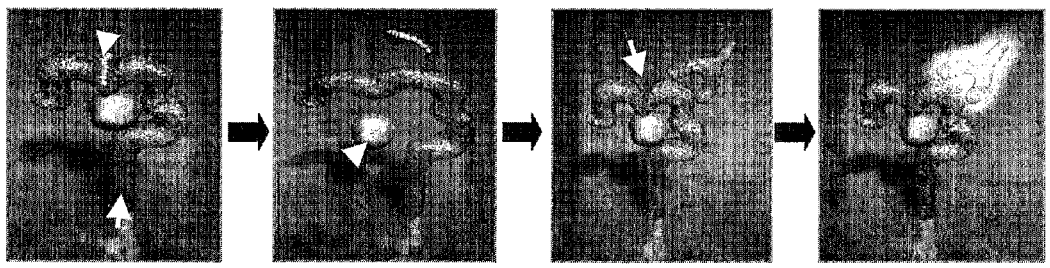

Figure 3 Graph of iScores for peptides 1-69
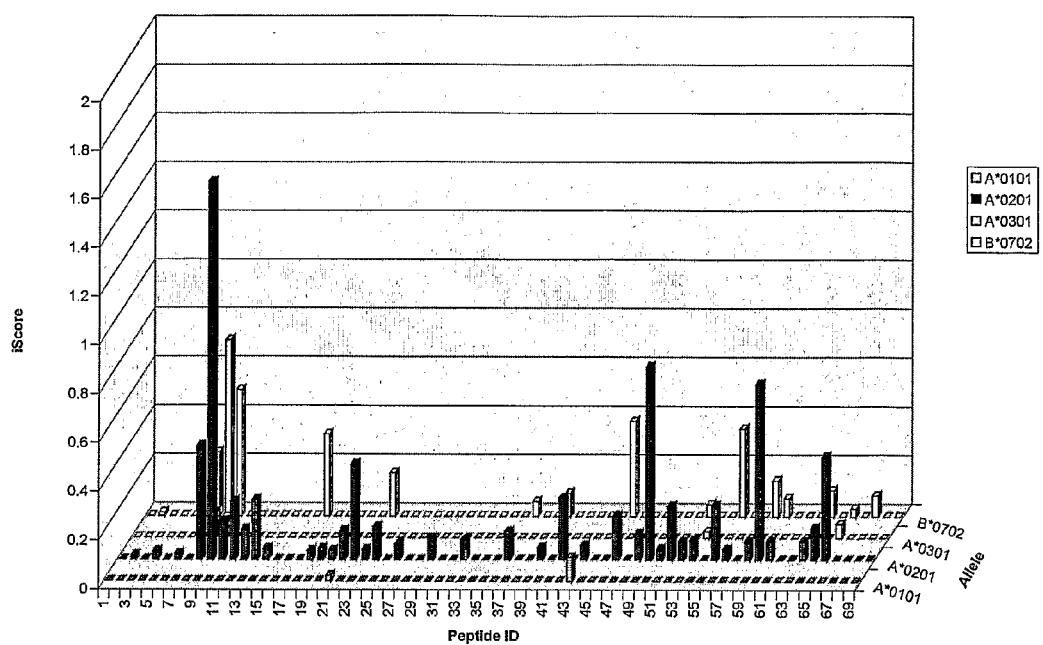
Figure 4: Graph of iScores for peptides 70-138
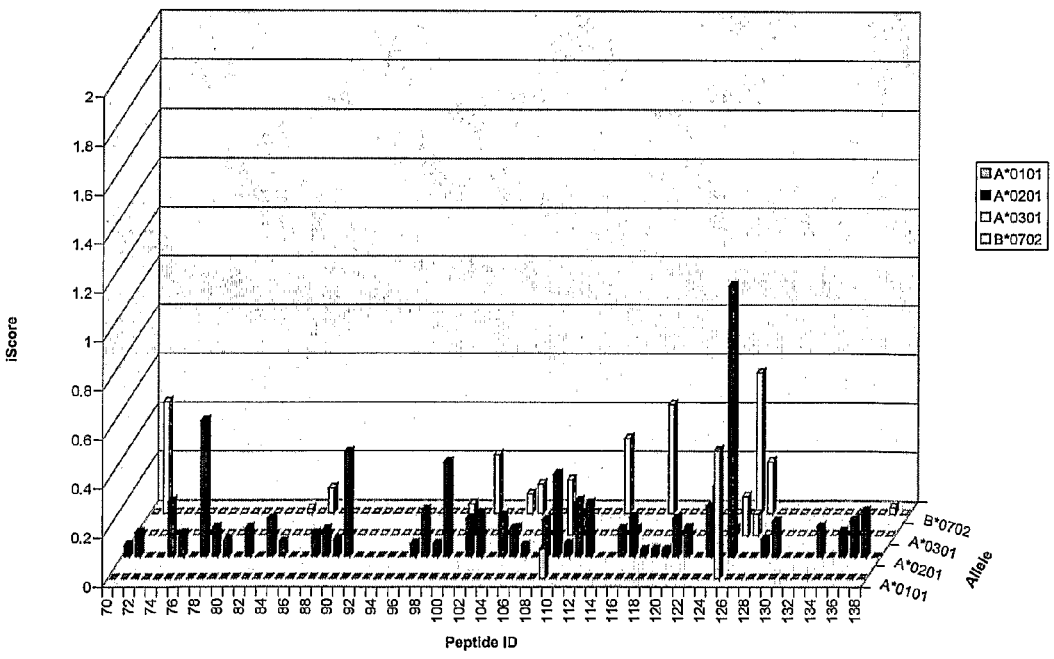

Figure 5: Graph of iScores for peptides 139-206
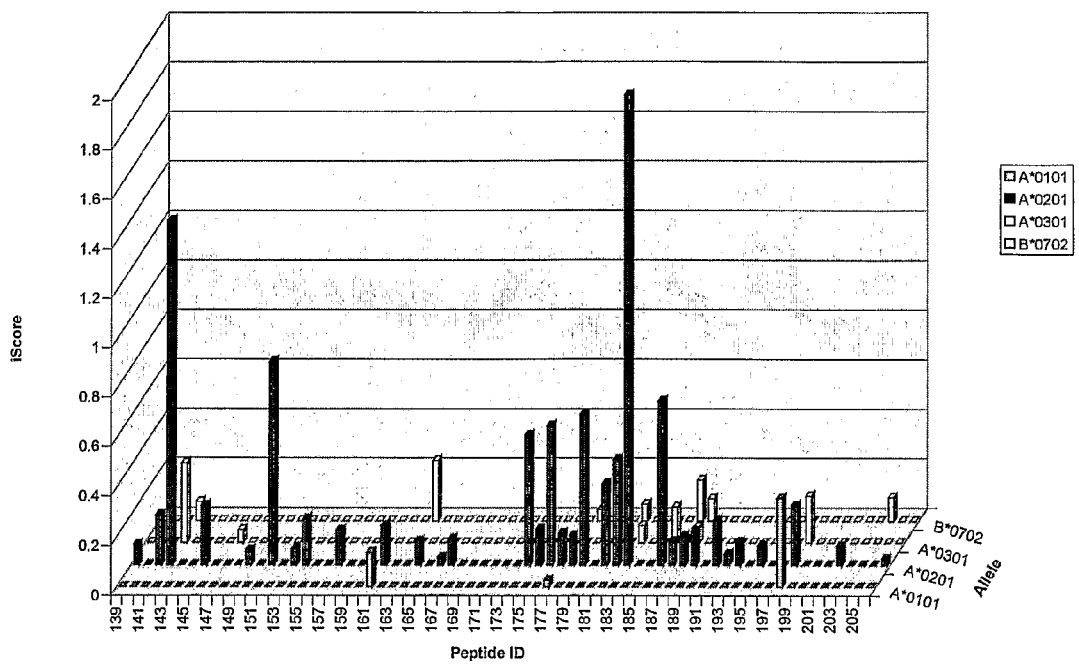

Figure 6: Example of the complete iTopia system used for 30 peptides with one MHC class I allele (B*0702)
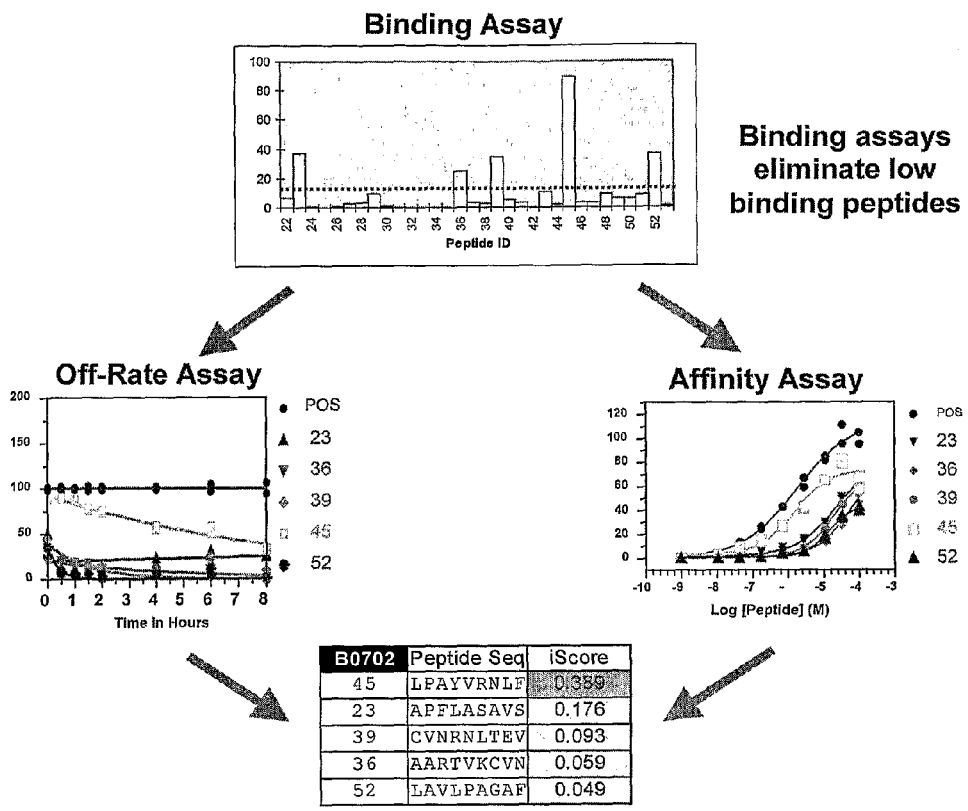

Figure 7: Graph showing iScore vs. iScore-rank for A*0101
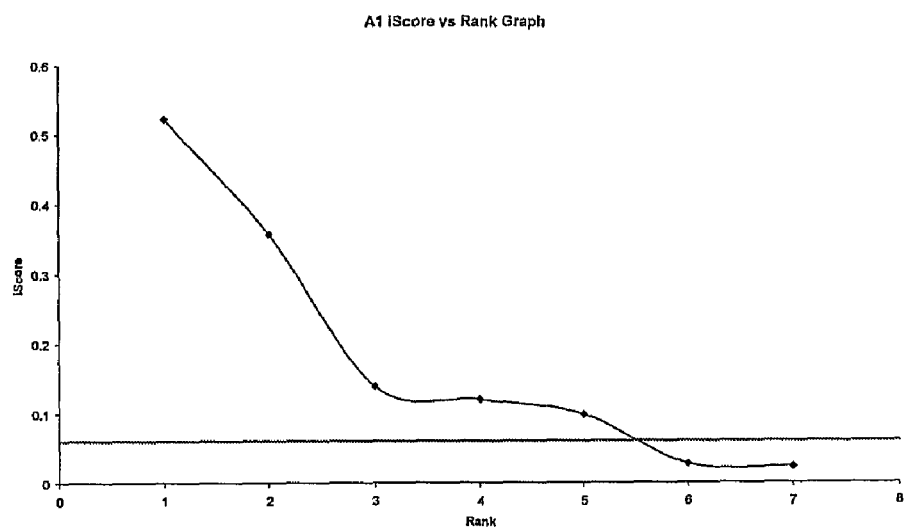

Figure 8: Graph showing iScore vs. iScore-rank for A*0201
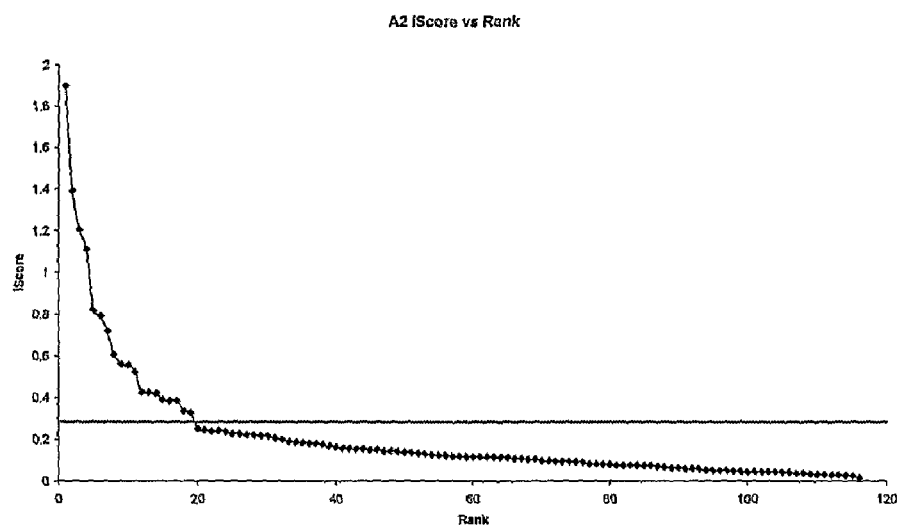

Figure 9: Graph showing iScore vs. iScore-rank for A*0301
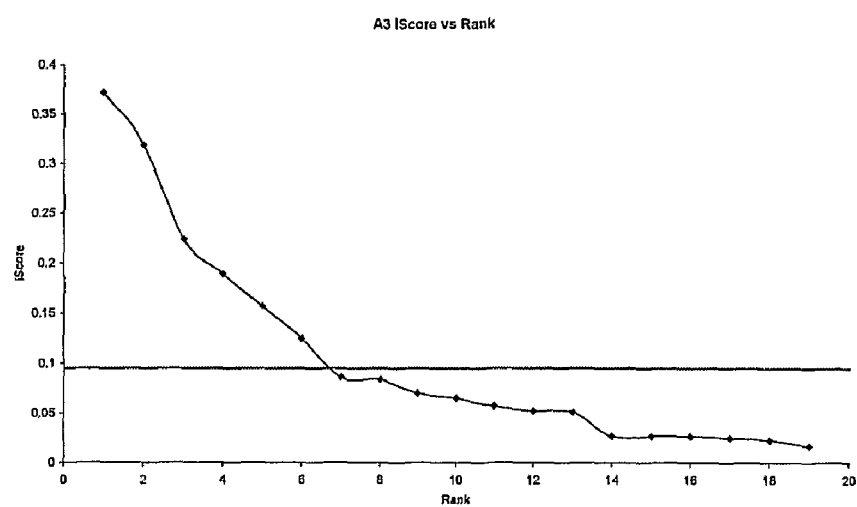

Figure 10: Graph showing iScore vs. iScore-rank for B*0702.
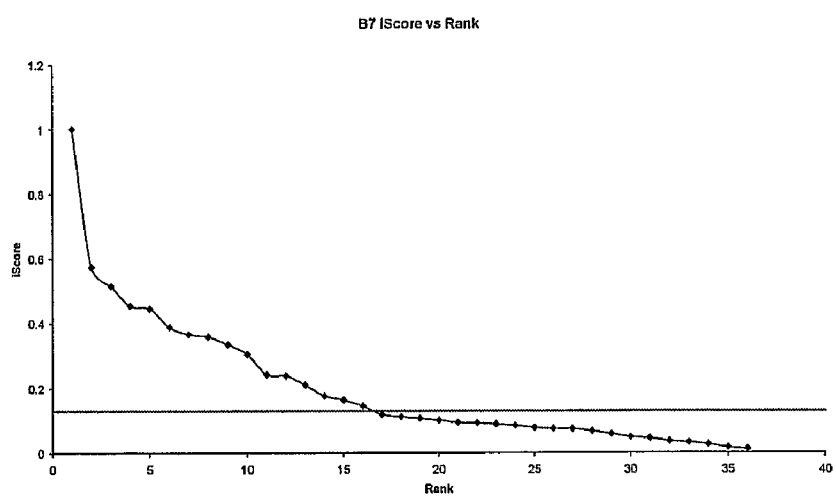

SEQUENCE LISTING

<160> NUMBER OF SEQ ID NOS: 356

<210> SEQ ID NO 1
<211> LENGTH: 9
<212> TYPE: PRT
<213> ORGANISM: Artificial
<220> FEATURE:
<223> OTHER INFORMATION: Synthetic peptide

<400> SEQUENCE: 1

Met Pro Gly Gly Cys Ser Arg Gly Pro
1               5

<210> SEQ ID NO 2
<211> LENGTH: 9
<212> TYPE: PRT
<213> ORGANISM: Artificial
<220> FEATURE:
<223> OTHER INFORMATION: Synthetic peptide

<400> SEQUENCE: 2

Gly Gly Cys Ser Arg Gly Pro Ala Ala
1               5

<210> SEQ ID NO 3
<211> LENGTH: 9
<212> TYPE: PRT
<213> ORGANISM: Artificial
<220> FEATURE:
<223> OTHER INFORMATION: Synthetic peptide

<400> SEQUENCE: 3

Cys Ser Arg Gly Pro Ala Ala Gly Asp
1               5

<210> SEQ ID NO 4
<211> LENGTH: 9
<212> TYPE: PRT
<213> ORGANISM: Artificial
<220> FEATURE:
<223> OTHER INFORMATION: Synthetic peptide

<400> SEQUENCE: 4

Arg Gly Pro Ala Ala Gly Asp Gly Arg
1               5

<210> SEQ ID NO 5
<211> LENGTH: 9
<212> TYPE: PRT
<213> ORGANISM: Artificial
<220> FEATURE:
<223> OTHER INFORMATION: Synthetic peptide

<400> SEQUENCE: 5

Pro Ala Ala Gly Asp Gly Arg Leu Arg
1               5

<210> SEQ ID NO 6
<211> LENGTH: 9
<212> TYPE: PRT
<213> ORGANISM: Artificial
<220> FEATURE:
<223> OTHER INFORMATION: Synthetic peptide

<400> SEQUENCE: 6

Ala Gly Asp Gly Arg Leu Arg Leu Ala

```
1               5

<210> SEQ ID NO 7
<211> LENGTH: 9
<212> TYPE: PRT
<213> ORGANISM: Artificial
<220> FEATURE:
<223> OTHER INFORMATION: Synthetic peptide

<400> SEQUENCE: 7

Asp Gly Arg Leu Arg Leu Ala Arg Leu
1               5

<210> SEQ ID NO 8
<211> LENGTH: 9
<212> TYPE: PRT
<213> ORGANISM: Artificial
<220> FEATURE:
<223> OTHER INFORMATION: Synthetic peptide

<400> SEQUENCE: 8

Arg Leu Arg Leu Ala Arg Leu Ala Leu
1               5

<210> SEQ ID NO 9
<211> LENGTH: 9
<212> TYPE: PRT
<213> ORGANISM: Artificial
<220> FEATURE:
<223> OTHER INFORMATION: Synthetic peptide

<400> SEQUENCE: 9

Arg Leu Ala Arg Leu Ala Leu Val Leu
1               5

<210> SEQ ID NO 10
<211> LENGTH: 9
<212> TYPE: PRT
<213> ORGANISM: Artificial
<220> FEATURE:
<223> OTHER INFORMATION: Synthetic peptide

<400> SEQUENCE: 10

Ala Arg Leu Ala Leu Val Leu Leu Gly
1               5

<210> SEQ ID NO 11
<211> LENGTH: 9
<212> TYPE: PRT
<213> ORGANISM: Artificial
<220> FEATURE:
<223> OTHER INFORMATION: Synthetic peptide

<400> SEQUENCE: 11

Leu Ala Leu Val Leu Leu Gly Trp Val
1               5

<210> SEQ ID NO 12
<211> LENGTH: 9
<212> TYPE: PRT
<213> ORGANISM: Artificial
<220> FEATURE:
<223> OTHER INFORMATION: Synthetic peptide

<400> SEQUENCE: 12

Leu Val Leu Leu Gly Trp Val Ser Ser
1               5
```

```
<210> SEQ ID NO 13
<211> LENGTH: 9
<212> TYPE: PRT
<213> ORGANISM: Artificial
<220> FEATURE:
<223> OTHER INFORMATION: Synthetic peptide

<400> SEQUENCE: 13

Leu Leu Gly Trp Val Ser Ser Ser Ser
1               5

<210> SEQ ID NO 14
<211> LENGTH: 9
<212> TYPE: PRT
<213> ORGANISM: Artificial
<220> FEATURE:
<223> OTHER INFORMATION: Synthetic peptide

<400> SEQUENCE: 14

Gly Trp Val Ser Ser Ser Ser Pro Thr
1               5

<210> SEQ ID NO 15
<211> LENGTH: 9
<212> TYPE: PRT
<213> ORGANISM: Artificial
<220> FEATURE:
<223> OTHER INFORMATION: Synthetic peptide

<400> SEQUENCE: 15

Val Ser Ser Ser Ser Pro Thr Ser Ser
1               5

<210> SEQ ID NO 16
<211> LENGTH: 9
<212> TYPE: PRT
<213> ORGANISM: Artificial
<220> FEATURE:
<223> OTHER INFORMATION: Synthetic peptide

<400> SEQUENCE: 16

Ser Ser Ser Pro Thr Ser Ser Ala Ser
1               5

<210> SEQ ID NO 17
<211> LENGTH: 9
<212> TYPE: PRT
<213> ORGANISM: Artificial
<220> FEATURE:
<223> OTHER INFORMATION: Synthetic peptide

<400> SEQUENCE: 17

Ser Pro Thr Ser Ser Ala Ser Ser Phe
1               5

<210> SEQ ID NO 18
<211> LENGTH: 9
<212> TYPE: PRT
<213> ORGANISM: Artificial
<220> FEATURE:
<223> OTHER INFORMATION: Synthetic peptide

<400> SEQUENCE: 18

Thr Ser Ser Ala Ser Ser Phe Ser Ser
1               5

<210> SEQ ID NO 19
```

```
<211> LENGTH: 9
<212> TYPE: PRT
<213> ORGANISM: Artificial
<220> FEATURE:
<223> OTHER INFORMATION: Synthetic peptide

<400> SEQUENCE: 19

Ser Ala Ser Ser Phe Ser Ser Ser Ala
1               5

<210> SEQ ID NO 20
<211> LENGTH: 9
<212> TYPE: PRT
<213> ORGANISM: Artificial
<220> FEATURE:
<223> OTHER INFORMATION: Synthetic peptide

<400> SEQUENCE: 20

Ser Ser Phe Ser Ser Ser Ala Pro Phe
1               5

<210> SEQ ID NO 21
<211> LENGTH: 9
<212> TYPE: PRT
<213> ORGANISM: Artificial
<220> FEATURE:
<223> OTHER INFORMATION: Synthetic peptide

<400> SEQUENCE: 21

Phe Ser Ser Ser Ala Pro Phe Leu Ala
1               5

<210> SEQ ID NO 22
<211> LENGTH: 9
<212> TYPE: PRT
<213> ORGANISM: Artificial
<220> FEATURE:
<223> OTHER INFORMATION: Synthetic peptide

<400> SEQUENCE: 22

Ser Ser Ala Pro Phe Leu Ala Ser Ala
1               5

<210> SEQ ID NO 23
<211> LENGTH: 9
<212> TYPE: PRT
<213> ORGANISM: Artificial
<220> FEATURE:
<223> OTHER INFORMATION: Synthetic peptide

<400> SEQUENCE: 23

Ala Pro Phe Leu Ala Ser Ala Val Ser
1               5

<210> SEQ ID NO 24
<211> LENGTH: 9
<212> TYPE: PRT
<213> ORGANISM: Artificial
<220> FEATURE:
<223> OTHER INFORMATION: Synthetic peptide

<400> SEQUENCE: 24

Phe Leu Ala Ser Ala Val Ser Ala Gln
1               5

<210> SEQ ID NO 25
<211> LENGTH: 9
<212> TYPE: PRT
```

<213> ORGANISM: Artificial
<220> FEATURE:
<223> OTHER INFORMATION: Synthetic peptide

<400> SEQUENCE: 25

Ala Ser Ala Val Ser Ala Gln Pro Pro
1               5

<210> SEQ ID NO 26
<211> LENGTH: 9
<212> TYPE: PRT
<213> ORGANISM: Artificial
<220> FEATURE:
<223> OTHER INFORMATION: Synthetic peptide

<400> SEQUENCE: 26

Ala Val Ser Ala Gln Pro Pro Leu Pro
1               5

<210> SEQ ID NO 27
<211> LENGTH: 9
<212> TYPE: PRT
<213> ORGANISM: Artificial
<220> FEATURE:
<223> OTHER INFORMATION: Synthetic peptide

<400> SEQUENCE: 27

Ser Ala Gln Pro Pro Leu Pro Asp Gln
1               5

<210> SEQ ID NO 28
<211> LENGTH: 9
<212> TYPE: PRT
<213> ORGANISM: Artificial
<220> FEATURE:
<223> OTHER INFORMATION: Synthetic peptide

<400> SEQUENCE: 28

Gln Pro Pro Leu Pro Asp Gln Cys Pro
1               5

<210> SEQ ID NO 29
<211> LENGTH: 9
<212> TYPE: PRT
<213> ORGANISM: Artificial
<220> FEATURE:
<223> OTHER INFORMATION: Synthetic peptide

<400> SEQUENCE: 29

Pro Leu Pro Asp Gln Cys Pro Ala Leu
1               5

<210> SEQ ID NO 30
<211> LENGTH: 9
<212> TYPE: PRT
<213> ORGANISM: Artificial
<220> FEATURE:
<223> OTHER INFORMATION: Synthetic peptide

<400> SEQUENCE: 30

Pro Asp Gln Cys Pro Ala Leu Cys Glu
1               5

<210> SEQ ID NO 31
<211> LENGTH: 9
<212> TYPE: PRT
<213> ORGANISM: Artificial
<220> FEATURE:

```
<223> OTHER INFORMATION: Synthetic peptide

<400> SEQUENCE: 31

Gln Cys Pro Ala Leu Cys Glu Cys Ser
1               5

<210> SEQ ID NO 32
<211> LENGTH: 9
<212> TYPE: PRT
<213> ORGANISM: Artificial
<220> FEATURE:
<223> OTHER INFORMATION: Synthetic peptide

<400> SEQUENCE: 32

Pro Ala Leu Cys Glu Cys Ser Glu Ala
1               5

<210> SEQ ID NO 33
<211> LENGTH: 9
<212> TYPE: PRT
<213> ORGANISM: Artificial
<220> FEATURE:
<223> OTHER INFORMATION: Synthetic peptide

<400> SEQUENCE: 33

Leu Cys Glu Cys Ser Glu Ala Ala Arg
1               5

<210> SEQ ID NO 34
<211> LENGTH: 9
<212> TYPE: PRT
<213> ORGANISM: Artificial
<220> FEATURE:
<223> OTHER INFORMATION: Synthetic peptide

<400> SEQUENCE: 34

Glu Cys Ser Glu Ala Ala Arg Thr Val
1               5

<210> SEQ ID NO 35
<211> LENGTH: 9
<212> TYPE: PRT
<213> ORGANISM: Artificial
<220> FEATURE:
<223> OTHER INFORMATION: Synthetic peptide

<400> SEQUENCE: 35

Ser Glu Ala Ala Arg Thr Val Lys Cys
1               5

<210> SEQ ID NO 36
<211> LENGTH: 9
<212> TYPE: PRT
<213> ORGANISM: Artificial
<220> FEATURE:
<223> OTHER INFORMATION: Synthetic peptide

<400> SEQUENCE: 36

Ala Ala Arg Thr Val Lys Cys Val Asn
1               5

<210> SEQ ID NO 37
<211> LENGTH: 9
<212> TYPE: PRT
<213> ORGANISM: Artificial
<220> FEATURE:
<223> OTHER INFORMATION: Synthetic peptide
```

```
<400> SEQUENCE: 37

Arg Thr Val Lys Cys Val Asn Arg Asn
1               5

<210> SEQ ID NO 38
<211> LENGTH: 9
<212> TYPE: PRT
<213> ORGANISM: Artificial
<220> FEATURE:
<223> OTHER INFORMATION: Synthetic peptide

<400> SEQUENCE: 38

Val Lys Cys Val Asn Arg Asn Leu Thr
1               5

<210> SEQ ID NO 39
<211> LENGTH: 9
<212> TYPE: PRT
<213> ORGANISM: Artificial
<220> FEATURE:
<223> OTHER INFORMATION: Synthetic peptide

<400> SEQUENCE: 39

Cys Val Asn Arg Asn Leu Thr Glu Val
1               5

<210> SEQ ID NO 40
<211> LENGTH: 9
<212> TYPE: PRT
<213> ORGANISM: Artificial
<220> FEATURE:
<223> OTHER INFORMATION: Synthetic peptide

<400> SEQUENCE: 40

Asn Arg Asn Leu Thr Glu Val Pro Thr
1               5

<210> SEQ ID NO 41
<211> LENGTH: 9
<212> TYPE: PRT
<213> ORGANISM: Artificial
<220> FEATURE:
<223> OTHER INFORMATION: Synthetic peptide

<400> SEQUENCE: 41

Asn Leu Thr Glu Val Pro Thr Asp Leu
1               5

<210> SEQ ID NO 42
<211> LENGTH: 9
<212> TYPE: PRT
<213> ORGANISM: Artificial
<220> FEATURE:
<223> OTHER INFORMATION: Synthetic peptide

<400> SEQUENCE: 42

Thr Glu Val Pro Thr Asp Leu Pro Ala
1               5

<210> SEQ ID NO 43
<211> LENGTH: 9
<212> TYPE: PRT
<213> ORGANISM: Artificial
<220> FEATURE:
<223> OTHER INFORMATION: Synthetic peptide

<400> SEQUENCE: 43
```

```
Val Pro Thr Asp Leu Pro Ala Tyr Val
1               5

<210> SEQ ID NO 44
<211> LENGTH: 9
<212> TYPE: PRT
<213> ORGANISM: Artificial
<220> FEATURE:
<223> OTHER INFORMATION: Synthetic peptide

<400> SEQUENCE: 44

Thr Asp Leu Pro Ala Tyr Val Arg Asn
1               5

<210> SEQ ID NO 45
<211> LENGTH: 9
<212> TYPE: PRT
<213> ORGANISM: Artificial
<220> FEATURE:
<223> OTHER INFORMATION: Synthetic peptide

<400> SEQUENCE: 45

Leu Pro Ala Tyr Val Arg Asn Leu Phe
1               5

<210> SEQ ID NO 46
<211> LENGTH: 9
<212> TYPE: PRT
<213> ORGANISM: Artificial
<220> FEATURE:
<223> OTHER INFORMATION: Synthetic peptide

<400> SEQUENCE: 46

Ala Tyr Val Arg Asn Leu Phe Leu Thr
1               5

<210> SEQ ID NO 47
<211> LENGTH: 9
<212> TYPE: PRT
<213> ORGANISM: Artificial
<220> FEATURE:
<223> OTHER INFORMATION: Synthetic peptide

<400> SEQUENCE: 47

Val Arg Asn Leu Phe Leu Thr Gly Asn
1               5

<210> SEQ ID NO 48
<211> LENGTH: 9
<212> TYPE: PRT
<213> ORGANISM: Artificial
<220> FEATURE:
<223> OTHER INFORMATION: Synthetic peptide

<400> SEQUENCE: 48

Asn Leu Phe Leu Thr Gly Asn Gln Leu
1               5

<210> SEQ ID NO 49
<211> LENGTH: 9
<212> TYPE: PRT
<213> ORGANISM: Artificial
<220> FEATURE:
<223> OTHER INFORMATION: Synthetic peptide

<400> SEQUENCE: 49

Phe Leu Thr Gly Asn Gln Leu Ala Val
1               5
```

```
<210> SEQ ID NO 50
<211> LENGTH: 9
<212> TYPE: PRT
<213> ORGANISM: Artificial
<220> FEATURE:
<223> OTHER INFORMATION: Synthetic peptide

<400> SEQUENCE: 50

Thr Gly Asn Gln Leu Ala Val Leu Pro
1               5

<210> SEQ ID NO 51
<211> LENGTH: 9
<212> TYPE: PRT
<213> ORGANISM: Artificial
<220> FEATURE:
<223> OTHER INFORMATION: Synthetic peptide

<400> SEQUENCE: 51

Asn Gln Leu Ala Val Leu Pro Ala Gly
1               5

<210> SEQ ID NO 52
<211> LENGTH: 9
<212> TYPE: PRT
<213> ORGANISM: Artificial
<220> FEATURE:
<223> OTHER INFORMATION: Synthetic peptide

<400> SEQUENCE: 52

Leu Ala Val Leu Pro Ala Gly Ala Phe
1               5

<210> SEQ ID NO 53
<211> LENGTH: 9
<212> TYPE: PRT
<213> ORGANISM: Artificial
<220> FEATURE:
<223> OTHER INFORMATION: Synthetic peptide

<400> SEQUENCE: 53

Val Leu Pro Ala Gly Ala Phe Ala Arg
1               5

<210> SEQ ID NO 54
<211> LENGTH: 9
<212> TYPE: PRT
<213> ORGANISM: Artificial
<220> FEATURE:
<223> OTHER INFORMATION: Synthetic peptide

<400> SEQUENCE: 54

Pro Ala Gly Ala Phe Ala Arg Arg Pro
1               5

<210> SEQ ID NO 55
<211> LENGTH: 9
<212> TYPE: PRT
<213> ORGANISM: Artificial
<220> FEATURE:
<223> OTHER INFORMATION: Synthetic peptide

<400> SEQUENCE: 55

Gly Ala Phe Ala Arg Arg Pro Pro Leu
1               5
```

```
<210> SEQ ID NO 56
<211> LENGTH: 9
<212> TYPE: PRT
<213> ORGANISM: Artificial
<220> FEATURE:
<223> OTHER INFORMATION: Synthetic peptide

<400> SEQUENCE: 56

Phe Ala Arg Arg Pro Pro Leu Ala Glu
1               5

<210> SEQ ID NO 57
<211> LENGTH: 9
<212> TYPE: PRT
<213> ORGANISM: Artificial
<220> FEATURE:
<223> OTHER INFORMATION: Synthetic peptide

<400> SEQUENCE: 57

Arg Arg Pro Pro Leu Ala Glu Leu Ala
1               5

<210> SEQ ID NO 58
<211> LENGTH: 9
<212> TYPE: PRT
<213> ORGANISM: Artificial
<220> FEATURE:
<223> OTHER INFORMATION: Synthetic peptide

<400> SEQUENCE: 58

Pro Pro Leu Ala Glu Leu Ala Ala Leu
1               5

<210> SEQ ID NO 59
<211> LENGTH: 9
<212> TYPE: PRT
<213> ORGANISM: Artificial
<220> FEATURE:
<223> OTHER INFORMATION: Synthetic peptide

<400> SEQUENCE: 59

Leu Ala Glu Leu Ala Ala Leu Asn Leu
1               5

<210> SEQ ID NO 60
<211> LENGTH: 9
<212> TYPE: PRT
<213> ORGANISM: Artificial
<220> FEATURE:
<223> OTHER INFORMATION: Synthetic peptide

<400> SEQUENCE: 60

Glu Leu Ala Ala Leu Asn Leu Ser Gly
1               5

<210> SEQ ID NO 61
<211> LENGTH: 9
<212> TYPE: PRT
<213> ORGANISM: Artificial
<220> FEATURE:
<223> OTHER INFORMATION: Synthetic peptide

<400> SEQUENCE: 61

Ala Ala Leu Asn Leu Ser Gly Ser Arg
1               5

<210> SEQ ID NO 62
<211> LENGTH: 9
```

```
<212> TYPE: PRT
<213> ORGANISM: Artificial
<220> FEATURE:
<223> OTHER INFORMATION: Synthetic peptide

<400> SEQUENCE: 62

Leu Asn Leu Ser Gly Ser Arg Leu Asp
1               5

<210> SEQ ID NO 63
<211> LENGTH: 9
<212> TYPE: PRT
<213> ORGANISM: Artificial
<220> FEATURE:
<223> OTHER INFORMATION: Synthetic peptide

<400> SEQUENCE: 63

Leu Ser Gly Ser Arg Leu Asp Glu Val
1               5

<210> SEQ ID NO 64
<211> LENGTH: 9
<212> TYPE: PRT
<213> ORGANISM: Artificial
<220> FEATURE:
<223> OTHER INFORMATION: Synthetic peptide

<400> SEQUENCE: 64

Gly Ser Arg Leu Asp Glu Val Arg Ala
1               5

<210> SEQ ID NO 65
<211> LENGTH: 9
<212> TYPE: PRT
<213> ORGANISM: Artificial
<220> FEATURE:
<223> OTHER INFORMATION: Synthetic peptide

<400> SEQUENCE: 65

Arg Leu Asp Glu Val Arg Ala Gly Ala
1               5

<210> SEQ ID NO 66
<211> LENGTH: 9
<212> TYPE: PRT
<213> ORGANISM: Artificial
<220> FEATURE:
<223> OTHER INFORMATION: Synthetic peptide

<400> SEQUENCE: 66

Asp Glu Val Arg Ala Gly Ala Phe Glu
1               5

<210> SEQ ID NO 67
<211> LENGTH: 9
<212> TYPE: PRT
<213> ORGANISM: Artificial
<220> FEATURE:
<223> OTHER INFORMATION: Synthetic peptide

<400> SEQUENCE: 67

Val Arg Ala Gly Ala Phe Glu His Leu
1               5

<210> SEQ ID NO 68
<211> LENGTH: 9
<212> TYPE: PRT
<213> ORGANISM: Artificial
```

```
<220> FEATURE:
<223> OTHER INFORMATION: Synthetic peptide

<400> SEQUENCE: 68

Ala Gly Ala Phe Glu His Leu Pro Ser
1               5

<210> SEQ ID NO 69
<211> LENGTH: 9
<212> TYPE: PRT
<213> ORGANISM: Artificial
<220> FEATURE:
<223> OTHER INFORMATION: Synthetic peptide

<400> SEQUENCE: 69

Ala Phe Glu His Leu Pro Ser Leu Arg
1               5

<210> SEQ ID NO 70
<211> LENGTH: 9
<212> TYPE: PRT
<213> ORGANISM: Artificial
<220> FEATURE:
<223> OTHER INFORMATION: Synthetic peptide

<400> SEQUENCE: 70

Glu His Leu Pro Ser Leu Arg Gln Leu
1               5

<210> SEQ ID NO 71
<211> LENGTH: 9
<212> TYPE: PRT
<213> ORGANISM: Artificial
<220> FEATURE:
<223> OTHER INFORMATION: Synthetic peptide

<400> SEQUENCE: 71

Leu Pro Ser Leu Arg Gln Leu Asp Leu
1               5

<210> SEQ ID NO 72
<211> LENGTH: 9
<212> TYPE: PRT
<213> ORGANISM: Artificial
<220> FEATURE:
<223> OTHER INFORMATION: Synthetic peptide

<400> SEQUENCE: 72

Ser Leu Arg Gln Leu Asp Leu Ser His
1               5

<210> SEQ ID NO 73
<211> LENGTH: 9
<212> TYPE: PRT
<213> ORGANISM: Artificial
<220> FEATURE:
<223> OTHER INFORMATION: Synthetic peptide

<400> SEQUENCE: 73

Arg Gln Leu Asp Leu Ser His Asn Pro
1               5

<210> SEQ ID NO 74
<211> LENGTH: 9
<212> TYPE: PRT
<213> ORGANISM: Artificial
<220> FEATURE:
<223> OTHER INFORMATION: Synthetic peptide
```

```
<400> SEQUENCE: 74

Leu Asp Leu Ser His Asn Pro Leu Ala
1               5

<210> SEQ ID NO 75
<211> LENGTH: 9
<212> TYPE: PRT
<213> ORGANISM: Artificial
<220> FEATURE:
<223> OTHER INFORMATION: Synthetic peptide

<400> SEQUENCE: 75

Leu Ser His Asn Pro Leu Ala Asp Leu
1               5

<210> SEQ ID NO 76
<211> LENGTH: 9
<212> TYPE: PRT
<213> ORGANISM: Artificial
<220> FEATURE:
<223> OTHER INFORMATION: Synthetic peptide

<400> SEQUENCE: 76

His Asn Pro Leu Ala Asp Leu Ser Pro
1               5

<210> SEQ ID NO 77
<211> LENGTH: 9
<212> TYPE: PRT
<213> ORGANISM: Artificial
<220> FEATURE:
<223> OTHER INFORMATION: Synthetic peptide

<400> SEQUENCE: 77

Pro Leu Ala Asp Leu Ser Pro Phe Ala
1               5

<210> SEQ ID NO 78
<211> LENGTH: 9
<212> TYPE: PRT
<213> ORGANISM: Artificial
<220> FEATURE:
<223> OTHER INFORMATION: Synthetic peptide

<400> SEQUENCE: 78

Ala Asp Leu Ser Pro Phe Ala Phe Ser
1               5

<210> SEQ ID NO 79
<211> LENGTH: 9
<212> TYPE: PRT
<213> ORGANISM: Artificial
<220> FEATURE:
<223> OTHER INFORMATION: Synthetic peptide

<400> SEQUENCE: 79

Leu Ser Pro Phe Ala Phe Ser Gly Ser
1               5

<210> SEQ ID NO 80
<211> LENGTH: 9
<212> TYPE: PRT
<213> ORGANISM: Artificial
<220> FEATURE:
<223> OTHER INFORMATION: Synthetic peptide

<400> SEQUENCE: 80
```

```
Pro Phe Ala Phe Ser Gly Ser Asn Ala
1               5
```

<210> SEQ ID NO 81
<211> LENGTH: 9
<212> TYPE: PRT
<213> ORGANISM: Artificial
<220> FEATURE:
<223> OTHER INFORMATION: Synthetic peptide

<400> SEQUENCE: 81

```
Ala Phe Ser Gly Ser Asn Ala Ser Val
1               5
```

<210> SEQ ID NO 82
<211> LENGTH: 9
<212> TYPE: PRT
<213> ORGANISM: Artificial
<220> FEATURE:
<223> OTHER INFORMATION: Synthetic peptide

<400> SEQUENCE: 82

```
Ser Gly Ser Asn Ala Ser Val Ser Ala
1               5
```

<210> SEQ ID NO 83
<211> LENGTH: 9
<212> TYPE: PRT
<213> ORGANISM: Artificial
<220> FEATURE:
<223> OTHER INFORMATION: Synthetic peptide

<400> SEQUENCE: 83

```
Ser Asn Ala Ser Val Ser Ala Pro Ser
1               5
```

<210> SEQ ID NO 84
<211> LENGTH: 9
<212> TYPE: PRT
<213> ORGANISM: Artificial
<220> FEATURE:
<223> OTHER INFORMATION: Synthetic peptide

<400> SEQUENCE: 84

```
Ala Ser Val Ser Ala Pro Ser Pro Leu
1               5
```

<210> SEQ ID NO 85
<211> LENGTH: 9
<212> TYPE: PRT
<213> ORGANISM: Artificial
<220> FEATURE:
<223> OTHER INFORMATION: Synthetic peptide

<400> SEQUENCE: 85

```
Val Ser Ala Pro Ser Pro Leu Val Glu
1               5
```

<210> SEQ ID NO 86
<211> LENGTH: 9
<212> TYPE: PRT
<213> ORGANISM: Artificial
<220> FEATURE:
<223> OTHER INFORMATION: Synthetic peptide

<400> SEQUENCE: 86

```
Ala Pro Ser Pro Leu Val Glu Leu Ile
```

```
<210> SEQ ID NO 87
<211> LENGTH: 9
<212> TYPE: PRT
<213> ORGANISM: Artificial
<220> FEATURE:
<223> OTHER INFORMATION: Synthetic peptide

<400> SEQUENCE: 87

Ser Pro Leu Val Glu Leu Ile Leu Asn
1               5

<210> SEQ ID NO 88
<211> LENGTH: 9
<212> TYPE: PRT
<213> ORGANISM: Artificial
<220> FEATURE:
<223> OTHER INFORMATION: Synthetic peptide

<400> SEQUENCE: 88

Leu Val Glu Leu Ile Leu Asn His Ile
1               5

<210> SEQ ID NO 89
<211> LENGTH: 9
<212> TYPE: PRT
<213> ORGANISM: Artificial
<220> FEATURE:
<223> OTHER INFORMATION: Synthetic peptide

<400> SEQUENCE: 89

Glu Leu Ile Leu Asn His Ile Val Pro
1               5

<210> SEQ ID NO 90
<211> LENGTH: 9
<212> TYPE: PRT
<213> ORGANISM: Artificial
<220> FEATURE:
<223> OTHER INFORMATION: Synthetic peptide

<400> SEQUENCE: 90

Ile Leu Asn His Ile Val Pro Pro Glu
1               5

<210> SEQ ID NO 91
<211> LENGTH: 9
<212> TYPE: PRT
<213> ORGANISM: Artificial
<220> FEATURE:
<223> OTHER INFORMATION: Synthetic peptide

<400> SEQUENCE: 91

Asn His Ile Val Pro Pro Glu Asp Glu
1               5

<210> SEQ ID NO 92
<211> LENGTH: 9
<212> TYPE: PRT
<213> ORGANISM: Artificial
<220> FEATURE:
<223> OTHER INFORMATION: Synthetic peptide

<400> SEQUENCE: 92

Ile Val Pro Pro Glu Asp Glu Arg Gln
1               5
```

<210> SEQ ID NO 93
<211> LENGTH: 9
<212> TYPE: PRT
<213> ORGANISM: Artificial
<220> FEATURE:
<223> OTHER INFORMATION: Synthetic peptide

<400> SEQUENCE: 93

Pro Pro Glu Asp Glu Arg Gln Asn Arg
1               5

<210> SEQ ID NO 94
<211> LENGTH: 9
<212> TYPE: PRT
<213> ORGANISM: Artificial
<220> FEATURE:
<223> OTHER INFORMATION: Synthetic peptide

<400> SEQUENCE: 94

Glu Asp Glu Arg Gln Asn Arg Ser Phe
1               5

<210> SEQ ID NO 95
<211> LENGTH: 9
<212> TYPE: PRT
<213> ORGANISM: Artificial
<220> FEATURE:
<223> OTHER INFORMATION: Synthetic peptide

<400> SEQUENCE: 95

Glu Arg Gln Asn Arg Ser Phe Glu Gly
1               5

<210> SEQ ID NO 96
<211> LENGTH: 9
<212> TYPE: PRT
<213> ORGANISM: Artificial
<220> FEATURE:
<223> OTHER INFORMATION: Synthetic peptide

<400> SEQUENCE: 96

Gln Asn Arg Ser Phe Glu Gly Met Val
1               5

<210> SEQ ID NO 97
<211> LENGTH: 9
<212> TYPE: PRT
<213> ORGANISM: Artificial
<220> FEATURE:
<223> OTHER INFORMATION: Synthetic peptide

<400> SEQUENCE: 97

Arg Ser Phe Glu Gly Met Val Val Ala
1               5

<210> SEQ ID NO 98
<211> LENGTH: 9
<212> TYPE: PRT
<213> ORGANISM: Artificial
<220> FEATURE:
<223> OTHER INFORMATION: Synthetic peptide

<400> SEQUENCE: 98

Phe Glu Gly Met Val Val Ala Ala Leu
1               5

<210> SEQ ID NO 99

```
<211> LENGTH: 9
<212> TYPE: PRT
<213> ORGANISM: Artificial
<220> FEATURE:
<223> OTHER INFORMATION: Synthetic peptide

<400> SEQUENCE: 99

Gly Met Val Val Ala Ala Leu Leu Ala
1               5

<210> SEQ ID NO 100
<211> LENGTH: 9
<212> TYPE: PRT
<213> ORGANISM: Artificial
<220> FEATURE:
<223> OTHER INFORMATION: Synthetic peptide

<400> SEQUENCE: 100

Gly Met Val Val Ala Ala Leu Leu Ala
1               5

<210> SEQ ID NO 101
<211> LENGTH: 9
<212> TYPE: PRT
<213> ORGANISM: Artificial
<220> FEATURE:
<223> OTHER INFORMATION: Synthetic peptide

<400> SEQUENCE: 101

Ala Ala Leu Leu Ala Gly Arg Ala Leu
1               5

<210> SEQ ID NO 102
<211> LENGTH: 9
<212> TYPE: PRT
<213> ORGANISM: Artificial
<220> FEATURE:
<223> OTHER INFORMATION: Synthetic peptide

<400> SEQUENCE: 102

Leu Leu Ala Gly Arg Ala Leu Gln Gly
1               5

<210> SEQ ID NO 103
<211> LENGTH: 9
<212> TYPE: PRT
<213> ORGANISM: Artificial
<220> FEATURE:
<223> OTHER INFORMATION: Synthetic peptide

<400> SEQUENCE: 103

Ala Gly Arg Ala Leu Gln Gly Leu Arg
1               5

<210> SEQ ID NO 104
<211> LENGTH: 9
<212> TYPE: PRT
<213> ORGANISM: Artificial
<220> FEATURE:
<223> OTHER INFORMATION: Synthetic peptide

<400> SEQUENCE: 104

Arg Ala Leu Gln Gly Leu Arg Arg Leu
1               5

<210> SEQ ID NO 105
<211> LENGTH: 9
<212> TYPE: PRT
```

```
<213> ORGANISM: Artificial
<220> FEATURE:
<223> OTHER INFORMATION: Synthetic peptide

<400> SEQUENCE: 105

Leu Gln Gly Leu Arg Arg Leu Glu Leu
1               5

<210> SEQ ID NO 106
<211> LENGTH: 9
<212> TYPE: PRT
<213> ORGANISM: Artificial
<220> FEATURE:
<223> OTHER INFORMATION: Synthetic peptide

<400> SEQUENCE: 106

Gly Leu Arg Arg Leu Glu Leu Ala Ser
1               5

<210> SEQ ID NO 107
<211> LENGTH: 9
<212> TYPE: PRT
<213> ORGANISM: Artificial
<220> FEATURE:
<223> OTHER INFORMATION: Synthetic peptide

<400> SEQUENCE: 107

Arg Arg Leu Glu Leu Ala Ser Asn His
1               5

<210> SEQ ID NO 108
<211> LENGTH: 9
<212> TYPE: PRT
<213> ORGANISM: Artificial
<220> FEATURE:
<223> OTHER INFORMATION: Synthetic peptide

<400> SEQUENCE: 108

Leu Glu Leu Ala Ser Asn His Phe Leu
1               5

<210> SEQ ID NO 109
<211> LENGTH: 9
<212> TYPE: PRT
<213> ORGANISM: Artificial
<220> FEATURE:
<223> OTHER INFORMATION: Synthetic peptide

<400> SEQUENCE: 109

Leu Ala Ser Asn His Phe Leu Tyr Leu
1               5

<210> SEQ ID NO 110
<211> LENGTH: 9
<212> TYPE: PRT
<213> ORGANISM: Artificial
<220> FEATURE:
<223> OTHER INFORMATION: Synthetic peptide

<400> SEQUENCE: 110

Ser Asn His Phe Leu Tyr Leu Pro Arg
1               5

<210> SEQ ID NO 111
<211> LENGTH: 9
<212> TYPE: PRT
<213> ORGANISM: Artificial
<220> FEATURE:
```

<223> OTHER INFORMATION: Synthetic peptide

<400> SEQUENCE: 111

His Phe Leu Tyr Leu Pro Arg Asp Val
1               5

<210> SEQ ID NO 112
<211> LENGTH: 9
<212> TYPE: PRT
<213> ORGANISM: Artificial
<220> FEATURE:
<223> OTHER INFORMATION: Synthetic peptide

<400> SEQUENCE: 112

Leu Tyr Leu Pro Arg Asp Val Leu Ala
1               5

<210> SEQ ID NO 113
<211> LENGTH: 9
<212> TYPE: PRT
<213> ORGANISM: Artificial
<220> FEATURE:
<223> OTHER INFORMATION: Synthetic peptide

<400> SEQUENCE: 113

Leu Pro Arg Asp Val Leu Ala Gln Leu
1               5

<210> SEQ ID NO 114
<211> LENGTH: 9
<212> TYPE: PRT
<213> ORGANISM: Artificial
<220> FEATURE:
<223> OTHER INFORMATION: Synthetic peptide

<400> SEQUENCE: 114

Arg Asp Val Leu Ala Gln Leu Pro Ser
1               5

<210> SEQ ID NO 115
<211> LENGTH: 9
<212> TYPE: PRT
<213> ORGANISM: Artificial
<220> FEATURE:
<223> OTHER INFORMATION: Synthetic peptide

<400> SEQUENCE: 115

Val Leu Ala Gln Leu Pro Ser Leu Arg
1               5

<210> SEQ ID NO 116
<211> LENGTH: 9
<212> TYPE: PRT
<213> ORGANISM: Artificial
<220> FEATURE:
<223> OTHER INFORMATION: Synthetic peptide

<400> SEQUENCE: 116

Ala Gln Leu Pro Ser Leu Arg His Leu
1               5

<210> SEQ ID NO 117
<211> LENGTH: 9
<212> TYPE: PRT
<213> ORGANISM: Artificial
<220> FEATURE:
<223> OTHER INFORMATION: Synthetic peptide

```
<400> SEQUENCE: 117

Leu Pro Ser Leu Arg His Leu Asp Leu
1               5

<210> SEQ ID NO 118
<211> LENGTH: 9
<212> TYPE: PRT
<213> ORGANISM: Artificial
<220> FEATURE:
<223> OTHER INFORMATION: Synthetic peptide

<400> SEQUENCE: 118

Ser Leu Arg His Leu Asp Leu Ser Asn
1               5

<210> SEQ ID NO 119
<211> LENGTH: 9
<212> TYPE: PRT
<213> ORGANISM: Artificial
<220> FEATURE:
<223> OTHER INFORMATION: Synthetic peptide

<400> SEQUENCE: 119

Arg His Leu Asp Leu Ser Asn Asn Ser
1               5

<210> SEQ ID NO 120
<211> LENGTH: 9
<212> TYPE: PRT
<213> ORGANISM: Artificial
<220> FEATURE:
<223> OTHER INFORMATION: Synthetic peptide

<400> SEQUENCE: 120

Leu Asp Leu Ser Asn Asn Ser Leu Val
1               5

<210> SEQ ID NO 121
<211> LENGTH: 9
<212> TYPE: PRT
<213> ORGANISM: Artificial
<220> FEATURE:
<223> OTHER INFORMATION: Synthetic peptide

<400> SEQUENCE: 121

Leu Ser Asn Asn Ser Leu Val Ser Leu
1               5

<210> SEQ ID NO 122
<211> LENGTH: 9
<212> TYPE: PRT
<213> ORGANISM: Artificial
<220> FEATURE:
<223> OTHER INFORMATION: Synthetic peptide

<400> SEQUENCE: 122

Asn Asn Ser Leu Val Ser Leu Thr Tyr
1               5

<210> SEQ ID NO 123
<211> LENGTH: 9
<212> TYPE: PRT
<213> ORGANISM: Artificial
<220> FEATURE:
<223> OTHER INFORMATION: Synthetic peptide

<400> SEQUENCE: 123
```

Ser Leu Val Ser Leu Thr Tyr Val Ser
1               5

<210> SEQ ID NO 124
<211> LENGTH: 9
<212> TYPE: PRT
<213> ORGANISM: Artificial
<220> FEATURE:
<223> OTHER INFORMATION: Synthetic peptide

<400> SEQUENCE: 124

Val Ser Leu Thr Tyr Val Ser Phe Arg
1               5

<210> SEQ ID NO 125
<211> LENGTH: 9
<212> TYPE: PRT
<213> ORGANISM: Artificial
<220> FEATURE:
<223> OTHER INFORMATION: Synthetic peptide

<400> SEQUENCE: 125

Leu Thr Tyr Val Ser Phe Arg Asn Leu
1               5

<210> SEQ ID NO 126
<211> LENGTH: 9
<212> TYPE: PRT
<213> ORGANISM: Artificial
<220> FEATURE:
<223> OTHER INFORMATION: Synthetic peptide

<400> SEQUENCE: 126

Tyr Val Ser Phe Arg Asn Leu Thr His
1               5

<210> SEQ ID NO 127
<211> LENGTH: 9
<212> TYPE: PRT
<213> ORGANISM: Artificial
<220> FEATURE:
<223> OTHER INFORMATION: Synthetic peptide

<400> SEQUENCE: 127

Ser Phe Arg Asn Leu Thr His Leu Glu
1               5

<210> SEQ ID NO 128
<211> LENGTH: 9
<212> TYPE: PRT
<213> ORGANISM: Artificial
<220> FEATURE:
<223> OTHER INFORMATION: Synthetic peptide

<400> SEQUENCE: 128

Arg Asn Leu Thr His Leu Glu Ser Leu
1               5

<210> SEQ ID NO 129
<211> LENGTH: 9
<212> TYPE: PRT
<213> ORGANISM: Artificial
<220> FEATURE:
<223> OTHER INFORMATION: Synthetic peptide

<400> SEQUENCE: 129

Leu Thr His Leu Glu Ser Leu His Leu
1               5

```
<210> SEQ ID NO 130
<211> LENGTH: 9
<212> TYPE: PRT
<213> ORGANISM: Artificial
<220> FEATURE:
<223> OTHER INFORMATION: Synthetic peptide

<400> SEQUENCE: 130

His Leu Glu Ser Leu His Leu Glu Asp
1               5

<210> SEQ ID NO 131
<211> LENGTH: 9
<212> TYPE: PRT
<213> ORGANISM: Artificial
<220> FEATURE:
<223> OTHER INFORMATION: Synthetic peptide

<400> SEQUENCE: 131

Glu Ser Leu His Leu Glu Asp Asn Ala
1               5

<210> SEQ ID NO 132
<211> LENGTH: 9
<212> TYPE: PRT
<213> ORGANISM: Artificial
<220> FEATURE:
<223> OTHER INFORMATION: Synthetic peptide

<400> SEQUENCE: 132

Leu His Leu Glu Asp Asn Ala Leu Lys
1               5

<210> SEQ ID NO 133
<211> LENGTH: 9
<212> TYPE: PRT
<213> ORGANISM: Artificial
<220> FEATURE:
<223> OTHER INFORMATION: Synthetic peptide

<400> SEQUENCE: 133

Leu Glu Asp Asn Ala Leu Lys Val Leu
1               5

<210> SEQ ID NO 134
<211> LENGTH: 9
<212> TYPE: PRT
<213> ORGANISM: Artificial
<220> FEATURE:
<223> OTHER INFORMATION: Synthetic peptide

<400> SEQUENCE: 134

Asp Asn Ala Leu Lys Val Leu His Asn
1               5

<210> SEQ ID NO 135
<211> LENGTH: 9
<212> TYPE: PRT
<213> ORGANISM: Artificial
<220> FEATURE:
<223> OTHER INFORMATION: Synthetic peptide

<400> SEQUENCE: 135

Ala Leu Lys Val Leu His Asn Gly Thr
1               5
```

```
<210> SEQ ID NO 136
<211> LENGTH: 9
<212> TYPE: PRT
<213> ORGANISM: Artificial
<220> FEATURE:
<223> OTHER INFORMATION: Synthetic peptide

<400> SEQUENCE: 136

Lys Val Leu His Asn Gly Thr Leu Ala
1               5

<210> SEQ ID NO 137
<211> LENGTH: 9
<212> TYPE: PRT
<213> ORGANISM: Artificial
<220> FEATURE:
<223> OTHER INFORMATION: Synthetic peptide

<400> SEQUENCE: 137

Leu His Asn Gly Thr Leu Ala Glu Leu
1               5

<210> SEQ ID NO 138
<211> LENGTH: 9
<212> TYPE: PRT
<213> ORGANISM: Artificial
<220> FEATURE:
<223> OTHER INFORMATION: Synthetic peptide

<400> SEQUENCE: 138

Asn Gly Thr Leu Ala Glu Leu Gln Gly
1               5

<210> SEQ ID NO 139
<211> LENGTH: 9
<212> TYPE: PRT
<213> ORGANISM: Artificial
<220> FEATURE:
<223> OTHER INFORMATION: Synthetic peptide

<400> SEQUENCE: 139

Thr Leu Ala Glu Leu Gln Gly Leu Pro
1               5

<210> SEQ ID NO 140
<211> LENGTH: 9
<212> TYPE: PRT
<213> ORGANISM: Artificial
<220> FEATURE:
<223> OTHER INFORMATION: Synthetic peptide

<400> SEQUENCE: 140

Ala Glu Leu Gln Gly Leu Pro His Ile
1               5

<210> SEQ ID NO 141
<211> LENGTH: 9
<212> TYPE: PRT
<213> ORGANISM: Artificial
<220> FEATURE:
<223> OTHER INFORMATION: Synthetic peptide

<400> SEQUENCE: 141

Leu Gln Gly Leu Pro His Ile Arg Val
1               5

<210> SEQ ID NO 142
<211> LENGTH: 9
```

```
<212> TYPE: PRT
<213> ORGANISM: Artificial
<220> FEATURE:
<223> OTHER INFORMATION: Synthetic peptide

<400> SEQUENCE: 142

Gly Leu Pro His Ile Arg Val Phe Leu
1               5

<210> SEQ ID NO 143
<211> LENGTH: 9
<212> TYPE: PRT
<213> ORGANISM: Artificial
<220> FEATURE:
<223> OTHER INFORMATION: Synthetic peptide

<400> SEQUENCE: 143

Pro His Ile Arg Val Phe Leu Asp Asn
1               5

<210> SEQ ID NO 144
<211> LENGTH: 9
<212> TYPE: PRT
<213> ORGANISM: Artificial
<220> FEATURE:
<223> OTHER INFORMATION: Synthetic peptide

<400> SEQUENCE: 144

Ile Arg Val Phe Leu Asp Asn Asn Pro
1               5

<210> SEQ ID NO 145
<211> LENGTH: 9
<212> TYPE: PRT
<213> ORGANISM: Artificial
<220> FEATURE:
<223> OTHER INFORMATION: Synthetic peptide

<400> SEQUENCE: 145

Val Phe Leu Asp Asn Asn Pro Trp Val
1               5

<210> SEQ ID NO 146
<211> LENGTH: 9
<212> TYPE: PRT
<213> ORGANISM: Artificial
<220> FEATURE:
<223> OTHER INFORMATION: Synthetic peptide

<400> SEQUENCE: 146

Leu Asp Asn Asn Pro Trp Val Cys Asp
1               5

<210> SEQ ID NO 147
<211> LENGTH: 9
<212> TYPE: PRT
<213> ORGANISM: Artificial
<220> FEATURE:
<223> OTHER INFORMATION: Synthetic peptide

<400> SEQUENCE: 147

Asn Asn Pro Trp Val Cys Asp Cys His
1               5

<210> SEQ ID NO 148
<211> LENGTH: 9
<212> TYPE: PRT
<213> ORGANISM: Artificial
```

<220> FEATURE:
<223> OTHER INFORMATION: Synthetic peptide

<400> SEQUENCE: 148

Pro Trp Val Cys Asp Cys His Met Ala
1               5

<210> SEQ ID NO 149
<211> LENGTH: 9
<212> TYPE: PRT
<213> ORGANISM: Artificial
<220> FEATURE:
<223> OTHER INFORMATION: Synthetic peptide

<400> SEQUENCE: 149

Val Cys Asp Cys His Met Ala Asp Met
1               5

<210> SEQ ID NO 150
<211> LENGTH: 9
<212> TYPE: PRT
<213> ORGANISM: Artificial
<220> FEATURE:
<223> OTHER INFORMATION: Synthetic peptide

<400> SEQUENCE: 150

Asp Cys His Met Ala Asp Met Val Thr
1               5

<210> SEQ ID NO 151
<211> LENGTH: 9
<212> TYPE: PRT
<213> ORGANISM: Artificial
<220> FEATURE:
<223> OTHER INFORMATION: Synthetic peptide

<400> SEQUENCE: 151

His Met Ala Asp Met Val Thr Trp Leu
1               5

<210> SEQ ID NO 152
<211> LENGTH: 9
<212> TYPE: PRT
<213> ORGANISM: Artificial
<220> FEATURE:
<223> OTHER INFORMATION: Synthetic peptide

<400> SEQUENCE: 152

Ala Asp Met Val Thr Trp Leu Lys Glu
1               5

<210> SEQ ID NO 153
<211> LENGTH: 9
<212> TYPE: PRT
<213> ORGANISM: Artificial
<220> FEATURE:
<223> OTHER INFORMATION: Synthetic peptide

<400> SEQUENCE: 153

Met Val Thr Trp Leu Lys Glu Thr Glu
1               5

<210> SEQ ID NO 154
<211> LENGTH: 9
<212> TYPE: PRT
<213> ORGANISM: Artificial
<220> FEATURE:
<223> OTHER INFORMATION: Synthetic peptide

```
<400> SEQUENCE: 154

Thr Trp Leu Lys Glu Thr Glu Val Val
1               5

<210> SEQ ID NO 155
<211> LENGTH: 9
<212> TYPE: PRT
<213> ORGANISM: Artificial
<220> FEATURE:
<223> OTHER INFORMATION: Synthetic peptide

<400> SEQUENCE: 155

Leu Lys Glu Thr Glu Val Val Gln Gly
1               5

<210> SEQ ID NO 156
<211> LENGTH: 9
<212> TYPE: PRT
<213> ORGANISM: Artificial
<220> FEATURE:
<223> OTHER INFORMATION: Synthetic peptide

<400> SEQUENCE: 156

Glu Thr Glu Val Val Gln Gly Lys Asp
1               5

<210> SEQ ID NO 157
<211> LENGTH: 9
<212> TYPE: PRT
<213> ORGANISM: Artificial
<220> FEATURE:
<223> OTHER INFORMATION: Synthetic peptide

<400> SEQUENCE: 157

Glu Val Val Gln Gly Lys Asp Arg Leu
1               5

<210> SEQ ID NO 158
<211> LENGTH: 9
<212> TYPE: PRT
<213> ORGANISM: Artificial
<220> FEATURE:
<223> OTHER INFORMATION: Synthetic peptide

<400> SEQUENCE: 158

Val Gln Gly Lys Asp Arg Leu Thr Cys
1               5

<210> SEQ ID NO 159
<211> LENGTH: 9
<212> TYPE: PRT
<213> ORGANISM: Artificial
<220> FEATURE:
<223> OTHER INFORMATION: Synthetic peptide

<400> SEQUENCE: 159

Gly Lys Asp Arg Leu Thr Cys Ala Tyr
1               5

<210> SEQ ID NO 160
<211> LENGTH: 9
<212> TYPE: PRT
<213> ORGANISM: Artificial
<220> FEATURE:
<223> OTHER INFORMATION: Synthetic peptide

<400> SEQUENCE: 160
```

Asp Arg Leu Thr Cys Ala Tyr Pro Glu
1               5

<210> SEQ ID NO 161
<211> LENGTH: 9
<212> TYPE: PRT
<213> ORGANISM: Artificial
<220> FEATURE:
<223> OTHER INFORMATION: Synthetic peptide

<400> SEQUENCE: 161

Leu Thr Cys Ala Tyr Pro Glu Lys Met
1               5

<210> SEQ ID NO 162
<211> LENGTH: 9
<212> TYPE: PRT
<213> ORGANISM: Artificial
<220> FEATURE:
<223> OTHER INFORMATION: Synthetic peptide

<400> SEQUENCE: 162

Cys Ala Tyr Pro Glu Lys Met Arg Asn
1               5

<210> SEQ ID NO 163
<211> LENGTH: 9
<212> TYPE: PRT
<213> ORGANISM: Artificial
<220> FEATURE:
<223> OTHER INFORMATION: Synthetic peptide

<400> SEQUENCE: 163

Tyr Pro Glu Lys Met Arg Asn Arg Val
1               5

<210> SEQ ID NO 164
<211> LENGTH: 9
<212> TYPE: PRT
<213> ORGANISM: Artificial
<220> FEATURE:
<223> OTHER INFORMATION: Synthetic peptide

<400> SEQUENCE: 164

Glu Lys Met Arg Asn Arg Val Leu Leu
1               5

<210> SEQ ID NO 165
<211> LENGTH: 9
<212> TYPE: PRT
<213> ORGANISM: Artificial
<220> FEATURE:
<223> OTHER INFORMATION: Synthetic peptide

<400> SEQUENCE: 165

Met Arg Asn Arg Val Leu Leu Glu Leu
1               5

<210> SEQ ID NO 166
<211> LENGTH: 9
<212> TYPE: PRT
<213> ORGANISM: Artificial
<220> FEATURE:
<223> OTHER INFORMATION: Synthetic peptide

<400> SEQUENCE: 166

Asn Arg Val Leu Leu Glu Leu Asn Ser

<210> SEQ ID NO 167
<211> LENGTH: 9
<212> TYPE: PRT
<213> ORGANISM: Artificial
<220> FEATURE:
<223> OTHER INFORMATION: Synthetic peptide

<400> SEQUENCE: 167

Val Leu Leu Glu Leu Asn Ser Ala Asp
1               5

<210> SEQ ID NO 168
<211> LENGTH: 9
<212> TYPE: PRT
<213> ORGANISM: Artificial
<220> FEATURE:
<223> OTHER INFORMATION: Synthetic peptide

<400> SEQUENCE: 168

Leu Glu Leu Asn Ser Ala Asp Leu Asp
1               5

<210> SEQ ID NO 169
<211> LENGTH: 9
<212> TYPE: PRT
<213> ORGANISM: Artificial
<220> FEATURE:
<223> OTHER INFORMATION: Synthetic peptide

<400> SEQUENCE: 169

Leu Asn Ser Ala Asp Leu Asp Cys Asp
1               5

<210> SEQ ID NO 170
<211> LENGTH: 9
<212> TYPE: PRT
<213> ORGANISM: Artificial
<220> FEATURE:
<223> OTHER INFORMATION: Synthetic peptide

<400> SEQUENCE: 170

Ser Ala Asp Leu Asp Cys Asp Pro Ile
1               5

<210> SEQ ID NO 171
<211> LENGTH: 9
<212> TYPE: PRT
<213> ORGANISM: Artificial
<220> FEATURE:
<223> OTHER INFORMATION: Synthetic peptide

<400> SEQUENCE: 171

Asp Leu Asp Cys Asp Pro Ile Leu Pro
1               5

<210> SEQ ID NO 172
<211> LENGTH: 9
<212> TYPE: PRT
<213> ORGANISM: Artificial
<220> FEATURE:
<223> OTHER INFORMATION: Synthetic peptide

<400> SEQUENCE: 172

Asp Cys Asp Pro Ile Leu Pro Pro Ser
1               5

```
<210> SEQ ID NO 173
<211> LENGTH: 9
<212> TYPE: PRT
<213> ORGANISM: Artificial
<220> FEATURE:
<223> OTHER INFORMATION: Synthetic peptide

<400> SEQUENCE: 173

Asp Pro Ile Leu Pro Pro Ser Leu Gln
1               5

<210> SEQ ID NO 174
<211> LENGTH: 9
<212> TYPE: PRT
<213> ORGANISM: Artificial
<220> FEATURE:
<223> OTHER INFORMATION: Synthetic peptide

<400> SEQUENCE: 174

Ile Leu Pro Pro Ser Leu Gln Thr Ser
1               5

<210> SEQ ID NO 175
<211> LENGTH: 9
<212> TYPE: PRT
<213> ORGANISM: Artificial
<220> FEATURE:
<223> OTHER INFORMATION: Synthetic peptide

<400> SEQUENCE: 175

Pro Pro Ser Leu Gln Thr Ser Tyr Val
1               5

<210> SEQ ID NO 176
<211> LENGTH: 9
<212> TYPE: PRT
<213> ORGANISM: Artificial
<220> FEATURE:
<223> OTHER INFORMATION: Synthetic peptide

<400> SEQUENCE: 176

Ser Leu Gln Thr Ser Tyr Val Phe Leu
1               5

<210> SEQ ID NO 177
<211> LENGTH: 9
<212> TYPE: PRT
<213> ORGANISM: Artificial
<220> FEATURE:
<223> OTHER INFORMATION: Synthetic peptide

<400> SEQUENCE: 177

Gln Thr Ser Tyr Val Phe Leu Gly Ile
1               5

<210> SEQ ID NO 178
<211> LENGTH: 9
<212> TYPE: PRT
<213> ORGANISM: Artificial
<220> FEATURE:
<223> OTHER INFORMATION: Synthetic peptide

<400> SEQUENCE: 178

Ser Tyr Val Phe Leu Gly Ile Val Leu
1               5

<210> SEQ ID NO 179
```

```
<211> LENGTH: 9
<212> TYPE: PRT
<213> ORGANISM: Artificial
<220> FEATURE:
<223> OTHER INFORMATION: Synthetic peptide

<400> SEQUENCE: 179

Val Phe Leu Gly Ile Val Leu Ala Leu
1               5

<210> SEQ ID NO 180
<211> LENGTH: 9
<212> TYPE: PRT
<213> ORGANISM: Artificial
<220> FEATURE:
<223> OTHER INFORMATION: Synthetic peptide

<400> SEQUENCE: 180

Leu Gly Ile Val Leu Ala Leu Ile Gly
1               5

<210> SEQ ID NO 181
<211> LENGTH: 9
<212> TYPE: PRT
<213> ORGANISM: Artificial
<220> FEATURE:
<223> OTHER INFORMATION: Synthetic peptide

<400> SEQUENCE: 181

Ile Val Leu Ala Leu Ile Gly Ala Ile
1               5

<210> SEQ ID NO 182
<211> LENGTH: 9
<212> TYPE: PRT
<213> ORGANISM: Artificial
<220> FEATURE:
<223> OTHER INFORMATION: Synthetic peptide

<400> SEQUENCE: 182

Leu Ala Leu Ile Gly Ala Ile Phe Leu
1               5

<210> SEQ ID NO 183
<211> LENGTH: 9
<212> TYPE: PRT
<213> ORGANISM: Artificial
<220> FEATURE:
<223> OTHER INFORMATION: Synthetic peptide

<400> SEQUENCE: 183

Leu Ile Gly Ala Ile Phe Leu Leu Val
1               5

<210> SEQ ID NO 184
<211> LENGTH: 9
<212> TYPE: PRT
<213> ORGANISM: Artificial
<220> FEATURE:
<223> OTHER INFORMATION: Synthetic peptide

<400> SEQUENCE: 184

Gly Ala Ile Phe Leu Leu Val Leu Tyr
1               5

<210> SEQ ID NO 185
<211> LENGTH: 9
<212> TYPE: PRT
```

```
<213> ORGANISM: Artificial
<220> FEATURE:
<223> OTHER INFORMATION: Synthetic peptide

<400> SEQUENCE: 185

Ile Phe Leu Leu Val Leu Tyr Leu Asn
1               5

<210> SEQ ID NO 186
<211> LENGTH: 9
<212> TYPE: PRT
<213> ORGANISM: Artificial
<220> FEATURE:
<223> OTHER INFORMATION: Synthetic peptide

<400> SEQUENCE: 186

Leu Leu Val Leu Tyr Leu Asn Arg Lys
1               5

<210> SEQ ID NO 187
<211> LENGTH: 9
<212> TYPE: PRT
<213> ORGANISM: Artificial
<220> FEATURE:
<223> OTHER INFORMATION: Synthetic peptide

<400> SEQUENCE: 187

Val Leu Tyr Leu Asn Arg Lys Gly Ile
1               5

<210> SEQ ID NO 188
<211> LENGTH: 9
<212> TYPE: PRT
<213> ORGANISM: Artificial
<220> FEATURE:
<223> OTHER INFORMATION: Synthetic peptide

<400> SEQUENCE: 188

Tyr Leu Asn Arg Lys Gly Ile Lys Lys
1               5

<210> SEQ ID NO 189
<211> LENGTH: 9
<212> TYPE: PRT
<213> ORGANISM: Artificial
<220> FEATURE:
<223> OTHER INFORMATION: Synthetic peptide

<400> SEQUENCE: 189

Asn Arg Lys Gly Ile Lys Lys Trp Met
1               5

<210> SEQ ID NO 190
<211> LENGTH: 9
<212> TYPE: PRT
<213> ORGANISM: Artificial
<220> FEATURE:
<223> OTHER INFORMATION: Synthetic peptide

<400> SEQUENCE: 190

Lys Gly Ile Lys Lys Trp Met His Asn
1               5

<210> SEQ ID NO 191
<211> LENGTH: 9
<212> TYPE: PRT
<213> ORGANISM: Artificial
<220> FEATURE:
```

<223> OTHER INFORMATION: Synthetic peptide

<400> SEQUENCE: 191

Ile Lys Lys Trp Met His Asn Ile Arg
1               5

<210> SEQ ID NO 192
<211> LENGTH: 9
<212> TYPE: PRT
<213> ORGANISM: Artificial
<220> FEATURE:
<223> OTHER INFORMATION: Synthetic peptide

<400> SEQUENCE: 192

Lys Trp Met His Asn Ile Arg Asp Ala
1               5

<210> SEQ ID NO 193
<211> LENGTH: 9
<212> TYPE: PRT
<213> ORGANISM: Artificial
<220> FEATURE:
<223> OTHER INFORMATION: Synthetic peptide

<400> SEQUENCE: 193

Met His Asn Ile Arg Asp Ala Cys Arg
1               5

<210> SEQ ID NO 194
<211> LENGTH: 9
<212> TYPE: PRT
<213> ORGANISM: Artificial
<220> FEATURE:
<223> OTHER INFORMATION: Synthetic peptide

<400> SEQUENCE: 194

Asn Ile Arg Asp Ala Cys Arg Asp His
1               5

<210> SEQ ID NO 195
<211> LENGTH: 9
<212> TYPE: PRT
<213> ORGANISM: Artificial
<220> FEATURE:
<223> OTHER INFORMATION: Synthetic peptide

<400> SEQUENCE: 195

Arg Asp Ala Cys Arg Asp His Met Glu
1               5

<210> SEQ ID NO 196
<211> LENGTH: 9
<212> TYPE: PRT
<213> ORGANISM: Artificial
<220> FEATURE:
<223> OTHER INFORMATION: Synthetic peptide

<400> SEQUENCE: 196

Ala Cys Arg Asp His Met Glu Gly Tyr
1               5

<210> SEQ ID NO 197
<211> LENGTH: 9
<212> TYPE: PRT
<213> ORGANISM: Artificial
<220> FEATURE:
<223> OTHER INFORMATION: Synthetic peptide

```
<400> SEQUENCE: 197

Arg Asp His Met Glu Gly Tyr His Tyr
1               5

<210> SEQ ID NO 198
<211> LENGTH: 9
<212> TYPE: PRT
<213> ORGANISM: Artificial
<220> FEATURE:
<223> OTHER INFORMATION: Synthetic peptide

<400> SEQUENCE: 198

His Met Glu Gly Tyr His Tyr Arg Tyr
1               5

<210> SEQ ID NO 199
<211> LENGTH: 9
<212> TYPE: PRT
<213> ORGANISM: Artificial
<220> FEATURE:
<223> OTHER INFORMATION: Synthetic peptide

<400> SEQUENCE: 199

Glu Gly Tyr His Tyr Arg Tyr Glu Ile
1               5

<210> SEQ ID NO 200
<211> LENGTH: 9
<212> TYPE: PRT
<213> ORGANISM: Artificial
<220> FEATURE:
<223> OTHER INFORMATION: Synthetic peptide

<400> SEQUENCE: 200

Tyr His Tyr Arg Tyr Glu Ile Asn Ala
1               5

<210> SEQ ID NO 201
<211> LENGTH: 9
<212> TYPE: PRT
<213> ORGANISM: Artificial
<220> FEATURE:
<223> OTHER INFORMATION: Synthetic peptide

<400> SEQUENCE: 201

Tyr Arg Tyr Glu Ile Asn Ala Asp Pro
1               5

<210> SEQ ID NO 202
<211> LENGTH: 9
<212> TYPE: PRT
<213> ORGANISM: Artificial
<220> FEATURE:
<223> OTHER INFORMATION: Synthetic peptide

<400> SEQUENCE: 202

Tyr Glu Ile Asn Ala Asp Pro Arg Leu
1               5

<210> SEQ ID NO 203
<211> LENGTH: 9
<212> TYPE: PRT
<213> ORGANISM: Artificial
<220> FEATURE:
<223> OTHER INFORMATION: Synthetic peptide

<400> SEQUENCE: 203
```

```
Ile Asn Ala Asp Pro Arg Leu Thr Asn
1               5

<210> SEQ ID NO 204
<211> LENGTH: 9
<212> TYPE: PRT
<213> ORGANISM: Artificial
<220> FEATURE:
<223> OTHER INFORMATION: Synthetic peptide

<400> SEQUENCE: 204

Ala Asp Pro Arg Leu Thr Asn Leu Ser
1               5

<210> SEQ ID NO 205
<211> LENGTH: 9
<212> TYPE: PRT
<213> ORGANISM: Artificial
<220> FEATURE:
<223> OTHER INFORMATION: Synthetic peptide

<400> SEQUENCE: 205

Pro Arg Leu Thr Asn Leu Ser Ser Asn
1               5

<210> SEQ ID NO 206
<211> LENGTH: 9
<212> TYPE: PRT
<213> ORGANISM: Artificial
<220> FEATURE:
<223> OTHER INFORMATION: Synthetic peptide

<400> SEQUENCE: 206

Leu Thr Asn Leu Ser Ser Asn Ser Asp
1               5

<210> SEQ ID NO 207
<211> LENGTH: 10
<212> TYPE: PRT
<213> ORGANISM: Artificial
<220> FEATURE:
<223> OTHER INFORMATION: Synthetic peptide

<400> SEQUENCE: 207

Met Pro Gly Gly Cys Ser Arg Gly Pro Ala
1               5                   10

<210> SEQ ID NO 208
<211> LENGTH: 10
<212> TYPE: PRT
<213> ORGANISM: Artificial
<220> FEATURE:
<223> OTHER INFORMATION: Synthetic peptide

<400> SEQUENCE: 208

Gly Gly Cys Ser Arg Gly Pro Ala Ala Gly
1               5                   10

<210> SEQ ID NO 209
<211> LENGTH: 10
<212> TYPE: PRT
<213> ORGANISM: Artificial
<220> FEATURE:
<223> OTHER INFORMATION: Synthetic peptide

<400> SEQUENCE: 209

Cys Ser Arg Gly Pro Ala Ala Gly Asp Gly
1               5                   10
```

```
<210> SEQ ID NO 210
<211> LENGTH: 10
<212> TYPE: PRT
<213> ORGANISM: Artificial
<220> FEATURE:
<223> OTHER INFORMATION: Synthetic peptide

<400> SEQUENCE: 210

Arg Gly Pro Ala Ala Gly Asp Gly Arg Leu
1               5                   10

<210> SEQ ID NO 211
<211> LENGTH: 10
<212> TYPE: PRT
<213> ORGANISM: Artificial
<220> FEATURE:
<223> OTHER INFORMATION: Synthetic peptide

<400> SEQUENCE: 211

Pro Ala Ala Gly Asp Gly Arg Leu Arg Leu
1               5                   10

<210> SEQ ID NO 212
<211> LENGTH: 10
<212> TYPE: PRT
<213> ORGANISM: Artificial
<220> FEATURE:
<223> OTHER INFORMATION: Synthetic peptide

<400> SEQUENCE: 212

Ala Gly Asp Gly Arg Leu Arg Leu Ala Arg
1               5                   10

<210> SEQ ID NO 213
<211> LENGTH: 10
<212> TYPE: PRT
<213> ORGANISM: Artificial
<220> FEATURE:
<223> OTHER INFORMATION: Synthetic peptide

<400> SEQUENCE: 213

Asp Gly Arg Leu Arg Leu Ala Arg Leu Ala
1               5                   10

<210> SEQ ID NO 214
<211> LENGTH: 10
<212> TYPE: PRT
<213> ORGANISM: Artificial
<220> FEATURE:
<223> OTHER INFORMATION: Synthetic peptide

<400> SEQUENCE: 214

Arg Leu Arg Leu Ala Arg Leu Ala Leu Val
1               5                   10

<210> SEQ ID NO 215
<211> LENGTH: 10
<212> TYPE: PRT
<213> ORGANISM: Artificial
<220> FEATURE:
<223> OTHER INFORMATION: Synthetic peptide

<400> SEQUENCE: 215

Arg Leu Ala Arg Leu Ala Leu Val Leu Leu
1               5                   10
```

```
<210> SEQ ID NO 216
<211> LENGTH: 10
<212> TYPE: PRT
<213> ORGANISM: Artificial
<220> FEATURE:
<223> OTHER INFORMATION: Synthetic peptide

<400> SEQUENCE: 216

Ala Arg Leu Ala Leu Val Leu Leu Gly Trp
1               5                   10

<210> SEQ ID NO 217
<211> LENGTH: 10
<212> TYPE: PRT
<213> ORGANISM: Artificial
<220> FEATURE:
<223> OTHER INFORMATION: Synthetic peptide

<400> SEQUENCE: 217

Asn Leu Thr Glu Val Pro Thr Asp Leu Pro
1               5                   10

<210> SEQ ID NO 218
<211> LENGTH: 10
<212> TYPE: PRT
<213> ORGANISM: Artificial
<220> FEATURE:
<223> OTHER INFORMATION: Synthetic peptide

<400> SEQUENCE: 218

Thr Glu Val Pro Thr Asp Leu Pro Ala Tyr
1               5                   10

<210> SEQ ID NO 219
<211> LENGTH: 10
<212> TYPE: PRT
<213> ORGANISM: Artificial
<220> FEATURE:
<223> OTHER INFORMATION: Synthetic peptide

<400> SEQUENCE: 219

Val Pro Thr Asp Leu Pro Ala Tyr Val Arg
1               5                   10

<210> SEQ ID NO 220
<211> LENGTH: 10
<212> TYPE: PRT
<213> ORGANISM: Artificial
<220> FEATURE:
<223> OTHER INFORMATION: Synthetic peptide

<400> SEQUENCE: 220

Thr Asp Leu Pro Ala Tyr Val Arg Asn Leu
1               5                   10

<210> SEQ ID NO 221
<211> LENGTH: 10
<212> TYPE: PRT
<213> ORGANISM: Artificial
<220> FEATURE:
<223> OTHER INFORMATION: Synthetic peptide

<400> SEQUENCE: 221

Leu Pro Ala Tyr Val Arg Asn Leu Phe Leu
1               5                   10

<210> SEQ ID NO 222
<211> LENGTH: 10
```

```
<212> TYPE: PRT
<213> ORGANISM: Artificial
<220> FEATURE:
<223> OTHER INFORMATION: Synthetic peptide

<400> SEQUENCE: 222

Ala Tyr Val Arg Asn Leu Phe Leu Thr Gly
1               5                   10

<210> SEQ ID NO 223
<211> LENGTH: 10
<212> TYPE: PRT
<213> ORGANISM: Artificial
<220> FEATURE:
<223> OTHER INFORMATION: Synthetic peptide

<400> SEQUENCE: 223

Val Arg Asn Leu Phe Leu Thr Gly Asn Gln
1               5                   10

<210> SEQ ID NO 224
<211> LENGTH: 10
<212> TYPE: PRT
<213> ORGANISM: Artificial
<220> FEATURE:
<223> OTHER INFORMATION: Synthetic peptide

<400> SEQUENCE: 224

Asn Leu Phe Leu Thr Gly Asn Gln Leu Ala
1               5                   10

<210> SEQ ID NO 225
<211> LENGTH: 10
<212> TYPE: PRT
<213> ORGANISM: Artificial
<220> FEATURE:
<223> OTHER INFORMATION: Synthetic peptide

<400> SEQUENCE: 225

Phe Leu Thr Gly Asn Gln Leu Ala Val Leu
1               5                   10

<210> SEQ ID NO 226
<211> LENGTH: 10
<212> TYPE: PRT
<213> ORGANISM: Artificial
<220> FEATURE:
<223> OTHER INFORMATION: Synthetic peptide

<400> SEQUENCE: 226

Thr Gly Asn Gln Leu Ala Val Leu Pro Ala
1               5                   10

<210> SEQ ID NO 227
<211> LENGTH: 10
<212> TYPE: PRT
<213> ORGANISM: Artificial
<220> FEATURE:
<223> OTHER INFORMATION: Synthetic peptide

<400> SEQUENCE: 227

Leu Pro Ser Leu Arg Gln Leu Asp Leu Ser
1               5                   10

<210> SEQ ID NO 228
<211> LENGTH: 10
<212> TYPE: PRT
<213> ORGANISM: Artificial
```

```
<220> FEATURE:
<223> OTHER INFORMATION: Synthetic peptide

<400> SEQUENCE: 228

Ser Leu Arg Gln Leu Asp Leu Ser His Asn
1               5                   10

<210> SEQ ID NO 229
<211> LENGTH: 10
<212> TYPE: PRT
<213> ORGANISM: Artificial
<220> FEATURE:
<223> OTHER INFORMATION: Synthetic peptide

<400> SEQUENCE: 229

Arg Gln Leu Asp Leu Ser His Asn Pro Leu
1               5                   10

<210> SEQ ID NO 230
<211> LENGTH: 10
<212> TYPE: PRT
<213> ORGANISM: Artificial
<220> FEATURE:
<223> OTHER INFORMATION: Synthetic peptide

<400> SEQUENCE: 230

Leu Asp Leu Ser His Asn Pro Leu Ala Asp
1               5                   10

<210> SEQ ID NO 231
<211> LENGTH: 10
<212> TYPE: PRT
<213> ORGANISM: Artificial
<220> FEATURE:
<223> OTHER INFORMATION: Synthetic peptide

<400> SEQUENCE: 231

Leu Ser His Asn Pro Leu Ala Asp Leu Ser
1               5                   10

<210> SEQ ID NO 232
<211> LENGTH: 10
<212> TYPE: PRT
<213> ORGANISM: Artificial
<220> FEATURE:
<223> OTHER INFORMATION: Synthetic peptide

<400> SEQUENCE: 232

His Asn Pro Leu Ala Asp Leu Ser Pro Phe
1               5                   10

<210> SEQ ID NO 233
<211> LENGTH: 10
<212> TYPE: PRT
<213> ORGANISM: Artificial
<220> FEATURE:
<223> OTHER INFORMATION: Synthetic peptide

<400> SEQUENCE: 233

Pro Leu Ala Asp Leu Ser Pro Phe Ala Phe
1               5                   10

<210> SEQ ID NO 234
<211> LENGTH: 10
<212> TYPE: PRT
<213> ORGANISM: Artificial
<220> FEATURE:
<223> OTHER INFORMATION: Synthetic peptide
```

<400> SEQUENCE: 234

Ala Asp Leu Ser Pro Phe Ala Phe Ser Gly
1               5                   10

<210> SEQ ID NO 235
<211> LENGTH: 10
<212> TYPE: PRT
<213> ORGANISM: Artificial
<220> FEATURE:
<223> OTHER INFORMATION: Synthetic peptide

<400> SEQUENCE: 235

Leu Ser Pro Phe Ala Phe Ser Gly Ser Asn
1               5                   10

<210> SEQ ID NO 236
<211> LENGTH: 10
<212> TYPE: PRT
<213> ORGANISM: Artificial
<220> FEATURE:
<223> OTHER INFORMATION: Synthetic peptide

<400> SEQUENCE: 236

Pro Phe Ala Phe Ser Gly Ser Asn Ala Ser
1               5                   10

<210> SEQ ID NO 237
<211> LENGTH: 10
<212> TYPE: PRT
<213> ORGANISM: Artificial
<220> FEATURE:
<223> OTHER INFORMATION: Synthetic peptide

<400> SEQUENCE: 237

Ala Phe Ser Gly Ser Asn Ala Ser Val Ser
1               5                   10

<210> SEQ ID NO 238
<211> LENGTH: 10
<212> TYPE: PRT
<213> ORGANISM: Artificial
<220> FEATURE:
<223> OTHER INFORMATION: Synthetic peptide

<400> SEQUENCE: 238

Ser Gly Ser Asn Ala Ser Val Ser Ala Pro
1               5                   10

<210> SEQ ID NO 239
<211> LENGTH: 10
<212> TYPE: PRT
<213> ORGANISM: Artificial
<220> FEATURE:
<223> OTHER INFORMATION: Synthetic peptide

<400> SEQUENCE: 239

Ser Asn Ala Ser Val Ser Ala Pro Ser Pro
1               5                   10

<210> SEQ ID NO 240
<211> LENGTH: 10
<212> TYPE: PRT
<213> ORGANISM: Artificial
<220> FEATURE:
<223> OTHER INFORMATION: Synthetic peptide

<400> SEQUENCE: 240

```
Ala Ser Val Ser Ala Pro Ser Pro Leu Val
1               5                   10

<210> SEQ ID NO 241
<211> LENGTH: 10
<212> TYPE: PRT
<213> ORGANISM: Artificial
<220> FEATURE:
<223> OTHER INFORMATION: Synthetic peptide

<400> SEQUENCE: 241

Val Ser Ala Pro Ser Pro Leu Val Glu Leu
1               5                   10

<210> SEQ ID NO 242
<211> LENGTH: 10
<212> TYPE: PRT
<213> ORGANISM: Artificial
<220> FEATURE:
<223> OTHER INFORMATION: Synthetic peptide

<400> SEQUENCE: 242

Ala Pro Ser Pro Leu Val Glu Leu Ile Leu
1               5                   10

<210> SEQ ID NO 243
<211> LENGTH: 10
<212> TYPE: PRT
<213> ORGANISM: Artificial
<220> FEATURE:
<223> OTHER INFORMATION: Synthetic peptide

<400> SEQUENCE: 243

Ser Pro Leu Val Glu Leu Ile Leu Asn His
1               5                   10

<210> SEQ ID NO 244
<211> LENGTH: 10
<212> TYPE: PRT
<213> ORGANISM: Artificial
<220> FEATURE:
<223> OTHER INFORMATION: Synthetic peptide

<400> SEQUENCE: 244

Leu Val Glu Leu Ile Leu Asn His Ile Val
1               5                   10

<210> SEQ ID NO 245
<211> LENGTH: 10
<212> TYPE: PRT
<213> ORGANISM: Artificial
<220> FEATURE:
<223> OTHER INFORMATION: Synthetic peptide

<400> SEQUENCE: 245

Glu Leu Ile Leu Asn His Ile Val Pro Pro
1               5                   10

<210> SEQ ID NO 246
<211> LENGTH: 10
<212> TYPE: PRT
<213> ORGANISM: Artificial
<220> FEATURE:
<223> OTHER INFORMATION: Synthetic peptide

<400> SEQUENCE: 246

Ile Leu Asn His Ile Val Pro Pro Glu Asp
```

```
<210> SEQ ID NO 247
<211> LENGTH: 10
<212> TYPE: PRT
<213> ORGANISM: Artificial
<220> FEATURE:
<223> OTHER INFORMATION: Synthetic peptide

<400> SEQUENCE: 247

His Phe Leu Tyr Leu Pro Arg Asp Val Leu
1               5                   10

<210> SEQ ID NO 248
<211> LENGTH: 10
<212> TYPE: PRT
<213> ORGANISM: Artificial
<220> FEATURE:
<223> OTHER INFORMATION: Synthetic peptide

<400> SEQUENCE: 248

Leu Tyr Leu Pro Arg Asp Val Leu Ala Gln
1               5                   10

<210> SEQ ID NO 249
<211> LENGTH: 10
<212> TYPE: PRT
<213> ORGANISM: Artificial
<220> FEATURE:
<223> OTHER INFORMATION: Synthetic peptide

<400> SEQUENCE: 249

Leu Pro Arg Asp Val Leu Ala Gln Leu Pro
1               5                   10

<210> SEQ ID NO 250
<211> LENGTH: 10
<212> TYPE: PRT
<213> ORGANISM: Artificial
<220> FEATURE:
<223> OTHER INFORMATION: Synthetic peptide

<400> SEQUENCE: 250

Arg Asp Val Leu Ala Gln Leu Pro Ser Leu
1               5                   10

<210> SEQ ID NO 251
<211> LENGTH: 10
<212> TYPE: PRT
<213> ORGANISM: Artificial
<220> FEATURE:
<223> OTHER INFORMATION: Synthetic peptide

<400> SEQUENCE: 251

Val Leu Ala Gln Leu Pro Ser Leu Arg His
1               5                   10

<210> SEQ ID NO 252
<211> LENGTH: 10
<212> TYPE: PRT
<213> ORGANISM: Artificial
<220> FEATURE:
<223> OTHER INFORMATION: Synthetic peptide

<400> SEQUENCE: 252

Ala Gln Leu Pro Ser Leu Arg His Leu Asp
1               5                   10
```

<210> SEQ ID NO 253
<211> LENGTH: 10
<212> TYPE: PRT
<213> ORGANISM: Artificial
<220> FEATURE:
<223> OTHER INFORMATION: Synthetic peptide

<400> SEQUENCE: 253

Leu Pro Ser Leu Arg His Leu Asp Leu Ser
1               5                   10

<210> SEQ ID NO 254
<211> LENGTH: 10
<212> TYPE: PRT
<213> ORGANISM: Artificial
<220> FEATURE:
<223> OTHER INFORMATION: Synthetic peptide

<400> SEQUENCE: 254

Ser Leu Arg His Leu Asp Leu Ser Asn Asn
1               5                   10

<210> SEQ ID NO 255
<211> LENGTH: 10
<212> TYPE: PRT
<213> ORGANISM: Artificial
<220> FEATURE:
<223> OTHER INFORMATION: Synthetic peptide

<400> SEQUENCE: 255

Arg His Leu Asp Leu Ser Asn Asn Ser Leu
1               5                   10

<210> SEQ ID NO 256
<211> LENGTH: 10
<212> TYPE: PRT
<213> ORGANISM: Artificial
<220> FEATURE:
<223> OTHER INFORMATION: Synthetic peptide

<400> SEQUENCE: 256

Leu Asp Leu Ser Asn Asn Ser Leu Val Ser
1               5                   10

<210> SEQ ID NO 257
<211> LENGTH: 10
<212> TYPE: PRT
<213> ORGANISM: Artificial
<220> FEATURE:
<223> OTHER INFORMATION: Synthetic peptide

<400> SEQUENCE: 257

Leu Ser Asn Asn Ser Leu Val Ser Leu Thr
1               5                   10

<210> SEQ ID NO 258
<211> LENGTH: 10
<212> TYPE: PRT
<213> ORGANISM: Artificial
<220> FEATURE:
<223> OTHER INFORMATION: Synthetic peptide

<400> SEQUENCE: 258

Asn Asn Ser Leu Val Ser Leu Thr Tyr Val
1               5                   10

<210> SEQ ID NO 259

```
<211> LENGTH: 10
<212> TYPE: PRT
<213> ORGANISM: Artificial
<220> FEATURE:
<223> OTHER INFORMATION: Synthetic peptide

<400> SEQUENCE: 259

Ser Leu Val Ser Leu Thr Tyr Val Ser Phe
1               5                   10

<210> SEQ ID NO 260
<211> LENGTH: 10
<212> TYPE: PRT
<213> ORGANISM: Artificial
<220> FEATURE:
<223> OTHER INFORMATION: Synthetic peptide

<400> SEQUENCE: 260

Val Ser Leu Thr Tyr Val Ser Phe Arg Asn
1               5                   10

<210> SEQ ID NO 261
<211> LENGTH: 10
<212> TYPE: PRT
<213> ORGANISM: Artificial
<220> FEATURE:
<223> OTHER INFORMATION: Synthetic peptide

<400> SEQUENCE: 261

Leu Thr Tyr Val Ser Phe Arg Asn Leu Thr
1               5                   10

<210> SEQ ID NO 262
<211> LENGTH: 10
<212> TYPE: PRT
<213> ORGANISM: Artificial
<220> FEATURE:
<223> OTHER INFORMATION: Synthetic peptide

<400> SEQUENCE: 262

Tyr Val Ser Phe Arg Asn Leu Thr His Leu
1               5                   10

<210> SEQ ID NO 263
<211> LENGTH: 10
<212> TYPE: PRT
<213> ORGANISM: Artificial
<220> FEATURE:
<223> OTHER INFORMATION: Synthetic peptide

<400> SEQUENCE: 263

Ser Phe Arg Asn Leu Thr His Leu Glu Ser
1               5                   10

<210> SEQ ID NO 264
<211> LENGTH: 10
<212> TYPE: PRT
<213> ORGANISM: Artificial
<220> FEATURE:
<223> OTHER INFORMATION: Synthetic peptide

<400> SEQUENCE: 264

Arg Asn Leu Thr His Leu Glu Ser Leu His
1               5                   10

<210> SEQ ID NO 265
<211> LENGTH: 10
<212> TYPE: PRT
```

```
<213> ORGANISM: Artificial
<220> FEATURE:
<223> OTHER INFORMATION: Synthetic peptide

<400> SEQUENCE: 265

Leu Thr His Leu Glu Ser Leu His Leu Glu
1               5                   10

<210> SEQ ID NO 266
<211> LENGTH: 10
<212> TYPE: PRT
<213> ORGANISM: Artificial
<220> FEATURE:
<223> OTHER INFORMATION: Synthetic peptide

<400> SEQUENCE: 266

His Leu Glu Ser Leu His Leu Glu Asp Asn
1               5                   10

<210> SEQ ID NO 267
<211> LENGTH: 10
<212> TYPE: PRT
<213> ORGANISM: Artificial
<220> FEATURE:
<223> OTHER INFORMATION: Synthetic peptide

<400> SEQUENCE: 267

Asp Leu Asp Cys Asp Pro Ile Leu Pro Pro
1               5                   10

<210> SEQ ID NO 268
<211> LENGTH: 10
<212> TYPE: PRT
<213> ORGANISM: Artificial
<220> FEATURE:
<223> OTHER INFORMATION: Synthetic peptide

<400> SEQUENCE: 268

Asp Cys Asp Pro Ile Leu Pro Pro Ser Leu
1               5                   10

<210> SEQ ID NO 269
<211> LENGTH: 10
<212> TYPE: PRT
<213> ORGANISM: Artificial
<220> FEATURE:
<223> OTHER INFORMATION: Synthetic peptide

<400> SEQUENCE: 269

Asp Pro Ile Leu Pro Pro Ser Leu Gln Thr
1               5                   10

<210> SEQ ID NO 270
<211> LENGTH: 10
<212> TYPE: PRT
<213> ORGANISM: Artificial
<220> FEATURE:
<223> OTHER INFORMATION: Synthetic peptide

<400> SEQUENCE: 270

Ile Leu Pro Pro Ser Leu Gln Thr Ser Tyr
1               5                   10

<210> SEQ ID NO 271
<211> LENGTH: 10
<212> TYPE: PRT
<213> ORGANISM: Artificial
<220> FEATURE:
```

<223> OTHER INFORMATION: Synthetic peptide

<400> SEQUENCE: 271

Pro Pro Ser Leu Gln Thr Ser Tyr Val Phe
1               5                   10

<210> SEQ ID NO 272
<211> LENGTH: 10
<212> TYPE: PRT
<213> ORGANISM: Artificial
<220> FEATURE:
<223> OTHER INFORMATION: Synthetic peptide

<400> SEQUENCE: 272

Ser Leu Gln Thr Ser Tyr Val Phe Leu Gly
1               5                   10

<210> SEQ ID NO 273
<211> LENGTH: 10
<212> TYPE: PRT
<213> ORGANISM: Artificial
<220> FEATURE:
<223> OTHER INFORMATION: Synthetic peptide

<400> SEQUENCE: 273

Gln Thr Ser Tyr Val Phe Leu Gly Ile Val
1               5                   10

<210> SEQ ID NO 274
<211> LENGTH: 10
<212> TYPE: PRT
<213> ORGANISM: Artificial
<220> FEATURE:
<223> OTHER INFORMATION: Synthetic peptide

<400> SEQUENCE: 274

Ser Tyr Val Phe Leu Gly Ile Val Leu Ala
1               5                   10

<210> SEQ ID NO 275
<211> LENGTH: 10
<212> TYPE: PRT
<213> ORGANISM: Artificial
<220> FEATURE:
<223> OTHER INFORMATION: Synthetic peptide

<400> SEQUENCE: 275

Val Phe Leu Gly Ile Val Leu Ala Leu Ile
1               5                   10

<210> SEQ ID NO 276
<211> LENGTH: 10
<212> TYPE: PRT
<213> ORGANISM: Artificial
<220> FEATURE:
<223> OTHER INFORMATION: Synthetic peptide

<400> SEQUENCE: 276

Leu Gly Ile Val Leu Ala Leu Ile Gly Ala
1               5                   10

<210> SEQ ID NO 277
<211> LENGTH: 10
<212> TYPE: PRT
<213> ORGANISM: Artificial
<220> FEATURE:
<223> OTHER INFORMATION: Synthetic peptide

```
<400> SEQUENCE: 277

Ile Val Leu Ala Leu Ile Gly Ala Ile Phe
1               5                   10

<210> SEQ ID NO 278
<211> LENGTH: 10
<212> TYPE: PRT
<213> ORGANISM: Artificial
<220> FEATURE:
<223> OTHER INFORMATION: Synthetic peptide

<400> SEQUENCE: 278

Leu Ala Leu Ile Gly Ala Ile Phe Leu Leu
1               5                   10

<210> SEQ ID NO 279
<211> LENGTH: 10
<212> TYPE: PRT
<213> ORGANISM: Artificial
<220> FEATURE:
<223> OTHER INFORMATION: Synthetic peptide

<400> SEQUENCE: 279

Leu Ile Gly Ala Ile Phe Leu Leu Val Leu
1               5                   10

<210> SEQ ID NO 280
<211> LENGTH: 10
<212> TYPE: PRT
<213> ORGANISM: Artificial
<220> FEATURE:
<223> OTHER INFORMATION: Synthetic peptide

<400> SEQUENCE: 280

Gly Ala Ile Phe Leu Leu Val Leu Tyr Leu
1               5                   10

<210> SEQ ID NO 281
<211> LENGTH: 10
<212> TYPE: PRT
<213> ORGANISM: Artificial
<220> FEATURE:
<223> OTHER INFORMATION: Synthetic peptide

<400> SEQUENCE: 281

Ile Phe Leu Leu Val Leu Tyr Leu Asn Arg
1               5                   10

<210> SEQ ID NO 282
<211> LENGTH: 10
<212> TYPE: PRT
<213> ORGANISM: Artificial
<220> FEATURE:
<223> OTHER INFORMATION: Synthetic peptide

<400> SEQUENCE: 282

Leu Leu Val Leu Tyr Leu Asn Arg Lys Gly
1               5                   10

<210> SEQ ID NO 283
<211> LENGTH: 10
<212> TYPE: PRT
<213> ORGANISM: Artificial
<220> FEATURE:
<223> OTHER INFORMATION: Synthetic peptide

<400> SEQUENCE: 283
```

Val Leu Tyr Leu Asn Arg Lys Gly Ile Lys
1               5                   10

<210> SEQ ID NO 284
<211> LENGTH: 10
<212> TYPE: PRT
<213> ORGANISM: Artificial
<220> FEATURE:
<223> OTHER INFORMATION: Synthetic peptide

<400> SEQUENCE: 284

Tyr Leu Asn Arg Lys Gly Ile Lys Lys Trp
1               5                   10

<210> SEQ ID NO 285
<211> LENGTH: 10
<212> TYPE: PRT
<213> ORGANISM: Artificial
<220> FEATURE:
<223> OTHER INFORMATION: Synthetic peptide

<400> SEQUENCE: 285

Asn Arg Lys Gly Ile Lys Lys Trp Met His
1               5                   10

<210> SEQ ID NO 286
<211> LENGTH: 10
<212> TYPE: PRT
<213> ORGANISM: Artificial
<220> FEATURE:
<223> OTHER INFORMATION: Synthetic peptide

<400> SEQUENCE: 286

Lys Gly Ile Lys Lys Trp Met His Asn Ile
1               5                   10

<210> SEQ ID NO 287
<211> LENGTH: 10
<212> TYPE: PRT
<213> ORGANISM: Artificial
<220> FEATURE:
<223> OTHER INFORMATION: Synthetic peptide

<400> SEQUENCE: 287

Ile Lys Lys Trp Met His Asn Ile Arg Asp
1               5                   10

<210> SEQ ID NO 288
<211> LENGTH: 10
<212> TYPE: PRT
<213> ORGANISM: Artificial
<220> FEATURE:
<223> OTHER INFORMATION: Synthetic peptide

<400> SEQUENCE: 288

Lys Trp Met His Asn Ile Arg Asp Ala Cys
1               5                   10

<210> SEQ ID NO 289
<211> LENGTH: 10
<212> TYPE: PRT
<213> ORGANISM: Artificial
<220> FEATURE:
<223> OTHER INFORMATION: Synthetic peptide

<400> SEQUENCE: 289

Met His Asn Ile Arg Asp Ala Cys Arg Asp
1               5                   10

<210> SEQ ID NO 290
<211> LENGTH: 10
<212> TYPE: PRT
<213> ORGANISM: Artificial
<220> FEATURE:
<223> OTHER INFORMATION: Synthetic peptide

<400> SEQUENCE: 290

Asn Ile Arg Asp Ala Cys Arg Asp His Met
1               5                   10

<210> SEQ ID NO 291
<211> LENGTH: 10
<212> TYPE: PRT
<213> ORGANISM: Artificial
<220> FEATURE:
<223> OTHER INFORMATION: Synthetic peptide

<400> SEQUENCE: 291

Arg Asp Ala Cys Arg Asp His Met Glu Gly
1               5                   10

<210> SEQ ID NO 292
<211> LENGTH: 10
<212> TYPE: PRT
<213> ORGANISM: Artificial
<220> FEATURE:
<223> OTHER INFORMATION: Synthetic peptide

<400> SEQUENCE: 292

Ala Cys Arg Asp His Met Glu Gly Tyr His
1               5                   10

<210> SEQ ID NO 293
<211> LENGTH: 10
<212> TYPE: PRT
<213> ORGANISM: Artificial
<220> FEATURE:
<223> OTHER INFORMATION: Synthetic peptide

<400> SEQUENCE: 293

Arg Asp His Met Glu Gly Tyr His Tyr Arg
1               5                   10

<210> SEQ ID NO 294
<211> LENGTH: 10
<212> TYPE: PRT
<213> ORGANISM: Artificial
<220> FEATURE:
<223> OTHER INFORMATION: Synthetic peptide

<400> SEQUENCE: 294

His Met Glu Gly Tyr His Tyr Arg Tyr Glu
1               5                   10

<210> SEQ ID NO 295
<211> LENGTH: 10
<212> TYPE: PRT
<213> ORGANISM: Artificial
<220> FEATURE:
<223> OTHER INFORMATION: Synthetic peptide

<400> SEQUENCE: 295

Glu Gly Tyr His Tyr Arg Tyr Glu Ile Asn
1               5                   10

```
<210> SEQ ID NO 296
<211> LENGTH: 10
<212> TYPE: PRT
<213> ORGANISM: Artificial
<220> FEATURE:
<223> OTHER INFORMATION: Synthetic peptide

<400> SEQUENCE: 296

Tyr His Tyr Arg Tyr Glu Ile Asn Ala Asp
1               5                   10

<210> SEQ ID NO 297
<211> LENGTH: 10
<212> TYPE: PRT
<213> ORGANISM: Artificial
<220> FEATURE:
<223> OTHER INFORMATION: Synthetic peptide

<400> SEQUENCE: 297

Tyr Arg Tyr Glu Ile Asn Ala Asp Pro Arg
1               5                   10

<210> SEQ ID NO 298
<211> LENGTH: 10
<212> TYPE: PRT
<213> ORGANISM: Artificial
<220> FEATURE:
<223> OTHER INFORMATION: Synthetic peptide

<400> SEQUENCE: 298

Tyr Glu Ile Asn Ala Asp Pro Arg Leu Thr
1               5                   10

<210> SEQ ID NO 299
<211> LENGTH: 10
<212> TYPE: PRT
<213> ORGANISM: Artificial
<220> FEATURE:
<223> OTHER INFORMATION: Synthetic peptide

<400> SEQUENCE: 299

Ile Asn Ala Asp Pro Arg Leu Thr Asn Leu
1               5                   10

<210> SEQ ID NO 300
<211> LENGTH: 10
<212> TYPE: PRT
<213> ORGANISM: Artificial
<220> FEATURE:
<223> OTHER INFORMATION: Synthetic peptide

<400> SEQUENCE: 300

Ala Asp Pro Arg Leu Thr Asn Leu Ser Ser
1               5                   10

<210> SEQ ID NO 301
<211> LENGTH: 10
<212> TYPE: PRT
<213> ORGANISM: Artificial
<220> FEATURE:
<223> OTHER INFORMATION: Synthetic peptide

<400> SEQUENCE: 301

Pro Arg Leu Thr Asn Leu Ser Ser Asn Ser
1               5                   10

<210> SEQ ID NO 302
<211> LENGTH: 10
```

```
<212> TYPE: PRT
<213> ORGANISM: Artificial
<220> FEATURE:
<223> OTHER INFORMATION: Synthetic peptide

<400> SEQUENCE: 302

Leu Thr Asn Leu Ser Ser Asn Ser Asp Val
1               5                   10

<210> SEQ ID NO 303
<211> LENGTH: 10
<212> TYPE: PRT
<213> ORGANISM: Artificial
<220> FEATURE:
<223> OTHER INFORMATION: Synthetic peptide

<400> SEQUENCE: 303

Ser Ser Ala Pro Phe Leu Ala Ser Ala Val
1               5                   10

<210> SEQ ID NO 304
<211> LENGTH: 10
<212> TYPE: PRT
<213> ORGANISM: Artificial
<220> FEATURE:
<223> OTHER INFORMATION: Synthetic peptide

<400> SEQUENCE: 304

Leu Ala Glu Leu Ala Ala Leu Asn Leu Ser
1               5                   10

<210> SEQ ID NO 305
<211> LENGTH: 10
<212> TYPE: PRT
<213> ORGANISM: Artificial
<220> FEATURE:
<223> OTHER INFORMATION: Synthetic peptide

<400> SEQUENCE: 305

Arg Leu Asp Glu Val Arg Ala Gly Ala Phe
1               5                   10

<210> SEQ ID NO 306
<211> LENGTH: 10
<212> TYPE: PRT
<213> ORGANISM: Artificial
<220> FEATURE:
<223> OTHER INFORMATION: Synthetic peptide

<400> SEQUENCE: 306

Gly Met Val Val Ala Ala Leu Leu Ala Gly
1               5                   10

<210> SEQ ID NO 307
<211> LENGTH: 10
<212> TYPE: PRT
<213> ORGANISM: Artificial
<220> FEATURE:
<223> OTHER INFORMATION: Synthetic peptide

<400> SEQUENCE: 307

Leu Ala Ser Asn His Phe Leu Tyr Leu Pro
1               5                   10

<210> SEQ ID NO 308
<211> LENGTH: 10
<212> TYPE: PRT
<213> ORGANISM: Artificial
```

<220> FEATURE:
<223> OTHER INFORMATION: Synthetic peptide

<400> SEQUENCE: 308

Gly Leu Pro His Ile Arg Val Phe Leu Asp
1               5                   10

<210> SEQ ID NO 309
<211> LENGTH: 10
<212> TYPE: PRT
<213> ORGANISM: Artificial
<220> FEATURE:
<223> OTHER INFORMATION: Synthetic peptide

<400> SEQUENCE: 309

His Met Ala Asp Met Val Thr Trp Leu Lys
1               5                   10

<210> SEQ ID NO 310
<211> LENGTH: 10
<212> TYPE: PRT
<213> ORGANISM: Artificial
<220> FEATURE:
<223> OTHER INFORMATION: Synthetic peptide

<400> SEQUENCE: 310

Ser Pro Thr Ser Ser Ala Ser Ser Phe Ser
1               5                   10

<210> SEQ ID NO 311
<211> LENGTH: 10
<212> TYPE: PRT
<213> ORGANISM: Artificial
<220> FEATURE:
<223> OTHER INFORMATION: Synthetic peptide

<400> SEQUENCE: 311

Ala Pro Phe Leu Ala Ser Ala Val Ser Ala
1               5                   10

<210> SEQ ID NO 312
<211> LENGTH: 10
<212> TYPE: PRT
<213> ORGANISM: Artificial
<220> FEATURE:
<223> OTHER INFORMATION: Synthetic peptide

<400> SEQUENCE: 312

Gly Ala Phe Ala Arg Arg Pro Pro Leu Ala
1               5                   10

<210> SEQ ID NO 313
<211> LENGTH: 10
<212> TYPE: PRT
<213> ORGANISM: Artificial
<220> FEATURE:
<223> OTHER INFORMATION: Synthetic peptide

<400> SEQUENCE: 313

Pro Pro Leu Ala Glu Leu Ala Ala Leu Asn
1               5                   10

<210> SEQ ID NO 314
<211> LENGTH: 10
<212> TYPE: PRT
<213> ORGANISM: Artificial
<220> FEATURE:
<223> OTHER INFORMATION: Synthetic peptide

```
<400> SEQUENCE: 314

Val Val Ala Ala Leu Leu Ala Gly Arg Ala
1               5                   10

<210> SEQ ID NO 315
<211> LENGTH: 10
<212> TYPE: PRT
<213> ORGANISM: Artificial
<220> FEATURE:
<223> OTHER INFORMATION: Synthetic peptide

<400> SEQUENCE: 315

Ala Ala Leu Leu Ala Gly Arg Ala Leu Gln
1               5                   10

<210> SEQ ID NO 316
<211> LENGTH: 10
<212> TYPE: PRT
<213> ORGANISM: Artificial
<220> FEATURE:
<223> OTHER INFORMATION: Synthetic peptide

<400> SEQUENCE: 316

Leu Ala Ser Asn His Phe Leu Tyr Leu Pro
1               5                   10

<210> SEQ ID NO 317
<211> LENGTH: 10
<212> TYPE: PRT
<213> ORGANISM: Artificial
<220> FEATURE:
<223> OTHER INFORMATION: Synthetic peptide

<400> SEQUENCE: 317

Gly Leu Pro His Ile Arg Val Phe Leu Asp
1               5                   10

<210> SEQ ID NO 318
<211> LENGTH: 10
<212> TYPE: PRT
<213> ORGANISM: Artificial
<220> FEATURE:
<223> OTHER INFORMATION: Synthetic peptide

<400> SEQUENCE: 318

Leu Thr Cys Ala Tyr Pro Glu Lys Met Arg
1               5                   10

<210> SEQ ID NO 319
<211> LENGTH: 10
<212> TYPE: PRT
<213> ORGANISM: Artificial
<220> FEATURE:
<223> OTHER INFORMATION: Synthetic peptide

<400> SEQUENCE: 319

Tyr Pro Glu Lys Met Arg Asn Arg Val Leu
1               5                   10

<210> SEQ ID NO 320
<211> LENGTH: 7
<212> TYPE: PRT
<213> ORGANISM: Artificial
<220> FEATURE:
<223> OTHER INFORMATION: Minimal epitope sequence

<400> SEQUENCE: 320
```

Arg Leu Ala Arg Leu Ala Leu
1               5

<210> SEQ ID NO 321
<211> LENGTH: 20
<212> TYPE: PRT
<213> ORGANISM: Artificial
<220> FEATURE:
<223> OTHER INFORMATION: Synthetic peptide

<400> SEQUENCE: 321

Leu Gln Gly Leu Pro His Ile Arg Val Phe Leu Asp Asn Asn Pro Trp
1               5                   10                  15

Val Cys Asp Cys
            20

<210> SEQ ID NO 322
<211> LENGTH: 20
<212> TYPE: PRT
<213> ORGANISM: Artificial
<220> FEATURE:
<223> OTHER INFORMATION: Synthetic peptide

<400> SEQUENCE: 322

Val Phe Leu Asp Asn Asn Pro Trp Val Cys Asp Cys His Met Ala Asp
1               5                   10                  15

Met Val Thr Trp
            20

<210> SEQ ID NO 323
<211> LENGTH: 20
<212> TYPE: PRT
<213> ORGANISM: Artificial
<220> FEATURE:
<223> OTHER INFORMATION: Synthetic peptide

<400> SEQUENCE: 323

Val Cys Asp Cys His Met Ala Asp Met Val Thr Trp Leu Lys Glu Thr
1               5                   10                  15

Glu Val Val Gln
            20

<210> SEQ ID NO 324
<211> LENGTH: 20
<212> TYPE: PRT
<213> ORGANISM: Artificial
<220> FEATURE:
<223> OTHER INFORMATION: Synthetic peptide

<400> SEQUENCE: 324

Met Val Thr Trp Leu Lys Glu Thr Glu Val Val Gln Gly Lys Asp Arg
1               5                   10                  15

Leu Thr Cys Ala
            20

<210> SEQ ID NO 325
<211> LENGTH: 20
<212> TYPE: PRT
<213> ORGANISM: Artificial
<220> FEATURE:
<223> OTHER INFORMATION: Synthetic peptide

<400> SEQUENCE: 325

Glu Val Val Gln Gly Lys Asp Arg Leu Thr Cys Ala Tyr Pro Glu Lys
1               5                   10                  15

```
Met Arg Asn Arg
            20

<210> SEQ ID NO 326
<211> LENGTH: 20
<212> TYPE: PRT
<213> ORGANISM: Artificial
<220> FEATURE:
<223> OTHER INFORMATION: Synthetic peptide

<400> SEQUENCE: 326

Leu Thr Cys Ala Tyr Pro Glu Lys Met Arg Asn Arg Val Leu Leu Glu
1               5                   10                  15

Leu Asn Ser Ala
            20

<210> SEQ ID NO 327
<211> LENGTH: 20
<212> TYPE: PRT
<213> ORGANISM: Artificial
<220> FEATURE:
<223> OTHER INFORMATION: Synthetic peptide

<400> SEQUENCE: 327

Met Arg Asn Arg Val Leu Leu Glu Leu Asn Ser Ala Asp Leu Asp Cys
1               5                   10                  15

Asp Pro Ile Leu
            20

<210> SEQ ID NO 328
<211> LENGTH: 20
<212> TYPE: PRT
<213> ORGANISM: Artificial
<220> FEATURE:
<223> OTHER INFORMATION: Synthetic peptide

<400> SEQUENCE: 328

Leu Asn Ser Ala Asp Leu Asp Cys Asp Pro Ile Leu Pro Pro Ser Leu
1               5                   10                  15

Gln Thr Ser Tyr
            20

<210> SEQ ID NO 329
<211> LENGTH: 20
<212> TYPE: PRT
<213> ORGANISM: Artificial
<220> FEATURE:
<223> OTHER INFORMATION: Synthetic peptide

<400> SEQUENCE: 329

Asp Pro Ile Leu Pro Pro Ser Leu Gln Thr Ser Tyr Val Phe Leu Gly
1               5                   10                  15

Ile Val Leu Ala
            20

<210> SEQ ID NO 330
<211> LENGTH: 20
<212> TYPE: PRT
<213> ORGANISM: Artificial
<220> FEATURE:
<223> OTHER INFORMATION: Synthetic peptide

<400> SEQUENCE: 330

Gln Thr Ser Tyr Val Phe Leu Gly Ile Val Leu Ala Leu Ile Gly Ala
1               5                   10                  15
```

Ile Phe Leu Leu
            20

<210> SEQ ID NO 331
<211> LENGTH: 20
<212> TYPE: PRT
<213> ORGANISM: Artificial
<220> FEATURE:
<223> OTHER INFORMATION: Synthetic peptide

<400> SEQUENCE: 331

Ala Ala Leu Asn Leu Ser Gly Ser Arg Leu Asp Glu Val Arg Ala Gly
1               5                   10                  15

Ala Phe Glu His
            20

<210> SEQ ID NO 332
<211> LENGTH: 20
<212> TYPE: PRT
<213> ORGANISM: Artificial
<220> FEATURE:
<223> OTHER INFORMATION: Synthetic peptide

<400> SEQUENCE: 332

Arg Leu Asp Glu Val Arg Ala Gly Ala Phe Glu His Leu Pro Ser Leu
1               5                   10                  15

Arg Gln Leu Asp
            20

<210> SEQ ID NO 333
<211> LENGTH: 20
<212> TYPE: PRT
<213> ORGANISM: Artificial
<220> FEATURE:
<223> OTHER INFORMATION: Synthetic peptide

<400> SEQUENCE: 333

Ala Phe Glu His Leu Pro Ser Leu Arg Gln Leu Asp Leu Ser His Asn
1               5                   10                  15

Pro Leu Ala Asp
            20

<210> SEQ ID NO 334
<211> LENGTH: 20
<212> TYPE: PRT
<213> ORGANISM: Artificial
<220> FEATURE:
<223> OTHER INFORMATION: Synthetic peptide

<400> SEQUENCE: 334

Arg Gln Leu Asp Leu Ser His Asn Pro Leu Ala Asp Leu Ser Pro Phe
1               5                   10                  15

Ala Phe Ser Gly
            20

<210> SEQ ID NO 335
<211> LENGTH: 20
<212> TYPE: PRT
<213> ORGANISM: Artificial
<220> FEATURE:
<223> OTHER INFORMATION: Synthetic peptide

<400> SEQUENCE: 335

Pro Leu Ala Asp Leu Ser Pro Phe Ala Phe Ser Gly Ser Asn Ala Ser
1               5                   10                  15

Val Ser Ala Pro
            20

<210> SEQ ID NO 336
<211> LENGTH: 20
<212> TYPE: PRT
<213> ORGANISM: Artificial
<220> FEATURE:
<223> OTHER INFORMATION: Synthetic peptide

<400> SEQUENCE: 336

Ala Phe Ser Gly Ser Asn Ala Ser Val Ser Ala Pro Ser Pro Leu Val
1               5                   10                  15

Glu Leu Ile Leu
            20

<210> SEQ ID NO 337
<211> LENGTH: 20
<212> TYPE: PRT
<213> ORGANISM: Artificial
<220> FEATURE:
<223> OTHER INFORMATION: Synthetic peptide

<400> SEQUENCE: 337

Val Ser Ala Pro Ser Pro Leu Val Glu Leu Ile Leu Asn His Ile Val
1               5                   10                  15

Pro Pro Glu Asp
            20

<210> SEQ ID NO 338
<211> LENGTH: 20
<212> TYPE: PRT
<213> ORGANISM: Artificial
<220> FEATURE:
<223> OTHER INFORMATION: Synthetic peptide

<400> SEQUENCE: 338

Glu Leu Ile Leu Asn His Ile Val Pro Pro Glu Asp Glu Arg Gln Asn
1               5                   10                  15

Arg Ser Phe Glu
            20

<210> SEQ ID NO 339
<211> LENGTH: 20
<212> TYPE: PRT
<213> ORGANISM: Artificial
<220> FEATURE:
<223> OTHER INFORMATION: Synthetic peptide

<400> SEQUENCE: 339

Pro Pro Glu Asp Glu Arg Gln Asn Arg Ser Phe Glu Gly Met Val Val
1               5                   10                  15

Ala Ala Leu Leu
            20

<210> SEQ ID NO 340
<211> LENGTH: 20
<212> TYPE: PRT
<213> ORGANISM: Artificial
<220> FEATURE:
<223> OTHER INFORMATION: Synthetic peptide

<400> SEQUENCE: 340

Arg Ser Phe Glu Gly Met Val Val Ala Ala Leu Leu Ala Gly Arg Ala
1               5                   10                  15

```
Leu Gln Gly Leu
            20

<210> SEQ ID NO 341
<211> LENGTH: 20
<212> TYPE: PRT
<213> ORGANISM: Artificial
<220> FEATURE:
<223> OTHER INFORMATION: Synthetic peptide

<400> SEQUENCE: 341

Ala Ala Leu Leu Ala Gly Arg Ala Leu Gln Gly Leu Arg Arg Leu Glu
1               5                   10                  15

Leu Ala Ser Asn
            20

<210> SEQ ID NO 342
<211> LENGTH: 20
<212> TYPE: PRT
<213> ORGANISM: Artificial
<220> FEATURE:
<223> OTHER INFORMATION: Synthetic peptide

<400> SEQUENCE: 342

Leu Gln Gly Leu Arg Arg Leu Glu Leu Ala Ser Asn His Phe Leu Tyr
1               5                   10                  15

Leu Pro Arg Asp
            20

<210> SEQ ID NO 343
<211> LENGTH: 20
<212> TYPE: PRT
<213> ORGANISM: Artificial
<220> FEATURE:
<223> OTHER INFORMATION: Synthetic peptide

<400> SEQUENCE: 343

Leu Ala Ser Asn His Phe Leu Tyr Leu Pro Arg Asp Val Leu Ala Gln
1               5                   10                  15

Leu Pro Ser Leu
            20

<210> SEQ ID NO 344
<211> LENGTH: 20
<212> TYPE: PRT
<213> ORGANISM: Artificial
<220> FEATURE:
<223> OTHER INFORMATION: Synthetic peptide

<400> SEQUENCE: 344

Leu Pro Arg Asp Val Leu Ala Gln Leu Pro Ser Leu Arg His Leu Asp
1               5                   10                  15

Leu Ser Asn Asn
            20

<210> SEQ ID NO 345
<211> LENGTH: 20
<212> TYPE: PRT
<213> ORGANISM: Artificial
<220> FEATURE:
<223> OTHER INFORMATION: Synthetic peptide

<400> SEQUENCE: 345

Leu Pro Ser Leu Arg His Leu Asp Leu Ser Asn Asn Ser Leu Val Ser
1               5                   10                  15
```

```
Leu Thr Tyr Val
            20

<210> SEQ ID NO 346
<211> LENGTH: 20
<212> TYPE: PRT
<213> ORGANISM: Artificial
<220> FEATURE:
<223> OTHER INFORMATION: Synthetic peptide

<400> SEQUENCE: 346

Leu Ser Asn Asn Ser Leu Val Ser Leu Thr Tyr Val Ser Phe Arg Asn
1               5                   10                  15

Leu Thr His Leu
            20

<210> SEQ ID NO 347
<211> LENGTH: 20
<212> TYPE: PRT
<213> ORGANISM: Artificial
<220> FEATURE:
<223> OTHER INFORMATION: Synthetic peptide

<400> SEQUENCE: 347

Leu Thr Tyr Val Ser Phe Arg Asn Leu Thr His Leu Glu Ser Leu His
1               5                   10                  15

Leu Glu Asp Asn
            20

<210> SEQ ID NO 348
<211> LENGTH: 20
<212> TYPE: PRT
<213> ORGANISM: Artificial
<220> FEATURE:
<223> OTHER INFORMATION: Synthetic peptide

<400> SEQUENCE: 348

Leu Thr His Leu Glu Ser Leu His Leu Glu Asp Asn Ala Leu Lys Val
1               5                   10                  15

Leu His Asn Gly
            20

<210> SEQ ID NO 349
<211> LENGTH: 20
<212> TYPE: PRT
<213> ORGANISM: Artificial
<220> FEATURE:
<223> OTHER INFORMATION: Synthetic peptide

<400> SEQUENCE: 349

Leu Glu Asp Asn Ala Leu Lys Val Leu His Asn Gly Thr Leu Ala Glu
1               5                   10                  15

Leu Gln Gly Leu
            20

<210> SEQ ID NO 350
<211> LENGTH: 20
<212> TYPE: PRT
<213> ORGANISM: Artificial
<220> FEATURE:
<223> OTHER INFORMATION: Synthetic peptide

<400> SEQUENCE: 350

Leu His Asn Gly Thr Leu Ala Glu Leu Gln Gly Leu Pro His Ile Arg
1               5                   10                  15
```

Val Phe Leu Asp
            20

<210> SEQ ID NO 351
<211> LENGTH: 20
<212> TYPE: PRT
<213> ORGANISM: Artificial
<220> FEATURE:
<223> OTHER INFORMATION: Synthetic peptide

<400> SEQUENCE: 351

Ile Val Leu Ala Leu Ile Gly Ala Ile Phe Leu Leu Val Leu Tyr Leu
1               5                   10                  15

Asn Arg Lys Gly
            20

<210> SEQ ID NO 352
<211> LENGTH: 20
<212> TYPE: PRT
<213> ORGANISM: Artificial
<220> FEATURE:
<223> OTHER INFORMATION: Synthetic peptide

<400> SEQUENCE: 352

Ile Phe Leu Leu Val Leu Tyr Leu Asn Arg Lys Gly Ile Lys Lys Trp
1               5                   10                  15

Met His Asn Ile
            20

<210> SEQ ID NO 353
<211> LENGTH: 20
<212> TYPE: PRT
<213> ORGANISM: Artificial
<220> FEATURE:
<223> OTHER INFORMATION: Synthetic peptide

<400> SEQUENCE: 353

Asn Arg Lys Gly Ile Lys Lys Trp Met His Asn Ile Arg Asp Ala Cys
1               5                   10                  15

Arg Asp His Met
            20

<210> SEQ ID NO 354
<211> LENGTH: 20
<212> TYPE: PRT
<213> ORGANISM: Artificial
<220> FEATURE:
<223> OTHER INFORMATION: Synthetic peptide

<400> SEQUENCE: 354

Met His Asn Ile Arg Asp Ala Cys Arg Asp His Met Glu Gly Tyr His
1               5                   10                  15

Tyr Arg Tyr Glu
            20

<210> SEQ ID NO 355
<211> LENGTH: 20
<212> TYPE: PRT
<213> ORGANISM: Artificial
<220> FEATURE:
<223> OTHER INFORMATION: Synthetic peptide

<400> SEQUENCE: 355

Arg Asp His Met Glu Gly Tyr His Tyr Arg Tyr Glu Ile Asn Ala Asp
1               5                   10                  15

```
Pro Arg Leu Thr
            20

<210> SEQ ID NO 356
<211> LENGTH: 20
<212> TYPE: PRT
<213> ORGANISM: Artificial
<220> FEATURE:
<223> OTHER INFORMATION: Synthetic peptide

<400> SEQUENCE: 356

Tyr Arg Tyr Glu Ile Asn Ala Asp Pro Arg Leu Thr Asn Leu Ser Ser
1               5                   10                  15

Asn Ser Asp Val
            20
```

PEPTIDE

FIELD OF THE INVENTION

The present invention relates to peptide epitopes of 5T4 antigen, and their use in immunotherapy.

BACKGROUND TO THE INVENTION

Prior to the identification of specific human tumour antigens, many clinical trials were performed attempting to immunise cancer patients against either whole cancer cells or subcellular fractions from cancer cells. The identification of genes encoding tumour antigens, however, has made it possible to develop specific immunotherapies based on attacking tumour cells bearing the identified antigens. A variety of clinical approaches utilising these genes or gene products are possible as summarised in the following table.

---

Active immunotherapy ("Cancer vaccines")

1. Immunisation with:
i) purified antigen
ii) immunodominant peptide (native or modified)
iii) "naked" DNA encoding the antigen
iv) recombinant viruses encoding the antigen
v) antigen presenting cells pulsed with protein or peptide
(or transfected with genes encoding the antigen)
2. Use of cytokine adjuvants such as IL-2 and IL-12 administered systemically or encoded by the immunising vector Passive immunotherapy ("Adoptive immunotherapy")

1. Transfer of cells sensitized in vitro to the specific antigen (bulk or cloned populations)
2. Transduction of effector cells (or stem cells) with genes encoding T cell receptors that recognise specific antigens.

---

Immunisation with intact protein has the potential advantage of simultaneously immunising against both class I and class II epitopes but requires extensive and time-consuming efforts to purify large amounts of tumour antigen. The identification of class I and class II peptide within a tumour antigen makes it possible to immunise with high levels of pure synthetic peptide. The peptide approach also has the advantage that one can choose between a class I (cellular) and a class II type response (or mixture) by choosing which epitopes to use. Immunisation with peptide also means that subdominant and/or cryptic epitopes can be chosen (as the need for antigen processing may be bypassed or reduced to a "trimming role") in order to stimulate a different subset of T cells. Also the peptide may be modified (for example at their HLA class I or II anchor sites) to increase their immunogenicity.

In the past few years, much attention has been given to the role of CD8+ T cells in tumour immunity. Tumour-specific CD8+ CTLs have been shown to be capable of lysing tumour cells directly and eradicating tumour masses in vivo in animal models. However, CD4+ T cells are also thought to play a critical role (Wang and Rosenberg (1999) Immunological Reviews 170:85-100) and it may be that optimal cancer vaccines require the participation of both CD4+ and CD8+ T cells.

A number of oncofoetal or tumour-associated antigens (TAAs) have been identified and characterised in human and animal tumours. In general, TAAs are antigens expressed during foetal development which are downregulated in adult cells, and are thus normally absent or present only at very low levels in adults. Tumour cells have been observed to resume expression of TAAs, and the application of TAAs for tumour diagnosis, targeting and immunotherapy has therefore been suggested.

The TAA 5T4 (see WO 89/07947) has been previously characterised. It is a 72 kDa membrane glycoprotein highly expressed on placental trophoblasts. Its expression on normal adult tissues is restricted to some specialised epithelia, but it is highly expressed and broadly distributed throughout a wide range (>75%) of carcinomas including gastric, colorectal, breast and ovarian cancer (see Table). It appears to be strongly correlated to metastasis in colorectal and gastric cancer. The full nucleic acid sequence of human 5T4 is known (Myers et al., 1994 J Biol Chem 169: 9319-24).

TABLE

Distribution of Human 5T4

| Tumour Type | 5T4 Frequency (%) |
|---|---|
| Breast | 84 |
| Ovarian | 71 |
| Gastric | 74 |
| Colorectal | 85 |

(Starzynska et al., Eur J Gastroenterol Hepatol 1998 June; 10(6):479-84; Starzynska et al., Br J Cancer 1994 May; 69(5):899-902; Starzynska et al., Br J Cancer 1992 November; 66(5):867-9)

5T4 has been proposed as a marker, with possible mechanistic involvement, for tumour progression and metastasis potential (Carsberg et al., (1996) Int J Cancer 1996 Sep. 27; 68(1):84-92). 5T4 has also been proposed for use as an immunotherapeutic agent (see WO 00/29428) and is used in TroVax® (Oxford Biomedica Ltd), a cancer vaccine in clinical development for delivery of 5T4 using an attenuated vaccinia virus vector (MVA). TroVax® is currently being evaluated in phase II clinical trials in late stage colorectal and renal cancer patients.

Cellular immune responses are directed against peptide sequences from an antigen's primary structure and are therefore less easily identified and monitored. CTL antigen receptors are only able to recognise antigens which have been processed and subsequently presented in the context of major histocompatibility complex (MHC) class I molecules on an antigen presenting or target cell. Presentation of antigens by MHC class I involves proteosome-mediated degradation of cytosolic proteins into peptides which are transported and bound to MHC class I molecules (in complex with $\beta_2$-Microglobulin ($\beta_2$M)) in the endoplasmic reticulum, before being translocated to the cell surface where they become available for T cell scrutiny.

Certain peptide epitopes of 5T4 that can bind specific MHCI (or MHCII) have been identified.

In addition, a number of epitope-predictive algorithms have been developed and are freely available. However, these are predominantly based on published data relating to the most common allele in the Caucasian population, HLA A*0201. Furthermore, while these are useful, such algorithms can produce high levels of false positive and negative results.

Accordingly there is a need for the identification of additional 5T4 epitopes and, in particular, there is a need for an increased repertoire of epitopes that can bind to a broader range of MHCI or MHCII.

This need is particularly relevant to 5T4. This is because 5T4 is a self-antigen meaning that the greatest challenge associated with mounting an effective anti-tumour immune response is the breaking of immunological tolerance. The magnitude of immunological responses induced against a self-antigen are usually lower than those observed against foreign pathogens such as viruses. This means that effective and sensitive monitoring of a broad range of immunological responses is essential in order to prove efficacy in breaking tolerance and inducing immune responses. Since cytotoxic T cells are thought to be a key mediator of tumour cell killing, the ability to detect and characterise 5T4 specific CTL responses is essential making the need for additional peptide epitopes of 5T4 particularly acute.

Additional epitopes will provide diagnostic tools allowing routine monitoring of clinical immune responses to become more focussed, streamlined, and sensitive and enable more robust assessments of possible correlations between 5T4-specific immune responses and clinical benefit.

SUMMARY OF THE INVENTION

The present inventors have identified a number of epitopes of 5T4. The identification of particular antigenic peptides provides new opportunities for the development of diagnostic and therapeutic strategies against cancer. In particular, the invention provides peptide epitopes of 5T4 antigen which are capable of being presented in conjunction with an MHC class I or a class II molecule such that they may be specifically recognised by a T cell. Accordingly, in a first aspect, there is provided a peptide epitope of 5T4 comprising an amino acid sequence as set out in any of SEQ ID NOs: 1-206. These peptides, and their corresponding SEQ. ID. NOs are set out in Table 1.

Suitably, a peptide epitope in accordance with this aspect of the invention binds a MHC class I allele.

In one embodiment there is provided a peptide epitope comprising an amino acid sequence as set out in any of SEQ ID NOs: 8, 9, 17, 22, 23, 43, 45, 49, 55, 58, 59, 65, 71, 77, 99, 100, 101, 109, 113, 117, 125, 126, 142, 151, 161, 163, 174, 176, 179, 181, 182, 183, 186, 187 and 198.

Suitably, a peptide epitope in accordance with the invention binds MHC class I allele A1.

Thus, in another embodiment there is provided a peptide epitope which comprises an amino acid sequence as set out in any of SEQ ID NOs: 43, 109, 125, 161 and 198.

In another embodiment there is provided a peptide epitope wherein said epitope binds MHC class I allele A2.

Thus, a further embodiment provides a peptide epitope which comprises an amino acid sequence as set out in any of SEQ ID NOs: 9, 22, 43, 49, 59, 65, 77, 99, 109, 125, 142, 151, 161, 174, 176, 179, 181, 182, 183, 186 and 198.

In yet another embodiment there is provided a peptide epitope wherein said epitope binds MHC class I allele A3.

Accordingly, another embodiment provides a peptide epitope which comprises an amino acid sequence as set out in any of SEQ ID NOs: 100, 109, 125, 142, 168 and 198.

Further, there is provided a peptide epitope wherein said epitope binds MHC class I allele B7.

Thus, another embodiment provides a peptide epitope which comprises an amino acid sequence as set out in any of SEQ ID NOs: 8, 9, 17, 23, 45, 55, 58, 71, 101, 113, 117, 125, 126, 163, 186 and 187.

In one embodiment, the peptide epitope of the invention comprises a sequence as set out in any of the preceding statements of the invention and consists of 6 to 18 amino acids. Suitably, said peptide consists of 8, 9, 10, 11, 12, 13, 14, 15, 16, 17 or 18 amino acids. Preferably, the peptide epitope comprises a sequence of 8 to 12 amino acids, suitably, 8 to 10 amino acids.

In another embodiment, a peptide epitope of the invention consists of an amino acid sequence as set out in any of SEQ ID NOs: 1-206.

In another aspect of the invention, there is provided a peptide epitope of 5T4 comprising an amino acid sequence as set out in Table 12. Suitably, a peptide epitope in accordance with this aspect of the invention binds a MHC class II allele.

Further aspects of the invention relate to:
a polyepitope string comprising such a peptide.
   such a peptide epitope, or such a polyepitope string in association with a cell penetrator.
   such a peptide epitope, or such a polyepitope string associated with an MHC multimer such as a tetramer or pentamer.
a nucleic acid sequence capable of encoding such a peptide epitope or polyepitope string (and optionally an associated cell penetrator).
a vector system capable of delivering such a nucleic acid sequence to a cell.
a cell pulsed with such a peptide epitope (or a precursor thereof).
a vaccine comprising such a peptide epitope, a polyepitope string, nucleic acid sequence, vector system and/or cell.
the use of such a vaccine in the manufacture of a medicament for use in the prevention and/or treatment of a disease.
a method for treating and/or preventing a disease in a subject in need of same which comprises the step of administering an effective amount of such a vaccine to the subject.
an agent capable of binding specifically to such a peptide and/or nucleic acid sequence.
a method which comprises the step of detecting the presence of such a peptide, nucleic acid or agent in a subject.
a T cell line or clone capable of specifically recognising such a peptide epitope in conjunction with an MHC class I or class II molecule.

Advantageously, identification of novel T cell epitopes will enable the production of MHC class I and class II multimers, tetramers and pentamers, useful as analytical tools delivering both increased sensitivity of immuno-monitoring and the ability to stain 5T4 reactive T-cells in tumour biopsy samples. In addition, the detection of 5T4 specific CTL in the periphery of individuals at risk of disease recurrence is a useful diagnostic tool.

Accordingly, in a further aspect of the invention there is provided an MHC multimer, tetramer or a pentamer comprising at least one of the MHC class I or II 5T4 peptide epitopes as described herein.

Other aspects of the present invention are presented in the accompanying claims and in the following description and discussion. These aspects are presented under separate section headings. However, it is to be understood that the teachings under each section heading are not necessarily limited to that particular section heading.

DETAILED DESCRIPTION OF THE INVENTION

Epitopes

The present invention relates to peptide epitopes.

The term "peptide" is used in the normal sense to mean a series of residues, typically L-amino acids, connected one to the other typically by peptide bonds between the α-amino and carboxyl groups of adjacent amino acids. The term includes modified peptides and synthetic peptide analogues.

A T cell epitope is a short peptide derivable from a protein antigen. Antigen presenting cells can internalise antigen and process it into short fragments which are capable of binding MHC molecules. The specificity of peptide binding to the MHC depends on specific interactions between the peptide and the peptide-binding groove of the particular MHC molecule.

Peptides which bind to MHC class I molecules (and are recognised by CD8+ T cells) are usually between 6 and 12, more usually between 8 and 12 amino or 8 and 10 amino acids in length. Typically, peptides are 9 amino acids in length. The amino-terminal amine group of the peptide makes contact with an invariant site at one end of the peptide groove, and the carboxylate group at the carboxy terminus binds to an invariant site at the other end of the groove. Thus, typically, such peptides have a hydrophobic or basic carboxy terminus and an absence of proline in the extreme amino terminus. The peptide lies in an extended confirmation along the groove with further contacts between main-chain atoms and conserved amino acid side chains that line the groove. Variations in peptide length are accommodated by a kinking in the peptide backbone, often at proline or glycine residues.

Peptides which bind to MHC class II molecules are usually at least 10 amino acids, for example about 13-18 amino acids in length, and can be much longer. These peptides lie in an extended confirmation along the MHC II peptide-binding groove which is open at both ends. The peptide is held in place mainly by main-chain atom contacts with conserved residues that line the peptide-binding groove. Binding of peptides to MHC class II is described for example by Rammensee, H.-G. 1995 Curr. Opin. Immunol. 7:85.

The peptide of the present invention may be made using chemical methods (Peptide Chemistry, A practical Textbook. Mikos Bodansky, Springer-Verlag, Berlin.). For example, peptides can be synthesized by solid phase techniques (Roberge J Y et al (1995) Science 269: 202-204), cleaved from the resin, and purified by preparative high performance liquid chromatography (e.g., Creighton (1983) Proteins Structures And Molecular Principles, WH Freeman and Co, New York N.Y.). Automated synthesis may be achieved, for example, using the ABI 43 1 A Peptide Synthesizer (Perkin Elmer) in accordance with the instructions provided by the manufacturer.

The peptide may alternatively be made by recombinant means, or by cleavage from a longer polypeptide. For example, the peptide may be obtained by cleavage from full-length 5T4. The composition of a peptide may be confirmed by amino acid analysis or sequencing (e.g., the Edman degradation procedure).

The term "peptide epitope" encompasses modified peptides. For example 5T4 peptides may be mutated, by amino acid insertion, deletion or substitution, so long as the MHC binding-specificity of the wild-type 5T4 peptide is retained. In a preferred embodiment the modified epitope has greater affinity for the peptide binding groove. Preferably the peptide contains 5 or fewer mutations from the wild-type sequence, more preferably 3 or fewer, most preferably 1 or 0 mutations.

Alternatively (or in addition) modifications may be made without changing the amino acid sequence of the peptide. For example, D-amino acids or other unnatural amino acids can be included, the normal amide bond can be replaced by ester or alkyl backbone bonds, N- or C-alkyl substituents, side chain modifications, and constraints such as disulphide bridges and side chain amide or ester linkages can be included. Such changes may result in greater in vivo stability of the peptide, and a longer biological lifetime.

Modification of epitopes may be performed based on predictions for more efficient T-cell induction derived using the program "Peptide Binding Predictions" devised by K. Parker (NIH) which may be found on the internet at www.bimas.d-crt.nih.gov/cgi-bin/molbio/ken_parker_comboform (see also Parker, K. C et al. 1994. J. Immunol. 152:163).

A "modified" 5T4 peptide epitope includes peptides which have been bound or otherwise associated to transporter peptides or adjuvants, in order to increase their ability to elicit an immune response. For example, peptides may be fused to TAP independent transporter peptides for efficient transport to HLA and interaction with HLA molecules to enhance CTL epitopes (for review see Yewdell et al., 1998 J Immunother 21:127-31; Fu et al., (1998) J Virol 72:1469-81).

In a further embodiment, 5T4 or 5T4 peptides may be fused to hepatitis B core antigen to enhance T helper and antibody responses (Schodel et al., 1996 Intervirology 39:104-10).

To be an epitope, the peptide should be capable of binding to the peptide-binding groove of a MHC class I or II molecule and be recognised by a T cell.

Cell surface presentation of peptides derived from a given antigen is not random and tends to be dominated by a small number of frequently occurring epitopes. The dominance of a particular peptide will depend on many factors, such as relative affinity for binding the MHC molecule, spatio-temporal point of generation within the APC and resistance to degradation. The epitope hierarchy for an antigen is thought to change with progression of an immune response. After a primary immune response to the immunodominant peptides, epitope "spreading" may occur to sub-dominant determinants (Lehmann et al (1992) Nature 358:155-157).

For any given antigen, cryptic epitopes may also exist. Cryptic epitopes are those which can stimulate a T cell response when administered as a peptide but which fail to produce such a response when administered as a whole antigen. It may be that during processing of the antigen into peptides in the APC the cryptic epitope is destroyed.

The peptide of the invention may be an immunodominant epitope, a sub-dominant epitope or a cryptic epitope of 5T4.

Epitopes for an antigen may be identified by measuring the T cell response to overlapping peptides spanning a portion of the antigen (see below) when presented by APC. Such studies usually result in "nested sets" of peptides, and the minimal epitope for a particular T cell line/clone can be assessed by measuring the response to truncated peptides.

The minimal epitope for an antigen may not be the best epitope for practical purposes. It may well be that amino acids flanking the minimal epitope will be required for optimal binding to the MHC.

The peptides are tested in an antigen presentation system which comprises antigen presenting cells and T cells. For example, the antigen presentation system may be a murine splenocyte preparation, a preparation of human cells from tonsil or PBMC. Alternatively, the antigen presentation system may comprise a particular T cell line/clone and/or a particular antigen presenting cell type.

T cell activation may be measured via T cell proliferation (for example using $^3$H-thymidine incorporation) or cytokine production. Activation of TH1-type CD4+ T cells can, for example be detected via IFNγ production which may be detected by standard techniques, such as an ELISPOT assay.

Polyepitope String

It has been found that a particularly effective way to induce an immune response to an antigen is by the use of a poly-epitope string, which contains a plurality of antigenic epitopes from one or more antigens linked together. For example, for malaria, a polyepitope string of mainly malaria (*P. falciparu*) CD8 T cell peptide epitopes has been described which also expresses CD4 T cell epitopes from tetanus toxoid and from the 38Kd mycobacterial antigen of various strains of *M. tuberculosis* and *M. bovis*.

The present invention also provides a polyepitope string comprising at least one peptide according to the present invention. Suitably a polyepitope string is made up of at least one, two, three, four or more peptide epitopes as described herein. In one embodiment, such polyepitope strings are distinguished from naturally occurring full length 5T4 by virtue of a composition which comprises multiple similar or identical epitopes. Suitably such epitopes are joined by additional sequences which are absent from the full length protein. The string may also comprise another epitope derivable from the 5T4 antigen or an epitope from another antigen—such as another TAA—or combinations thereof. The string may also comprise both MHC class I and MHC class II epitopes. A polyepitope string may optionally comprise additional intervening amino acids between the 5T4 epitopes.

TAAs have been characterised either as membrane proteins or altered carbohydrate molecules of glycoproteins and glycolipids, however their functions remain largely unknown. One TAA family, the transmembrane 4 superfamily (TM4SF), usually has four well-conserved membrane-spanning regions, certain cysteine residues and short sequence motifs. There is evidence that TM4SF antigens exist in close association with other important membrane receptors including CD4 and CD8 of T cells (Imai & Yoshie (1993) *J. Immunol.* 151, 6470-6481). It has also been suggested that TM4SF antigens may play a role in signal transduction which in turn, affects cell development, activation and motility. Examples of TM4SF antigens include human melanoma-associated antigen ME491, human and mouse leukocyte surface antigen CD37, and human lymphoblastic leukemia-associated TALLA-1 (Hotta, H. et al. (1988) Cancer Res. 48, 2955-2962; Classon, B. J. et al. (1989) J. Exp. Med. 169: 1497-1502; Tomlinson, M. G. et al. (1996) Mol. Immun. 33: 867-872; Takagi, S. et al. (1995) Int. J. Cancer 61: 706-715).

Further examples of TAAs also include, but are not limited to, TAAs in the following classes: cancer testis antigens (HOM-MEL-40), differentiation antigens (HOM-MEL-55), overexpressed gene products (HOM-MD-21), mutated gene products (NY-COL-2), splice variants (HOM-MD-397), gene amplification products (HOM-NSCLC-11) and cancer related autoantigens (HOM-MEL-2.4) as reviewed in Cancer Vaccines and Immunotherapy (2000) Eds Stem, Beverley and Carroll, Cambridge University Press, Cambridge. Further examples include, MART-1 (Melanoma Antigen Recognised by T cells-1) MAGE-A (MAGE-A1, MAGE-A2, MAGE-A3, MAGE-A4, MAGE-A6, MAGE-A8, MAGE-A10, MAGE-A12), MAGE B (MAGE-B1-MAGE-B24), MAGE-C (MAGE-C1/CT7, CT10), GAGE (GAGE-1, GAGE-8, PAGE-1, PAGE-4, XAGE-1, XAGE-3), LAGE (LAGE-1a (1S), -1b(1L), NY-ESO-1), SSX (SSX1-SSX-5), BAGE, SCP-1, PRAME (MAPE), SART-1, SART-3, CTp11, TSP50, CT9/BRDT, gp100, MART-1, TRP-1, TRP-2, MELAN-A/MART-1, Carcinoembryonic antigen (CEA), prostate-specific antigen (PSA), MUCIN (MUC-1) and Tyrosinase. TAAs are reviewed in Cancer Immunology (2001) Kluwer Academic Publishers, The Netherlands.

Cell Penetrators

The present invention also provides a peptide epitope, or a polyepitope string in association with a cell penetrator.

Antigen presenting cells (such as dendritic cells) pulsed with peptides have proven effective in enhancing antitumour immunity (Celluzzi et al (1996) J. Exp. Med. 183 283-287; Young et al (1996) J. Exp. Med. 183 7-11). It has been shown that it is possible to prolong the presentation of a peptide by dendritic cells (and thus enhance antitumour immunity) by linking it to a cell penetrating peptide (CPP) (Wang and Wang (2002) Nature Biotechnology 20 149-154).

A cell penetrator may be any entity which enhances the intracellular delivery of the peptide/polyepitope string to the antigen presenting cell. For example, the cell penetrator may be a lipid which, when associated with the peptide, enhances its capacity to cross the plasma membrane. Alternatively, the cell penetrator may be a peptide. Several cell penetrating peptide (CPPs) have been identified from proteins, including the Tat protein of HIV (Frankel and Pabo (1988) Cell 55 1189-1193), the VP22 protein of HSV (Elliott and O'Hare (1997) Cell 88 223-233) and fibroblast growth factor (Lin et al (1995) J. Biol. Chem. 270 14255-14258).

The term "associated with" is intended to include direct linkage, for example by a covalent bond. Examples of covalent bonds for linking amino acids include disulphide bridges and peptide bonds. In a preferred embodiment, the peptide/polyepitope string and a CPP are linked by a peptide bond to create a fusion protein.

The term also includes non-covalent linkage, such as association by electrostatic bonding, hydrogen bonding and van der Waals' forces. The cell penetrator and peptide/polyepitope string may be associated without covalent or non-covalent bonding. For example the cell penetrator may be a lipid which encapsulates the peptide/polyepitope string (e.g. a. liposome).

5T4

5T4 has been previously characterised, for example, in WO89/07947. The sequence of human 5T4 appears in GenBank at accession no. Z29083. The peptide may also be derived from a corresponding 5T4 antigen from a different species, such as murine 5T4 (WO00/29428), canine 5T4 (WO01/36486) or feline 5T4. The peptide may also be derived from a naturally occurring variant of 5T4 found with a particular species, preferably a mammal. Such a variant may be encoded by a related gene of the same gene family, by an allelic variant of a particular gene, or represent an alternative splicing variant of the 5T4 gene.

A peptide derived from 5T4 from a different species or a splice variant may have a different amino acid sequence from the analogous human wild-type 5T4 peptide. However, as long as the peptide retains the same qualitative binding specificity as the human peptide (i.e. it binds in the peptide binding groove of an MHC molecule of the same haplotype) then it is still an epitope in accordance with the present invention.

Nucleic Acid

The present invention also relates to a nucleic acid sequence capable of encoding a peptide epitope or polyepitope string according to the first aspect of the invention.

A "nucleic acid", as referred to herein, may be DNA or RNA, naturally-occurring or synthetic, or any combination thereof. Nucleic acids according to the invention are limited only in that they serve the function of encoding a 5T4 peptide in such a way that it may be translated by the machinery of the cells of a host organism. Thus, natural nucleic acids may be modified, for example to increase the stability thereof. DNA and/or RNA, but especially RNA, may be modified in order to improve nuclease resistance of the members. For example, known modifications for ribonucleotides include 2'-O-methyl, 2'-fluoro, 2'—$NH_2$, and 2'-O-allyl. The modified nucleic acids according to the invention may comprise chemical modifications which have been made in order to increase the in vivo stability of the nucleic acid, enhance or mediate the delivery thereof, or reduce the clearance rate from the body. Examples of such modifications include chemical substitutions at the ribose and/or phosphate and/or base positions of a given RNA sequence. See, for example, WO 92/03568; U.S. Pat. No. 5,118,672; Hobbs et al., (1973) Biochemistry 12:5138; Guschlbauer et al., (1977) Nucleic Acids Res. 4:1933; Schibaharu et al., (1987) Nucleic Acids Res. 15:4403; Pieken et al., (1991) Science 253:314, each of which is specifically incorporated herein by reference.

The present invention also encompasses nucleic acids which will hybridise to a nucleic acid sequence capable of encoding a peptide epitope or polyepitope string according to the first aspect of the invention.

Stringency of hybridisation refers to conditions under which polynucleic acid hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M $Na^+$ at 65-68° C. High stringency conditions can be provided, for example, by hybridisation in an aqueous solution containing 6×SSC, 5×Denhardt's, 1% SDS (sodium dodecyl sulphate), 0.1 $Na^+$ pyrophosphate and 0.1 mg/ml denatured salmon sperm DNA as non specific competitor. Following hybridisation, high stringency washing may be done in several steps, with a final wash (about 30 min) at the hybridisation temperature in 0.2-0.1×SSC, 0.1% SDS.

Moderate stringency refers to conditions equivalent to hybridisation in the above described solution but at about 60-62° C. In that case the final wash is performed at the hybridisation temperature in 1×SSC, 0.1% SDS.

Low stringency refers to conditions equivalent to hybridisation in the above described solution at about 50-52° C. In that case, the final wash is performed at the hybridisation temperature in 2×SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

Given the guidance provided herein, the nucleic acids of the invention are obtainable according to methods well known in the art. For example, a DNA of the invention is obtainable by chemical synthesis, using polymerase chain reaction (PCR) or direct cleavage from a longer polynucleotide, such as the entire 5T4 coding sequence or a fragment thereof.

Chemical methods for synthesis of a nucleic acid of interest are known in the art and include triester, phosphite, phosphoramidite and H-phosphonate methods, PCR and other autoprimer methods as well as oligonucleotide synthesis on solid supports. These methods may be used if the entire nucleic acid sequence of the nucleic acid is known, or the sequence of the nucleic acid complementary to the coding strand is available. Alternatively, if the target amino acid sequence is known, one may infer potential nucleic acid sequences using known and preferred coding residues for each amino acid residue.

It is envisaged that the nucleic acid of the invention can be modified by nucleotide substitution, nucleotide deletion, nucleotide insertion or inversion of a nucleotide stretch, and any combination thereof. Such mutants can be used e.g. to produce a 5T4 peptide that has an amino acid sequence differing from the wild-type 5T4 epitope. Such a peptide is still a peptide in accordance with the present invention if it retains the capacity to act as a T cell epitope. Mutagenesis may be predetermined (site-specific) or random. A mutation which is not a silent mutation should not place sequences out of reading frames and preferably will not create complementary regions that could hybridise to produce secondary mRNA structure such as loops or hairpins.

Variants/Fragments/Homologues/Derivatives

The present invention encompasses the use of nucleotide and amino acid sequences and variants, homologues, derivatives and fragments thereof.

The term "variant" is used to mean a naturally occurring polypeptide or nucleotide sequence which differs from a wild-type sequence.

The term "fragment" indicates that a polypeptide or nucleotide sequence comprises a fraction of a subject sequence. Preferably the sequence comprises at least 50%, more preferably at least 65%, more preferably at least 80%, more preferably at least 90%, most preferably at least 90% of the subject sequence. If the fragment is a fragment of an amino acid then preferably, for a MHC class I peptide, the fragments are 6-12 amino acids in length. More preferably, the fragments are 8, 9 or 10 amino acids in length. For a MHC class II peptide, suitably the fragments are 12 to 25 amino acids in length. Suitably such fragments are capable of binding MHC class I or MHC class II.

The term "homologue" means an entity having a certain homology with the subject amino acid sequences and the subject nucleotide sequences. Here, the term "homology" can be equated with "identity".

In the present context, a homologous sequence is taken to include an amino acid sequence, which may be at least 75, 85 or 90% identical, preferably at least 95 or 98% identical to the subject sequence. Typically, the homologues will comprise the same activity as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence, which may be at least 75, 85 or 90% identical, preferably at least 95 or 98% identical to the subject sequence. Typically, the homologues will comprise the same activity as the subject sequence. Although homology can also be considered in terms of similarity (i.e. amino acid residues having similar chemical properties/functions), in the context of the present invention it is preferred to express homology in terms of sequence identity.

Homology comparisons may be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped"

alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix—such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues, which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example, according to the Table below. Amino acids in the same block in the second column and preferably in the same line in the third column may be substituted for each other:

| ALIPHATIC | Non-polar | G A P |
|---|---|---|
| | | I L V |
| | Polar-uncharged | C S T M |
| | | N Q |
| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e. like-for-like substitution—such as basic for basic, acidic for acidic, polar for polar etc. Non-homologous substitution may also occur i.e. from one class of residue to another or alternatively involving the inclusion of unnatural amino acids—such as ornithine (hereinafter referred to as Z), diaminobutyric acid ornithine (hereinafter referred to as B), norleucine ornithine (hereinafter referred to as 0), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids—such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ϵ-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe)—such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups—such as methyl, ethyl or propyl groups—in addition to amino acid spacers—such as glycine or β-alanine residues. A further form of variation involves the presence of one or more amino acid residues in peptoid form will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example, Simon R J et al., PNAS (1992) 89(20), 9367-9371 and Horwell D C, Trends Biotechnol. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences may be modified by any method available in the art. Such modifications may be carried out to enhance the in vivo activity or life span of nucleotide sequences useful in the present invention.

Vector System

The nucleic acid sequence of the present invention may be delivered to a cell by way of a vector system.

As used herein, a "vector" may be any agent capable of delivering or maintaining nucleic acid in a host cell, and includes viral vectors, plasmids, naked nucleic acids, nucleic acids complexed with polypeptide or other molecules and nucleic acids immobilised onto solid phase particles. Such vectors are described in detail below. It will be understood that the present invention, in its broadest form, is not limited to any specific vector for delivery of the 5T4 peptide-encoding nucleic acid.

The vector may be a prokaryotic or eukaryotic vector.

Nucleic acids encoding 5T4 epitopes and polyepitope strings in accordance with the present invention can be delivered by viral or non-viral techniques.

Non-viral delivery systems include but are not limited to DNA transfection methods. Here, transfection includes a process using a non-viral vector to deliver a 5T4 gene to a target mammalian cell.

Typical transfection methods include electroporation, nucleic acid biolistics, lipid-mediated transfection, compacted nucleic acid-mediated transfection, liposomes, immunoliposomes, lipofectin, cationic agent-mediated, cationic facial amphiphiles (CFAs) (Nature Biotechnology 1996 14; 556), multivalent cations such as spermine, cationic lipids or polylysine, 1, 2,-bis(oleoyloxy)-3-(trimethylammonio) propane (DOTAP)-cholesterol complexes (Wolff and Trubetskoy 1998 Nature Biotechnology 16: 421) and combinations thereof.

Non-viral delivery systems may also include, but are not limited to, bacterial delivery systems. The use of bacteria as anticancer agents and as delivery agents for anticancer drugs has been reviewed in Expert Opin Biol Ther 2001 March; 1(2):291-300.

Suitable bacteria include, but are not limited to, bacterial pathogens and non-pathogenic commensal bacteria. By way of example, suitable genera may be selected from *Salmonella, Mycobacterium, Yersinia, Shigella, Listeria* and *Brucella*. Recent advances in the pathogenesis and molecular biology of these bacteria have allowed the rational development of new and improved bacterial carriers and more effective gene expression systems. These advances have improved the performance and versatility of these delivery systems.

The bacteria may be invasive intracellular bacteria that are able to transfer eukaryotic expression plasmids into mammalian host cells in vitro and in vivo. Plasmid transfer may take place when the recombinant bacterium dies within the host cell, either due to metabolic attenuation or induction of autolysis. Alternatively, antibiotics may be used and spontaneous transfer has also been observed, indicating that this phenomenon might also occur under physiological conditions. Plasmid transfer has been reported for *Shigella flexneri, Salmonella typhimurium, S. typhi, Listeria monocytogenes* and recombinant *Escherichia coli*, but other invasive bacteria may also be used.

Bacteria may be used for DNA vaccine delivery. Such bacteria may enter the host cell cytosol after phagocytosis, for example, *Shigella* and *Listeria*, or they remain in the phagosomal compartment—such as *Salmonella*. Both intracellular localisations may be suitable for successful delivery of DNA vaccine vectors.

The bacterial delivery systems may utilise *Mycobacterium* in the form of non pathogenic *Mycobacterium* strains, genetic transfer systems in the form of cloning and expression vectors, and related technologies to provide products containing, for example, non toxic immuno-regulating *Mycobacterium* adjuvants, non toxic immuno-stimulating exogenous antigens specific for a variety of diseases, and non toxic amounts of cytokines that boost the TH-1 pathway (Tunis Med 2001 February; 79(2):65-81).

*Salmonella* strains—such as attenuated strains—which comprise defined gene deletions, may be used as suitable delivery systems—such as the delivery of antigens. A number of strategies for delivery by these strains have been attempted, ranging from plasmid-based to chromosomal integration systems. By way of example, Rosenkranz et al. Vaccine 2003, 21(7-8), 798-801 describe eukaryotic expression plasmids encoding cytokines, and assessed their capacity to modulate immune responses in different experimental models. Plasmids encoding mouse IL-4 and IL-18 under cytomegalovirus promoter were constructed and transformed into live attenuated *Salmonella enterica* serovar Typhi strain CVD 908-htrA, and *Salmonella enterica* serovar Typhimurium strain SL3261.

The use of attenuated *Salmonella typhimurium* as a potential gene delivery vector has been reviewed in Anticancer Res 2002, 22(6A):3261-6.

*Brucella abortus* may also be used as a suitable delivery system as described by Vemulapalli et al. Infect Immun (2000) 68(6):3290-6. *Brucella abortus* strain RB51 is a stable, rough, attenuated mutant widely used as a live vaccine for bovine brucellosis. This strain may be used as a delivery vector, for example, in the delivery of protective antigens of other intracellular pathogens to which the induction of a strong Th1 type of immune response is needed for effective protection.

Boyd et al. Eur J Cell Biol (2000) 79 (10) 659-71 describe the use of *Yersinia enterocolitica* for the delivery of proteins into a wide range of cell types. *Y. enterocolitica* translocates virulence proteins, called Yop effectors, into the cytosol of eukaryotic cells. No limit to the range of eukaryotic cells into which *Y. enterocolitica* can translocate Yops was reported. The Yop effectors YopE, YopH and YopT were each cytotoxic for the adherent cell types tested, showing that not only is *Y. enterocolitica* not selective in its translocation of particular Yop effectors into each cell type, but also that the action of these Yop effectors is not cell type specific. To use the *Yersinia* translocation system for broad applications, a *Y. enterocolitica* translocation strain and vector for the delivery of heterologous proteins into eukaryotic cells was constructed. This strain and vector combination lacks the translocated Yop effectors and allows delivery into eukaryotic cells of heterologous proteins fused to the minimal N-terminal secretion/translocation signal of YopE.

U.S. Pat. No. 5,965,381 describes a recombinant *Yersinia* for the delivery of proteins into eukaryotic cells. Such *Yers-*

*inia* are deficient in the production of functional effector proteins, but are endowed with a functional secretion and translocation system.

Cell adhesion molecules are a large group of molecules involved in a variety of cell-to-cell and cell-to-extra-cellular matrix (ECM) interactions and are exploited by a number of pathogenic micro-organisms as receptors for cell entry. These molecules may be used for the targeting and uptake of both gene and drug delivery systems. Cell adhesion molecules and their use in gene transfer has been reviewed in Adv Drug Deliv Rev 2000 Nov. 15; 44(2-3):135-52.

The gene gun delivery system may also be used for the delivery of DNA, which is a highly reliable method compared to intramuscular inoculation (Jpn J Pharmacol 2000 July; 83(3):167-74).

Viral delivery systems include but are not limited to adenovirus vectors, adeno-associated viral (AAV) vectors, herpes viral vectors, retroviral vectors, lentiviral vectors or baculoviral vectors, venezuelan equine encephalitis virus (VEE), poxviruses such as: canarypox virus (Taylor et al 1995 Vaccine 13:539-549), entomopox virus (Li Y et al 1998 XIIth International Poxvirus Symposium p 144. Abstract), penguine pox (Standard et al. J Gen Virol. 1998 79:1637-46) alphavirus, and alphavirus based DNA vectors.

Examples of retroviruses include but are not limited to: murine leukaemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukaemia virus (Mo-MLV), FBR murine osteosarcoma virus (FBR MSV), Moloney murine sarcoma virus (Mo-MSV), Abelson murine leukaemia virus (A-MLV), Avian myelocytomatosis virus-29 (MC29), and Avian erythroblastosis virus (AEV).

A detailed list of retroviruses may be found in Coffin et al ("Retroviruses" 1997 Cold Spring Harbour Laboratory Press Eds: J M Coffin, S M Hughes, H E Varmus pp 758-763).

Lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells (Lewis et al 1992 EMBO. J 11: 3053-3058; Lewis and Emerman 1994 J. Virol. 68: 510-516). In contrast, other retroviruses—such as MLV—are unable to infect non-dividing cells such as those that make up, for example, muscle, brain, lung and liver tissue.

The vector of the present invention may be configured as a split-intron vector. A split intron vector is described in PCT patent applications WO 99/15683 and WO 99/15684.

If the features of adenoviruses are combined with the genetic stability of retroviruses/lentiviruses then essentially the adenovirus can be used to transduce target cells to become transient retroviral producer cells that could stably infect neighbouring cells. Such retroviral producer cells engineered to express 5T4 antigen can be implanted in organisms such as animals or humans for use in the treatment of angiogenesis and/or cancer.

The vector of the present invention may be configured as a psuedotyped vector.

In the design of retroviral vectors it may be desirable to engineer particles with different target cell specificities to the native virus, to enable the delivery of genetic material to an expanded or altered range of cell types. One manner in which to achieve this is by engineering the virus envelope protein to alter its specificity. Another approach is to introduce a heterologous envelope protein into the vector particle to replace or add to the native envelope protein of the virus.

The term pseudotyping means incorporating in at least a part of, or substituting a part of, or replacing all of, an env gene of a viral genome with a heterologous env gene, for example an env gene from another virus. Pseudotyping is not a new phenomenon and examples may be found in WO 99/61639, WO-A-98/05759, WO-A-98/05754, WO-A-97/17457, WO-A-96/09400, WO-A-91/00047 and Mebatsion et al 1997 Cell 90, 841-847.

Pseudotyping can improve retroviral vector stability and transduction efficiency. A pseudotype of murine leukemia virus packaged with lymphocytic choriomeningitis virus (LCMV) has been described (Miletic et al (1999) J. Virol. 73:6114-6116) and shown to be stable during ultracentrifugation and capable of infecting several cell lines from different species.

Poxvirus Vectors

TAAs are weakly immunogenic, being recognised as "self" by the immune system and thus tolerated to a large extent. The use of poxvirus vectors is sometimes able to cause the antigens to be presented such that this tolerance may be overcome at least in part, (especially if immune evasion genes are deleted—see below) thus enabling a host to raise an immune response.

Poxvirus vectors are preferred for use in the present invention. Pox viruses are engineered for recombinant gene expression and for the use as recombinant live vaccines. This entails the use of recombinant techniques to introduce nucleic acids encoding foreign antigens into the genome of the pox virus. If the nucleic acid is integrated at a site in the viral DNA which is non-essential for the life cycle of the virus, it is possible for the newly produced recombinant pox virus to be infectious, that is to say to infect foreign cells and thus to express the integrated DNA sequence. The recombinant pox viruses prepared in this way can be used as vaccines for the prophylaxis and/or treatment of pathologic and infectious disease.

Expression of 5T4 peptide(s) in recombinant pox viruses, such as vaccinia viruses, requires the ligation of vaccinia promoters to the nucleic acid encoding the 5T4 peptide(s). Plasmid vectors (also called insertion vectors), have been constructed to insert nucleic acids into vaccinia virus through homologous recombination between the viral sequences flanking the nucleic acid in a donor plasmid and homologous sequence present in the parental virus (Mackett et al 1982 PNAS 79: 7415-7419). One type of insertion vector is composed of: (a) a vaccinia virus promoter including the transcriptional initiation site; (b) several unique restriction endonuclease cloning sites located downstream from the transcriptional start site for insertion of nucleic acid; (c) nonessential vaccinia virus sequences (such as the Thymidine Kinase (TK) gene) flanking the promoter and cloning sites which direct insertion of the nucleic acid into the homologous nonessential region of the virus genome; and (d) a bacterial origin of replication and antibiotic resistance marker for replication and selection in *E. Coli*. Examples of such vectors are described by Mackett (Mackett et al 1984, J. Virol. 49: 857-864).

The isolated plasmid containing the nucleic acid to be inserted is transfected into a cell culture, e.g., chick embryo fibroblasts, along with the parental virus, e.g., poxvirus. Recombination between homologous pox DNA in the plasmid and the viral genome respectively results in a recombinant poxvirus modified by the presence of the promoter-gene construct in its genome, at a site which does not affect virus viability.

As noted above, the nucleic acid is inserted into a region (insertion region) in the virus which does not affect virus viability of the resultant recombinant virus. Such regions can be readily identified in a virus by, for example, randomly testing segments of virus DNA for regions that allow recombinant formation without seriously affecting virus viability of the recombinant. One region that can readily be used and is present in many viruses is the thymidine kinase (TK) gene. For example, the TK gene has been found in all pox virus genomes examined [leporipoxvirus: Upton, et al J. Virology 60:920 (1986) (shope fibroma virus); capripoxvirus: Gershon, et al J. Gen. Virol. 70:525 (1989) (Kenya sheep-1); orthopoxvirus: Weir, et al J. Virol 46:530 (1983) (vaccinia); Esposito, et al Virology 135:561 (1984) (monkeypox and variola virus); Hruby, et al PNAS, 80:3411 (1983) (vaccinia); Kilpatrick, et al Virology 143:399 (1985) (Yaba monkey tumour virus); avipoxvirus: Binns, et al J. Gen. Virol 69:1275 (1988) (fowlpox); Boyle, et al Virology 156:355 (1987) (fowlpox); Schnitzlein, et al J. Virological Method, 20:341 (1988) (fowlpox, quailpox); entomopox (Lytvyn, et al J. Gen. Virol 73:3235-3240 (1992)].

In vaccinia, in addition to the TK region, other insertion regions include, for example, HindIII M.

In fowlpox, in addition to the TK region, other insertion regions include, for example, BamHI J [Jenkins, et al AIDS Research and Human Retroviruses 7:991-998 (1991)] the EcoRI-HindIII fragment, BamHI fragment, EcoRV-HindIII fragment, BamHI fragment and the HindIII fragment set forth in EPO Application No. 0 308 220 A1. [Calvert, et al J. of Virol 67:3069-3076 (1993); Taylor, et al Vaccine 6:497-503 (1988); Spehner, et al (1990) and Boursnell, et al J. of Gen. Virol 71:621-628 (1990)].

In swinepox preferred insertion sites include the thymidine kinase gene region.

A promoter can readily be selected depending on the host and the target cell type. For example in poxviruses, pox viral promoters should be used, such as the vaccinia 7.5K, or 40K or fowlpox C1. Artificial constructs containing appropriate pox sequences can also be used. Enhancer elements can also be used in combination to increase the level of expression. Furthermore, the use of inducible promoters, which are also well known in the art, are preferred in some embodiments.

Foreign gene expression can be detected by enzymatic or immunological assays (for example, immuno-precipitation, radioimmunoassay, or immunoblotting). Naturally occurring membrane glycoproteins produced from recombinant vaccinia infected cells are glycosylated and may be transported to the cell surface. High expressing levels can be obtained by using strong promoters.

Other requirements for viral vectors for use in vaccines include good immunogenicity and safety. MVA is a replication-impaired vaccinia strain with a good safety record. In most cell types and normal human tissue, MVA does not replicate. Replication of MVA is observed in a few transformed cell types such as BHK21 cells. Carroll et al (1997) have shown that the recombinant MVA is equally as good as conventional recombinant vaccinia vectors at generating a protective CD8+T cell response and is an efficacious alternative to the more commonly used replication competent vaccinia virus. The vaccinia virus strains derived from MVA, or independently developed strains having the features of MVA which make MVA particularly suitable for use in a vaccine, are also suitable for use in the present invention.

Preferably, the vector is a vaccinia virus vector such as MVA or NYVAC. Most preferred is the vaccinia strain modified virus ankara (MVA) or a strain derived therefrom. Alternatives to vaccinia vectors include avipox vectors such as fowlpox or canarypox known as ALVAC and strains derived therefrom which can infect and express recombinant proteins in human cells but are unable to replicate.

In one aspect of the present invention at least one immune evasion gene is deleted from the poxvirus vector.

Viruses, especially large viruses such a poxviruses which have an extensive coding capacity and can thus encode a variety of genes, have developed a number of techniques for evading the immune system of their hosts. For example, they are able to evade non-specific defences such as complement, interferons and the inflammatory response, as well as to interfere with or block the function of cytokines. A number of these immune evasion polypeptides have been deleted from MVA, with the exception of the interferon resistance protein in the left terminal region.

Poxviruses in general, being large DNA viruses which establish acute, rather than latent, infections. They encode so many antigenic proteins that antigenic variation is difficult, thus relying on active immune evasion to protect themselves from the mammalian immune system. They possess a number of genes which encode polypeptides which are responsible for interfering with a number of aspects of the immune system: they disrupt interferon action, interfere with complement, cytokine activity, inflammatory responses and CTL recognition (for a review, Smith et al., (1997) Immunol Rev 159:137-154). Removal of these proteins is beneficial in promoting the ability of weak immunogens encoded on a poxvirus vector to elicit an immune response in a subject.

An immune evasion gene or polypeptide is a gene, or its product, which assists the virus in evading the mammalian immune system. Preferably, the gene or gene product interferes with the working of the immune system, at least one level. This may be achieved in a number of ways, such as by interfering in signalling pathways by providing competitors for signalling molecules, by providing soluble cytokine receptor mimics and the like.

Immune evasion genes include, but are not limited to, the following:

Interferon evasion genes. Vaccinia possesses at least three genes which interfere with IFN action. The E3L gene expresses a 25 Kd polypeptide which competes with P1 protein kinase for binding to dsRNA, an event which leads to activation of P1, phosphorylation of eIF2α and resultant failure of translation initiation complex assembly. This pathway is ordinarily responsive to IFN activation, but is impeded by E3L expression thus allowing translation initiation to proceed unimpeded.

The K3L gene expresses a 10.5 Kd polypeptide which also interferes with P1 activity, since it is effectively an eIF2α mimic and acts as a competitor for P1 protein kinase. Its mode of action is thus similar to E3L.

The A18R gene is predicted to encode a helicase, which appears to interfere with the 2',5'-oligoadenylate pathway, which is in turn IFN responsive. 2',5'-A activates RNAse L, which acts to prevent viral translation. Expression of A18R appears to reduce 2',5'-A levels in infected cells.

Complement. The product of the B5R gene of vaccinia is known to be highly related to factor H, a regulator of the alternative complement pathway. This pathway may be activated by antigen alone, unlike the classical pathway. The B5R gene product thus may interfere with the alternative complement pathway.

The C21L gene is in turn related to C4b-binding protein in humans, and interacts with cells bearing C4b on the surface to prevent binding to the CR1 complement receptor.

Soluble Cytokine Receptors. The product of the vaccinia WR B15R gene (B16R in Copenhagen strain vaccinia) is related to IL1-R.

The WR gene ORF SalF19R, A53R in Copenhagen strain vaccinia, encodes a TNF receptor. However, in wild-type virus both of these genes are believed to be inactive due to fragmentation of the ORFs.

The B8R gene is believed to encode a soluble IFN-γ receptor, providing the virus with yet another IFN evasion mechanism.

Inflammation. A number of genes are believed to be involved in the prevention of inflammatory responses to viral infection. These include A44L, K2L, B13R and B22R.

In one aspect of the present invention, the majority of the immune evasion genes are deleted from the recombinant poxvirus vector. Preferably, all the immune evasion genes are deleted. Thus, in one aspect of the present invention, the recombinant poxvirus vector is a recombinant MVA vector in which the K3L interferon resistance protein gene has been disrupted or deleted.

Preferred are poxviruses which are non-hazardous to the intended subject. Thus, for example, for use in humans, poxviruses which are either host-range restricted, such as avipox viruses, or otherwise attenuated, such as attenuated strains of vaccinia (including NYVAC and MVA) are preferred. Most preferred are attenuated vaccinia virus strains, although non-vaccinia strains are usefully employed in subjects with pre-existing smallpox immunity.

A construct which contains at least one nucleic acid which codes for 5T4 epitope(s) flanked by MVA DNA sequences adjacent to a naturally occurring deletion, e.g. deletion II, within the MVA genome, is introduced into cells infected with MVA, to allow homologous recombination.

Once the construct has been introduced into the eukaryotic cell and the 5T4 epitope DNA has recombined with the viral DNA, the desired recombinant vaccinia virus, can be isolated, preferably with the aid of a marker (Nakano et al Proc. Natl. Acad. Sci. USA 79, 1593-1596 [1982], Franke et al Mol. Cell. Biol. 1918-1924 [1985], Chakrabarti et al Mol. Cell. Biol. 3403-3409 [1985], Fathi et al Virology 97-105 [1986]).

The construct to be inserted can be linear or circular. A circular DNA is preferred, especially a plasmid. The construct contains sequences flanking the left and the right side of a naturally occurring deletion, e.g. deletion II, within the MVA genome (Altenburger, W., Suter, C. P. and Altenburger J. (1989) Arch. Virol. 105, 15-27). The foreign DNA sequence is inserted between the sequences flanking the naturally occurring deletion.

For the expression of at least one nucleic acid, it is necessary for regulatory sequences, which are required for the transcription of the nucleic acid to be present upstream of the nucleic acid. Such regulatory sequences are known to those skilled in the art, and includes for example those of the vaccinia 11 kDa gene as are described in EP-A-198,328, and those of the 7.5 kDa gene (EP-A-110,385).

The construct can be introduced into the MVA infected cells by transfection, for example by means of calcium phosphate precipitation (Graham et al Virol. 52, 456-467 [1973; Wigler et al Cell 777-785 [1979] by means of electroporation (Neumann et al EMBO J. 1, 841-845 [1982]), by microinjection (Graessmann et al Meth. Enzymology 101, 482-492 (1983)), by means of liposomes (Straubinger et al Methods in Enzymology 101, 512-527 (1983)), by means of spheroplasts (Schaffner, Proc. Natl. Acad. Sci. USA 77, 2163-2167 (1980)) or by other methods known to those skilled in the art. Transfection by means of liposomes is preferred.

The recombinant priming and boosting vectors of the present invention can have a tropism for a specific cell type in the mammal. By way of example, the recombinant vectors of the present invention can be engineered to infect professional APCs such as dendritic cells and macrophages. Dendritic cells are known to be orchestrators of a successful immune response especially that of a cell mediated response. It has been shown that ex vivo treatment of dendritic cells with antigen or viral vectors containing such a target antigen, will induce efficacious immune responses when infused into syngeneic animals or humans (see Nestle F O, et al. Vaccination_of melanoma patients with peptide- or tumor lysate-pulsed dendritic cells, Nat. Med. 1998 March; 4(3):328-32 and Kim C J, et al. Dendritic cells infected with poxviruses encoding MART-1/Melan A sensitize T lymphocytes in vitro. J. Immunother. 1997 July; 20(4):276-86. The recombinant vectors can also infect tumour cells. Alternatively, the recombinant vectors are able to infect any cell in the mammal.

Other examples of vectors include ex vivo delivery systems, which include but are not limited to DNA transfection methods such as electroporation, DNA biolistics, lipid-mediated transfection and compacted DNA-mediated transfection.

The vector may be a plasmid DNA vector. As used herein, "plasmid" refers to discrete elements that are used to introduce heterologous DNA into cells for either expression or replication thereof. Selection and use of such vehicles are well within the skill of the artisan.

Pulsed Cells

The present invention also provides cells pulsed with peptides of the first aspect of the invention.

Preferably the cells to be pulsed are capable of expressing MHC class I or class II.

MHC class I molecules can be expressed on nearly all cell types, but expression of MHC class II molecules is limited to so-called "professional" antigen presenting cells (APCs); B cells, dendritic cells and macrophages. However, expression of MHC class II can be induced on other cell types by treating with IFNγ.

Expression of MHC class I or MHC class II molecules can also be achieved by genetic engineering (i.e. provision of a gene encoding the relevant MHC molecule to the cell to be pulsed). This approach has the advantage that an appropriate MHC haplotype(s) can be chosen which bind specifically to the peptide(s).

Preferably the cell to be pulsed is an antigen presenting cell, i.e. a cell which, in a normal immune response, is capable of processing an antigen and presenting it at the cell surface in conjunction with an MHC molecule. Antigen presenting cells include B cells, macrophages and dendritic cells. In an especially preferred embodiment, the cell is a dendritic cell.

Preferably the cell is capable of expressing an MHC molecule which binds a peptide according to the first aspect of the invention in its peptide binding groove. For example, the cell may express one of the following HLA restriction elements: B7, B8, Cw7 A1, A2 or A3 (for MHC class I).

Peptide pulsing protocols are known in the art (see for example Redchenko and Rickinson (1999) J. Virol. 334-342; Nestle et al (1998) Nat. Med. 4 328-332; Tjandrawan et al (1998) J. Immunotherapy 21 149-157). For example, in a standard protocol for loading dendritic cells with peptides, cells are incubated with peptide at 50 μg/ml with 3 μg/ml β-2 microglobulin for two hours in serum free medium. The unbound peptide is then washed off.

The pulsed cell of the present invention may be used as a vaccine, for example to stimulate a prophylactic or therapeutic anti-5T4 immune response.

The present invention therefore also provides a method for treating and/or preventing a disease which comprises the step of administering a peptide-pulsed cell to a subject in need of same.

Vaccine/Pharmaceutical Composition

The present invention also provides a vaccine/pharmaceutical composition comprising a peptide epitope, a polyepitope string, a nucleic acid sequence, a vector system and/or a cell according to previous aspects of the invention.

The vaccine/pharmaceutical composition may be for prophylactic or therapeutic use. In addition, the vaccine/pharmaceutical composition of the invention may be used in a combination therapy, for example, in cancer therapy, the vaccine/pharmaceutical composition of the invention may be used in a combination with a conventional chemotherapeutic agent.

The vaccine may by prepared as an injectable, either as liquid solution or suspension; solid form suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further examples of adjuvants and other agents include aluminium hydroxide, aluminium phosphate, aluminium potassium sulphate (alum), beryllium sulphate, silica, kaolin, carbon, water-in-oil emulsions, oil-in-water emulsions, muramyl dipeptide, bacterial endotoxin, lipid X, *Corynebacteriu parvum* (*Propionobacterium acnes*), *Bordetella pertussis*, polyribonucleotides, sodium alginate, lanolin, lysolecithin, vitamin A, saponin, liposomes, levamisole, DEAE-dextran, blocked copolymers, biodegradeable microspheres, immunostimulatory complexes (ISCOMs) or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

Typically, adjuvants such as AMPHIGEN™ (oil-in-water), ALHYDROGEL™ (aluminium hydroxide), or a mixture of AMPHIGEN™ and ALHYDROGEL™ adjuvants are used. Only aluminium hydroxide is approved for human use.

The proportion of immunogen and adjuvant can be varied over a broad range so long as both are present in effective amounts. For example, aluminium hydroxide can be present in an amount of about 0.5% of the vaccine mixture ($Al_2O_3$ basis). Conveniently, the vaccines are formulated to contain a final concentration of immunogen in the range of from 0.2 to 200 µg/ml, preferably 5 to 50 µg/ml, most preferably 15 µg/ml.

After formulation, the vaccine may be incorporated into a sterile container which is then sealed and stored at a low temperature, for example 4° C., or it may be freeze-dried. Lyophilisation permits long-term storage in a stabilised form.

The vaccine may be administered in a convenient manner such as by the oral, intravenous (where water soluble), intramuscular, subcutaneous, intranasal, intradermal or suppository routes or implanting (e.g. using slow release molecules).

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer.

Capsules, tablets and pills for oral administration to a patient may be provided with an enteric coating comprising, for example, EUDRAGIT™ coating "S", EUDRAGIT™ coating "L", cellulose acetate, cellulose acetate phthalate or hydroxypropylmethyl cellulose.

5T4 peptides may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

5T4 peptides may be administered with costimulatory molecules such as those involved in the interaction between receptor-ligand pairs expressed on the surface of antigen presenting cells and T cells. Such costimulatory molecules can be administered by administration of the protein molecule or of the corresponding nucleic acid encoding the protein molecule. Suitable costimulatory molecules include CD40, B7-1, B7-2, CD54, members of the ICAM family (eg ICAM-1, -2, or -3), CD58, SLAM ligands, polypeptides that bind heat stable antigen, polypeptides which bind to members or the TNF receptor family (eg 4-1BBL, TRAF-1, TRAF-2, TRAF-3, OX40L, TRAF-5, CD70) and CD 154. Peptides may also be administered in combination with stimulatory chemokines or cytokines including, for example, IL-2, IL-3, IL4, SCF, IL-6, IL7, IL-12, IL15, IL16, IL18, G-CSF, GM-CSF, IL-1alpha, IL-11, MIP-11, LIF, c-kit ligand, thrombopoietin and flt3 ligand, TNF-α and interferons such as IFN-α or IFN-γ. Chemokines may also be used in combination with the peptides, such as CCL3 or CCL5 or may be fused with the peptides of the invention (eg CXCL10 and CCL7). Where the peptides are administered by administering a nucleic acid encoding the peptide, the costimulatory molecule may also be administered by administering the corresponding nucleic acid encoding the costimulatory molecule.

It is also known in the art that suppressive or negative regulatory immune mechanisms may be blocked which results in enhanced immune responses. For example, treatment with anti-CTLA-4, anti-CD25, anti-CD4, the fusion protein IL13Ra2-Fc, and combinations thereof (such as anti-CTLA-4 and anti-CD25) have been shown to upregulate anti-tumour immune responses and would be suitable to be used in combination with the peptides of the present invention. The regulatory T-cell (Treg) inhibitor ONTAK (IL-2 diptheria toxin conjugate $DAB_{389}IL2$) has also been shown to enhance vaccine-mediated antitumour, thus inhibitors of Tregs are also suitable for use with the peptides.

Heterologous Vaccination Regimes

Regimes for administration of vaccines/pharmaceutic compositions according to the present invention may be determined by conventional efficacy testing. Especially preferred, however, are regimes which include successive priming and boosting steps. It is observed that such regimes achieve superior breaking of immune tolerance and induction of T cell responses (see Schneider et al., 1998 Nat Med 4:397-402).

Prime-boost regimes may be homologous (where the same composition is administered in subsequent doses) or heterologous (where the priming and boosting compositions are different). For example, the priming composition may be a non-viral vector (such as a plasmid) encoding a 5T4 antigen and the boosting composition may be a viral vector (such as a poxvirus vector) encoding a 5T4 antigen, wherein either or both of said "5T4 antigens" is an epitope or polyepitope string of the present invention. Alternatively, the priming composition may be a viral vector derived from one type of virus while the boosting composition may be a viral vector derived from a different type for virus.

Combination Therapies

The present invention thus also relates to the sequential use of a vaccine according to the present invention. Thus, the invention further relates to a peptide of the invention or a vector encoding a peptide of the invention and a chemotherapeutic compound, for separate, simultaneous separate or combined use in the treatment of tumours. Suitable chemotherapeutic agents include standard compounds used in chemotherapy such as 5-fluoruracil, leukovorin, oxaliplatin, intercalating agents, taxanes, anthracyclines, topoisomerase inhibitors (including irinotecan) and platinum-containing compounds (including oxaliplatin and carboplatin) and High Dose IL2, for example.

The invention further relates to a peptide of the invention or a vector encoding a peptide of the invention and a kinase inhibitor, for separate, simultaneous separate or combined use in the treatment of tumours. Suitable kinase inhibitors include those which have been shown to possess anti-tumour activity (such as gefitinib (Iressa) and erlotinib (Tarceva) and these could be used in combination with the peptides. The receptor tyrosine kinase inhibitors, such as Sunitinib malate and Sorafenib which have been shown to be effective in the treatment of renal cell carcinoma are also suitable to be used in combination.

Diagnostic Methods

The present invention also provides an agent capable of binding specifically to a peptide according to the present invention and/or a nucleic acid sequence which encodes such a peptide.

An agent is considered to "bind specifically" to a peptide/nucleic acid sequence of the present invention if there is a greater than 10 fold difference, and preferably a 25, 50 or 100 fold difference between the binding of the agent to a peptide/nucleic acid sequence of the present invention and another peptide/nucleic acid sequence.

The agent may be any compound capable of binding specifically to a peptide and/or a nucleic acid sequence. The term "compound" refers to a chemical compound (naturally occurring or synthesised), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule.

Preferably the agent is identifiable by screening a library of candidate compounds. Libraries of compounds may be screened in multi-well plates (e.g., 96-well plates), with a different test compound in each well. In particular, the library of candidate compounds may be a combinatorial library. A variety of combinatorial libraries of random-sequence oligonucleotides, polypeptides, or synthetic oligomers have been proposed and numbers of small-molecule libraries have also been developed. Combinatorial libraries of oligomers may be formed by a variety of solution-phase or solid-phase methods in which mixtures of different subunits are added stepwise to growing oligomers or parent compound, until a desired oligomer size is reached (typically hexapeptide or heptapeptide). A library of increasing complexity can be formed in this manner, for example, by pooling multiple choices of reagents with each additional subunit step. Alternatively, the library may be formed by solid-phase synthetic methods in which beads containing different-sequence oligomers that form the library are alternately mixed and separated, with one of a selected number of subunits being added to each group of separated beads at each step. Libraries, including combinatorial libraries are commercially available from pharmaceutical companies and specialty library suppliers.

Where the agent recognises a nucleic acid according to the present invention, the agent may comprise an antisense sequence.

Where the agent recognises a peptide according to the present invention, the agent may comprise an MHC molecule or part thereof which comprises the peptide binding groove. Alternatively the agent may comprise an anti-peptide antibody.

As used herein, "antibody" includes a whole immunoglobulin molecule or a part thereof or a bioisostere or a mimetic thereof or a derivative thereof or a combination thereof. Examples of a part thereof include: Fab, F(ab)'$_2$, and Fv. Examples of a bioisostere include single chain Fv (ScFv) fragments, chimeric antibodies, bifunctional antibodies.

The term "mimetic" relates to any chemical which may be a peptide, polypeptide, antibody or other organic chemical which has the same binding specificity as the antibody.

The term "derivative" as used herein in relation to antibodies includes chemical modification of an antibody. Illustrative of such modifications would be replacement of hydrogen by an alkyl, acyl, or amino group.

A whole immunoglobulin molecule is divided into two regions: binding (Fab) domains that interact with the antigen and effector (Fc) domains that signal the initiation of processes such as phagocytosis. Each antibody molecule consists of two classes of polypeptide chains, light (L) chains and heavy (H) chains. A single antibody has two identical copies of the L chain and two of the H chain. The N-terminal domain from each chain forms the variable regions, which constitute the antigen-binding sites. The C-terminal domain is called the constant region. The variable domains of the H ($V_H$) and L ($V_L$) chains constitute an Fv unit and can interact closely to form a single chain Fv (ScFv) unit. In most H chains, a hinge region is found. This hinge region is flexible and allows the Fab binding regions to move freely relative to the rest of the molecule. The hinge region is also the place on the molecule most susceptible to the action of protease which can split the antibody into the antigen binding site (Fab) and the effector (Fc) region.

The domain structure of the antibody molecule is favourable to protein engineering, facilitating the exchange between molecules of functional domains carrying antigen-binding activities (Fabs and Fvs) or effector functions (Fc). The structure of the antibody also makes it easy to produce antibodies with an antigen recognition capacity joined to molecules such as toxins, lymphocytes or growth factors.

Chimeric antibody technology involves the transplantation of whole mouse antibody variable domains onto human antibody constant domains. Chimeric antibodies are less immunogenic than mouse antibodies but they retain their antibody specificity and show reduced HAMA responses.

In chimeric antibodies, the variable region remains completely murine. However, the structure of the antibody makes it possible to produce variable regions of comparable specificity which are predominantly human in origin. The antigen-combining site of an antibody is formed from the six complementarity-determining regions (CDRs) of the variable portions of the heavy and light chains. Each antibody domain consists of seven antiparallel β-sheets forming a P-barrel with loops connecting the β-strands. Among the loops are the CDR regions. It is feasible to move the CDRs and their associated specificity from one scaffolding β-barrel to another. This is called CDR-grafting. CDR-grafted antibodies appear in early clinical studies not to be as strongly immunogenic as either mouse or chimaeric antibodies. Moreover, mutations may be made outside the CDR in order to increase the binding activity thereof, as in so-called humanised antibodies.

Fab, Fv, and single chain Fv (ScFv) fragments with VH and VL joined by a polypeptide linker exhibit specificities and affinities for antigen similar to the original monoclonal antibodies. The ScFv fusion proteins can be produced with a non-antibody molecule attached to either the amino or carboxy terminus. In these molecules, the Fv can be used for specific targeting of the attached molecule to a cell expressing the appropriate antigen. Bifunctional antibodies can also be created by engineering two different binding specificities into a single antibody chain. Bifunctional Fab, Fv and ScFv antibodies may comprise engineered domains such as CDR grafted or humanised domains.

Procedures for identifying, characterising, cloning, producing and engineering polyclonal and monoclonal antibodies and their derivatives are well established, for example using hybridomas derived from mice or transgenic mice, phage-display libraries or scFv libraries. Genes encoding immunoglobulins or immunoglobulin-like molecules can be expressed in a variety of heterologous expression systems. Large glycosylated proteins including immunoglobulins are efficiently secreted and assembled from eukaryotic cells, particularly mammalian cells. Small, non-glycosylated fragments such as Fab, Fv, or scFv fragments can be produced in functional form in mammalian cells or bacterial cells.

The agent may recognise the peptide/nucleic acid of the present invention alone, or in conjunction with another compound. For example, the agent may be capable of binding specifically to the peptide when presented by an MHC molecule. In this case, the agent of the present invention may comprise a T cell receptor (TCR) molecule or part thereof. TCRs are useful for screening or therapeutic purposes.

Single-chain TCRs are artificial constructs comprising a single amino acid strand, which like native heterodimeric TCRs bind to MHC-peptide complexes. WO 2004/033685 describes a class of alpha/beta-analogue single-chain TCRs which are characterised by the presence of a disulphide bond between residues of the single amino acid strand, which contributes to the stability of the molecule. WO 99/60119 describes synthetic multivalent TCR complexes with a plurality of TCR binding sites and increased avidity.

The TCR may be associated with another molecule such as CD4 (for MHC class II epitopes) or CD8 (for MHC class I epitopes). Alternatively, or in addition, the receptor may be associated with CD3.

It is also possible to engineer T cells to express chimeric immune receptors (CIRs) on their surfaces which comprise a tumour antigen recognition function and a T cell signalling function (such as the ζ chain of the TCR). Antibody-based and TCR-based chimeric CIRs have been reported. Thus monoclonal antibodies or TCRs which recognise tumour antigens such as 5T4 or the peptides of the invention could be used to generate such engineered T cells with enhanced anti-tumour efficacy.

If the agent occurs naturally in the human body, then preferably the agent of the present invention is in a substantially isolated form.

The present invention also provides a method which comprises the step of detecting the presence of a peptide, nucleic acid or agent of the present invention in a subject.

In a preferred embodiment, the method is used to detect the presence of T cells capable of specifically recognising a peptide epitope according to the present invention in conjunction with an MHC molecule.

The diagnostic method may, for example, be for diagnosing or monitoring the progression of a disease or for monitoring the progression of an immune response in a subject.

As mentioned above, as an immune response progresses, the dominance of particular epitopes may change, and sub-dominant epitopes can predominate. Thus by detecting the presence of a particular epitope, or a TCR/T cell capable of recognising such an epitope, information can be gained about the progression of the immune response.

The method may be carried out in vivo, or more preferably on an ex vivo sample.

Thus the present invention also provides a diagnostic method which comprises the following steps:
 (i) isolating a sample from a subject;
 (ii) detecting in the sample ex vivo the presence of T cells capable of specifically recognising a peptide epitope according to the present invention in conjunction with an MHC molecule.

In a preferred embodiment, the method is for diagnosing or monitoring the progression of a cancerous disease.

The nature of the method will depend on whether a peptide, nucleic acid or agent of the present invention is being detected (and if it is an agent, on the nature of that agent).

In order to detect a peptide of the present invention, an agent of the present invention (such as an antibody or an MHC molecule) may be used. Methods of screening with antibodies (such as ELISAs, immunoblotting, western blotting, competitive assays, two site capture assays) are well known in the art.

In order to detect peptides or specific T cells, an antigen presentation assay may be used. When a T cell successfully recognises an MHC:peptide complex, it is stimulated. This stimulation can be monitored by proliferation of the T cells (for example by incorporation of $^3$H) and/or by production of cytokines by the T cells (for example by an ELISPOT assay). Thus it is possible to detect the presence of a specific peptide by using appropriate APCs and T cells lines, and to detect the presence of a specific T cell by using appropriate APCs and peptide/antigen.

The presence of a particular cell surface molecule (such as a TCR or MHC molecule) can also be investigated using fluorescence activated cell scanning (FACS).

Where the method is to detect the presence of a nucleic acid, numerous methods are known in the art such as PCR, southern blotting (for DNA) and northern blotting (for RNA).

Antibodies

The present invention further relates to the use of peptides in accordance with the invention to raise antibodies as well as the use of those antibodies in therapeutic methods. Such therapeutic methods include, for example, delivery of therapeutic toxins including radiolabels, for example, through antibody targetting of 5T4-expressing cells.

T cells

The present invention also relates to a T cell, such as a T cell clone, or line, which is capable of specifically recognising a peptide epitope according to the present invention in conjunction with an MHC molecule. Several methods for generating T cell lines and clones are known in the art. One method for generating T cell lines is as follows:

Mice are primed with antigen (usually subcutaneously in the rear footpad), and the draining lymph nodes (in this case the popliteal and inguinal) are removed 1 week later and set up in co-culture with the antigen and with syngeneic feeder cells i.e. cells from mice of the same inbred line (e.g. normal thymocytes or splenocytes). After 4 days the lymphoblasts are isolated and induced to proliferate with IL-2. When the population of cells has expanded sufficiently, they are checked for antigen and MHC specificity in a lymphocyte transformation test, and are maintained by alternate cycles of culture on antigen-treated feeder cells and culture in IL-2-containing medium.

The definitive T-cell lineage marker is the T-cell receptor (TCR). There are presently two defined types of TCR, both of which are heterodimers of two disulphide-linked polypeptides. One type consist of α and β chains, the other type consists of γ and δ chains. Approximately 90-95% of blood T cells express α/β, TCR, the other 5-10% expressing γ/δ TCR.

T cells can be divided into two distinct populations: a subset which carries the CD4 marker and mainly "helps" or "induces" immune responses ($T_H$) and a subset which carries the CD8 marker and is predominantly cytotoxic ($T_C$). CD4+ T cells recognise peptides in association with MHC class II molecules, whereas CD8+ T cells recognise peptides in association with Class I molecules, so the presence of CD4 or CD8 restricts the types of cell with which the T cell can interact.

The CD4 set has been functionally sub-divided into two further subsets:

(i) T cells that positively influence the response of T cells and B cells (the helper T cell function) are CD29+. Practically all the cells in this population also express a low molecular weight isoform of the CD45 leucocyte common antigen, designated CD45RO.

(ii) Cells that induce the supressor/cytotoxic functions of CD8+ cells (the suppressor/inducer function) express a different form of the CD45 molecule, CD45RA.

Functional diversity has also been demonstrated by functional analysis of $T_H$ clones for cytokine secretion patterns. The $T_H1$ subset of CD4+ T cells secrete IL-2 and IFN-γ, whereas the $T_H2$ subset produces IL-4, IL-5, IL-6 and IL-10.

$T_H1$ cells mediate several functions associated with cytotoxicity and local inflammatory reactions. Consequently these cells are important for combating intracellular pathogens, including viruses, bacteria and parasites. $T_H2$ cells are more effective at stimulating B cells to proliferate and produce antibodies, and therefore in normal immune responses function to protect against free-living organisms.

Expression of all of the markers described above can readily be detected using specific antibodies, so the type of T cell can be selected/determined using FACS. Expression of particular cytokines can also be detected by methods known in the art, such as ELISPOT assay.

Prophylactic/Therapeutic Methods

The present invention also provides the use of a vaccine according to the present invention in the manufacture of a medicament for use in the prevention and/or treatment of a disease.

There is also provided a method for treating and/or preventing a disease in a subject which comprises the step of administering an effective amount of a vaccine according to the present invention.

Administration of the vaccine may elicit an immune response in the subject. In a preferred embodiment, administration of the vaccine breaks immune tolerance to 5T4 in the subject.

Where the peptide is a class I epitope, the immune response elicited may involve the activation of 5T4 specific cytotoxic T-lymphocytes. Where the peptide is a class II epitope, the immune response elicited may involve the activation of $T_H1$ and/or $T_H2$ cells.

Advantageously, the response is an anti-tumour immunotherapeutic response which is effective to inhibit, arrest or reverse the development of a tumour in a subject.

Targeting Molecules

The invention further relates to the use of 5T4 targeting molecules, such as anti-5T4 antibodies, for example anti-5T4 scFvs. These antibodies may be used to (i) to target natural or exogenous 5T4 in situ and/or (ii) deliver immune enhancer molecules, such as B7.1, to natural or exogenous 5T4 in situ (Carroll et al. (1998) J Natl Cancer Inst 90(24):1881-7). This potentiates the immunogenicity of 5T4 in the subject.

Clinical trials using HLA class I restricted eptiopes have demonstrated that such peptides can be delivered safely, generate T cell response and may have clinical benefit (Jager et al., PNAS (2000), 97, 10917-10922.). However, to maximise vaccine efficacy, an immune response against a broad range of HLA class I and II epitopes is required. Indeed, the use of class II helper T cell epitopes derived from the tumour antigen Her-2/neu administered in combination with known class I epitopes from the same antigen resulted in stronger and more long-lived immune responses than class I epitopes delivered alone (Knutson et al., J. Clin. Invest (2001) 107; 477-484). The class II epitopes of the present invention could be used along with class I epitopes from 5T4 in this way.

The present invention thus also relates to the sequential use of a vaccine according to the present invention and anti-5T4 antibodies, for example anti-5T4 scFvs. The anti-5T4 scFvs antibodies may be administered as naked DNA encoding the antibodies (for example, in a plasmid comprising the encoding DNA together with a short promoter region to control its production), in an expression vector (which may be viral or non-viral) comprising the encoding sequence or in a protein form. Thus, the invention provides a vector encoding a 5T4 peptide antigen and an agent capable of binding 5T4 which is optionally fused with an immunostimulatory molecule, for separate, such as sequential use, in the treatment of tumours.

In a further embodiment, the invention encompasses a combination therapy including enzyme/prodrug therapy and immunotherapy with 5T4. For example, the enzyme/prodrug therapy may comprise intratumoural or systemic delivery of P450, delivered optionally using an retroviral or lentiviral vector, and cyclophosphamide (CPA) followed by systemic immunotherapeutic induction with 5T4.

Thus, the invention further relates to a vector encoding 5T4 peptide antigen and a prodrug/enzyme combination, for separate, simultaneous separate or combined use in the treatment of tumours.

Diseases

5T4 is a tumour associated antigen. Presence of 5T4 on cancer cells is associated with metastasis and has been shown to be an independent indicator of prognosis in a number of different cancers.

In a preferred embodiment, the disease (which is preventable/treatable using a vaccine according to the present invention) is a cancer. In particular the disease may be a carcinoma of, for example, the breast, lung, stomach, pancreas, endometrium, cervix, colorectal, renal or prostate.

WO89/07947 describes an immunohistochemical screen of neoplastic tissues using an anti-5T4 monoclonal antibody (see Tables II and VI). Preferably, the disease is a cancer which can be shown to be 5T4 positive by diagnostic testing (such as with an anti-5T4 antibody), for example: invasive carcinoma of the Ampulla of Vater, carcinoma$_{[kh1]}$ of breast, colon, endometrium, pancreas, or stomach, bladder such as a squamous carcinoma of the bladder, cervix, lung or oesophagus; colon, such as a tubulovillous adenoma of the colon; endometrium such as a malignant mixed Mullerian tumour of the endometrium kidney such as a clear cell carcinoma of the kidney; lung including lung cancers (large cell undifferentiated, giant cell carcinoma, broncho-alveolar carcinoma, metastatic leiomyosarcoma); an ovary including ovarian cancer (a Brenner tumour, cystadenocarcinoma, solid teratoma); a cancer of the testis (such as seminoma, mature cystic teratoma); a soft tissue fibrosarcoma; a teratoma such as anaplastic germ cell tumours); or a trophoblast cancer (choriocarcimoma (e.g. in uterus, lung or brain), tumour of placental site (hydatidiform mole).

MHC Multimers

The present invention also provides 5T4 peptide epitope associated with (eg. folded with) MHC multimers (such as tetramers and pentamers) and uses thereof.

Tetramers are fluorescent reagents that allow for the direct visualisation of antigen-specific T-cells (Altman et al. (1996) Science 271, 94-96). They consist of individual peptides epitopes refolded with HLA class I protein and bind to T cells that are specific for that particular epitope. They allow for the direct quantification of antigen specific lymphocytes and have been applied widely in human and murine immunology.

The tetramers may be prepared using the methods described by Altman et al. (1996) Science 271, 94-96. Briefly, tetramers may be prepared by adding biotinylated protein to streptavidin PE at a ratio of 4:1. Tetramer bound cells may be selected using magnetic activated cell sorting (MACS). MACS has been described in Radbruch et al. (1994) Methods in Cell Biology 42, 387-403.

Advantageously, the use of tetramers allows for the tracking of a 5T4-specific immune response before, during and after vaccination; to purify autologous CD4+ T cells from individual patients and expand/manipulate them ex vivo for possible re-infusion; as a diagnostic indicator, for example, in subjects prone to colorectal and other 5T4-positive cancers. Accordingly, the present invention also relates to the use of a 5T4 peptide epitope tetramer for monitoring a 5T4-specific immune response before, during or after vaccination. The present invention further relates to the use of a 5T4 peptide epitope tetramer for the purification of autologous CD4+ T cells from individual patients. The present invention still further relates to the use of a 5T4 peptide epitope tetramer as a diagnostic indicator in subjects prone to 5T4-positive cancers—such as colorectal cancers.

Class II tetramers have been described, for example, by Novak, E J et al 1999 *J. Clin. Invest* 104:R63-R67.

Pentamers

The present invention also provides 5T4 peptide epitope associated with pentamers and uses thereof.

Pentamers are similar to tetramers but include 5 refolded peptide epitopes. Suitable pentamers include Pro5 T MHC Pentamers contain 5 MHC-peptide complexes that are multimerised by a self-assembling coiled-coil-domain. All 5 MHC-peptide complexes are held facing in the same direction, similar to a bouquet of flowers. Therefore, with Pro5$_{[RH2]}$™ MHC Pentamer technology, all 5 MHC-peptide complexes are available for binding to T cell receptors (TCRs), resulting in an interaction with very high avidity.

Each Pro5™ MHC Pentamer also contains up to 5 fluorescent molecules yielding an improved fluorescence intensity of the complex. Pro5™ MHC Pentamers are fully compatible with existing applications for MHC tetramers. They can also be used in combination with other technologies such as intracellular cytokine staining (e.g. IFNg/IL-2) and/or surface markers (e.g. CD69/CD45RO) to establish an accurate profile of the functional phenotype of antigen specific T cell subsets.

Suitable said pentamers can be generated to comprise 5T4 peptide epitopes of the invention.

Pentamers can be used, for example, for tracking antigen-specific T Cells in situ For example, Pro5™ MHC Pentamers can be used to stain viable tissue sections from lymphoid organs, peripheral tissues and tumour infiltrate. By carrying out double-staining with fluorescent anti-CD8 antibody and fluorescent MHC Pentamers, the antigen-specific T cells can be visualised by confocal microscopy. (see, for example, Skinner P J and Haase A T. (2002). In situ tetramer staining. J. Immunol. Methods 268: 29-34. [PubMedID: 12213340]; Haanen J B, et al. (2000). In situ detection of virus- and tumor-specific T-cell immunity. Nat Med 6:1056-1060. [PubMedID:10973329] and Skinner P J, et al. (2000). Cutting edge: In situ tetramer staining of antigen-specific T cells in tissues. J Immunol 165:613-617. [PubMedID: 10878330]).

The invention is further described, for the purposes of illustration only, in the following examples in which reference is made to the following Figures.

FIG. 1 shows a schematic work-plan illustrating the method for identifying 5T4 CTL epitopes.

FIG. 2 shows the basic iTopia binding assay.

FIG. 3 shows a graph of iScores for peptides 1-69.

FIG. 4 shows a graph of iScores for peptides 70-138.

FIG. 5 shows a graph of iScores for peptides 139-206.

FIG. 6 shows an example of the complete iTopia system. (SEQ ID NOs 45, 23, 36, and 52 (from top to bottom) are provided in table of FIG. 6)

FIG. 7 shows a graph showing iScore vs iScore-rank for A*0101.

FIG. 8 shows a graph showing iScore vs iScore-rank for A*0201.

FIG. 9 shows a graph showing iScore vs iScore-rank for A*0301.

FIG. 10 shows a graph showing iScore vs iScore-rank for B*0702.

Figure 15:
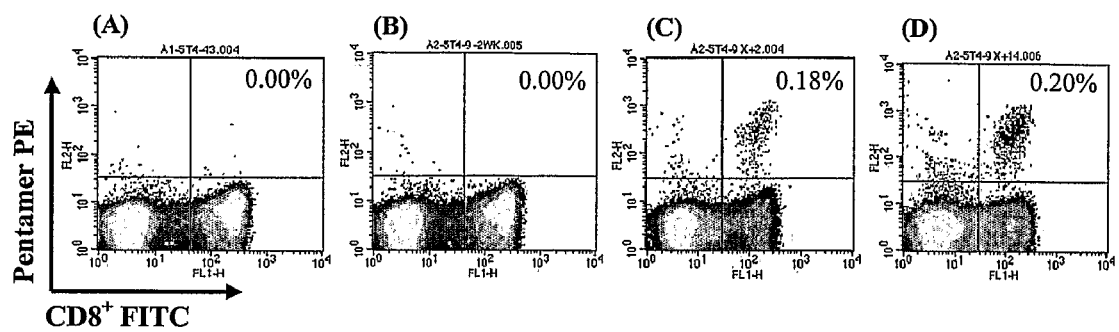

FIG. 15 shows analysis of HLA-A2/9 specific CD8 positive T cells in TV2-018 patient at −2 wk (Plot B), X+2 wk (Plot C) and X+14 wk (Plot D). The percentages in the top right quadrant indicate pentamer/CD8 double positive cells as a proportion of total lymphocytes. A HLA-type mismatched pentamer complex, HLA-A1/43, was used at X+2 wk as a control for non-specific background binding (Plot A).

Figure 16:
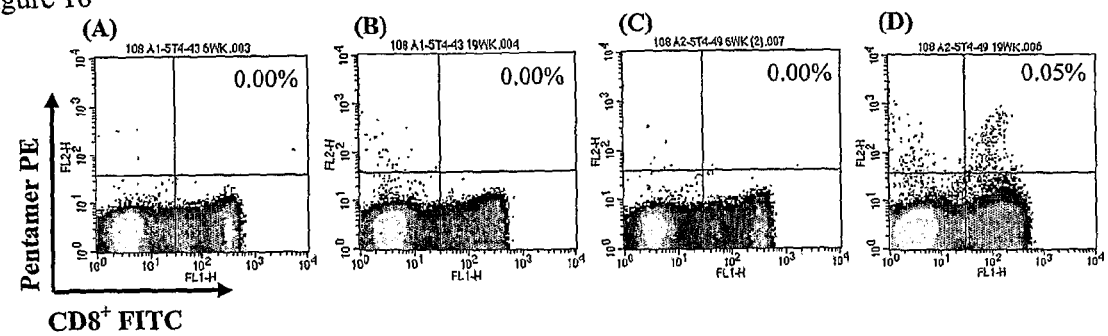

FIG. 16 shows analysis of HLA-A2/49-specific CD8 positive T cells in TV2-108 patient at 6 wk (Plot C), 19 wk (Plot D). The percentages in the top right quadrant indicate pentamer/CD8 double positive cells as a proportion of total lymphocytes. A HLA-type mismatched pentamer complex HLA-A1/43 was used at 6 wk (Plot A) and 19 wk (Plot B) as a control for non-specific background binding.

Table 1 shows physical data for 9-mer peptides synthesised by JPT Peptide Technologies GmbH Table 2 shows peptide binding assay results.

Table 3 shows off-rate assay results

Table 4 shows affinity assay results.

Table 5 shows iScore results from all peptides tested.

Table 6 shows a summary of iTopia results.

Table 7 shows peptides selected for further functional analysis in descending order of iScore.

Table 8a shows constituents of the 5T4 iTopia hit peptide pools used in the immunomonitoring of patients' IFNγ ELISpot responses. The table illustrates the peptide ID and amino acid sequence for components of the A2 iTopia hit pool and the combined A1/A3/B7 iTopia hit pool.

Table 8b shows constituents of the 5T4 peptide pools used in the immunomonitoring of patients' IFNγ ELISpot responses. The table illustrates the peptide ID and amino acid sequence for components of each peptide pool. (Sequences listed in Table 8b correspond to SEQ ID NOs 1 to 302 (listed from top to bottom and left to right))

Table 9 shows positive IFNγ ELISpot responses detected in PBMCs (recovered from TroVax treated patients) following stimulation with 5T4 peptide pools. The table details results where a positive ELISpot response was detected to a 5T4 peptide pool which contained an iTopia hit for either HLA A1, A2, A3 or B7 and the responding patient had a matching allele.

Table 10 shows positive IFNγ ELISpot responses detected in PBMCs (recovered from TroVax treated patients) following stimulation with iTopia hit peptides. The table lists patients who showed a positive ELISpot response to the A2 peptide pool or the A1/A3/B7 pool and had the same corresponding HLA type.

Table 11 shows dissection of positive IFNγ ELISpot responses detected in PBMCs (recovered from TroVax treated patients) following stimulation with 5T4 peptides. The table details patients who had initially shown a positive IFNγ ELISpot response to 5T4 peptide pools 1, 5, 13 or 20 or the individual peptide 77. Following dissection of the peptide pool into its constituents, the single peptide responsible for the positive ELISpot response is tabulated. In some cases, the MHC restriction of the response is known (either through use of a blocking antibody or a previously identified CTL epitope) and is listed. The HLA restriction of these CTL epitopes predicted by iTopia is also shown. Finally, pentamers have been synthesised for 2 of HLA A2 eptiopes (9 and 49) and also demonstrated positive responses in PBMCs from 2 patients Table 12: Details of individual class II peptides and class II peptide pools Table 13: Positive IFNγ ELISpot responses detected in PBMCs (recovered from TroVax treated patients) following stimulation with 5T4 20 mer peptides 39.2 and 41.2.

Table 14: Positive proliferative responses detected in PBMCs (recovered from TroVax treated patients) following stimulation with 5T4 20 mer peptides and peptide pools.

Table 15: HLA-type distribution among positive proliferative responses to 5T4 20 mer peptides and peptide pools detected in PBMCs (recovered from TroVax treated patients). The number of individuals responding to a particular antigen is shown as a fraction of the total number of responding patients (whose HLA type is known) for that antigen.

The invention will now be further described by way of Examples, which are meant to serve to assist one of ordinary skill in the art in carrying out the invention and are not intended in any way to limit the scope of the invention.

EXAMPLES

Example 1—Class I

A schematic of the methods, showing the stages involved, is illustrated in FIG. 1.

Methods

Peptides 206 9 mers overlapping by 7 amino acids spanning the entire 5T4 protein were generated and synthesised by JPT Technologies GmbH (Jerini) using standard techniques.

Table 1 presents data for all 206 test peptides. These peptides are allocated SEQ ID NOs: as shown.

Testing

The peptides were dissolved at $1 \times 10^{-2}$ M, in DMSO prior to use.

The 9 mers were tested for Peptide Binding, Off Rate and Affinity using iTopia Epitope Discovery System in accordance with the manufacturer's instructions. Briefly, 96 well microtitre plates coated with MHC molecules representing different MHC alleles are used to identify candidate peptides. MHC class I alleles A*0101 (A1), A*0201 (A2), A*0301 (A3), and B*0702 (B7) were used. Determinations are performed in duplicate using an ELISA plate reader and included allele specific positive controls.

i) Peptide Binding—This assay measures the ability of individual peptides to bind to the MHC molecules under standardized optimal binding conditions. The assay is performed for all the test peptides across the selected MHC alleles. The test peptides identified as "binders" are characterized further in terms of affinity and dissociation experiments.

The basic binding assay is illustrated in FIG. 2.

Briefly, MHC class I monomers, bound via biotin to streptavadin-coated microtitre plates (A), first have their stabilising placeholder peptide and $\beta_2M$ removed (B), before being reconstituted with test peptide and fresh $\beta_2M$ in the presence of fluorescently labelled detection antibody (C). Following a period of binding under optimal conditions, excess antibody is removed and a measurement of total fluorescence taken (D).

Manipulation of binding conditions in subsequent assays then allows quantification of the relative binding properties of candidate peptide sequences which passed the initial screen and enables assessment of the overall quality of binding for each.

The binding of the test peptides to the MHC molecules was performed at $1.11 \times 10^{-5}$ M of peptide under optimal, standardised test conditions. A control peptide was run in parallel on the same plate and at the same concentration as the test peptides.

Off-rate Assay—This assay evaluates the dissociation of previously bound peptide at defined time points.

Briefly, the off-rate assay shifts binding from optimal to suboptimal conditions to determine the rate at which a peptides dissociates from MHC complexes. Results are expressed as the amount of time needed to achieve 50% dissociation of the peptide from the MHC complex, or the t1/2 value, represented in hours. This essentially indicates the stability of the MHC-peptide complexes and has high biological relevance as it relates to the length of time available for a particular MHC-peptide complex to reach the cell surface and interact with a T cell receptor (TCR), a factor thought to be of importance in the ability to activate a T cell. Results from this assay constitute a major share of the final iScore.

iii) Affinity Assay—Candidate peptides identified in the initial peptide binding assay are incubated at increasing concentrations for a given period to determine their relative binding affinities for the MHC molecules. The affinity is expressed as quantity of peptide needed to achieve 50% binding or ED50 value.

Briefly, the affinity assay assesses the binding potential of decreasing concentrations of peptide as a means of determining their relative affinities, with results expressed as the concentration of peptide needed to achieve 50% binding, or the ED50 value, and also contributes in part to the final iScore.

iScore

Finally, multiparametric analysis is performed on the results from these assays and an iScore is generated. The iScore represents a measure of the overall quality of peptide-MHC binding, enabling candidate peptides to be ranked in order of binding quality and allowing rational prioritisation of peptides for functional cellular follow-up studies.

Interpretation of the iScore

As part of the validation of the iTopia system, a panel of overlapping peptides derived from the CMV pp 65 protein were used and their binding properties for the A*0201 allele analysed. A number of T cell epitopes restricted by HLA A*0201 had already been identified (by more conventional methodologies) by other researchers for this protein. In the iTopia study, it was reported that an iScore of: >0.5 represented "good quality binding"; between 0.25 and 0.5 represented "medium quality binding"; and <0.25 represented "poor quality binding". Six of the 20 peptides which gave a "good" iScore (>0.5) for A*0201, represented previously characterised CMV pp 65 A*0201 epitopes. Of the 14 other peptides which gave a "good" iScore, 13 showed positive responses by ELISPOT and/or tetramer staining using PBMCs from CMV positive donors demonstrating that these represented functional and novel CTL epitopes. This demonstrated that the binding properties of a peptide, quantified by the peptides' iScore, gave a high probability of predicting functional epitopes accurately.

Each MHC class I allele has different binding properties and affinities for peptides which they bind. Therefore, information obtained with HLA A*0201 in which peptides are ranked as good, medium or poor binders using >0.5, 0.25-0.5 and <0.25 as thresholds is not necessarily transferable between alleles. Also, different proteins are likely to have distinct immunogenic profiles and the affinities between peptides and MHC class I molecules will be different between proteins. This may be particularly relevant in the case of self-antigens where immunogenicity is likely to be lower than in foreign proteins.

Results

Table 2 shows the results of the initial binding by allele for each peptide. The level of binding is expressed as a percent of positive control peptide binding for each allele. Peptides with values of ≧15% of control have been highlighted and these were further characterised for affinity and off-rate.

Of the 206 overlapping 9-mer peptides screened for each of the MHC class I alleles in this initial binding assay the following results were obtained:

A*0101: 8 peptides exhibited binding of >15% compared with controls.

A*0201: 115 peptides exhibited binding of >15% compared with controls.

A*0301: 19 peptides exhibited binding of >15% compared with controls.

B*0702: 36 peptides exhibited binding of >15% compared with controls.

Off-Rate Analysis

The peptides initially identified as binders were evaluated for stability based on their ability to remain bound to MHC molecules at 37° C. over the course of 8 hours. The values obtained for each time point (in duplicate) have been expressed as a percentage of the positive control. A one-phase exponential decay curve, with a plateau given equal to 0, was generated using GraphPad Prism® software, which calculated the t1/2 and goodness-of-fit, as measured by $r^2$, for each peptide. Results are presented in Table 3.

Affinity Analysis

Dose-response curves of peptide binding to MHC were prepared by peptide titration to determine the ED50 measurement for each peptide. Values for the concentrations tested (in duplicate) were obtained as a percentage of the highest (9000x) concentration of the positive control peptide. A dose-response curve was generated using GraphPad Prism® curve fitting software, which automatically calculated the ED50 (in Molarity) for each peptide. Results are presented in Table 4.

Multi-Parametric Analysis-iScore

Multi-parametric analysis permits the integration of half-life and ED50 parameters in an integrated iScore. This reflects the capability of a peptide to reconstitute with MHC molecules in a stable complex, defining its overall level of binding i.e. the iScore value represents the overall quality of peptide-MHC binding and is used to rank candidate peptides as an indicator of functional relevance. The lead candidate epitopes for each allele are selected for cellular functional analysis to confirm their biological relevance.

FIGS. 3 to 5 provide a visual graphical representation of iScores for all tested peptides across all tested alleles. Table 5 shows iScore results from all peptides tested.

FIG. 6 gives an example of the complete iTopia system.

FIG. 6 graphically demonstrates the use of the iTopia system using the example of 30 5T4 peptides (22-52) screened against the B*0702 allele. Five peptides exhibited >15% binding compared to the positive control peptide in the initial binding assay and these were analysed in the off-rate and affinity assays. When multiparametric analysis was performed, a single peptide, #45, stood out as having a higher iScore then the rest (0.389) and this is clearly reflected in the low off-rate and relatively high affinity seen for this peptide.

Table 6 summarises the results obtained in this study and categorised according to iScore per allele.

The range of iScores differed considerably between alleles, the highest iScore (Rank #1) seen with A*0101 was 0.522, 1.897 for A*0201, 0.375 for A*0301 and 1.001 for B*0702. The arbitrary thresholds (>0.5=good, 0.5 to 0.25=medium, and <0.25=poor) assigned by Beckman in their previous investigation of A*0201 epitopes in the CMV pp 65 protein (see "Interpretation of the iScore", page 6) are not suitable for use with the above data due to the inter-allelic variation.

By plotting iScore against iScore-rank, as displayed in FIGS. 7 to 10, it is possible to see distinct populations of iScores, as indicated by a change in the gradient of the graphs. These shifts suggest points at which to discriminate between groups of peptides with different binding properties and by which to set inclusion thresholds for further functional analyses. The changes in gradient of the graphs in FIGS. 7 to 10 are indicated by a line which delineates the populations of iScores forming the basis of discrimination for further functional studies.

FIG. 7: Graph showing iScore vs. iScore-rank for A*0101. A change in gradient can be seen above 0.06 (indicated by the pink line) and this will form the threshold above which peptides will be included in functional analysis. Five peptides will therefore be included in functional analysis.

FIG. 8: Graph showing iScore vs. iScore-rank for A*0201. A change in gradient can be seen above 0.285 (indicated by the pink line) and this will form the threshold above which peptides will be included in functional analysis. Nineteen peptides will therefore be included in functional analysis.

FIG. 9: Graph showing iScore vs. iScore-rank for A*0301. A change in gradient can be seen above 0.095 (indicated by the pink line) and this will form the threshold above which peptides will be included in functional analysis. Six peptides will therefore be included in functional analysis.

FIG. 10: Graph showing iScore vs. iScore-rank for B*0702. A change in gradient can be seen above 0.13 (indicated by the pink line) and this will form the threshold above which peptides will be included in functional analysis. Sixteen peptides will therefore be included in functional analysis.

Table 7 displays the peptides selected for functional analysis (as shown in FIGS. 7 to 10) ranked in descending order of iScore.

Peptides are Tested in an ELISpot Assay.

The ELISpot assay is performed as described elsewhere (Czerkinsky et al (1988) in "Theoretical and Technical Aspects of ELISA and Other Solid Phase Immunoassays (D. M. Kemeny and S J. Challacombe, eds.) pp 217-239 John Wiley & Sons, New York).

5T4-specific CTLs can be generated from healthy donors following several rounds of in vitro stimulation with peptide-loaded dendritic cells (DCs). Briefly, PBMCs from donors are HLA typed and those which are HLA-A1, A2, A3 or B7 positive donors are used for subsequent experiments. Autologous dendritic cells generated from the adherent fraction of PBMC in the presence of cytokines are pulsed with candidate peptides. Autologous PBMCs are subsequently co-cultured with peptide pulsed DCs. After several rounds of stimulation with freshly generated peptide-pulsed DCs, resulting bulk cell culture is tested for the presence of peptide-specific cells by ELISPOT as follows.

Alternatively, PBMCs are recovered from patients treated with TroVax® (TV) and interrogated with test peptides. Briefly, PBMCs, previously obtained by separation on Histopaque-1077 and frozen, are thawed and recovered overnight before being plated out at concentration of $2 \times 10^5$ cells per well of PVDF 96-well plate covered with interferon-capturing antibody. Peptides, in pools or individually, are added to each well at final concentration of 5 µg/ml per peptide. Wells with DMSO and PHA can serve as negative and positive controls respectively. Also CEF peptides (A pool of 23 T-cell epitopes from human cytomegalovirus, Epstein-Barr virus and influenza virus, which stimulates the release of IFN-γ from CD8+ T-cells) can be included as positive control. After O/N incubation a plate is washed with PBS-Tween, a second-step antibody is added, followed by a third-step enzyme and a chromogenic substrate. The number of spots is counted by automated ELISPOT plate reader.

Positive IFNγ ELISPOT responses from patients of known HLA type against appropriate peptides (i.e. peptides which were shown to bind to a HLA molecule shared by the responding patient) confirm the peptide as a CTL epitope. Antibodies capable of interfering with the presentation of epitopes by specific alleles can be used to further demonstrate allelic restriction.

10 Mer Experiments 10 mer peptides corresponding to 9 mer peptides listed in Table 1, but with an additional amino acid at their carboxy termini, as set out below, were tested to identify individual peptide epitopes responsible for the cellular responses observed with the peptide pools.

Patient TV2-018, from the Trovax® phase II clinical trial TV2, that was treated with the chemotherapeutic agents irinotecan and 5FU alongside Trovax® has been shown to have the following HLA Type: A2, A3, B44, B60, Cw3, Cw5.

The TV2 clinical trial regimen involves six Trovax® vaccinations and 12 cycles of chemotherapy. The end of chemotherapy is designated 'X' and time-points following are named X+n, where n is the number of weeks after chemotherapy ended.

Immuno-monitoring of this patient using IFNγ ELISPOT, identified strong ex-vivo responses to a number of 10 mer peptide pools, namely pools #5, #20, and #1. These responses were dissected to identify the individual peptides responsible, as detailed below.

The antigens and reagents used were as follows:
PHA (phytohaemagglutinin—used as a non-specific positive control)
CEF (Pool of 5 T-cell epitopes from human cytomegalovirus, Epstein-Barr virus and influenza virus.—used as a positive control)
MVA (modified vaccinia Ankara)
10 mer Peptide pool #1 (containing 10 mer peptides 1-10)
10 mer peptide #1 (MPGGCSRGPA) (SEQ ID NO 207)
10 mer peptide #2 (GGCSRGPAAG) (SEQ ID NO 208)
10 mer peptide #3 (CSRGPAAGDG) (SEQ ID NO 209)
10 mer peptide #4 (RGPAAGDGRL) (SEQ ID NO 210)
10 mer peptide #5 (PAAGDGRLRL) (SEQ ID NO 211)
10 mer peptide #6 (AGDGRLRLAR) (SEQ ID NO 212)
10 mer peptide #7 (DGRLRLARLA) (SEQ ID NO 213)
10 mer peptide #8 (RLRLARLALV) (SEQ ID NO 214)
10 mer peptide #9 (RLARLALVLL) (SEQ ID NO 215)
10 mer peptide #10 (ARLALVLLGW) (SEQ ID NO 216)
10 mer Peptide pool #5 (containing 10 mer peptides 41-50)
10 mer peptide #41 (NLTEVPTDLP) (SEQ ID NO 217)
10 mer peptide #42 (TEVPTDLPAY) (SEQ ID NO 218)
10 mer peptide #43 (VPTDLPAYVR) (SEQ ID NO 219)
10 mer peptide #44 (TDLPAYVRNL) (SEQ ID NO 220)
10 mer peptide #45 (LPAYVRNLFL) (SEQ ID NO 221)
10 mer peptide #46 (AYVRNLFLTG) (SEQ ID NO 222)
10 mer peptide #47 (VRNLFLTGNQ) (SEQ ID NO 223)
10 mer peptide #48 (NLFLTGNQLA) (SEQ ID NO 224)
10 mer peptide #49 (FLTGNQLAVL) (SEQ ID NO 225)
10 mer peptide #50 (TGNQLAVLPA) (SEQ ID NO 226)
10 mer Peptide pool #20 (containing 10 mer peptides 191-200)
10 mer peptide #191 (IKKWMHNIRD) (SEQ ID NO 287)

10 mer peptide #192 (KWMHNIRDAC) (SEQ ID NO 288)
10 mer peptide #193 (MHNIRDACRD) (SEQ ID NO 289)
10 mer peptide #194 (NIRDACRDHM) (SEQ ID NO 290)
10 mer peptide #195 (RDACRDHMEG) (SEQ ID NO 291)
10 mer peptide #196 (ACRDHMEGYH) (SEQ ID NO 292)
10 mer peptide #197 (RDHMEGYHYR) (SEQ ID NO 293)
10 mer peptide #198 (HMEGYHYRYE) (SEQ ID NO 294)
10 mer peptide #199 (EGYHYRYEIN) (SEQ ID NO 295)
10 mer peptide #200 (YHYRYEINAD) (SEQ ID NO 296)

The ELISPOT was performed in accordance with the procedures and documents detailed above.

Results

Figure 11:
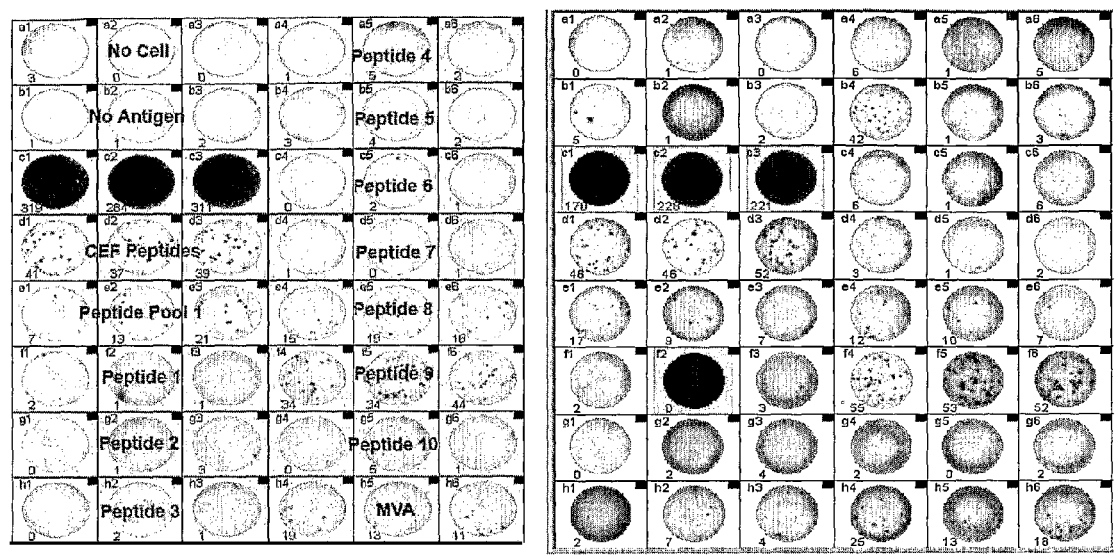
FIG. 11 shows Class 1 Peptide pool 1 retested as individual peptides at X+6 wk (left) and X+10 wk (right).

FIG. 11 shows Class 1 Peptide pool 1 retested as individual peptides at X+6 wk (left) and X+10 wk (right).

It is possible to see from the ELISPOT in FIG. 11 that, in the no cell and no antigen wells, there is a low background, which demonstrates there are few non-specific responding cells, and that CEF and MVA have induced IFNγ responses. Peptide pool 1 (containing 10 mer peptides 1-10) has produced a response at both time points and when the peptides in pool 1 are tested individually, it is clear that there is a response to peptides 8 (RLRLARLALV) (SEQ ID NO 214) and 9 (RLARLALVLL) (SEQ ID NO 215).

Figure 12:
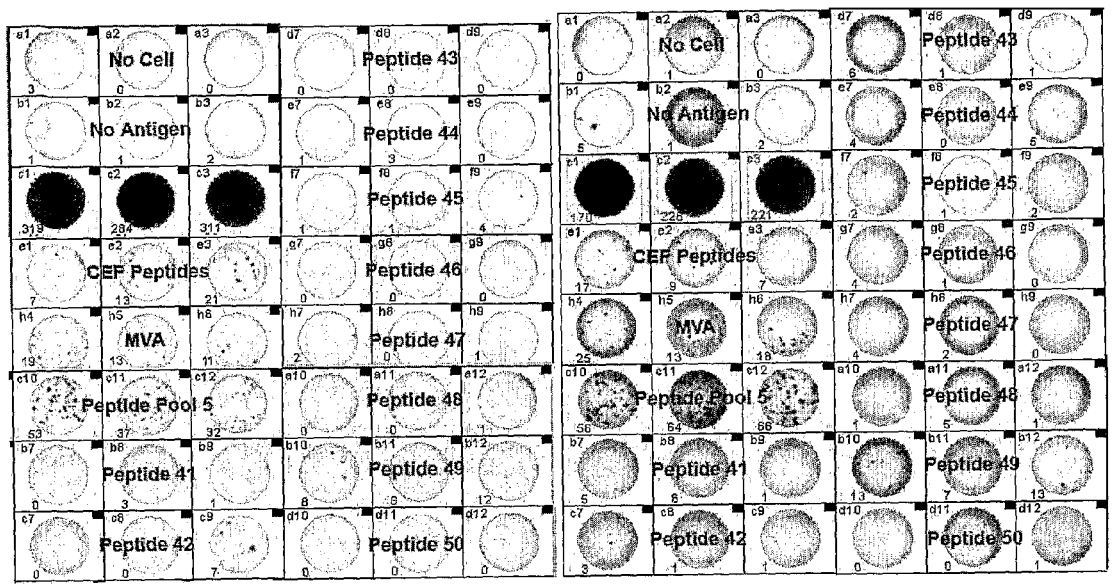
FIG. 12 shows Class 1 Peptide pool 5 retested as individual peptides at X+6 wk (left) and X+10 wk (right).

FIG. 12 shows Class 1 Peptide pool 5 retested as individual peptides at X+6 wk (left) and X+10 wk (right).

It is possible to see from the ELISPOT in FIG. 12 that, in the no cell and no antigen wells, there is a low background, which demonstrates there are few non-specific responding cells, and that CEF and MVA have induced IFNγ responses. Peptide pool 5 (containing 10 mer peptides 41-50) has produced a response at both time points as previously observed and when the peptides in pool 5 are tested individually, it is clear that there is a response to peptide 49 (FLTGNQLAVL) (SEQ ID NO 225).

Figure 13:
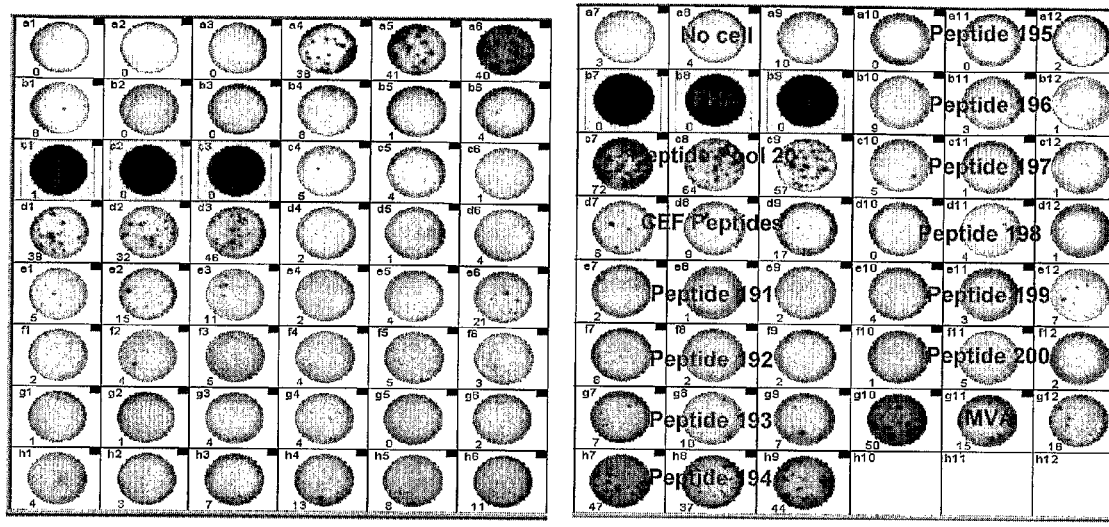
FIG. 13 shows Class 1 Peptide pool 20 retested as individual peptides at X+6 wk (left) and X+10 wk (right).

FIG. 13 shows Class 1 Peptide pool 20 retested as individual peptides at X+6 wk (left) and X+10 wk (right).

It is possible to see from the ELISPOT in FIG. 13 that, in the no cell and no antigen wells, there is a low background, which demonstrates there are few non-specific responding cells, and that CEF and MVA have induced IFNγ responses. Peptide pool 20 (containing 10 mer peptides 191-200) has produced a response at both time points as previously observed and when the peptides in pool 20 are tested individually, it is clear that there is a response to peptide 194 (NIRDACRDHM). Although the HLA allelic restriction of this peptide has not been defined, it must be restricted by at least one of the HLA alleles expressed by this patient, namely HLA A2, A3, B44, B60, Cw3, or Cw5.

Discussion:

It is clear from the above results that the 5T4 10 mer peptides 8, 9, 49, and 194 are capable of inducing an ex-vivo IFNγ response in PBMCs from an individual immunised with Trovax®. As this patient's HLA type is A2, A3, B44, B60, Cw3, Cw5, these responses must be restricted to one of these alleles in this patient. 9 mer peptides 9 and 49, which are identical to the 10 mer peptides but shorter by a single carboxy terminal amino acid residue, were identified as putative HLA-A2 epitopes using the iTopia epitope discovery system (peptide 9 being ranked 4th and peptide 49 6th). As patient 018 has an A2 HLA type, it is possible that the responses to these peptides are occurring via HLA A2 mediated presentation, although this will need to be verified.

9 Mer Experiments

To verify that the some of the individual 10 mer peptides seen to stimulate IFN γ production in the previous experiment are also capable of stimulating a response as 9 mer peptides, the following peptides were tested:

Antigens and Reagents:
A2 blocking antibody clone BB7.2 Serotec (Cat: MCA2090XZ)
MVA (modified vaccinia Ankara)
10 mer Peptide pool #1 (containing 10 mer peptides 1-10)
10 mer peptide #1 (MPGGCSRGPA) (SEQ ID NO 207)
10 mer peptide #8 (RLRLARLALV) (SEQ ID NO 214)
10 mer peptide #9 (RLARLALVLL) (SEQ ID NO 215)
10 mer peptide #10 (ARLALVLLGW) (SEQ ID NO 216)
9 mer Peptide pool #1 (containing 9 mer peptides 1-10)
9 mer peptide #1 (MPGGCSRGP) (SEQ ID NO 1)
9 mer peptide #8 (RLRLARLAL) (SEQ ID NO 8)
9 mer peptide #9 (RLARLALVL) (SEQ ID NO 9)
9 mer peptide #10 (ARLALVLLG) (SEQ ID NO 10)
10 mer Peptide pool #5 (containing 10 mer peptides 41-50)
10 mer peptide #41 (NLTEVPTDLP) (SEQ ID NO 217)
10 mer peptide #48 (NLFLTGNQLA) (SEQ ID NO 224)
10 mer peptide #49 (FLTGNQLAVL) (SEQ ID NO 225)
10 mer peptide #50 (TGNQLAVLPA) (SEQ ID NO 226)
9 mer Peptide pool #5 (containing 9 mer peptides 41-50)
9 mer peptide #41 (NLTEVPTDL) (SEQ ID NO 41)
9 mer peptide #48 (NLFLTGNQL) (SEQ ID NO 48)
9 mer peptide #49 (FLTGNQLAV) (SEQ ID NO 49)
9 mer peptide #50 (TGNQLAVLP) (SEQ ID NO 50)

The ELISPOT was performed in accordance with the procedures and documents detailed above. The A2 blocking antibody (clone BB7.2) has been used in the past to demonstrate A2 restriction of responses in cytotoxic T cell assays and is being used in this assay to demonstrate that particular peptide epitopes are A2 restricted.

Figure 14:
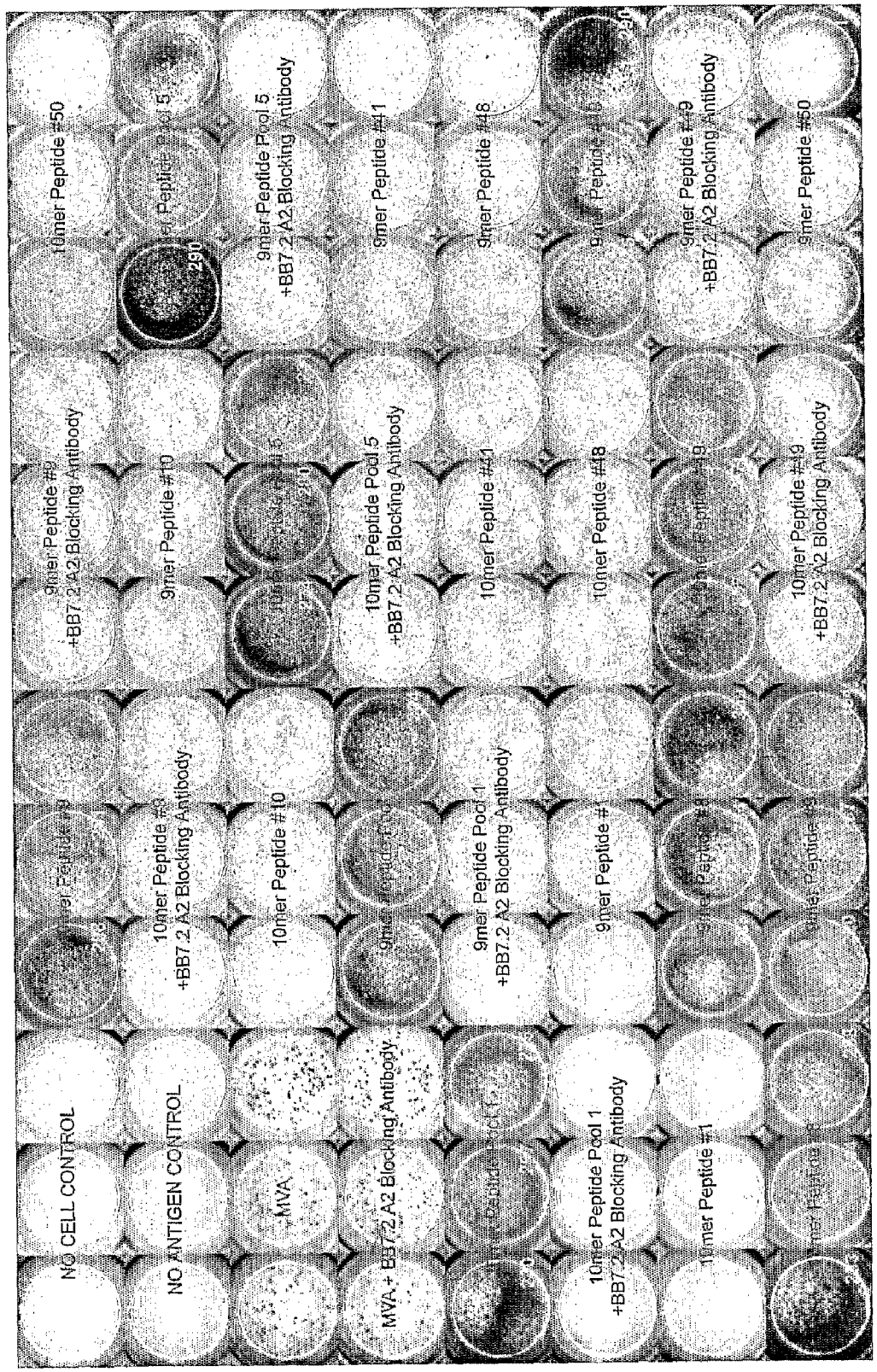
FIG. 14 shows 10 mer peptides and peptide pools compared to 9 mer peptides and pools in the presence and absence of an A2 blocking antibody (clone BB7.2) as indicated.

Results and Discussion:

FIG. 14 shows 10 mer peptides and peptide pools compared to 9 mer peptides and pools in the presence and absence of an A2 blocking antibody (clone BB7.2) as indicated.

It is possible to see from the ELISPOT in FIG. 14 that there is a clean background, indicated by the absence of spots in the No cell and No antigen wells, which demonstrates there are few non-specific responding cells; and there is a response to MVA.

The fact that there is no significant reduction in response to MVA in the presence of the A2 blocking antibody, indicates that the A2 blocking antibody does not appear to have any toxic effect on the PBMCs.

10 mer pool 1 has shown a response, which is completely ablated by the A2 blocking antibody, indicating that the peptide epitope(s) in this pool for this patient is/are A2 restricted. 10 mer peptide 1 (MPGGCSRGPA) (SEQ ID NO 207) shows no response and nor does peptide 10 (ARLALVLLGW) (SEQ ID NO 216). Peptides 8 (RLRLARLALV) (SEQ ID NO 214) and 9 (RLARLALVLL) (SEQ ID NO 215) both show a response and using the A2 blocking antibody with peptide 9, it is possible to see that this is A2 restricted.

The 9 mer pool 1 peptides showed an identical pattern of responses to the 10 mer pool 1 peptides. 9 mer pool 1 has shown a response, which is completely ablated by the A2 blocking antibody, indicating that the peptide epitope(s) in this pool for this patient is/are A2 restricted. 9 mer peptide 1 (MPGGCSRGP) (SEQ ID NO 1) shows no response and nor does peptide 10 (ARLALVLLG) (SEQ ID NO 10). Peptides 8 (RLRLARLAL) (SEQ ID NO 8) and 9 (RLARLALVL) (SEQ ID NO 9) both show a response and using the A2 blocking antibody with peptide 9, it is possible to see that this is A2 restricted. Peptide 9 was identified as a putative A2 epitope (ranked 3rd) using iTopia and the above result validates this peptide as a true class I epitope and verifies that it is HLA-A2 restricted (although it does not preclude the possibility that it is also restricted by an other allele not expressed by this individual). As peptide 8 and 9 share an overlapping sequence of 7 amino acids (RLARLAL) (SEQ ID NO 320) suggesting that this represents a minimal epitope. It is also likely that their structure, with the anchor residues at positions 2 and 4 filled by leucine residues in both cases, accounts for the fact that they are both capable of stimulating a response. Without the use of the A2 blocking antibody in this case, it is not possible to define the allelic restriction of peptide 8 other than that it must be presented by one of A2, A3, B44, B60, Cw3, and Cw5.

10 mer pool 5 has shown a response, which is completely ablated by the A2 blocking antibody, indicating that the peptide epitope(s) in this pool for this patient is/are A2 restricted. 10 mer peptide 41 (NLTEVPTDLP) (SEQ ID NO 217) shows no response and nor does peptide 48 (NLFLTGNQLA) (SEQ ID NO 224) or 50 (TGNQLAVLPA) (SEQ NO 226). Peptide 49 (FLTGNQLAVL) (SEQ ID NO 225) shows a response and using the A2 blocking antibody with peptide 49, it is possible to see that this is A2 restricted. The fact that neither of the flanking peptides elicit a response, indicates that the epitope is defined by the sequence of peptide 49.

The 9 mer pool 5 peptides showed an identical pattern of responses to the 10 mer pool 5 peptides. 9 mer pool 5 has shown a response, which is completely ablated by the A2 blocking antibody, indicating that the peptide epitope(s) in this pool for this patient is/are A2 restricted. 9 mer peptide 41 shows no response and nor does peptide 48 or 50. Peptide 49 shows a response and using the A2 blocking antibody with peptide 49, it is possible to see that this is A2 restricted. Peptide 49 was identified as a putative A2 epitope (ranked 6$^{th}$) using iTopia and the above result validates this peptide as a true class I epitope and verifies that it is HLA-A2 restricted (although it does not preclude the possibility that it is also restricted by an other allele not expressed by this individual).
Reactivity of PBMCs from TroVax Vaccinated Patients to 5T4 Peptide Pools Containing iTopia hits.
Introduction:

Briefly, as part of the immunomonitoring of the phase II TroVax trial TV2, PBMCs, from colorectal cancer patients who had been vaccinated with TroVax, were interrogated with pools of 10 mer peptides (these were identical to the 9 mer peptides except that they have an additional c-terminal amino acid).

Two pools of 5T4 peptides were made up of iTopia hits, one contained the A2 hits (X peptides) and the other contained all of the A1, A3 and B7 hits (Y peptides). Additional pools of peptides were also used to interrogate PBMCs; these contained adjacent 5T4 peptides.
Materials:

The peptide pools were made up as detailed in Tables 8a (iTopia hits) and 8b (pools of adjacent peptides) such that the final concentrations of peptide used in the IFNγ ELISpot were 5 μg/ml per peptide.
Results:

A library of overlapping 5T4 peptides has been used to interrogate IFNγ ELISpot responses in PBMCs recovered from patients vaccinated with TroVax. As detailed above, each pool contained 10 adjacent peptides (with the exception of the 2 iTopia peptide pools). A number of these pools contain peptides which are predicted (by iTopia) to be CTL epitopes restricted through HLA A1, A2, A3 or B7. Analysis of IFNγ ELISpot responses showed a number of patients who responded to a peptide pool following, but not before, vaccination with TroVax. We have identified patients who responded to a peptide pool that contained a putative CTL epitope which was predicted by iTopia to be restricted through a HLA allele which was present in the responding patient. Table 9 lists all of the instances where this has occurred.

In addition to interrogating patients' PBMCs with a panel of over-lapping peptides, pools of peptides containing iTopia A2 hits and combined A1/A3/B7 hits were also used. Results in Table 10 detail patients who showed a positive IFNγ ELISpot response to these peptide pools and had a matching HLA allele.

Where availability of a responding patient's PBMCs has allowed, the peptide pools have been dissected into their constituents with the aim of identifying the individual peptide which induced the positive IFNγ ELISpot response (Table 11). By dissecting positive responses from peptide pools, 4 individual peptides (9, 49, 125 and 194) were identified which were responsible for the positive IFNγ ELISpot response. It has been possible to use a blocking antibody specific for HLA-A2 to confirm the restriction through this allele for peptides 9 and 49. Peptide 77 has been identified previously as being restricted through HLA A2 and was identified as an A2 hit by iTopia. Following the identification of positive IFNγ ELISpot responses to individual peptides, MHC multimers (Pentamers) were synthesised for 2 HLA-A2 epitopes (9 and 49). Positive pentamer responses were detected in patient 018 to both pentamers and in patient 108 to pentamer 49.
Conclusion:

By analysing IFNγ ELISpot responses from patients vaccinated with TroVax, we have been able to identify peptide pools which induced a positive response and contained an iTopia hit of a HLA allele which the patient possessed. The peptide pools used to interrogate patients' PBMCs contained all of the iTopia hit peptides and, positive responses were detected in pools of peptides containing all of the iTopia hits. Therefore, the iTopia hits are genuine epitopes eliciting cellular responses. Where dissections of responding peptide pools have been carried out, it was shown that the iTopia hit contained within the pool elicited the response. Indeed, 5 peptides predicted to be CTL epitopes by iTopia have now been confirmed to be CTL epitopes.
Use of Multimeric MHC/Peptide Complexes (Pentamers) for the Validation of iTopia Hits.
Introduction Multimeric MHC/peptide complexes (pentamers in this case) can be used for direct ex vivo analysis of the frequency and phenotype of antigen-specific T cells. The assay relies upon the interaction between the MHC/peptide complex and T cell receptor clusters on the surface of T cells. The method is known to be robust, and can detect antigen-specific populations at frequencies as low as 1:5,000 CD8+ T-cells (approximately 1:50,000 PBMC).

Analysis of PBMCs from patient TV2-018 (HLA type: A2, A3, B44, B60, Cw3, Cw5) and TV2-108 (HLA type A2, A3, B8, B64 Cw7, Cw8) was done using HLA-A2 pentamers specific for peptides 9 (HLA-A2/9; peptide sequence RLARLALVL) (SEQ ID NO 9) and 49 (HLA-A2/49; peptide sequence FLTGNQLAV) (SEQ ID NO 49). A pentamer with a mismatched HLA type (HLA-A1/43; peptide sequence VPTDLPAYV) (SEQ ID NO 43) was used as a negative control for binding.
Materials:
  PBMCs from patient TV2-018 at the −2 wk, X+2 wk, and X+14 wk timepoints, and patient TV2-108 at the 6 wk and 19 wk timepoints
  Class I. MHC Pro5 Pentamers HLA-A2/9 (RLARLALVL), HLA-A2/49 (FLTGNQLAV) and HLA-A1/43 (VPTDLPAYV). (from ProImmune).

Fluorescent labelled anti-CD8 antibody (CD8 FITC from BD Biosciences).

Methods:

Briefly, PBMCs were thawed and incubated with a primary layer consisting of the pentamer complex, followed by a secondary layer consisting of a fluorescent (PE-labelled) pentamer tag and fluorescent (FITC labelled) anti-CD8 antibody. Samples were then analysed by flow cytometry.

Results

The results are shown in FIGS. 15 and 16.

Conclusion:

Distinct populations of CD8+ T cells specific for HLA-A2/9 can be seen for patient TV2-018 at the X+2 wk and X+14 wk time points. This is in agreement with previous ELISpot results and confirms the HLA restriction of this epitope as A2. Distinct populations of CD8+ T cells specific for HLA-A2/49 can be seen for patient TV2-108 at the 19 wk time point. This is also in agreement with previous ELISpot results and confirms the HLA restriction of this epitope as A2.

Use of a HLA-A2 Transgenic Mouse Model for the Validation of iTopia Hits.

HLA-A2 transgenic mice are vaccinated with TroVax®. Following vaccination, splenocytes are isolated. These cells are tested for evidence of specificity against the peptides identified as HLA-A2 binders by iTopia using ELISpot assay.

Example 2—Class II

Reactivity of PBMCs from TROVAX® Vaccinated Patients to 5T4 20 Mer Peptides.

Introduction:

Briefly, as part of the immunomonitoring of the phase II TROVAX® trial TV2, PBMCs, from colorectal cancer patients who had been vaccinated with TROVAX®, were interrogated with two 20 mer peptides, number 39.2 (MVTWLKETEVVQGKDRLTCA) (SEQ ID NO 324) and 41.2 (LTCAYPEKMRNRVLLELNSA) (SEQ ID NO 326) in ELISpot assays and with ten individual 20 mer peptides and seven pools of 20 mer peptides in cellular proliferation assays.

Materials:

The peptides were included in TV2 ELISpot assays such that the final concentration of peptide was 5 µg/ml. Table 12 displays the individual peptides and constituents of the peptide pools.

Methods:

ELISpot is described previously.

Cellular proliferation assay is described briefly as follows. PBMCs, freshly obtained by separation on Histopaque-1077, are plated out at concentration of $1 \times 10^5$ cells per well of 96-well plate. Peptides, individually or in pools, are added to each well at final concentration of 2 µg/ml per peptide. Wells with media alone and PHA can serve as negative and positive controls respectively. Also Tetanus toxin can be included as an antigen specific positive control. After 6 days incubation (37° C.; 5% $CO_2$), 1 µCi of tritiated thymidine (3H-Thymidine) is added to each well and, following an additional overnight incubation, cells are harvested and tritiated thymidine incorporation is measured using a scintillation counter.

Results:

The class II 5T4 20 mer peptides 39.2 and 41.2 were used to interrogate IFNγ ELISpot responses in PBMCs recovered from patients vaccinated with TroVax. Analysis of IFNγ ELISpot responses showed a number of patients responded to a peptide following, but not before, vaccination with TroVax. Table 13 lists all of the instances where this has occurred. Similarly, when individual class II 5T4 20 mer peptides as well as pools of class II 5T4 peptide pools were used to interrogate cellular proliferative responses in PBMCs recovered from patients vaccinated with TroVax, numerous responses were seen following, but not before, vaccination with TroVax. Table 14 lists all of the instances where this has occurred.

When the HLA types of the patients responding to a particular peptide or pool are analysed, as shown in Table 15, the likely HLA restriction of a particular peptide or pool can be determined by the frequency with which a particular HLA type is represented amongst the responding patients. Amongst the single peptides the most likely HLA restriction of peptide 36.2 is either DQ2, DR7, or DR53 as each were represented by 3 out of 7 responders. The most likely HLA restriction of peptide 37.2 is either DQ2, DR52, or DR53 as DQ2 was represented by 7 out of 10 responders and DR52 or DR53 were each represented by 5 out of 10. The most likely HLA restriction of peptide 38.2 is either DQ2, DQ6, or DR52 as each were represented by 5 out of 10 responders. The most likely HLA restriction of peptide 39.2 is either DQ6, DR51, or DR52 as DQ6 was represented by 6 out of 10 responders and DR51 and DR52 were represented by 5 out of 10 responders. The most likely HLA restriction of peptide 40.2 is either DQ6, DR15, DR51, or DR52 as DQ6 was represented by 8 out of 12 responders and DR15, DR51 and DR52 were represented by 6 out of 12 responders. The most likely HLA restriction of peptide 41.2 is either DQ6, DR51, or DR15 as DQ6 was represented by 9 out of 13 responders, DR51 was represented by 7 out of 13 responders and DR15 was represented by 6 out of 13 responders. The most likely HLA restriction of peptide 42.2 is either DQ6, DR51, DQ5, or DR15 as DQ6 was represented by 8 out of 12 responders, DR51 was represented by 7 out of 12 responder and DQ5 and DR15 were represented by 6 out of 12 responders. The most likely HLA restriction of peptide 43.2 is either DQ6, DR15, or DR51 as DQ6 was represented by 7 out of 11 responders and DR15 and DR51 were represented by 6 out of 11 responders. The most likely HLA restriction of peptide 44.2 is either DQ6, DR15, DR51, or DR52 as they were each represented by 5 out of 9 responders. The most likely HLA restriction of peptide 45.2 is either DQ6, DR53, DR15, or DR51 as DQ6 and DR53 were represented by 5 out of 8 responders and DR15 and DR51 were represented by 4 out of 8 responders. The most likely HLA restriction of peptides contained in pool 4.2 are either DQ2, DQ6, DR52, or DR53 as they were each represented by 6 out of 15 responders or DQ7 which was represented by 5 out of 15 responders. The most likely HLA restriction of peptides contained in pool 5.2 are either DR52, DQ2, DR17, or DQ6 as DR52 was represented by 9 out of 13 responders, DQ2 was represented by 7 out of 13 responders, DR17 was represented by 6 out of 13 responders, and DQ6 was represented by 5 out of 13 responders. The most likely HLA restriction of peptides contained in pool 6.2 are either DQ2, DR52, DQ6, DR7, or DR17 as DQ2 and DR52 were represented by 7 out of 13 responders, and DQ6, DR7 and DR17 were represented by 5 out of 13 responders. The most likely HLA restriction of peptides contained in pool 7.2 are either DQ6, DR52, DQ2, DR15, or DR51 as DQ6 was represented by 8 out of 13 responders, DR52 was represented by 6 out of 13 responders, and DQ2, DR15 and DR51 were represented by 5 out of 13 responders. The most likely HLA restriction of peptides contained in pool 8.2 are either DQ2, DQ6, DR52, DR15, or DR51 as DQ2, DQ6, and DR52 were represented by 8 out of 18 responders and DR15 and DR51 were represented by 7 out of 18 responders. The most likely HLA restriction of peptides contained in pool 9.2 are either DQ6, DR15, DR51, DQ2, or DR53 as DQ6 was represented by 8 out of 12 responders, DR15 and DR51 were represented by 7 out of 12 responders and DQ2 and DR53 were represented by 5 out of 12 responders. The most likely HLA restriction of peptides contained in pool 10.2 are either DQ6, DR52, DQ2, DR15, or DR51 as DQ6 and DR52 were represented by 8 out of 15 responders, DQ2 was represented by 7 out of 15 responders and DR15 and DR51 were represented by 6 out of 16 responders.

Conclusion:

By analysing IFNγ ELISpot as well as cellular proliferative responses from patients vaccinated with TroVax, we have been able to identify peptides which induced a positive response. It is also possible to determine the likely HLA restriction.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

Physical data for 9-mer peptides

| Peptide No (SEQ ID NO:) | Peptide Sequence | Peptide Lot Number | Experimental Molecular Weight (mg/mmole) | Theoretical (Manoisotopic) Molecular Weight (mg/mmole) | Theoretical Molecular Weight + TFA[1] (mg/mmole) | Purity (%) | Peptide Mass (mg) | DMSO Volume (µl) |
|---|---|---|---|---|---|---|---|---|
| 1 | MPGGCSRGP | 050704Y2-33 | 861.3 | 860 | 1088 | 80 | 3.4 | 250 |
| 2 | GGCSRGPAA | 220704S-33 | 775.3 | 774 | 1002 | 88.4 | 4.6 | 406 |
| 3 | CSRGPAAGD | 050704Y1-25 | 832.3 | 832 | 1060 | 93.2 | 4.3 | 378 |
| 4 | RGPAAGDGR | 050704Y2-50 | 856.5 | 855 | 1197 | 85.1 | 3.1 | 220 |
| 5 | PAAGDGRLR | 050704Y2-51 | 912.5 | 911 | 1253 | 85.6 | 3 | 205 |
| 6 | AGDGRLRLA | 050704Y1-2 | 928.4 | 928 | 1270 | 82 | 3.6 | 232 |
| 7 | DGRLRLARL | 050704Y1-74 | 1069.7 | 1069 | 1525 | 80.3 | 4.4 | 232 |
| 8 | RLRLARLAL | 050704Y1-75 | 1081.7 | 1061 | 1537 | 82.9 | 3 | 162 |
| 9 | RLARLALVL | 050704Y1-76 | 1024.7 | 1024 | 1366 | 81.5 | 4.5 | 268 |
| 10 | ARLALVLLG | 050704Y1-50 | 925.7 | 925 | 1153 | 86.5 | 4.6 | 345 |
| 11 | LALVLLGWV | 130704Y3-61 | 983.7 | 983 | 1097 | 92.2 | 3.9 | 328 |
| 12 | LVLLGWVSS | 050704Y2-64 | 973.7 | 973 | 1087 | 81.3 | 3 | 224 |
| 13 | LLGWVSSSS | 050704Y2-65 | 935.5 | 934 | 1048 | 88.4 | 3 | 253 |
| 14 | GWVSSSSPT | 130704Y3-62 | 907.4 | 906 | 1020 | 91.5 | 4.4 | 395 |
| 15 | VSSSSPTSS | 050704Y2-66 | 838.4 | 837 | 951 | 91.8 | 3 | 290 |
| 16 | SSSPTSSAS | 050704Y2-67 | 810.3 | 809 | 923 | 94.1 | 3 | 306 |
| 17 | SPTSSASSF | 050704Y1-45 | 870.4 | 869 | 983 | 87.8 | 4.8 | 429 |
| 18 | TSSASSFSS | 050704Y2-68 | 860.4 | 859 | 973 | 93.4 | 3 | 288 |
| 19 | SASSFSSSA | 050704Y1-3 | 830.3 | 829 | 943 | 94.6 | 3.6 | 361 |
| 20 | SSFSSSAPF | 050704Y1-46 | 916.5 | 915 | 1029 | 80.6 | 4.6 | 360 |
| 21 | FSSSAPFLA | 050704Y1-4 | 926.5 | 925 | 1039 | 80.8 | 4.7 | 366 |
| 22 | SSAPFLASA | 050704Y1-5 | 850.5 | 849 | 963 | 83.7 | 3.2 | 278 |
| 23 | APFLASAVS | 050704Y2-69 | 862.5 | 861 | 975 | 80.2 | 4 | 329 |
| 24 | FLASAVSAQ | 220704S-53 | 893.4 | 892 | 1006 | 91.3 | 4.5 | 408 |
| 25 | ASAVSAQPP | 130704Y3-63 | 827.4 | 826 | 940 | 80 | 3 | 255 |
| 26 | AVSAQPPLP | 220704S-47 | 879.5 | 878 | 992 | 96 | 4.9 | 474 |
| 27 | SAQPPLPDQ | 050704Y2-47 | 952.5 | 951 | 1065 | 95 | 3 | 268 |

TABLE 1-continued

Physical data for 9-mer peptides

| Peptide No (SEQ ID NO:) | Peptide Sequence | Peptide Lot Number | Experimental Molecular Weight (mg/mmole) | Theoretical (Manoisotopic) Molecular Weight (mg/mmole) | Theoretical Molecular Weight + TFA[1] (mg/mmole) | Purity (%) | Peptide Mass (mg) | DMSO Volume (µl) |
|---|---|---|---|---|---|---|---|---|
| 28 | QPPLPDQCP | 220704S-48 | 994.3 | 993 | 1107 | 83.1 | 4.5 | 338 |
| 29 | PLPDQCPAL | 050704Y1-77 | 952.8 | 952 | 1066 | 87.7 | 5 | 411 |
| 30 | PDQCPALCE | 050704Y1-34 | 975.4 | 974 | 1088 | 90.7 | 3.8 | 317 |
| 31 | QCPALCECS | 220704S-54 | 953.3 | 952 | 1066 | 80.2 | 4 | 301 |
| 32 | PALCECSEA | 050704Y1-6 | 920.2 | 921 | 1035 | 80 | 4.4 | 340 |
| 33 | LCECSEAAR | 050704Y2-52 | 981.3 | 980 | 1208 | 80.5 | 3 | 200 |
| 34 | ECSEAARTV | 220704S-60 | 965.3 | 964 | 1192 | 84.2 | 4.1 | 290 |
| 35 | SEAARTVKC | 220704S-36 | 964.3 | 963 | 1305 | 84 | 4.1 | 264 |
| 36 | AARTVKCVN | 050704Y2-20 | 961.3 | 961 | 1303 | 81.3 | 3 | 187 |
| 37 | RTVKCVNRN | 220704S-43 | 1090.4 | 1089 | 1545 | 84.3 | 3.7 | 202 |
| 38 | VKCVNRNLT | 050704Y2-84 | 1045.9 | 1046 | 1388 | 85.6 | 4.7 | 290 |
| 39 | CVNRNLTEV | 220704S-38 | 1047.4 | 1047 | 1275 | 80.2 | 4.7 | 296 |
| 40 | NRNLTEVPT | 050704Y2-85 | 1043.6 | 1043 | 1271 | 82.4 | 3.1 | 201 |
| 41 | NLTEVPTDL | 050704Y1-78 | 1001.6 | 1001 | 1115 | 84.1 | 4.8 | 362 |
| 42 | TEVPTDLPA | 050704Y1-7 | 942.7 | 941 | 1055 | 85.8 | 3.5 | 285 |
| 43 | VPTDLPAYV | 050704Y2-92 | 974.6 | 974 | 1088 | 92.7 | 3.6 | 307 |
| 44 | TDLPAYVRN | 220704S-44 | 1048.4 | 1048 | 1276 | 91 | 3.1 | 221 |
| 45 | LPAYVRNLF | 050704Y1-47 | 1092.6 | 1092 | 1320 | 83.7 | 3.4 | 216 |
| 46 | AYVRNLFLT | 050704Y2-86 | 1096.7 | 1096 | 1324 | 82.5 | 3.4 | 212 |
| 47 | VRNLFLTGN | 220704S-45 | 1033.5 | 1033 | 1261 | 86.7 | 4 | 275 |
| 48 | NLFLTGNQL | 050704Y1-79 | 1019.7 | 1019 | 1133 | 80.5 | 4 | 284 |
| 49 | FLTGNQLAV | 050704Y2-93 | 962.7 | 962 | 1076 | 80.3 | 4 | 299 |
| 50 | TGNQLAVLP | 220704S-49 | 912.5 | 912 | 1026 | 85.8 | 4.3 | 360 |
| 51 | NQLAVLPAG | 050704Y1-51 | 882.5 | 881 | 995 | 92.3 | 3 | 278 |
| 52 | LAVLPAGAF | 050704Y1-48 | 858.5 | 858 | 972 | 86.8 | 3 | 268 |
| 53 | VLPAGAFAR | 050704Y2-53 | 901.6 | 901 | 1129 | 89.5 | 3.3 | 262 |
| 54 | PAGAFARRP | 130704Y3-64 | 942.5 | 942 | 1284 | 80 | 3 | 187 |
| 55 | GAFARRPPL | 050704Y1-80 | 984.6 | 984 | 1326 | 90.5 | 4.8 | 328 |
| 56 | FARRPPLAE | 060704Y1-35 | 1056.6 | 1056 | 1398 | 94.8 | 3.6 | 244 |
| 57 | RRPPLAELA | 050704Y1-8 | 1022.6 | 1022 | 1364 | 96 | 4.9 | 345 |
| 58 | PPLAELAAL | 220704A3 | 894.5 | 894 | 1008 | 94.4 | 4.9 | 459 |
| 59 | LAELAALNL | 050704Y1-82 | 927.7 | 927 | 1041 | 81.3 | 4.5 | 351 |
| 60 | ELAALNLSG | 050704Y1-52 | 887.5 | 888 | 1000 | 96.9 | 4.8 | 465 |
| 61 | AALNLSGSR | 050704Y2-54 | 888.5 | 887 | 1115 | 96.7 | 3.1 | 269 |
| 62 | LNLSGSRLD | 050704Y1-26 | 974.5 | 974 | 1202 | 80.2 | 3.8 | 254 |
| 63 | LSGSRLDEV | 050704Y2-94 | 975.6 | 975 | 1203 | 80.2 | 4.5 | 300 |

TABLE 1-continued

Physical data for 9-mer peptides

| Peptide No (SEQ ID NO:) | Peptide Sequence | Peptide Lot Number | Experimental Molecular Weight (mg/mmole) | Theoretical (Manoisotopic) Molecular Weight (mg/mmole) | Theoretical Molecular Weight + TFA[1] (mg/mmole) | Purity (%) | Peptide Mass (mg) | DMSO Volume (µl) |
|---|---|---|---|---|---|---|---|---|
| 64 | GSRLDEVRA | 050704Y1-9 | 1002.5 | 1002 | 1344 | 80.1 | 4 | 238 |
| 65 | RLDEVRAGA | 060704Y1-10 | 986.5 | 986 | 1328 | 91.9 | 4.6 | 318 |
| 66 | DEVRAGAFE | 050704Y1-36 | 993.5 | 992 | 1220 | 96.3 | 3.5 | 276 |
| 67 | VRAGAFEHL | 220704S-39 | 999.5 | 999 | 1341 | 89 | 4.5 | 299 |
| 68 | AGAFEHLPS | 220704S-55 | 928.3 | 927 | 1155 | 92.3 | 4.2 | 336 |
| 69 | AFEHLPSLR | 050704Y2-55 | 1069.6 | 1069 | 1411 | 91.7 | 3 | 195 |
| 70 | EHLPSLRQL | 050704Y1-84 | 1092.7 | 1092 | 1434 | 86.4 | 4.7 | 283 |
| 71 | LPSLRQLDL | 050704Y1-85 | 1054.7 | 1054 | 1282 | 93.1 | 4 | 290 |
| 72 | SLRQLDLSH | 050704Y1-58 | 1068.4 | 1068 | 1410 | 100 | 3.9 | 277 |
| 73 | RQLDLSHNP | 130704Y3-65 | 1079.4 | 1079 | 1421 | 92.3 | 3 | 195 |
| 74 | LDLSHNPLA | 050704Y1-11 | 979.5 | 979 | 1207 | 81.3 | 5 | 337 |
| 75 | LSHNPLADL | 050704Y1-86 | 979.5 | 979 | 1207 | 83.6 | 4.5 | 312 |
| 76 | HNPLADLSP | 130704Y3-66 | 963.5 | 962 | 1190 | 84.4 | 3 | 213 |
| 77 | PLADLSPFA | 050704Y1-12 | 930.5 | 929 | 1043 | 81.2 | 4.8 | 374 |
| 78 | ADLSPFAFS | 050704Y2-72 | 954.3 | 953 | 1067 | 97.8 | 4.7 | 431 |
| 79 | LSPFAFSGS | 050704Y2-73 | 912.5 | 911 | 1025 | 82.7 | 3.4 | 274 |
| 80 | PFAFSGSNA | 05D704Y1-13 | 897.4 | 896 | 1010 | 81.4 | 4.6 | 371 |
| 81 | AFSGSNASV | 050704Y2-95 | 839.5 | 838 | 952 | 82.9 | 3.4 | 296 |
| 82 | SGSNASVSA | 050704Y1-14 | 779.3 | 778 | 892 | 92.7 | 4.6 | 478 |
| 83 | SNASVSAPS | 130704Y3-67 | 819.3 | 818 | 932 | 89.8 | 5 | 482 |
| 84 | ASVSAPSPL | 050704Y1-67 | 828.5 | 827 | 941 | 92.9 | 4.8 | 474 |
| 85 | VSAPSPLVE | 050704Y1-37 | 898.5 | 897 | 1011 | 91.3 | 3.3 | 298 |
| 86 | APSPLVELI | 050704Y1-63 | 938.8 | 938 | 1052 | 92.3 | 4.5 | 395 |
| 87 | SPLVELILN | 050704Y2-24 | 997.5 | 997 | 1111 | 80.3 | 4.8 | 347 |
| 88 | LVELILNHI | 050704Y1-64 | 1063.7 | 1063 | 1291 | 97.5 | 3.3 | 249 |
| 89 | ELILNHIVP | 130704Y3-68 | 1047.6 | 1047 | 1275 | 80.1 | 4.6 | 289 |
| 90 | ILNHIVPPE | 050704Y1-38 | 1031.6 | 1031 | 1259 | 82.4 | 4.6 | 301 |
| 91 | NHIVPPEDE | 050704Y1-39 | 1049.4 | 1048 | 1276 | 89.3 | 3.7 | 259 |
| 92 | IVPPEDERQ | 050704Y2-48 | 1082.6 | 1082 | 1310 | 98.4 | 4.6 | 346 |
| 93 | PPEDERQNR | 050704Y2-56 | 1140.6 | 1140 | 1482 | 95.1 | 4 | 257 |
| 94 | EDERQNRSF | 050704Y1-49 | 1180.5 | 1180 | 1522 | 89 | 4.1 | 240 |
| 95 | ERQNRSFEG | 050704Y1-53 | 1122.5 | 1122 | 1464 | 96.7 | 4.8 | 317 |
| 96 | QNRSFEGMV | 060704Y2-96 | 1067.5 | 1066 | 1294 | 80.6 | 3.6 | 224 |
| 97 | RSFEGMVVA | 050704Y1-15 | 995.5 | 994 | 1222 | 95.6 | 4.2 | 329 |
| 98 | FEGMVVAAL | 050704Y1-88 | 936.3 | 935 | 1049 | 94 | 4.9 | 439 |
| 99 | GMVVAALLA | 050704Y1-16 | 844.6 | 843 | 957 | 88 | 4.9 | 451 |

TABLE 1-continued

Physical data for 9-mer peptides

| Peptide No (SEQ ID NO:) | Peptide Sequence | Peptide Lot Number | Experimental Molecular Weight (mg/mmole) | Theoretical (Manoisotopic) Molecular Weight (mg/mmole) | Theoretical Molecular Weight + TFA[1] (mg/mmole) | Purity (%) | Peptide Mass (mg) | DMSO Volume (μl) |
|---|---|---|---|---|---|---|---|---|
| 100 | VVAALLAGR | 050704Y2-57 | 869.5 | 869 | 1097 | 80.4 | 3.2 | 235 |
| 101 | AALLAGRAL | 050704Y1-89 | 865.6 | 855 | 1083 | 80.7 | 3.1 | 231 |
| 102 | LLAGRALQG | 050704Y1-54 | 898.6 | 898 | 1126 | 80 | 3.8 | 270 |
| 103 | AGRALQGLR | 050704Y2-58 | 941.6 | 941 | 1283 | 88.2 | 3 | 206 |
| 104 | RALQGLRRL | 050704Y1-90 | 1082.6 | 1082 | 1538 | 87.9 | 3.5 | 200 |
| 105 | LQGLRRLEL | 050704Y1-91 | 1097.6 | 1097 | 1439 | 94.3 | 4.2 | 275 |
| 106 | GLRRLELAS | 220704S-56 | 1014.5 | 1014 | 1356 | 82.3 | 4.6 | 279 |
| 107 | RRLELASNH | 050704Y1-59 | 1095.5 | 1095 | 1551 | 81.6 | 3.3 | 174 |
| 108 | LELASNHFL | 050704Y1-92 | 1043.6 | 1043 | 1271 | 80 | 4.4 | 277 |
| 109 | LASNHFLYL | 050704Y1-93 | 1077.6 | 1077 | 1305 | 84.4 | 4.1 | 265 |
| 110 | SNHFLYLPR | 050704Y2-59 | 1146.7 | 1148 | 1488 | 80.4 | 3.2 | 173 |
| 111 | HFLYLPRDV | 050704Y3-1 | 1159.7 | 1159 | 1501 | 84.3 | 3.6 | 202 |
| 112 | LYLPRDVLA | 050704Y1-17 | 1059.6 | 1059 | 1287 | 84.5 | 4.2 | 276 |
| 113 | LPRDVLAQL | 050704Y1-94 | 1024.5 | 1024 | 1252 | 93 | 4.5 | 334 |
| 114 | RDVLAQLPS | 053704Y2-76 | 998.7 | 998 | 1226 | 88.2 | 3 | 216 |
| 115 | VLAQLPSLR | 050704Y2-50 | 996.7 | 996 | 1224 | 92.1 | 3 | 228 |
| 118 | AQLPSLRHL | 220704S-40 | 1034.5 | 1034 | 1376 | 83.9 | 5 | 305 |
| 117 | LPSLRHLDL | 220704S-41 | 1063.5 | 1063 | 1405 | 84.6 | 4.4 | 265 |
| 116 | SLRHDLSN | 050704Y2-25 | 1054.6 | 1054 | 1396 | 88.6 | 3.8 | 241 |
| 119 | RHLDLSNNS | 050704Y2-77 | 1055.6 | 1055 | 1397 | 93.3 | 3 | 200 |
| 120 | LDLSNNSLV | 050704Y3-2 | 974.5 | 974 | 1088 | 86.2 | 4.2 | 333 |
| 121 | LSNNSLVSL | 130704Y3-69 | 946.5 | 946 | 1060 | 86.7 | 4.5 | 368 |
| 122 | NNSLVSLTY | 050704Y3-9 | 1010.5 | 1010 | 1124 | 87.4 | 4.8 | 373 |
| 123 | SLVSLTYVS | 220704S-57 | 968.4 | 968 | 1082 | 100 | 4.5 | 416 |
| 124 | VSLTYVSFR | 050704Y2-61 | 1071.6 | 1071 | 1299 | 90.3 | 3.6 | 250 |
| 125 | LTYVSFRNL | 050704Y2-2 | 1112.7 | 1112 | 1340 | 80.2 | 5 | 299 |
| 128 | YVSFRNLTH | 050704Y1-60 | 1136.4 | 1136 | 1478 | 98.1 | 4.6 | 305 |
| 127 | SFRNLTHLE | 050704Y1-40 | 1116.6 | 1116 | 1458 | 97.9 | 4.4 | 295 |
| 128 | RNLTHLESL | 050704Y2-3 | 1082.6 | 1082 | 1424 | 82.9 | 4.1 | 239 |
| 129 | LTHLESLHL | 050704Y2-4 | 1062.4 | 1062 | 1404 | 96.7 | 4.7 | 324 |
| 130 | HLESLHLED | 050704Y1-27 | 1092.5 | 1092 | 1434 | 93.5 | 3 | 196 |
| 131 | ESLHLEDNA | 050704Y1-18 | 1027.4 | 1026 | 1254 | 91.9 | 4.5 | 330 |
| 132 | LHLEDNALK | 130704Y3-70 | 1052.6 | 1052 | 1394 | 84.6 | 3.8 | 231 |
| 133 | LEDNALKVL | 050704Y2-5 | 1014.6 | 1014 | 1242 | 91.7 | 3.6 | 266 |
| 134 | DNALKVLHN | 050704Y2-26 | 1023.5 | 1023 | 1365 | 93.3 | 3.4 | 232 |
| 135 | ALKVLHNGT | 050704Y2-87 | 952.6 | 952 | 1294 | 84.8 | 3.7 | 242 |

TABLE 1-continued

Physical data for 9-mer peptides

| Peptide No (SEQ ID NO:) | Peptide Sequence | Peptide Lot Number | Experimental Molecular Weight (mg/mmole) | Theoretical (Manoisotopic) Molecular Weight (mg/mmole) | Theoretical Molecular Weight + TFA[1] (mg/mmole) | Purity (%) | Peptide Mass (mg) | DMSO Volume (μl) |
|---|---|---|---|---|---|---|---|---|
| 136 | KVLHNGTLA | 050704Y1-19 | 952.5 | 952 | 1294 | 86.6 | 3.4 | 228 |
| 137 | LHNGTLAEL | 050704Y2-6 | 967.5 | 967 | 1195 | 89.4 | 4.1 | 307 |
| 136 | NGTLAELQG | 050704Y1-55 | 902.5 | 901 | 1015 | 90.5 | 4.8 | 428 |
| 139 | TLAELQGLP | 220704S-50 | 941.4 | 941 | 1055 | 81.3 | 4 | 308 |
| 140 | AELQGLPHI | 050704Y1-65 | 977.6 | 977 | 1205 | 89.7 | 5 | 372 |
| 141 | LQGLPHIRV | 050704Y3-3 | 1032.6 | 1032 | 1374 | 94.4 | 4.2 | 289 |
| 142 | GLPHIRVFL | 050704Y2-7 | 1051.7 | 1051 | 1393 | 80.2 | 3.6 | 207 |
| 143 | PHIRVFLDN | 220704S-46 | 1110.4 | 1110 | 1452 | 94.9 | 4.4 | 288 |
| 144 | IRVFLDNNP | 220704S-51 | 1087.5 | 1087 | 1315 | 84.4 | 4 | 257 |
| 145 | VFLDNNPWV | 050704Y3-4 | 1103.6 | 1103 | 1217 | 81.4 | 5 | 334 |
| 145 | LDNNPWVCD | 220704S-37 | 1075.3 | 1074 | 1186 | 96.6 | 3.2 | 260 |
| 147 | NNPWVCDCH | 050704Y1-61 | 1085.4 | 1086 | 1314 | 81.1 | 4.3 | 265 |
| 148 | PWVCDCHMA | 220704S-34 | 1061.3 | 1060 | 1286 | 88.9 | 4 | 276 |
| 149 | VCDCHMADM | 050704Y2-17 | 1024.2 | 1023 | 1251 | 80.9 | 4.4 | 285 |
| 150 | DCHMADMVT | 220704S-59 | 1022.3 | 1021 | 1249 | 80 | 4.1 | 263 |
| 151 | HMADMVTWL | 050704Y2-8 | 1103.4 | 1102 | 1330 | 92.3 | 3.2 | 222 |
| 152 | ADMVTWLKE | 050704Y1-41 | 1092.5 | 1092 | 1320 | 80.5 | 4.6 | 281 |
| 153 | MVTWLKETE | 050704Y1-42 | 1136.6 | 1136 | 1364 | 86.9 | 4.1 | 261 |
| 154 | TWLKETEVV | 050704Y3-5 | 1104.6 | 1104 | 1332 | 83.2 | 4.1 | 256 |
| 155 | LKETEVVQG | 050704Y1-56 | 1002.5 | 1002 | 1230 | 88 | 3.8 | 272 |
| 156 | ETEVVQGKD | 050704Y1-29 | 1004.5 | 1003 | 1231 | 96.1 | 4.3 | 336 |
| 157 | EVVQGKDRL | 050704Y2-9 | 1043.6 | 1043 | 1385 | 89.2 | 4.8 | 309 |
| 158 | VQGKDRLTC | 050704Y1-24 | 1018.5 | 1019 | 1361 | 83.9 | 4.3 | 265 |
| 159 | GKDRLTCAY | 050704Y3-10 | 1026.4 | 1025 | 1367 | 80.3 | 3.8 | 223 |
| 160 | DRLTCAYPE | 050704Y1-43 | 1066.9 | 1066 | 1294 | 88.2 | 3.3 | 225 |
| 161 | LTCAYPEKM | 050704Y2-18 | 1055.4 | 1054 | 1282 | 80.7 | 3.4 | 214 |
| 162 | CAYPEKMRN | 050704Y2-28 | 1110.4 | 1110 | 1452 | 95.9 | 3 | 198 |
| 163 | YPEKMRNRV | 050704Y3-6 | 1192.7 | 1192 | 1648 | 87 | 3.7 | 195 |
| 164 | EKMRNRVLL | 050704Y2-10 | 1158.6 | 1158 | 1614 | 100 | 4.6 | 285 |
| 165 | MRNRVLLEL | 050704Y2-11 | 1143.6 | 1143 | 1485 | 100 | 4 | 269 |
| 166 | NRVLLELNS | 050704Y2-79 | 1057.5 | 1057 | 1285 | 81.3 | 3 | 190 |
| 167 | VLLELNSAD | 050704Y1-30 | 973.5 | 973 | 1087 | 92 | 4.3 | 364 |
| 168 | LELNSADLD | 050704Y1-31 | 989.5 | 988 | 1102 | 91.7 | 5 | 416 |
| 169 | LNSADLDCD | 050704Y1-32 | 964.5 | 964 | 1078 | 80.6 | 4.2 | 314 |
| 170 | SADLDCDPI | 050704Y1-66 | 947.6 | 947 | 1061 | 90.8 | 3.8 | 325 |
| 171 | DLDCDPILP | 220704S-52 | 1000.3 | 999 | 1113 | 96.2 | 4.2 | 363 |

TABLE 1-continued

Physical data for 9-mer peptides

| Peptide No (SEQ ID NO:) | Peptide Sequence | Peptide Lot Number | Experimental Molecular Weight (mg/mmole) | Theoretical (Manoisotopic) Molecular Weight (mg/mmole) | Theoretical Molecular Weight + TFA[1] (mg/mmole) | Purity (%) | Peptide Mass (mg) | DMSO Volume (μl) |
|---|---|---|---|---|---|---|---|---|
| 172 | DCDPILPPS | 220704S-58 | 956.3 | 955 | 1069 | 81.2 | 5 | 380 |
| 173 | DPILPPSLQ | 050704Y2-49 | 979.7 | 979 | 1093 | 97.7 | 4.1 | 366 |
| 174 | ILPPSLQTS | 050704Y2-81 | 955.6 | 955 | 1069 | 96.9 | 3 | 272 |
| 175 | PPSLQTSYV | 050704Y3-7 | 991.5 | 991 | 1105 | 91.4 | 3.6 | 298 |
| 176 | SLQTSYVFL | 050704Y2-12 | 1057.6 | 1057 | 1171 | 83.6 | 3 | 214 |
| 177 | QTSYVFLGI | 050704Y1-67 | 1027.6 | 1027 | 1141 | 80.5 | 4.3 | 303 |
| 178 | SYVFLGIVL | 050704Y2-13 | 1010.7 | 1010 | 1124 | 80.1 | 5 | 356 |
| 179 | VFLGIVLAL | 050704Y2-14 | 944.5 | 944 | 1058 | 81.2 | 4.8 | 368 |
| 180 | LGIVLALIG | 050704Y1-57 | 868.7 | 868 | 982 | 85 | 4.1 | 355 |
| 181 | IVLALIGAI | 050704Y1-68 | 882.7 | 882 | 996 | 85.6 | 5 | 430 |
| 182 | LALIGAIFL | 050704Y2-15 | 930.5 | 930 | 1044 | 89.2 | 4.9 | 419 |
| 183 | LIGAIFLLV | 050704Y3-8 | 958.5 | 958 | 1072 | 87.3 | 4.2 | 342 |
| 184 | GAIFLLVLY | 050704Y3-11 | 1008.5 | 1008 | 1122 | 80 | 3.7 | 264 |
| 185 | IFLLVLYLN | 080704Y2-29 | 1107.6 | 1107 | 1221 | 80 | 4.2 | 275 |
| 186 | LLVLYLNRK | 050704Y1-72 | 1131.7 | 1131 | 1473 | 80.8 | 3.6 | 197 |
| 187 | VLYLNRKGI | 050704Y1-69 | 1075.5 | 1075 | 1417 | 93.8 | 4.4 | 291 |
| 188 | YLNRKGIKK | 050704Y1-73 | 1119.7 | 1119 | 1689 | 92.4 | 3.1 | 170 |
| 189 | NRKGIKKWM | 050704Y2-19 | 1160.7 | 1160 | 1730 | 91 | 5 | 263 |
| 190 | KGIKKWMHN | 050704Y2-30 | 1141.6 | 1141 | 1711 | 84.6 | 3.8 | 188 |
| 191 | IKKWMHNIR | 130704Y3-71 | 1225.7 | 1225 | 1795 | 85.7 | 5 | 239 |
| 192 | KWMHNIRDA | 220704S-35 | 1170.4 | 1170 | 1626 | 93 | 4.2 | 240 |
| 193 | MHNIRDACR | 050704Y2-63 | 1114.6 | 1115 | 1571 | 84.3 | 3 | 161 |
| 194 | NIRDACRDH | 050704Y1-62 | 1098.9 | 1098 | 1554 | 83.8 | 4.9 | 264 |
| 195 | RDACRDHME | 130704Y3-72 | 1132.3 | 1131 | 1587 | 93.1 | 5 | 293 |
| 196 | ACRDHMEGY | 050704Y3-12 | 1080.4 | 1080 | 1422 | 88 | 3.4 | 210 |
| 197 | RDHMEGYHY | 050704Y3-13 | 1207.4 | 1206 | 1662 | 83.1 | 3.1 | 155 |
| 198 | HMEGYHYRY | 050704Y3-14 | 1255.5 | 1255 | 1711 | 91.5 | 4.6 | 246 |
| 199 | EGYHYRYEI | 050704Y1-70 | 1229.3 | 1229 | 1571 | 80.4 | 3.2 | 164 |
| 200 | YHYRYEINA | 050704Y1-22 | 1229.3 | 1228 | 1570 | 89.8 | 4.3 | 246 |
| 201 | YRYEINADP | 130704Y3-73 | 1140.5 | 1140 | 1368 | 80.1 | 3 | 176 |
| 202 | YEINADPRL | 220704S-42 | 1090.4 | 1090 | 1318 | 87 | 4.2 | 277 |
| 203 | INADPRLTN | 050704Y2-31 | 1013.5 | 1013 | 1241 | 89.8 | 4.3 | 311 |
| 204 | ADPRLTNLS | 050704Y2-82 | 986.5 | 986 | 1214 | 80.4 | 3.3 | 219 |
| 205 | PRLTNLSSN | 050704Y2-32 | 1001.6 | 1001 | 1229 | 90.8 | 3.5 | 259 |
| 206 | LTNLSSNSD | 050704Y1-33 | 950.5 | 949 | 1063 | 80.4 | 3.9 | 295 |

[1]Trifluoroacetic acid

TABLE 2

Peptide binding assay results.

| Peptide | | MHC Class I Molecule | | | |
|---|---|---|---|---|---|
| No | Sequence | A*0101 | A*0201 | A*0301 | B*0702 |
| 1 | MPGGCSRGP | 0 | 9 | 0 | 3 |
| 2 | GGCSRGPAA | 0 | 30 | 1 | 18 |
| 3 | CSRGPAAGD | 0 | 3 | 5 | 3 |
| 4 | RGPAAGDGR | 4 | 19 | 10 | 6 |
| 5 | PAAGDGRLR | 4 | 5 | 4 | 5 |
| 6 | AGDGRLRLA | 4 | 30 | 2 | 6 |
| 7 | DGRLRLARL | 0 | 14 | 4 | 41 |
| 8 | RLRLARLAL | 3 | 17 | 43 | 46 |
| 9 | RLARLALVL | 2 | 65 | 48 | 84 |
| 10 | ARLALVLLG | 0 | 26 | 1 | 10 |
| 11 | LALVLLGWV | 2 | 42 | 0 | 2 |
| 12 | LVLLGWVSS | 5 | 34 | 3 | 7 |
| 13 | LLGWVSSSS | 6 | 71 | 10 | 8 |
| 14 | GWVSSSSPT | 4 | 20 | 0 | 2 |
| 15 | VSSSSPTSS | 3 | 9 | 2 | 2 |
| 16 | SSSPTSSAS | 4 | 7 | 2 | 8 |
| 17 | SPTSSASSF | 2 | 4 | 0 | 62 |
| 18 | TSSASSFSS | 3 | 22 | 0 | 11 |
| 19 | SASSFSSSA | 5 | 48 | 0 | 10 |
| 20 | SSFSSSAPF | 8 | 31 | 4 | 12 |
| 21 | FSSSAPFLA | 32 | 77 | 1 | 6 |
| 22 | SSAPFLASA | 6 | 85 | 1 | 7 |
| 23 | APFLASAVS | 1 | 15 | 0 | 37 |
| 24 | FLASAVSAQ | 2 | 58 | 0 | 1 |
| 25 | ASAVSAQPP | 2 | 5 | 0 | 0 |
| 26 | AVSAQPPLP | 1 | 21 | 0 | 0 |
| 27 | SAQPPLPDQ | 2 | 13 | 0 | 3 |
| 28 | QPPLPDQCP | 6 | 5 | 1 | 3 |
| 29 | PLPDQCPAL | 6 | 23 | 0 | 9 |
| 30 | PDQCPALCE | 5 | 3 | 0 | 1 |
| 31 | QCPALCECS | 3 | 2 | 0 | 0 |
| 32 | PALCECSEA | 4 | 19 | 0 | 0 |
| 33 | LCECSEAAR | 3 | 8 | 0 | 0 |
| 34 | ECSEAARTV | 2 | 4 | 0 | 0 |
| 35 | SEAARTVKC | 5 | 1 | 0 | 0 |
| 36 | AARTVKCVN | 7 | 16 | 1 | 24 |
| 37 | RTVKCVNRN | 7 | 12 | 12 | 3 |
| 38 | VKCVNRNLT | 6 | 3 | 0 | 2 |
| 39 | CVNRNLTEV | 2 | 22 | 0 | 34 |
| 40 | NRNLTEVPT | 1 | 6 | 0 | 5 |
| 41 | NLTEVPTDL | 1 | 55 | 0 | 3 |
| 42 | TEVPTDLPA | 3 | 7 | 0 | 0 |
| 43 | VPTDLPAYV | 33 | 29 | 0 | 11 |
| 44 | TDLPAYVRN | 7 | 3 | 1 | 2 |
| 45 | LPAYVRNLF | 7 | 14 | 2 | 90 |
| 46 | AYVRNLFLT | 8 | 32 | 1 | 3 |
| 47 | VRNLFLTGN | 0 | 5 | 0 | 3 |
| 48 | NLFLTGNQL | 2 | 59 | 0 | 9 |
| 49 | FLTGNQLAV | 4 | 90 | 3 | 6 |
| 50 | TGNQLAVLP | 6 | 18 | 2 | 6 |
| 51 | NQLAVLPAG | 6 | 65 | 3 | 9 |
| 52 | LAVLPAGAF | 6 | 29 | 9 | 37 |
| 53 | VLPAGAFAR | 1 | 20 | 51 | 1 |
| 54 | PAGAFARRP | 2 | 4 | 3 | 7 |
| 55 | GAFARRPPL | 0 | 41 | 3 | 91 |
| 56 | FARRPPLAE | 1 | 29 | 5 | 6 |
| 57 | RRPPLAELA | 2 | 11 | 2 | 9 |
| 58 | PLAELAAL | 6 | 19 | 4 | 33 |
| 59 | LAELAALNL | 15 | 63 | 3 | 16 |
| 60 | ELAALNLSG | 5 | 26 | 2 | 7 |
| 61 | AALNLSGSR | 3 | 6 | 13 | 3 |
| 62 | LNLSGSRLD | 2 | 7 | 2 | 7 |
| 63 | LSGSRLDEV | 5 | 45 | 1 | 25 |
| 64 | GSRLDEVRA | 2 | 25 | 2 | 5 |
| 65 | RLDEVRAGA | 4 | 69 | 17 | 32 |
| 66 | DEVRAGAFE | 6 | 9 | 7 | 12 |
| 67 | VRAGAFEHL | 7 | 12 | 3 | 52 |
| 68 | AGAFEHLPS | 6 | 10 | 3 | 7 |
| 69 | AFEHLPSLR | 1 | 11 | 11 | 0 |
| 70 | EHLPSLRQL | 0 | 16 | 1 | 12 |
| 71 | LPSLRQLDL | 0 | 27 | 0 | 82 |
| 72 | SLRQLDLSH | 0 | 6 | 11 | 13 |
| 73 | RQLDLSHNP | 2 | 8 | 2 | 4 |
| 74 | LDLSHNPLA | 6 | 40 | 3 | 7 |

TABLE 2-continued

Peptide binding assay results.

| Peptide | | MHC Class I Molecule | | | |
|---|---|---|---|---|---|
| No | Sequence | A*0101 | A*0201 | A*0301 | B*0702 |
| 75 | LSHNPLADL | 6 | 33 | 3 | 13 |
| 76 | HNPLADLSP | 5 | 7 | 3 | 5 |
| 77 | PLADLSPFA | 1 | 67 | 0 | 10 |
| 78 | ADLSPFAFS | 1 | 33 | 3 | 8 |
| 79 | LSPFAFSGS | 1 | 41 | 0 | 8 |
| 80 | PFAFSGSNA | 0 | 13 | 3 | 7 |
| 81 | AFSGSNASV | 2 | 55 | 2 | 14 |
| 82 | SGSNASVSA | 5 | 15 | 3 | 11 |
| 83 | SNASVSAPS | 6 | 21 | 3 | 10 |
| 84 | ASVSAPSPL | 6 | 47 | 3 | 20 |
| 85 | VSAPSPLVE | 3 | 13 | 7 | 3 |
| 86 | APSPLVELI | 2 | 8 | 1 | 26 |
| 87 | SPLVELILN | 1 | 25 | 0 | 2 |
| 88 | LVELILNHI | 0 | 54 | 0 | 0 |
| 89 | ELILNHIVP | 3 | 30 | 1 | 2 |
| 90 | ILNHIVPPE | 5 | 63 | 4 | 7 |
| 91 | NHIVPPEDE | 6 | 11 | 3 | 5 |
| 92 | IVPPEDERQ | 6 | 12 | 3 | 3 |
| 93 | PPEDERQNR | 0 | 2 | 0 | 0 |
| 94 | EDERQNRSF | 0 | 2 | 4 | 4 |
| 95 | ERQNRSFEG | 0 | 1 | 1 | 1 |
| 96 | QNRSFEGMV | 1 | 18 | 2 | 8 |
| 97 | RSFEGMVVA | 2 | 86 | 8 | 4 |
| 98 | FEGMVVAAL | 0 | 28 | 2 | 2 |
| 99 | GMVVAALLA | 0 | 71 | 0 | 0 |
| 100 | VVAALLAGR | 9 | 11 | 49 | 7 |
| 101 | AALLAGRAL | 1 | 38 | 0 | 59 |
| 102 | LLAGRALQG | 2 | 43 | 3 | 5 |
| 103 | AGRALQGLR | 0 | 2 | 2 | 1 |
| 104 | RALQGLRRL | 4 | 74 | 42 | 79 |
| 105 | LQGLRRLEL | 3 | 38 | 2 | 89 |
| 106 | GLRRLELAS | 2 | 37 | 6 | 5 |
| 107 | RRLELASNH | 0 | 5 | 3 | 3 |
| 108 | LELASNHFL | 5 | 51 | 2 | 5 |
| 109 | LASNHFLYL | 26 | 78 | 18 | 49 |
| 110 | SNHFLYLPR | 0 | 18 | 16 | 5 |
| 111 | HFLYLPRDV | 1 | 54 | 1 | 2 |
| 112 | LYLPRDVLA | 4 | 48 | 3 | 7 |
| 113 | LPRDVLAQL | 3 | 10 | 3 | 79 |
| 114 | RDVLAQLPS | 1 | 15 | 3 | 4 |
| 115 | VLAQLPSLR | 0 | 50 | 55 | 0 |
| 116 | AQLPSLRHL | 0 | 74 | 3 | 8 |
| 117 | LPSLRHLDL | 0 | 16 | 1 | 96 |
| 118 | SLRHLDLSN | 0 | 25 | 2 | 5 |
| 119 | RHLDLSNNS | 0 | 15 | 1 | 1 |
| 120 | LDLSNNSLV | 7 | 42 | 3 | 3 |
| 121 | LSNNSLVSL | 4 | 57 | 3 | 19 |
| 122 | NNSLVSLTY | 8 | 12 | 4 | 0 |
| 123 | SLVSLTYVS | 0 | 67 | 0 | 0 |
| 124 | VSLTYVSFR | 1 | 7 | 39 | 0 |
| 125 | LTYVSFRNL | 28 | 25 | 20 | 58 |
| 126 | YVSFRNLTH | 12 | 7 | 36 | 43 |
| 127 | SFRNLTHLE | 1 | 1 | 1 | 0 |
| 128 | RNLTHLESL | 3 | 45 | 3 | 13 |
| 129 | LTHLESLHL | 12 | 69 | 3 | 6 |
| 130 | HLESLHLED | 4 | 3 | 2 | 2 |
| 131 | ESLHLEDNA | 2 | 8 | 0 | 0 |
| 132 | LHLEDNALK | 4 | 4 | 5 | 0 |
| 133 | LEDNALKVL | 2 | 21 | 0 | 0 |
| 134 | DNALKVLHN | 1 | 5 | 0 | 0 |
| 135 | ALKVLHNGT | 3 | 33 | 1 | 0 |
| 136 | KVLHNGTLA | 5 | 50 | 6 | 4 |
| 137 | LHNGTLAEL | 4 | 40 | 2 | 16 |
| 138 | NGTLAELQG | 3 | 9 | 3 | 0 |
| 139 | TLAELQGLP | 0 | 50 | 1 | 5 |
| 140 | AELQGLPHI | 0 | 9 | 1 | 0 |
| 141 | LQGLPHIRV | 0 | 82 | 2 | 2 |
| 142 | GLPHIRVFL | 0 | 101 | 18 | 33 |
| 143 | PHIRVFLDN | 0 | 2 | 3 | 10 |
| 144 | IRVFLDNNP | 0 | 4 | 3 | 5 |
| 145 | VFLDNNPWV | 0 | 70 | 1 | 0 |
| 146 | LDNNPWVCD | 0 | 0 | 2 | 3 |
| 147 | NNPWVCDCH | 0 | 0 | 16 | 4 |
| 148 | PWVCDCHMA | 0 | 0 | 0 | 0 |

TABLE 2-continued

Peptide binding assay results.

| Peptide | | MHC Class I Molecule | | | |
|---|---|---|---|---|---|
| No | Sequence | A*0101 | A*0201 | A*0301 | B*0702 |
| 149 | VCDCHMADM | 0 | 21 | 2 | 4 |
| 150 | DCHMADMVT | 0 | 7 | 3 | 5 |
| 151 | HMADMVTWL | 0 | 95 | 5 | 7 |
| 152 | ADMVTWLKE | 0 | 6 | 4 | 8 |
| 153 | MVTWLKETE | 0 | 17 | 3 | 3 |
| 154 | TWLKETEVV | 0 | 29 | 4 | 5 |
| 155 | LKETEVVQG | 0 | 3 | 4 | 3 |
| 156 | ETEVVQGKD | 0 | 1 | 3 | 1 |
| 157 | EVVQGKDRL | 0 | 16 | 3 | 3 |
| 158 | VQGKDRLTC | 0 | 4 | 6 | 6 |
| 159 | GKDRLTCAY | 3 | 6 | 6 | 4 |
| 160 | DRLTCAYPE | 0 | 6 | 5 | 3 |
| 161 | LTCAYPEKM | 16 | 40 | 8 | 5 |
| 162 | CAYPEKMRN | 0 | 11 | 4 | 3 |
| 163 | YPEKMRNRV | 0 | 6 | 4 | 70 |
| 164 | EKMRNRVLL | 0 | 15 | 4 | 12 |
| 165 | MRNRVLLEL | 0 | 6 | 4 | 13 |
| 166 | NRVLLELNS | 0 | 16 | 6 | 5 |
| 167 | VLLELNSAD | 0 | 48 | 6 | 7 |
| 168 | LELNSADLD | 0 | 3 | 5 | 3 |
| 169 | LNSADLDCD | 0 | 0 | 3 | 0 |
| 170 | SADLDCDPI | 0 | 4 | 4 | 3 |
| 171 | DLDCDPILP | 0 | 0 | 4 | 3 |
| 172 | DCDPILPPS | 0 | 0 | 3 | 0 |
| 173 | DPILPPSLQ | 0 | 7 | 4 | 0 |
| 174 | ILPPSLQTS | 0 | 81 | 6 | 3 |
| 175 | PPSLQTSYV | 0 | 17 | 6 | 13 |
| 176 | SLQTSYVFL | 0 | 59 | 12 | 4 |
| 177 | QTSYVFLGI | 25 | 61 | 5 | 8 |
| 178 | SYVFLGIVL | 0 | 30 | 3 | 17 |
| 179 | VFLGIVLAL | 0 | 62 | 3 | 1 |
| 180 | LGIVLALIG | 0 | 10 | 1 | 0 |
| 181 | IVLALIGAI | 0 | 67 | 4 | 1 |
| 182 | LALIGAIFL | 0 | 55 | 5 | 38 |
| 183 | LIGAIFLLV | 0 | 76 | 28 | 1 |
| 184 | GAIFLLVLY | 0 | 5 | 5 | 0 |
| 185 | IFLLVLYLN | 0 | 8 | 0 | 2 |
| 186 | LLVLYLNRK | 13 | 16 | 54 | 5 |
| 187 | VLYLNRKGI | 1 | 58 | 31 | 35 |
| 188 | YLNRKGIKK | 4 | 31 | 93 | 18 |
| 189 | NRKGIKKWM | 6 | 28 | 3 | 9 |
| 190 | KGIKKWMHN | 3 | 14 | 3 | 6 |
| 191 | IKKWMHNIR | 0 | 28 | 5 | 1 |
| 192 | KWMHNIRDA | 0 | 23 | 2 | 3 |
| 193 | MHNIRDACR | 0 | 19 | 8 | 3 |
| 194 | NIRDACRDH | 0 | 1 | 0 | 6 |
| 195 | RDACRDHME | 0 | 24 | 1 | 3 |
| 196 | ACRDHMEGY | 3 | 8 | 4 | 7 |
| 197 | RDHMEGYHY | 11 | 6 | 3 | 5 |
| 198 | HMEGYHYRY | 114 | 47 | 64 | 5 |
| 199 | EGYHYRYEI | 0 | 9 | 0 | 4 |
| 200 | YHYRYEINA | 0 | 7 | 1 | 5 |
| 201 | YRYEINADP | 0 | 0 | 1 | 3 |
| 202 | YEINADPRL | 0 | 39 | 0 | 3 |
| 203 | INADPRLTN | 0 | 3 | 1 | 4 |
| 204 | ADPRLTNLS | 2 | 6 | 3 | 23 |
| 205 | PRLTNLSSN | 2 | 8 | 2 | 11 |
| 206 | LTNLSSNSD | 2 | 19 | 1 | 6 |

TABLE 3

Off-rate assay results.

| | | MHC Class I Molecule Half life [(t1/2 (Hours)] | | | | | | | |
|---|---|---|---|---|---|---|---|---|---|
| Peptide | | A*0101 | | A*0201 | | A*0301 | | B*0701 | |
| No | Sequence | t1/2 | R² | t1/2 | R² | t1/2 | R² | t1/2 | R² |
| 2 | GGCSRGPAA | | | 0.5 | 0.66 | | | 1.3 | 0.22 |
| 4 | RGPAAGDGR | | | 1.2 | 0.93 | | | | |
| 6 | AGDGRLRLA | | | 0.1 | 0.94 | | | | |
| 7 | DGRLRLARL | | | | | | | 2.6 | 0.15 |
| 8 | RLRLARLAL | | | 7.2 | 0.59 | 0.2 | 0.95 | 3.1 | 0.66 |
| 9 | RLARLALVL | | | 15.9 | 0.35 | 0.3 | 0.99 | 2 | 0.09 |
| 10 | ARLALVLLG | | | 1.2 | 0.7 | | | | |
| 11 | LALVLLGWV | | | 1.6 | 0.93 | | | | |
| 12 | LVLLGWVSS | | | 2.6 | 0.92 | | | | |
| 13 | LLGWVSSSS | | | 1.8 | 0.99 | | | | |
| 14 | GWVSSSSPT | | | 1 | 0.94 | | | | |
| 17 | SPTSSASSF | | | | | | | 2.6 | 0.23 |
| 18 | TSSASSFSS | | | 0.7 | 0.97 | | | | |
| 19 | SASSFSSSA | | | 0.2 | 0.91 | | | | |
| 20 | SSFSSSAPF | | | 0.4 | 0.65 | | | | |
| 21 | FSSSAPFLA | 0.2 | 0.88 | 0.3 | 0.95 | | | | |
| 22 | SSAPFLASA | | | 1.3 | 0.98 | | | | |
| 23 | APFLASAVS | | | 1.6 | 0.67 | | | 2.6 | 0.02 |
| 24 | FLASAVSAQ | | | 0.7 | 0.97 | | | | |
| 26 | AVSAQPPLP | | | 1.7 | 0.89 | | | | |
| 29 | PLPDQCPAL | | | 2.8 | 0.77 | | | | |
| 32 | PALCECSEA | | | 2.2 | 0.81 | | | | |
| 36 | AARTVKCVN | | | 11.1 | 0.31 | | | 1.4 | 0.69 |
| 39 | CVNRNLTEV | | | 1.3 | 0.89 | | | 0.7 | 0.44 |
| 41 | NLTEVPTDL | | | 1.4 | 0.98 | | | | |
| 43 | VPTDLPAYV | 1.8 | 0.87 | 1.1 | 0.91 | | | | |
| 45 | LPAYVRNLF | | | | | | | 1.7 | 0.95 |
| 46 | AYVRNLFLT | | | 6.8 | 0.77 | | | | |
| 48 | NLFLTGNQL | | | 0.5 | 0.98 | | | | |
| 49 | FLTGNQLAV | | | 10.6 | 0.74 | | | | |
| 50 | TGNQLAVLP | | | 6.7 | 0.08 | | | | |
| 51 | NQLAVLPAG | | | 3.2 | 0.92 | | | | |
| 52 | LAVLPAGAF | | | 3.6 | 0.63 | | | 0.3 | 0.84 |
| 53 | VLPAGAFAR | | | 2.2 | 0.9 | 0.5 | 0.58 | | |
| 55 | GAFARRPPL | | | 1.9 | 0.98 | | | 1.3 | 0.91 |
| 56 | FARRPPLAE | | | 0.3 | 0.94 | | | | |
| 58 | PPLAELAAL | | | 4.6 | 0.49 | | | 3 | 0.11 |
| 59 | LAELAALNL | 2.5 | 0.25 | 13.1 | 0.33 | | | 3.2 | 0.42 |
| 60 | ELAALNLSG | | | 1.6 | 0.64 | | | | |
| 63 | LSGSRLDEV | | | 0.5 | 0.9 | | | 2.9 | 0.11 |
| 64 | GSRLDEVRA | | | 1.9 | 0.94 | | | | |
| 65 | RLDEVRAGA | | | 9.7 | 0.59 | 0.2 | 0.94 | 0.2 | 0.75 |
| 67 | VRAGAFEHL | | | | | | | 0.4 | 0.44 |
| 70 | EHLPSLRQL | | | 1.4 | 0.84 | | | | |
| 71 | LPSLRQLDL | | | 1.4 | 0.89 | | | 3.1 | 0.88 |
| 74 | LDLSHNPLA | | | 5.4 | 0.79 | | | | |
| 75 | LSHNPLADL | | | 1.3 | 0.72 | | | | |
| 77 | PLADLSPFA | | | 4.8 | 0.93 | | | | |
| 78 | ADLSPFAFS | | | 2.5 | 0.91 | | | | |
| 79 | LSPFAFSGS | | | 0.4 | 0.85 | | | | |
| 81 | AFSGSNASV | | | 0.7 | 0.95 | | | | |
| 83 | SNASVSAPS | | | 15.8 | 0.02 | | | | |
| 84 | ASVSAPSPL | | | 0.4 | 0.87 | | | 0.1 | 0.67 |
| 86 | APSPLVELI | | | | | | | 1.6 | 0.26 |
| 87 | SPLVELILN | | | 2.4 | 0.63 | | | | |
| 88 | LVELILNHI | | | 0.3 | 0.84 | | | | |
| 89 | ELILNHIVP | | | 1.1 | 0.78 | | | | |
| 90 | ILNHIVPPE | | | 13 | 0.46 | | | | |
| 96 | QNRSFEGMV | | | 2.4 | 0.87 | | | | |
| 97 | RSFEGMVVA | | | 0.7 | 0.99 | | | | |
| 98 | FEGMVVAAL | | | 1.1 | 0.96 | | | | |
| 99 | GMVVAALLA | | | 1.8 | 0.93 | | | | |
| 100 | VVAALLAGR | | | | | 8.1 | 0.01 | | |
| 101 | AALLAGRAL | | | 1.9 | 0.79 | | | 1.6 | 0.1 |
| 102 | LLAGRALQG | | | 1.4 | 0.9 | | | | |
| 104 | RALQGLRRL | | | 0.6 | 0.95 | 0.4 | 0.61 | 0.1 | 0.68 |
| 105 | LQGLRRLEL | | | 2.1 | 0.77 | | | 0.2 | 0.68 |
| 106 | GLRRLELAS | | | 0.4 | 0.93 | | | | |
| 108 | LELASNHFL | | | 1.4 | 0.95 | | | | |
| 109 | LASNHFLYL | 3 | 0.15 | 1.2 | 0.97 | 3.6 | 0.96 | 0.2 | 0.86 |
| 110 | SNHFLYLPR | | | 1.2 | 0.85 | 0.9 | 0.94 | | |

TABLE 3-continued

Off-rate assay results.

| | | MHC Class I Molecule Half life [(t1/2 (Hours)] | | | | | | |
|---|---|---|---|---|---|---|---|---|
| Peptide | | A*0101 | | A*0201 | | A*0301 | | B*0701 | |
| No | Sequence | t1/2 | $R^2$ | t1/2 | $R^2$ | t1/2 | $R^2$ | t1/2 | $R^2$ |
| 111 | HFLYLPRDV | | | 2.9 | 0.82 | | | | |
| 112 | LYLPRDVLA | | | 3.4 | 0.66 | | | | |
| 113 | LPRDVLAQL | | | | | | | 3.3 | 0.87 |
| 115 | VLAQLPSLR | | | 0.6 | 0.77 | 0.2 | 0.97 | | |
| 116 | AQLPSLRHL | | | 0.7 | 0.95 | | | | |
| 117 | LPSLRHLDL | | | 0.7 | 0.81 | | | 3 | 0.81 |
| 118 | SLRHLDLSN | | | 0.4 | 0.93 | | | | |
| 119 | RHLDLSNNS | | | 1.1 | 0.82 | | | | |
| 120 | LDLSNNSLV | | | 3.4 | 0.76 | | | | |
| 121 | LSNNSLVSL | | | 0.8 | 0.75 | | | 4.1 | 0.38 |
| 123 | SLVSLTYVS | | | 0.9 | 0.96 | | | | |
| 124 | VSLTYVSFR | | | | | 0.2 | 0.95 | | |
| 125 | LTYVSFRNL | 3.9 | 0.12 | 8.1 | 0.2 | 0.7 | 0.99 | 6 | 0.73 |
| 126 | YVSFRNLTH | | | | | 0.9 | 0.95 | 2.6 | 0 |
| 128 | RNLTHLESL | | | 0.9 | 0.83 | | | | |
| 129 | LTHLESLHL | | | 1 | 0.8 | | | | |
| 133 | LEDNALKVL | | | 5.7 | 0.57 | | | | |
| 135 | ALKVLHNGT | | | 1.5 | 0.84 | | | | |
| 136 | KVLHNGTLA | | | 2.2 | 0.78 | | | | |
| 137 | LHNGTLAEL | | | 4.2 | 0.58 | | | 0.3 | 0.95 |
| 139 | TLAELQGLP | | | 0.7 | 0.89 | | | | |
| 141 | LQGLPHIRV | | | 1.1 | 0.87 | | | | |
| 142 | GLPHIRVFL | | | 12.9 | 0.42 | 6 | 0.64 | 0.9 | 0.82 |
| 145 | VFLDNNPWV | | | 1.2 | 0.93 | | | | |
| 147 | NNPWVCDCH | | | | | 0.2 | 0.96 | | |
| 149 | VCDCHMADM | | | 1.4 | 0.85 | | | | |
| 151 | HMADMVTWL | | | 7.9 | 0.84 | | | | |
| 153 | MVTWLKETE | | | 1.2 | 0.75 | | | | |
| 154 | TWLKETEVV | | | 6.4 | 0.75 | | | | |
| 157 | EVVQGKDRL | | | 11 | 0.11 | | | | |
| 161 | LTCAYPEKM | 3.7 | 0.18 | 3.1 | 0.72 | | | | |
| 163 | YPEKMRNRV | | | | | | | 1.9 | 0.76 |
| 164 | EKMRNRVLL | | | 7 | 0.3 | | | | |
| 166 | NRVLLELNS | | | 1.3 | 0.63 | | | | |
| 167 | VLLELNSAD | | | 0.8 | 0.81 | | | | |
| 174 | ILPPSLQTS | | | 5 | 0.93 | | | | |
| 175 | PPSLQTSYV | | | 12.7 | 0.08 | | | | |
| 176 | SLQTSYVFL | | | 12.4 | 0.33 | | | | |
| 177 | QTSYVFLGI | 0.2 | 0.76 | 0.6 | 0.87 | | | | |
| 178 | SYVFLGIVL | | | 5.1 | 0.78 | | | 0.9 | 0.69 |
| 179 | VFLGIVLAL | | | 15 | 0.26 | | | | |
| 181 | IVLALIGAI | | | 1.3 | 0.95 | | | | |
| 182 | LALIGAIFL | | | 3.2 | 0.9 | | | 0.5 | 0.94 |
| 183 | LIGAIFLLV | | | 19.4 | 0.02 | 0.5 | 0.84 | | |
| 186 | LLVLYLNRK | | | 21.4 | 0 | 3.2 | 0.77 | | |
| 187 | VLYLNRKGI | | | 0.6 | 0.83 | 1.4 | 0.37 | 2.9 | 0.04 |
| 188 | YLNRKGIKK | | | 6.5 | 0.57 | 0.7 | 0.9 | 3.3 | 0.79 |
| 189 | NRKGIKKWM | | | 10 | 0.31 | | | | |
| 191 | IKKWMHNIR | | | 14.6 | 0.05 | | | | |
| 192 | KWMHNIRDA | | | 1.4 | 0.85 | | | | |
| 193 | MHNIRDACR | | | 5.3 | 0.6 | | | | |
| 195 | RDACRDHME | | | 3 | 0.68 | | | | |
| 198 | HMEGYHYRY | 1.3 | 0.97 | 6.3 | 0.74 | 1.7 | 0.88 | | |
| 202 | YEINADPRL | | | 0.6 | 0.8 | | | | |
| 204 | ADPRLTNLS | | | | | | | 3.1 | 0.35 |
| 206 | LTNLSSNSD | | | 0.7 | 0.71 | | | | |

TABLE 4

Affinity assay results.

| | | MHC Class I Molecule Affinity | | | | | | | |
|---|---|---|---|---|---|---|---|---|---|
| | Peptide | A*0101 | | A*0201 | | A*0301 | | B*0701 | |
| No | Sequence | ED50 | $R^2$ | ED50 | $R^2$ | ED50 | $R^2$ | ED50 | $R^2$ |
| 2 | GGCSRGPAA | | | 3.00E−05 | 0.99 | | | 3.00E−05 | 0.4 |
| 4 | RGPAAGDGR | | | 4.00E−05 | 0.95 | | | | |
| 6 | AGDGRLRLA | | | 2.00E−05 | 1 | | | | |
| 7 | DGRLRLARL | | | | | | | 3.00E−06 | 0.65 |
| 8 | RLRLARLAL | | | 6.00E−08 | 0.56 | 4.00E−07 | 0.95 | 2.00E−08 | 0.45 |
| 9 | RLARLALVL | | | 9.00E−08 | 0.59 | 3.00E−06 | 0.98 | 7.00E−07 | 0.81 |
| 10 | ARLALVLLG | | | 9.00E−08 | 0.5 | | | | |
| 11 | LALVLLGWV | | | 4.00E−07 | 0.97 | | | | |
| 12 | LVLLGWVSS | | | 1.00E−05 | 1 | | | | |
| 13 | LLGWVSSSS | | | 5.00E−06 | 1 | | | | |
| 14 | GWVSSSPT | | | 1.00E−05 | 0.99 | | | | |
| 17 | SPTSSASSF | | | | | | | 2.00E−06 | 0.93 |
| 18 | TSSASSFSS | | | 2.00E−05 | 0.99 | | | | |
| 19 | SASSFSSSA | | | 2.00E−05 | 0.99 | | | | |
| 20 | SSFSSSAPF | | | 9.00E−06 | 0.97 | | | | |
| 21 | FSSSAPFLA | 2.00E−05 | 1 | 2.00E−06 | 0.99 | | | | |
| 22 | SSAPFLASA | | | 3.00E−07 | 0.95 | | | | |
| 23 | APFLASAVS | | | 2.00E−05 | 0.98 | | | 2.00E−05 | 1 |
| 24 | FLASAVSAQ | | | 5.00E−06 | 0.99 | | | | |
| 26 | AVSAQPPLP | | | 2.00E−05 | 1 | | | | |
| 29 | PLPDQCPAL | | | 8.00E−06 | 0.97 | | | | |
| 32 | PALCECSEA | | | 4.00E−06 | 0.89 | | | | |
| 36 | AARTVKCVN | | | 2.00E−05 | 0.99 | | | 6.00E−05 | 0.98 |
| 39 | CVNRNLTEV | | | 8.00E−06 | 0.98 | | | 2.00E−05 | 0.99 |
| 41 | NLTEVPTDL | | | 6.00E−07 | 0.88 | | | | |
| 43 | VPTDLPAYV | 2.00E−05 | 0.97 | 2.00E−05 | 1 | | | | |
| 45 | LPAYVRNLF | | | | | | | 2.00E−06 | 0.96 |
| 46 | AYVRNLFLT | | | 8.00E−06 | 0.99 | | | | |
| 48 | NLFLTGNQL | | | 2.00E−06 | 0.98 | | | | |
| 49 | FLTGNQLAV | | | 1.00E−06 | 0.99 | | | | |
| 50 | TGNQLAVLP | | | 5.00E−05 | 0.99 | | | | |
| 51 | NQLAVLPAG | | | 4.00E−06 | 0.98 | | | | |
| 52 | LAVLPAGAF | | | 1.00E−05 | 0.99 | | | 2.00E−05 | 0.99 |
| 53 | VLPAGAFAR | | | 2.00E−05 | 0.99 | 7.00E−06 | 1 | | |
| 55 | GAFARRPPL | | | 8.00E−07 | 0.84 | | | 1.00E−06 | 0.9 |
| 56 | FARRPPLAE | | | 2.00E−05 | 1 | | | | |
| 58 | PPLAELAAL | | | 4.00E−05 | 0.97 | | | 3.00E−05 | 0.99 |
| 59 | LAELAALNL | | | 2.00E−05 | 0.94 | | | 2.00E−05 | 1 |
| 60 | ELAALNLSG | | | 2.00E−06 | 0.98 | | | | |
| 63 | LSGSRLDEV | | | 9.00E−06 | 0.99 | | | 3.00E−05 | 1 |
| 64 | GSRLDEVRA | | | 2.00E−06 | 0.79 | | | | |
| 65 | RLDEVRAGA | | | 2.00E−05 | 0.75 | 4.00E−05 | 1 | 2.00E−05 | 1 |
| 67 | VRAGAFEHL | | | | | | | 1.00E−05 | 0.99 |
| 70 | EHLPSLRQL | | | 2.00E−05 | 0.67 | | | | |
| 71 | LPSLRQLDL | | | 5.00E−06 | 0.96 | | | 3.00E−06 | 0.97 |
| 74 | LDLSHNPLA | | | 1.00E−05 | 0.98 | | | | |
| 75 | LSHNPLADL | | | 1.00E−06 | 1 | | | | |
| 77 | PLADLSPFA | | | 2.00E−06 | 0.99 | | | | |
| 78 | ADLSPFAFS | | | 2.00E−05 | 0.99 | | | | |
| 79 | LSPFAFSGS | | | 1.00E−05 | 0.99 | | | | |
| 81 | AFSGSNASV | | | 7.00E−06 | 0.99 | | | | |
| 83 | SNASVSAPS | | | 3.00E−05 | 0.99 | | | | |
| 84 | ASVSAPSPL | | | 9.00E−06 | 1 | | | 3.00E−06 | 0.99 |
| 86 | APSPLVELI | | | | | | | 2.00E−05 | 1 |
| 87 | SPLVELILN | | | 6.00E−05 | 0.99 | | | | |
| 88 | LVELILNHI | | | 2.00E−06 | 0.96 | | | | |
| 89 | ELILNHIVP | | | 3.00E−05 | 0.98 | | | | |
| 90 | ILNHIVPPE | | | 6.00E−06 | 0.99 | | | | |
| 96 | QNRSFEGMV | | | 2.00E−05 | 1 | | | | |
| 97 | RSFEGMVVA | | | 2.00E−06 | 0.98 | | | | |
| 98 | FEGMVVAAL | | | 1.00E−05 | 0.99 | | | | |
| 99 | GMVVAALLA | | | 6.00E−07 | 0.94 | | | | |
| 100 | VVAALLAGR | | | | | 1.00E−05 | 1 | | |
| 101 | AALLAGRAL | | | 4.00E−06 | 0.97 | | | 7.00E−06 | 0.99 |
| 102 | LLAGRALQG | | | 2.00E−06 | 0.96 | | | | |
| 104 | RALQGLRRL | | | 3.00E−06 | 0.99 | 2.00E−05 | 1 | 7.00E−06 | 1 |
| 105 | LQGLRRLEL | | | 1.00E−05 | 0.99 | | | 5.00E−06 | 0.99 |
| 106 | GLRRLELAS | | | 1.00E−05 | 0.98 | | | | |
| 108 | LELASNHFL | | | 5.00E−06 | 0.99 | | | | |
| 109 | LASNHFLYL | 2.00E−05 | 0.99 | 6.00E−07 | 0.99 | 3.00E−05 | 0.98 | | |
| 110 | SNHFLYLPR | | | 1.00E−05 | 0.99 | 3.00E−05 | 1 | | |

TABLE 4-continued

Affinity assay results.

| | | MHC Class I Molecule Affinity | | | | | | | |
|---|---|---|---|---|---|---|---|---|---|
| Peptide | | A*0101 | | A*0201 | | A*0301 | | B*0701 | |
| No | Sequence | ED50 | $R^2$ | ED50 | $R^2$ | ED50 | $R^2$ | ED50 | $R^2$ |
| 111 | HFLYLPRDV | | | 1.00E−05 | 0.99 | | | | |
| 112 | LYLPRDVLA | | | 9.00E−06 | 0.99 | | | | |
| 113 | LPRDVLAQL | | | | | | | 1.00E−05 | 0.99 |
| 115 | VLAQLPSLR | | | 1.00E−05 | 1 | 1.00E−05 | 1 | | |
| 116 | AQLPSLRHL | | | 3.00E−06 | 0.98 | | | | |
| 117 | LPSLRHLDL | | | 2.00E−05 | 0.98 | | | 5.00E−06 | 1 |
| 118 | SLRHLDLSN | | | 2.00E−05 | 1 | | | | |
| 119 | RHLDLSNNS | | | 3.00E−05 | 0.98 | | | | |
| 120 | LDLSNNSLV | | | 2.00E−05 | 0.99 | | | | |
| 121 | LSNNSLVSL | | | 1.00E−05 | 1 | | | 2.00E−05 | 0.99 |
| 123 | SLVSLTYVS | | | 3.00E−06 | 0.95 | | | | |
| 124 | VSLTYVSFR | | | | | 1.00E−05 | 0.99 | | |
| 125 | LTYVSFRNL | 3.00E−06 | 0.43 | 4.00E−07 | 0.45 | 3.00E−06 | 0.67 | 3.00E−06 | 0.95 |
| 126 | YVSFRNLTH | | | | | 3.00E−05 | 0.99 | 1.00E−05 | 0.98 |
| 128 | RNLTHLESL | | | 2.00E−05 | 0.99 | | | | |
| 129 | LTHLESLHL | | | 9.00E−06 | 0.99 | | | | |
| 133 | LEDNALKVL | | | 3.00E−05 | 0.99 | | | | |
| 135 | ALKVLHNGT | | | 1.00E−05 | 0.99 | | | | |
| 136 | KVLHNGTLA | | | 2.00E−05 | 1 | | | | |
| 137 | LHNGTLAEL | | | 2.00E−05 | 0.98 | | | 3.00E−05 | 0.99 |
| 139 | TLAELQGLP | | | 1.00E−05 | 1 | | | | |
| 141 | LQGLPHIRV | | | 5.00E−06 | 1 | | | | |
| 142 | GLPHIRVFL | | | 2.00E−07 | 0.95 | 1.00E−05 | 0.99 | 2.00E−05 | 0.99 |
| 145 | VFLDNNPWV | | | 2.00E−06 | 0.99 | | | | |
| 147 | NNPWVCDCH | | | | | 3.00E−06 | 0.93 | | |
| 149 | VCDCHMADM | | | 2.00E−05 | 0.99 | | | | |
| 151 | HMADMVTWL | | | 2.00E−06 | 0.99 | | | | |
| 153 | MVTWLKETE | | | 8.00E−06 | 0.95 | | | | |
| 154 | TWLKETEVV | | | 1.00E−05 | 0.97 | | | | |
| 157 | EVVQGKDRL | | | 2.00E−05 | 0.99 | | | | |
| 161 | LTCAYPEKM | 2.00E−05 | 1 | 1.00E−05 | 0.99 | | | | |
| 163 | YPEKMRNRV | | | | | | | 1.00E−05 | 0.99 |
| 164 | EKMRNRVLL | | | 3.00E−05 | 0.99 | | | | |
| 166 | NRVLLELNS | | | 2.00E−05 | 1 | | | | |
| 167 | VLLELNSAD | | | 5.00E−06 | 0.98 | | | | |
| 174 | ILPPSLQTS | | | 2.00E−06 | 0.99 | | | | |
| 175 | PPSLQTSYV | | | 2.00E−05 | 0.98 | | | | |
| 176 | SLQTSYVFL | | | 6.00E−06 | 0.99 | | | | |
| 177 | QTSYVFLGI | 2.00E−05 | 1 | 2.00E−06 | 0.99 | | | | |
| 178 | SYVFLGIVL | | | 3.00E−05 | 0.95 | | | 1.00E−05 | 0.97 |
| 179 | VFLGIVLAL | | | 4.00E−06 | 0.99 | | | | |
| 181 | IVLALIGAI | | | 2.00E−07 | 0.92 | | | | |
| 182 | LALIGAIFL | | | 1.00E−07 | 0.96 | | | 1.00E−05 | 0.99 |
| 183 | LIGAIFLLV | | | 5.00E−08 | 0.97 | 2.00E−07 | 0.98 | | |
| 186 | LLVLYLNRK | | | 3.0E−06 | 0.76 | 5.00E−07 | 0.91 | | |
| 187 | VLYLNRKGI | | | 1.00E−05 | 1 | 3.00E−05 | 0.98 | 2.00E−05 | 0.99 |
| 188 | YLNRKGIKK | | | 7.00E−06 | 0.98 | 3.00E−06 | 1 | 2.00E−05 | 0.96 |
| 189 | NRKGIKKWM | | | 2.00E−06 | 0.98 | | | | |
| 191 | IKKWMHNIR | | | 4.00E−05 | 0.99 | | | | |
| 192 | KWMHNIRDA | | | 3.00E−05 | 0.99 | | | | |
| 193 | MHNIRDACR | | | 2.00E−05 | 0.99 | | | | |
| 195 | RDACRDHME | | | 4.00E−05 | 0.97 | | | | |
| 198 | HMEGYHYRY | 3.00E−06 | 1 | 3.00E−05 | 0.99 | 2.00E−05 | 1 | | |
| 202 | YEINADPRL | | | 2.00E−05 | 1 | | | | |
| 204 | ADPRLTNLS | | | | | | | 3.00E−05 | 0.99 |
| 206 | LTNLSSNSD | | | 1.00E−05 | 0.98 | | | | |

TABLE 5 iScore results from all peptides tested.

Level of Binding
>0.5
0.25-0.5
<0.25

| No | Peptide Sequence | A*0101 | A*0201 | A*0301 | B*0702 |
|---|---|---|---|---|---|
| 1 | MPGGCSRGP | 0 | 0 | 0 | 0 |
| 2 | GGCSRGPAA | 0 | 0.016 | 0 | 0.012 |
| 3 | CSRGPAAGD | 0 | 0 | 0 | 0 |
| 4 | RGPAAGDGR | 0 | 0.032 | 0 | 0 |
| 5 | PAAGDGRLR | 0 | 0 | 0 | 0 |
| 6 | AGDGRLRLA | 0 | 0.023 | 0 | 0 |
| 7 | DGRLRLARL | 0 | 0 | 0 | 0.038 |
| 8 | RLRLARLAL | 0 | 0.216 | 0.027 | 1.001 |
| 9 | RLARLALVL | 0 | 1.205 | 0.052 | 0.515 |
| 10 | ARLALVLLG | 0 | 0.143 | 0 | 0 |
| 11 | LALVLLGWV | 0 | 0.237 | 0 | 0 |
| 12 | LVLLGWVSS | 0 | 0.122 | 0 | 0 |
| 13 | LLGWVSSSS | 0 | 0.243 | 0 | 0 |
| 14 | GWVSSSSPT | 0 | 0.044 | 0 | 0 |
| 15 | VSSSSPTSS | 0 | 0 | 0 | 0 |
| 16 | SSSPTSSAS | 0 | 0 | 0 | 0 |
| 17 | SPTSSASSF | 0 | 0 | 0 | 0.335 |
| 18 | TSSASSFSS | 0 | 0.037 | 0 | 0 |
| 19 | SASSFSSSA | 0 | 0.045 | 0 | 0 |
| 20 | SSFSSSAPF | 0 | 0.037 | 0 | 0 |
| 21 | FSSSAPFLA | 0.023 | 0.116 | 0 | 0 |
| 22 | SSAPFLASA | 0 | 0.389 | 0 | 0 |
| 23 | APFLASAVS | 0 | 0.041 | 0 | 0.176 |
| 24 | FLASAVSAQ | 0 | 0.134 | 0 | 0 |
| 25 | ASAVSAQPP | 0 | 0 | 0 | 0 |
| 26 | AVSAQPPLP | 0 | 0.062 | 0 | 0 |
| 27 | SAQPPLPDQ | 0 | 0 | 0 | 0 |
| 28 | QPPLPDQCP | 0 | 0 | 0 | 0 |
| 29 | PLPDQCPAL | 0 | 0.088 | 0 | 0 |
| 30 | PDQCPALCE | 0 | 0 | 0 | 0 |
| 31 | QCPALCECS | 0 | 0 | 0 | 0 |
| 32 | PALCECSEA | 0 | 0.082 | 0 | 0 |
| 33 | LCECSEAAR | 0 | 0 | 0 | 0 |
| 34 | ECSEAARTV | 0 | 0 | 0 | 0 |
| 35 | SEAARTVKC | 0 | 0 | 0 | 0 |
| 36 | AARTVKCVN | 0 | 0.115 | 0 | 0.059 |
| 37 | RTVKCVNRN | 0 | 0 | 0 | 0 |
| 38 | VKCVNRNLT | 0 | 0 | 0 | 0 |
| 39 | CVNRNLTEV | 0 | 0.05 | 0 | 0.093 |
| 40 | NRNLTEVPT | 0 | 0 | 0 | 0 |
| 41 | NLTEVPTDL | 0 | 0.253 | 0 | 0 |
| 42 | TEVPTDLPA | 0 | 0 | 0 | 0 |
| 43 | VPTDLPAYV | 0.098 | 0.059 | 0 | 0 |
| 44 | TDLPAYVRN | 0 | 0 | 0 | 0 |
| 45 | LPAYVRNLF | 0 | 0 | 0 | 0.389 |
| 46 | AYVRNLFLT | 0 | 0.18 | 0 | 0 |
| 47 | VRNLFLTGN | 0 | 0 | 0 | 0 |
| 48 | NLFLTGNQL | 0 | 0.107 | 0 | 0 |
| 49 | FLTGNQLAV | 0 | 0.791 | 0 | 0 |
| 50 | TGNQLAVLP | 0 | 0.044 | 0 | 0 |
| 51 | NQLAVLPAG | 0 | 0.22 | 0 | 0 |
| 52 | LAVLPAGAF | 0 | 0.074 | 0 | 0.049 |
| 53 | VLPAGAFAR | 0 | 0.081 | 0.027 | 0 |
| 54 | PAGAFARRP | 0 | 0 | 0 | 0 |
| 55 | GAFARRPPL | 0 | 0.222 | 0 | 0.359 |
| 56 | FARRPPLAE | 0 | 0.042 | 0 | 0 |
| 57 | RRPPLAELA | 0 | 0 | 0 | 0 |
| 58 | PPLAELAAL | 0 | 0.075 | 0 | 0.145 |
| 59 | LAELAALNL | 0 | 0.72 | 0 | 0.074 |
| 60 | ELAALNLSG | 0 | 0.075 | 0 | 0 |
| 61 | AALNLSGSR | 0 | 0 | 0 | 0 |
| 62 | LNLSGSRLD | 0 | 0 | 0 | 0 |
| 63 | LSGSRLDEV | 0 | 0.075 | 0 | 0.107 |
| 64 | GSRLDEVRA | 0 | 0.13 | 0 | 0 |
| 65 | RLDEVRAGA | 0 | 0.422 | 0.057 | 0.032 |
| 66 | DEVRAGAFE | 0 | 0 | 0 | 0 |
| 67 | VRAGAFEHL | 0 | 0 | 0 | 0.085 |
| 68 | AGAFEHLPS | 0 | 0 | 0 | 0 |
| 69 | AFEHLPSLR | 0 | 0 | 0 | 0 |
| 70 | EHLPSLRQL | 0 | 0.046 | 0 | 0 |
| 71 | LPSLRQLDL | 0 | 0.098 | 0 | 0.454 |
| 72 | SLRQLDLSH | 0 | 0 | 0 | 0 |
| 73 | RQLDLSHNP | 0 | 0 | 0 | 0 |
| 74 | LDLSHNPLA | 0 | 0.226 | 0 | 0 |
| 75 | LSHNPLADL | 0 | 0.095 | 0 | 0 |
| 76 | HNPLADLSP | 0 | 0 | 0 | 0 |
| 77 | PLADLSPFA | 0 | 0.556 | 0 | 0 |
| 78 | ADLSPFAFS | 0 | 0.116 | 0 | 0 |
| 79 | LSPFAFSGS | 0 | 0.064 | 0 | 0 |
| 80 | PFAFSGSNA | 0 | 0 | 0 | 0 |
| 81 | AFSGSNASV | 0 | 0.116 | 0 | 0 |
| 82 | SGSNASVSA | 0 | 0 | 0 | 0 |
| 83 | SNASVSAPS | 0 | 0.154 | 0 | 0 |
| 84 | ASVSAPSPL | 0 | 0.059 | 0 | 0.017 |
| 85 | VSAPSPLVE | 0 | 0 | 0 | 0 |
| 86 | APSPLVELI | 0 | 0 | 0 | 0.101 |
| 87 | SPLVELILN | 0 | 0.094 | 0 | 0 |
| 88 | LVELILNHI | 0 | 0.109 | 0 | 0 |
| 89 | ELILNHIVP | 0 | 0.067 | 0 | 0 |
| 90 | ILNHIVPPE | 0 | 0.426 | 0 | 0 |
| 91 | NHIVPPEDE | 0 | 0 | 0 | 0 |
| 92 | IVPPEDERQ | 0 | 0 | 0 | 0 |
| 93 | PPEDERQNR | 0 | 0 | 0 | 0 |
| 94 | EDERQNRSF | 0 | 0 | 0 | 0 |
| 95 | ERQNRSFEG | 0 | 0 | 0 | 0 |
| 96 | QNRSFEGMV | 0 | 0.052 | 0 | 0 |
| 97 | RSFEGMVVA | 0 | 0.189 | 0 | 0 |
| 98 | FEGMVVAAL | 0 | 0.051 | 0 | 0 |
| 99 | GMVVAALLA | 0 | 0.384 | 0 | 0 |
| 100 | VVAALLAGR | 0 | 0 | 0.125 | 0 |
| 101 | AALLAGRAL | 0 | 0.156 | 0 | 0.238 |
| 102 | LLAGRALQG | 0 | 0.176 | 0 | 0 |
| 103 | AGRALQGLR | 0 | 0 | 0 | 0 |
| 104 | RALQGLRRL | 0 | 0.168 | 0.027 | 0.078 |
| 105 | LQGLRRLEL | 0 | 0.114 | 0 | 0.119 |
| 106 | GLRRLELAS | 0 | 0.046 | 0 | 0 |
| 107 | RRLELASNH | 0 | 0 | 0 | 0 |
| 108 | LELASNHFL | 0 | 0.151 | 0 | 0 |
| 109 | LASNHFLYL | 0.12 | 0.337 | 0.224 | 0 |
| 110 | SNHFLYLPR | 0 | 0.051 | 0.084 | 0 |
| 111 | HFLYLPRDV | 0 | 0.227 | 0 | 0 |
| 112 | LYLPRDVLA | 0 | 0.218 | 0 | 0 |
| 113 | LPRDVLAQL | 0 | 0 | 0 | 0.305 |
| 114 | RDVLAQLPS | 0 | 0 | 0 | 0 |
| 115 | VLAQLPSLR | 0 | 0.113 | 0.023 | 0 |
| 116 | AQLPSLRHL | 0 | 0.162 | 0 | 0 |
| 117 | LPSLRHLDL | 0 | 0.028 | 0 | 0.445 |
| 118 | SLRHLDLSN | 0 | 0.03 | 0 | 0 |
| 119 | RHLDLSNNS | 0 | 0.029 | 0 | 0 |
| 120 | LDLSNNSLV | 0 | 0.158 | 0 | 0 |
| 121 | LSNNSLVSL | 0 | 0.116 | 0 | 0.112 |
| 122 | NNSLVSLTY | 0 | 0 | 0 | 0 |
| 123 | SLVSLTYVS | 0 | 0.206 | 0 | 0 |
| 124 | VSLTYVSFR | 0 | 0 | 0.025 | 0 |
| 125 | LTYVSFRNL | 0.522 | 1.11 | 0.157 | 0.574 |
| 126 | YVSFRNLTH | 0 | 0 | 0.086 | 0.21 |
| 127 | SFRNLTHLE | 0 | 0 | 0 | 0 |
| 128 | RNLTHLESL | 0 | 0.072 | 0 | 0 |
| 129 | LTHLESLHL | 0 | 0.143 | 0 | 0 |
| 130 | HLESLHLED | 0 | 0 | 0 | 0 |
| 131 | ESLHLEDNA | 0 | 0 | 0 | 0 |
| 132 | LHLEDNALK | 0 | 0 | 0 | 0 |
| 133 | LEDNALKVL | 0 | 0.122 | 0 | 0 |
| 134 | DNALKVLHN | 0 | 0 | 0 | 0 |
| 135 | ALKVLHNGT | 0 | 0.104 | 0 | 0 |
| 136 | KVLHNGTLA | 0 | 0.15 | 0 | 0 |
| 137 | LHNGTLAEL | 0 | 0.187 | 0 | 0.026 |
| 138 | NGTLAELQG | 0 | 0 | 0 | 0 |
| 139 | TLAELQGLP | 0 | 0.083 | 0 | 0 |
| 140 | AELQGLPHI | 0 | 0 | 0 | 0 |

TABLE 5-continued iScore results from all peptides tested.

| | | | | Level of Binding >0.5 0.25-0.5 <0.25 | |
|---|---|---|---|---|---|
| Peptide | | MHC Class I Molecule | | | |
| No | Sequence | A*0101 | A*0201 | A*0301 | B*0702 |
| 141 | LQGLPHIRV | 0 | 0.2 | 0 | 0 |
| 142 | GLPHIRVFL | 0 | 1.39 | 0.319 | 0.075 |
| 143 | PHIRVFLDN | 0 | 0 | 0 | 0 |
| 144 | IRVFLDNNP | 0 | 0 | 0 | 0 |
| 145 | VFLDNNPWV | 0 | 0.239 | 0 | 0 |
| 146 | LDNNPWVCD | 0 | 0 | 0 | 0 |
| 147 | NNPWVCDCH | 0 | 0 | 0.051 | 0 |
| 148 | PWVCDCHMA | 0 | 0 | 0 | 0 |
| 149 | VCDCHMADM | 0 | 0.061 | 0 | 0 |
| 150 | DCHMADMVT | 0 | 0 | 0 | 0 |
| 151 | HMADMVTWL | 0 | 0.821 | 0 | 0 |
| 152 | ADMVTWLKE | 0 | 0 | 0 | 0 |
| 153 | MVTWLKETE | 0 | 0.051 | 0 | 0 |
| 154 | TWLKETEVV | 0 | 0.184 | 0 | 0 |
| 155 | LKETEVVQG | 0 | 0 | 0 | 0 |
| 156 | ETEVVQGKD | 0 | 0 | 0 | 0 |
| 157 | EVVQGKDRL | 0 | 0.139 | 0 | 0 |
| 158 | VQGKDRLTC | 0 | 0.074 | 0 | 0 |
| 159 | GKDRLTCAY | 0 | 0 | 0 | 0 |
| 160 | DRLTCAYPE | 0 | 0 | 0 | 0 |
| 161 | LTCAYPEKM | 0.139 | 0.158 | 0 | 0 |
| 162 | CAYPEKMRN | 0 | 0 | 0 | 0 |
| 163 | YPEKMRNRV | 0 | 0 | 0 | 0.242 |
| 164 | EKMRNRVLL | 0 | 0.096 | 0 | 0 |
| 165 | MRNRVLLEL | 0 | 0 | 0 | 0 |
| 166 | NRVLLELNS | 0 | 0.031 | 0 | 0 |
| 167 | VLLELNSAD | 0 | 0.105 | 0 | 0 |
| 168 | LELNSADLD | 0 | 0 | 0 | 0 |
| 169 | LNSADLDCD | 0 | 0 | 0 | 0 |
| 170 | SADLDCDPI | 0 | 0 | 0 | 0 |
| 171 | DLDCDPILP | 0 | 0 | 0 | 0 |
| 172 | DCDPILPPS | 0 | 0 | 0 | 0 |
| 173 | DPILPPSLQ | 0 | 0 | 0 | 0 |
| 174 | ILPPSLQTS | 0 | 0.523 | 0 | 0 |
| 175 | PPSLQTSYV | 0 | 0.145 | 0 | 0 |
| 176 | SLQTSYVFL | 0 | 0.561 | 0 | 0 |
| 177 | QTSYVFLGI | 0.027 | 0.127 | 0 | 0 |
| 178 | SYVFLGIVL | 0 | 0.118 | 0 | 0.045 |
| 179 | VFLGIVLAL | 0 | 0.606 | 0 | 0 |
| 180 | LGIVLALIG | 0 | 0 | 0 | 0 |
| 181 | IVLALIGAI | 0 | 0.326 | 0 | 0 |
| 182 | LALIGAIFL | 0 | 0.425 | 0 | 0.067 |
| 183 | LIGAIFLLV | 0 | 1.897 | 0.07 | 0 |
| 184 | GAIFLLVLY | 0 | 0 | 0 | 0 |
| 185 | IFLLVLYLN | 0 | 0 | 0 | 0 |
| 186 | LLVLYLNRK | 0 | 0.386 | 0.372 | 0.366 |
| 187 | VLYLNRKGI | 0 | 0.095 | 0.014 | 0.164 |
| 188 | YLNRKGIKK | 0 | 0.118 | 0.065 | 0.089 |
| 189 | NRKGIKKWM | 0 | 0.138 | 0 | 0 |
| 190 | KGIKKWMHN | 0 | 0 | 0 | 0 |
| 191 | IKKWMHNIR | 0 | 0.181 | 0 | 0 |
| 192 | KWMHNIRDA | 0 | 0.045 | 0 | 0 |
| 193 | MHNIRDACR | 0 | 0.093 | 0 | 0 |
| 194 | NIRDACRDH | 0 | 0 | 0 | 0 |
| 195 | RDACRDHME | 0 | 0.08 | 0 | 0 |
| 196 | ACRDHMEGY | 0 | 0 | 0 | 0 |
| 197 | RDHMEGYHY | 0 | 0 | 0 | 0 |
| 198 | HMEGYHYRY | 0.357 | 0.24 | 0.189 | 0 |
| 199 | EGYHYRYEI | 0 | 0 | 0 | 0 |
| 200 | YHYRYEINA | 0 | 0 | 0 | 0 |
| 201 | YRYEINADP | 0 | 0 | 0 | 0 |
| 202 | YEINADPRL | 0 | 0.077 | 0 | 0 |
| 203 | INADPRLTN | 0 | 0 | 0 | 0 |
| 204 | ADPRLTNLS | 0 | 0 | 0 | 0.094 |
| 205 | PRLTNLSSN | 0 | 0 | 0 | 0 |
| 206 | LTNLSSNSD | 0 | 0.027 | 0 | 0 |

TABLE 6

Summary of iTopia results

| | MHC class I Allele (% of Caucasian population) | | | |
|---|---|---|---|---|
| iScore | A1 (16%) | A2 (28%) | A3 (14%) | B7 (13%) |
| >0.5 | 1 | 11 | 0 | 3 |
| 0.25-0.5 | 1 | 9 | 2 | 7 |
| <0.25 | 5 | 95 | 17 | 26 |

TABLE 7

Candidate Peptides in Descending Order of iScore

| Peptide No (SEQ ID NO) | Sequence | iTopia |
|---|---|---|
| | A*0101 | |
| 125 | LTYVSFRNL | 0.522 |
| 198 | HMEGYHYRY | 0.357 |
| 161 | LTCAYPEKM | 0.139 |
| 109 | LASNHFLYL | 0.12 |
| 43 | VPTDLPAYV | 0.098 |
| | A*0201 | |
| 183 | LIGAIFLLV | 1.897 |
| 142 | GLPHIRVFL | 1.39 |
| 9 | RLARLALVL | 1.205 |
| 125 | LTYVSFRNL | 1.11 |
| 151 | HMADMVTWL | 0.821 |
| 49 | FLTGNQLAV | 0.791 |
| 59 | LAELAALNL | 0.72 |
| 179 | VFLGIVLAL | 0.606 |
| 176 | SLQTSYVFL | 0.561 |
| 77 | PLADLSPFA | 0.556 |
| 174 | ILPPSLQTS | 0.523 |
| 90 | ILNHIVPPE | 0.426 |
| 182 | LALIGAIFL | 0.425 |
| 65 | RLDEVRAGA | 0.422 |
| 22 | SSAPFLASA | 0.389 |
| 186 | LLVLYLNRK | 0.386 |
| 99 | GMVVAALLA | 0.384 |
| 109 | LASNHFLYL | 0.337 |
| 181 | IYLALIGAI | 0.326 |
| | A*0301 | |
| 186 | LLVLYLNRK | 0.375 |
| 142 | GLPHIRVFL | 0.319 |
| 109 | LASNHFLYL | 0.224 |
| 198 | HMEGYHYRY | 0.189 |
| 125 | LTYVSFRNL | 0.157 |
| 100 | VVAALLAGR | 0.125 |
| | B*0702 | |
| 8 | RLRLARLAL | 1.001 |
| 125 | LTYVSFRNL | 0.574 |
| 9 | RLARLALVL | 0.515 |
| 71 | LPSLRQLDL | 0.454 |
| 117 | LPSLRHLDL | 0.445 |
| 45 | LPAYVRNLF | 0.389 |
| 186 | LLVLYLNRK | 0.366 |
| 55 | GAFARRPPL | 0.359 |
| 17 | SPTSSASSF | 0.335 |
| 113 | LPRDVLAQL | 0.305 |
| 163 | YPEKMRNRV | 0.242 |
| 101 | AALLAGRAL | 0.238 |
| 126 | YVSFRNLTH | 0.21 |
| 23 | APFLASAVS | 0.176 |
| 187 | VLYLNRKGI | 0.164 |
| 58 | PPLAELAAL | 0.145 |

TABLE 8a

| Peptide ID | SEQ ID NO | Sequence |
|---|---|---|
| | A2 iTopia hit pool | |
| 9 | 215 | RLARLALVLL |
| 22 | 303 | SSAPFLASV |
| 49 | 225 | FLTGNQLAVL |
| 59 | 304 | LAELAALNLS |
| 65 | 305 | RLDEVRAGAF |
| 77 | 233 | PLADLSPFAF |
| 90 | 246 | ILNHIVPPED |
| 99 | 306 | GMVVAALLAG |
| 109 | 307 | LASNHFLYLP |
| 125 | 261 | LTYVSFRNLT |
| 142 | 308 | GLPHIRVFLD |
| 151 | 309 | HMADMVTWLK |
| 174 | 270 | ILPPSLQTSY |
| 176 | 272 | SLQTSYVFLG |
| 179 | 275 | VFLGIVLALI |
| 181 | 277 | IVLALIGAIF |
| 182 | 278 | LALIGAIFLL |
| 183 | 279 | LIGAIFLLVL |
| 168 | 282 | LLVLYLNRKG |
| | A1/A3/B7 iTopia hit pool | |
| 8 | 214 | RLRLARLALV |
| 9 | 215 | RLARLALVLL |
| 17 | 310 | SPTSSASSFS |
| 23 | 311 | APFLASAVSA |
| 43 | 219 | VPTDLPAYVR |
| 45 | 221 | LPAYVRNLFL |
| 55 | 312 | GAFARRPPLA |
| 58 | 313 | PPLAELAALN |
| 71 | 227 | LPSLRQLDLS |
| 100 | 314 | VVAALLAGRA |
| 101 | 315 | AALLAGRALQ |
| 109 | 316 | LASNHFLYLP |
| 113 | 249 | LPRDVLAQLP |
| 117 | 253 | LPSLRHLDLS |
| 125 | 261 | LTYVSFRNLT |
| 126 | 262 | YVSFRNLTHL |
| 142 | 317 | GLPHIRVFLD |
| 161 | 318 | LTCAYPEKMR |
| 163 | 319 | YPEKMRNRVL |
| 186 | 282 | LLVLYLNRKG |
| 187 | 283 | VLYLNRKGIK |
| 198 | 294 | HMEGYHYRYE |

TABLE 8b

| Peptide ID | Sequence |
|---|---|
| | Peptide pool 1 |
| 1 | MPGGCSRGPA |
| 2 | GGCSRGPAAG |
| 3 | CSRGPAAGDG |
| 4 | RGPAAGDGRL |
| 5 | PAAGDGRLRL |
| 6 | AGDGRLRLAR |
| 7 | DGRLRLARLA |
| 8 | RLRLARLALV |
| 9 | RLARLALVLL |
| 10 | ARLALVLLGW |
| | Peptide pool 5 |
| 41 | NLTEVPTDLP |
| 42 | TEVPTDLPAY |
| 43 | VPTDLPAYVR |
| 44 | TDLPAYVRNL |
| 45 | LPAYVRNLFL |
| 46 | AYVRNLFLTG |
| 47 | VRNLFLTGNQ |
| 48 | NLFLTGNQLA |
| 49 | FLTGNQLAVL |
| 50 | TGNQLAVLPA |
| | Peptide pool 8 |
| 71 | LPSLRQLDLS |
| 72 | SLRQLDLSHN |
| 73 | RQLDLSHNPL |
| 74 | LDLSHNPLAD |
| 75 | LSHNPLADLS |
| 76 | HNPLADLSPF |
| 77 | PLADLSPFAF |
| 78 | ADLSPFAFSG |
| 79 | LSPFAFSGSN |
| 80 | PFAFSGSNAS |
| | Peptide pool 9 |
| 81 | AFSGSNASVS |
| 82 | SGSNASVSAP |
| 83 | SNASVSAPSP |
| 84 | ASVSAPSPLV |
| 85 | VSAPSPLVEL |
| 86 | APSPLVELIL |
| 87 | SPLVELILNH |
| 88 | LVELILNHIV |
| 89 | ELILNHIVPP |
| 90 | ILNHIVPPED |
| | Peptide pool 12 |
| 111 | HFLYLPRDVL |
| 112 | LYLPRDVLAQ |
| 113 | LPRDVLAQLP |
| 114 | RDVLAQLPSL |
| 115 | VLAQLPSLRH |
| 116 | AQLPSLRHLD |
| 117 | LPSLRHLDLS |
| 118 | SLRHLDLSNN |
| 119 | RHLDLSNNSL |
| 120 | LDLSNNSLVS |
| | Peptide pool 13 |
| 121 | LSNNSLVSLT |
| 122 | NNSLVSLTYV |
| 123 | SLVSLTYVSF |
| 124 | VSLTYVSFRN |
| 125 | LTYVSFRNLT |
| 126 | YVSFRNLTHL |
| 127 | SFRNLTHLES |
| 128 | RNLTHLESLH |
| 129 | LTHLESLHLE |
| 130 | HLESLHLEDN |
| | Peptide pool 18 |
| 171 | DLDCDPILPP |
| 172 | DCDPILPPSL |
| 173 | DPILPPSLQT |
| 174 | ILPPSLQTSY |
| 175 | PPSLQTSYVF |
| 176 | SLQTSYVFLG |
| 177 | QTSYVFLGIV |
| 178 | SYVFLGIVLA |
| 179 | VFLGIVLALI |
| 180 | LGIVLALIGA |
| | Peptide pool 19 |
| 181 | IVLALIGAIF |
| 182 | LALIGAIFLL |
| 183 | LIGAIFLLVL |
| 184 | GAIFLLVLYL |
| 185 | IFLLVLYLNR |
| 186 | LLVLYLNRKG |

TABLE 8b-continued

| Peptide ID | Sequence |
|---|---|
| 187 | VLYLNRKGIK |
| 188 | YLNRKGIKKW |
| 189 | NRKGIKKWMH |
| 190 | KGIKKWMHNI |
| Peptide pool 20 | |
| 191 | IKKWMHNIRD |
| 192 | KWMHNIRDAC |
| 193 | MHNIRDACRD |
| 194 | NIRDACRDHM |
| 195 | RDACRDHMEG |

TABLE 8b-continued

| Peptide ID | Sequence |
|---|---|
| 196 | ACRDHMEGYH |
| 197 | RDHMEGYHYR |
| 198 | HMEGYHYRYE |
| 199 | EGYHYRYEIN |
| 200 | YHYRYEINAD |
| 201 | YRYEINADPR |
| 202 | YEINADPRLT |
| 203 | INADPRLTNL |
| 204 | ADPRLTNLSS |
| 205 | PRLTNLSSNS |
| 206 | LTNLSSNSDV |

TABLE 9

| iTopia Hit MHC restriction | Peptide No (SEQ ID NO) | Peptide sequence | Peptide contained in pool: | Responding patient ID | Responding patient MHC type | Assay |
|---|---|---|---|---|---|---|
| A1 | 43 | VPTDLPAYV | Peptide pool 5 | TV2-005 | A1, A2, B8, B35, Cw4, Cw7 | ELISpot |
| | | | | TV2-101 | A1, A29, B8, B45, Cw6, Cw7 | ELISpot |
| A1 | 125 | LTYVSFRNL | Peptide pool 13 | TV2-005 | A1, A2, B8, B35, Cw4, Cw7 | ELISpot |
| | | | | TV2-105 | A1, B8, Cw7 | ELISpot |
| A1 | 198 | HMEGYHYRY | Peptide pool 20 | TV2-005 | A1, A2, B8, B35, Cw4, Cw7 | ELISpot |
| | | | | TV2-105 | A1, B8, Cw7 | ELISpot |
| A2 | 9 | RLARLALVL | Peptide pool 1 | TV2-005 | A1, A2, B8, B35, Cw4, Cw7 | ELISpot |
| | | | | TV2-012 | A2, B7, B44, Cw5, Cw7 | ELISpot |
| | | | | TV2-018 | A2, A3, B44, B60, Cw3, Cw5 | ELISpot |
| | | | | TV2-103 | A2, A30, B18, B44, Cw5 | ELISpot |
| | | | | TV2-107 | A1, A2, B35, B62, Cw4, Cw10 | ELISpot |
| | | | | TV2-108 | A2, A3, B8, B64, Cw7, Cw8 | ELISpot |
| A2 | 49 | FLTGNQLAV | Peptide pool 5 | TV2-005 | A1, A2, B8, B35, Cw4, Cw7 | ELISpot |
| | | | | TV2-012 | A1, B7, B44, Cw5, Cw7 | ELISpot |
| | | | | TV2-018 | A2, A3, B44, B60, Cw3, Cw5 | ELISpot |
| | | | | TV2-103 | A1, A30, B18, B44, Cw5 | ELISpot |
| | | | | TV2-108 | A2, A3, B8, B64, Cw7, Cw8 | ELISpot |
| A2 | 77 | PLADLSPFA | Peptide 77 | TV2-005 | A1, A2, B8, B35, Cw4, Cw7 | ELISpot |
| | | | | TV2-012 | A2, B7, B44, Cw5, Cw7 | ELISpot |
| A2 | 77 | PLADLSPFA | Peptide pool 8 | TV2-012 | A2, B7, B44, Cw5, Cw7 | ELISpot |
| | | | | TV2-012 | A2, B7, B44, Cw5, Cw7 | ELISpot |
| A2 | 90 | ILNHIVPPE | Peptide pool 9 | TV2-005 | A1, A2, B8, B35, Cw4, Cw7 | ELISpot |
| | | | | TV2-012 | A2, B7, B44, Cw5, Cw7 | ELISpot |
| | | | | TV2-013 | A2, A3, B7, B35, Cw4, Cw7 | ELISpot |
| A2 | 125 | LTYVSFRNL | Peptide pool 13 | TV2-005 | A1, A2, B8, B35, Cw4, Cw7 | ELISpot |
| | | | | TV2-012 | A2, B7, B44, Cw5, Cw7 | ELISpot |
| | | | | TV2-108 | A2, A3, B8, B64, Cw7, Cw8 | ELISpot |
| A2 | 174 | ILPPSLQTS | Peptide pool 18 | TV2-005 | A1, A2, B8, B35, Cw4, Cw7 | ELISpot |
| | | | | TV2-012 | A2, B7, B44, Cw5, Cw7 | ELISpot |
| | | | | TV2-013 | A2, A3, B7, B35, Cw4, Cw7 | ELISpot |
| A2 | 176 | SLQTSYVFL | Peptide pool 18 | TV2-005 | A1, A2, B8, B35, Cw4, Cw7 | ELISpot |
| | | | | TV2-012 | A2, B7, B44, Cw5, Cw7 | ELISpot |
| | | | | TV2-013 | A2, A3, B7, B35, Cw4, Cw7 | ELISpot |
| A2 | 179 | VFLGIVLAL | Peptide pool 18 | TV2-005 | A1, A2, B8, B35, Cw4, Cw7 | ELISpot |
| | | | | TV2-012 | A2, B7, B44, Cw5, Cw7 | ELISpot |
| | | | | TV2-013 | A2, A3, B7, B35, Cw4, Cw7 | ELISpot |
| A2 | 181 | IVLALIGAI | Peptide pool 19 | TV2-005 | A1, A2, B8, B35, Cw4, Cw7 | ELISpot |
| | | | | TV2-012 | A2, B7, B44, Cw5, Cw7 | ELISpot |
| A2 | 182 | LALIGAIFL | Peptide pool 19 | TV2-005 | A1, A2, B8, B35, Cw4, Cw7 | ELISpot |
| | | | | TV2-012 | A2, B7, B44, Cw5, Cw7 | ELISpot |
| A2 | 183 | LIGALFLLV | Peptide pool 19 | TV2-005 | A1, A2, B8, B35, Cw4, Cw7 | ELISpot |
| | | | | TV2-012 | A2, B7, B44, Cw5, Cw7 | ELISpot |

TABLE 9-continued

| iTopia Hit MHC restriction | Peptide No (SEQ ID NO) | Peptide sequence | Peptide contained in pool: | Responding patient ID | Responding patient MHC type | Assay |
|---|---|---|---|---|---|---|
| A2 | 186 | LLVLYLNRK | Peptide pool 19 | TV2-005 | A1, A2, B8, B35, Cw4, Cw7 | ELISpot |
| | | | | TV2-012 | A2, B7, B44, Cw5, Cw7 | ELISpot |
| A3 | 125 | LTYVSFRNL | Peptide pool 13 | TV2-009 | A3, B7, Cw7 | ELISpot |
| | | | | TV2-017 | A3, A24, B18, B39, Cw7, Cw12 | ELISpot |
| | | | | TV2-104 | A3, A68, B8, B18, Cw7 | ELISpot |
| | | | | TV2-108 | A2, A3, B8, B64, Cw7, Cw8 | ELISpot |
| A3 | 198 | HMEGYHYRY | Peptide pool 20 | TV2-009 | A3, B7, Cw7 | ELISpot |
| | | | | TV2-013 | A2, A3, B7, B35, Cw4, Cw7 | ELISpot |
| | | | | TV2-018 | A2, A3, B44, B60, Cw3, Cw5 | ELISpot |
| B7 | 8 | RLRLARLAL | Peptide pool 1 | TV2-012 | A2, B7, B44, Cw5, Cw7 | ELISpot |
| B7 | 9 | RLARLALVL | Peptide pool 1 | TV2-012 | A2, B7, B44, Cw5, Cw7 | ELISpot |
| B7 | 45 | LPAYVRNLF | Peptide pool 5 | TV2-009 | A3, B7, Cw7 | ELISpot |
| | | | | TV2-012 | A2, B7, B44, Cw5, Cw7 | ELISpot |
| B7 | 71 | LPSLRQLDL | Peptide pool 8 | TV2-012 | A2, B7, B44, Cw5, Cw7 | ELISpot |
| B7 | 113 | LPRDVLAQL | Peptide pool 12 | TV2-012 | A2, B7, B44, Cw5, Cw7 | ELISpot |
| | | | | TV2-113 | A11, A24, B7, B45, Cw6, Cw7 | ELISpot |
| B7 | 117 | LPSLRHLDL | Peptide pool 12 | TV2-012 | A2, B7, B44, Cw5, Cw7 | ELISpot |
| | | | | TV2-113 | A11, A24, B7, B45, Cw6, Cw7 | ELISpot |
| B7 | 125 | LTYVSFRNL | Peptide pool 13 | TV2-009 | A3, B7, Cw7 | ELISpot |
| | | | | TV2-012 | A2, B7, B44, Cw5, Cw7 | ELISpot |
| B7 | 126 | YVSFRNLTH | Peptide pool 13 | TV2-009 | A3, B7, Cw7 | ELISpot |
| | | | | TV2-012 | A2, B7, B44, Cw5, Cw7 | ELISpot |
| B7 | 187 | VLYLNRKGI | Peptide pool 19 | TV2-012 | A2, B7, B44, Cw5, Cw7 | ELISpot |
| | | | | TV2-012 | A2, B7, B44, Cw5, Cw7 | ELISpot |

TABLE 10

| iTopia Hit MHC restriction | Peptide contained in pool: | Responding patient ID | Responding patient MHC type | Assay |
|---|---|---|---|---|
| A1 | A1/A3/B7 peptide pool | TV2-002 | A1, A24, B7, B35, Cw4, Cw7 | ELISpot |
| | | TV2-005 | A1, A2, B8, B35, Cw4, Cw7 | ELISpot |
| | | TV2-019 | A1, A24, B7, B8, Cw7 | ELISpot |
| | | TV2-107 | A1, A2, B35, B62, Cw4, Cw10 | ELISpot |
| A2 | A2 peptide pool | TV2-005 | A1, A2, B8, B35, Cw4, Cw7 | ELISpot |
| | | TV2-012 | A2, B7, B44, Cw5, Cw7 | ELISpot |
| | | TV2-107 | A1, A2, B35, B62, Cw4, Cw10 | ELISpot |
| A3 | A1/A3/B7 peptide pool | TV2-017 | A3, A24, B18, B39, Cw7, Cw12 | ELISpot |
| | | TV2-104 | A3, A68, B8, B18, Cw7 | ELISpot |
| B7 | A1/A3/B7 peptide pool | TV2-002 | A1, A24, B7, B35, Cw4, Cw7 | ELISpot |
| | | TV2-012 | A2, B7, B44, Cw5, Cw7 | ELISpot |
| | | TV2-019 | A1, A24, B7, B8, Cw7 | ELISpot |

TABLE 11

| Patient No. | HLA Type | Initial +ve Responses | Response Dissected | Epitope Identified? | MHC Restriction* | iTopia Hit? | Pentamer Available | Pentamer +ve? |
|---|---|---|---|---|---|---|---|---|
| 005 | A1, A2, B35, B8, Cw4, Cw7 | Peptide 77 | N/A | 77 | A2 | A2 | No | |
| 012 | A2, B7, B44, Cw5, Cw7 | Peptide 77 | N/A | 77 | A2 | A2 | No | |
| 018 | A2, A3, B44, B60, Cw3, Cw5 | Pool 5 | Yes | 49 | A2 | A2 | Yes | Yes |
| | | Pool 20 | Yes | 194 | Unknown | No | | |
| | | Pool 1 | Yes | 9 | A2 | A2/B7 | Yes | Yes |
| 105 | A1, B8, Cw7 | Pool 13 | Yes | 125 | A1 | A1/A2/A3/B7 | No | |
| 108 | A2, A3, B8, B64, Cw7, Cw8 | Pool 5 | Yes | 49 | A2 | A2 | Yes | Yes |

*MHC restriction confirmed using a blocking antibody or identified previously.

TABLE 12

| Class II peptide ID | Constituent peptide(s) | Peptide sequence |
|---|---|---|
| Peptide 36.2 | 36.2 | LQGLPHIRVFLDNNPWVCDC |
| Peptide 37.2 | 37.2 | VFLDNNPWVCDCHMADMVTW |
| Peptide 38.2 | 38.2 | VCDCHMADMVTWLKETEVVQ |
| Peptide 39.2 | 39.2 | MVTWLKETEVVQGKDRLTCA |
| Peptide 40.2 | 40.2 | EVVQGKDRLTCAYPEKMRNR |
| Peptide 41.2 | 41.2 | LTCAYPEKMRNRVLLELNSA |
| Peptide 42.2 | 42.2 | MRNRVLLELNSADLDCDPIL |
| Peptide 43.2 | 43.2 | LNSADLDCDPILPPSLQTSY |
| Peptide 44.2 | 44.2 | DPILPPSLQTSYVFLGIVLA |
| Peptide 45.2 | 45.2 | QTSYVFLGIVLALIGAIFLL |
| Pool 4.2 | 16.2 | AALNLSGSRLDEVRAGAFEH |
|  | 17.2 | RLDEVRAGAFEHLPSLRQLD |
|  | 18.2 | AFEHLPSLRQLDLSHNPLAD |
|  | 19.2 | RQLDLSHNPLADLSPFAFSG |
|  | 20.2 | PLADLSPFAFSGSNASVSAP |
| Pool 5.2 | 21.2 | AFSGSNASVSAPSPLVELIL |
|  | 22.2 | VSAPSPLVELILNHIVPPED |
|  | 23.2 | ELILNHIVPPEDERQNRSFE |
|  | 24.2 | PPEDERQNRSFEGMVVAALL |
|  | 25.2 | RSFEGMVVAALLAGRALQGL |
| Pool 6.2 | 26.2 | AALLAGRALQGLRRLELASN |
|  | 27.2 | LQGLRRLELASNHFLYLPRD |
|  | 28.2 | LASNHFLYLPRDVLAQLPSL |
|  | 29.2 | LPRDVLAQLPSLRHLDLSNN |
|  | 30.2 | LPSLRHLDLSNNSLVSLTYV |
| Pool 7.2 | 31.2 | LSNNSLVSLTYVSFRNLTHL |
|  | 32.2 | LTYVSFRNLTHLESLHLEDN |
|  | 33.2 | LTHLESLHLEDNALKVLHNG |
|  | 34.2 | LEDNALKVLHNGTLAELQGL |
|  | 35.2 | LHNGTLAELQGLPHIRVFLD |
| Pool 8.2 | 36.2 | LQGLPHIRVFLDNNPWVCDC |
|  | 37.2 | VFLDNNPWVCDCHMADMVTW |
|  | 38.2 | VCDCHMADMVTWLKETEVVQ |
|  | 39.2 | MVTWLKETEVVQGKDRLTCA |
|  | 40.2 | EVVQGKDRLTCAYPEKMRNR |
| Pool 9.2 | 41.2 | LTCAYPEKMRNRVLLELNSA |
|  | 42.2 | MRNRVLLELNSADLDCDPIL |
|  | 43.2 | LNSADLDCDPILPPSLQTSY |
|  | 44.2 | DPILPPSLQTSYVFLGIVLA |
|  | 45.2 | QTSYVFLGIVLALIGAIFLL |
| Pool 10.2 | 46.2 | IVLALIGAIFLLVLYLNRKG |
|  | 47.2 | IFLLVLYLNRKGIKKWMHNI |
|  | 48.2 | NRKGIKKWMHNIRDACRDHM |
|  | 49.2 | MHNIRDACRDHMEGYHYRYE |
|  | 50.2 | RDHMEGYHYRYEINADPRLT |
|  | 51.2 | YRYEINADPRLTNLSSNSDV |

TABLE 13

| Class II Peptide ID | Peptide sequence | Responding patient ID | Responding patient MHC type | Assay |
|---|---|---|---|---|
| 39.2 | MVTWLKETEVVQGKDRLTCA | TV2-005 | DR17, DR52, DQ2 | ELISpot |
|  |  | TV2-012 | DR4, DR15, DR51, DR53, DQ6, DQ7 | ELISpot |
|  |  | TV2-102 | DR7, DR13, DR52, DR53, DQ2, DQ6 | ELISpot |
|  |  | TV2-103 | DR15, DR17, DR51, DR52, DQ2, DQ6 | ELISpot |
|  |  | TV2-104 | DR4, DR17, DR52, DR53, DQ2, DQ8 | ELISpot |
|  |  | TV2-110 | DR9, DR12, DR52, DR53, DQ7, DQ9 | ELISpot |
| 41.2 | LTCAYPEKMRNRVLLELNSA | TV2-002 | DR11, DR13, DR52, DQ6, DQ7 | ELISpot |
|  |  | TV2-005 | DR17, DR52, DQ2 | ELISpot |
|  |  | TV2-012 | DR4, DR15, DR51, DR53, DQ6, DQ7 | ELISpot |
|  |  | TV2-015 | DR1, DR15, DR51, DQ5, DQ6 | ELISpot |
|  |  | TV2-016 | DR13, DR15, DR51, DR52, DQ6 | ELISpot |

TABLE 14

| Class II Peptide ID | Peptide sequence | Peptide contained in pool: | Responding patient ID | Responding patient MHC type | Assay |
|---|---|---|---|---|---|
| 36.2 | LQGLPHIRVFLDNNPWVCDC | Peptide 362 | TV2-007 | DR7, DR53, DQ2 | Proliferation |
|  |  |  | TV2-009 | DR1, DR7, DR53N, DQ5, DQ9 | Proliferation |
|  |  |  | TV2-010 | DR4, DR9, DR53, DQ7, DQ9 | Proliferation |
|  |  |  | TV2-016 | DR13, DR15, DR51, DR52, DQ6 | Proliferation |
|  |  |  | TV2-106 |  | Proliferation |
|  |  |  | TV2-113 | DR7, DR15, DR51, DR53, DQ2, DQ6 | Proliferation |
|  |  |  | TV2-114 | DR1, DQ5 | Proliferation |
|  |  |  | TV2-116 | DR11, DR17, DR52, DQ2, DQ7 | Proliferation |

TABLE 14-continued

| Class II Peptide ID | Peptide sequence | Peptide contained in pool: | Responding patient ID | Responding patient MHC type | Assay |
|---|---|---|---|---|---|
| 37.2 | VFLDNMPWVCDCHMADMVTW | Peptide 37.2 | TV2-007 | DR7, DR53, DQ2 | Proliferation |
| | | | TV2-010 | DR4, DR9, DR53, DQ7, DQ9 | Proliferation |
| | | | TV2-015 | DR1, DR15, DR51, DQ5, DQ6 | Proliferation |
| | | | TV2-102 | DR7, DR13, DR52, DR53, DQ2, DQ6 | Proliferation |
| | | | TV2-103 | DR15, DR17, DR51, DR52, DQ2, DQ6 | Proliferation |
| | | | TV2-104 | DR4, DR17, DR52, DR53, DQ2, DQ8 | Proliferation |
| | | | TV2-113 | DR7, DR15, DR51, DR53, DQ2, DQ6 | Proliferation |
| | | | TV2-114 | DR1, DQ5 | Proliferation |
| | | | TV2-116 | DR11, DR17, DR52, DQ2, DQ7 | Proliferation |
| | | | TV2-117 | DR1, DR17, DR52, DQ2, DQ5 | Proliferation |
| 38.2 | VCDCHMADMVTWLKETEVVQ | Peptide 38.2 | TV2-007 | DR7, DR53, DQ2 | Proliferation |
| | | | TV2-012 | DR4, DR15, DR51, DR53, DQ6, DQ7 | Proliferation |
| | | | TV2-013 | DR1, DR13, DR52, DQ5, DQ6 | Proliferation |
| | | | TV2-014 | DR15, DR51, DQ6 | Proliferation |
| | | | TV2-015 | DR1, DR15, DR51, DQ5, DQ6 | Proliferation |
| | | | TV2-103 | DR15, DR17, DR51, DR52, DQ2, DQ6 | Proliferation |
| | | | TV2-104 | DR4, DR17, DR52, DR53, DQ2, DQ8 | Proliferation |
| | | | TV2-105 | DR17, DR52, DQ2 | Proliferation |
| | | | TV2-106 | | Proliferation |
| | | | TV2-114 | DR1, DQ5 | Proliferation |
| | | | TV2-116 | DR11, DR17, DR52, DQ2, DQ7 | Proliferation |
| 39.2 | MVTWLKETEVVQGKDRLTCA | Peptide 39.2 | TV2-007 | DR7, DR53, DQ2 | Proliferation |
| | | | TV2-014 | DR15, DR51, DQ6 | Proliferation |
| | | | TV2-016 | DR13, DR15, DR51, DR52, DQ6 | Proliferation |
| | | | TV2-017 | DR11, DR16, DR51, DR52, DQ5, DQ6 | Proliferation |
| | | | TV2-019 | DR4, DR15, DR51, DR53, DQ6, DQ7 | Proliferation |
| | | | TV2-102 | DR7, DR13, DR52, DR53, DQ2, DQ6 | Proliferation |
| | | | TV2-103 | DR15, DR17, DR51, DR52, DQ2, DQ6 | Proliferation |
| | | | TV2-107 | DR1, DQ5 | Proliferation |
| | | | TV2-109 | | Proliferation |
| | | | TV2-114 | DR1, DQ5 | Proliferation |
| | | | TV2-116 | DR11, DR17, DR52, DQ2, DQ7 | Proliferation |
| 40.2 | EVVQGKDRLTCAYPEKMRNR | Peptide 40.2 | TV2-001 | DR15, DR51, DR103, DQ5, DQ6 | Proliferation |
| | | | TV2-003 | DR13, DR17, DR52, DQ2, DQ6 | Proliferation |
| | | | TV2-014 | DR15, DR51, DQ6 | Proliferation |
| | | | TV2-016 | DR13, DR15, DR51, DR52, DQ6 | Proliferation |
| | | | TV2-018 | DR7, DR8, DR53N, DQ4, DQ9 | Proliferation |
| | | | TV2-102 | DR7, DR13, DR52, DR53, DQ2, DQ6 | Proliferation |
| | | | TV2-103 | DR15, DR17, DR51, DR52, DQ2, DQ6 | Proliferation |
| | | | TV2-106 | | Proliferation |
| | | | TV2-110 | DR9, DR12, DR52, DR53, DQ7, DQ9 | Proliferation |
| | | | TV2-112 | DR4, DR15, DR51, DR53, DQ6, DQ7 | Proliferation |
| | | | TV2-113 | DR7, DR15, DR51, DR53, DQ2, DQ6 | Proliferation |

TABLE 14-continued

| Class II Peptide ID | Peptide sequence | Peptide contained in pool: | Responding patient ID | Responding patient MHC type | Assay |
|---|---|---|---|---|---|
| | | | TV2-114 | DR1, DQ5 | Proliferation |
| | | | TV2-116 | DR11, DR17, DR52, DQ2, DQ7 | Proliferation |
| 41.2 | LTCAYPEKMRNRVLLELNSA | Peptide 41.2 | TV2-001 | DR15, DR51, DR103, DQ5, DQ6 | Proliferation |
| | | | TV2-002 | DR11, DR13, DR52, DQ6, DQ7 | Proliferation |
| | | | TV2-007 | DR7, DR53, DQ2 | Proliferation |
| | | | TV2-012 | DR4, DR15, DR51, DR53, DQ6, DQ7 | Proliferation |
| | | | TV2-014 | DR15, DR51, DQ6 | Proliferation |
| | | | TV2-015 | DR1, DR15, DR51, DQ5, DQ6 | Proliferation |
| | | | TV2-017 | DR11, DR16, DR51, DR52, DQ5, DQ6 | Proliferation |
| | | | TV2-102 | DR7, DR13, DR52, DR53, DQ2, DQ6 | Proliferation |
| | | | TV2-103 | DR15, DR17, DR51, DR52, DQ2, DQ6 | Proliferation |
| | | | TV2-106 | | Proliferation |
| | | | TV2-107 | DR1, DQ5 | Proliferation |
| | | | TV2-109 | | Proliferation |
| | | | TV2-113 | DR7, DR15, DR51, DR53, DQ2, DQ6 | Proliferation |
| | | | TV2-114 | DR1, DQ5 | Proliferation |
| | | | TV2-116 | DR11, DR17, DR52, DQ2, DQ7 | Proliferation |
| 42.2 | MRNRVLLELNSADLDCDPIL | Peptide 42.2 | TV2-001 | DR15, DR51, DR103, DQ5, DQ6 | Proliferation |
| | | | TV2-009 | DR1, DR7, DR53N, DQ5, DQ9 | Proliferation |
| | | | TV2-014 | DR15, DR51, DQ6 | Proliferation |
| | | | TV2-015 | DR1, DR15, DR51, DQ5, DQ6 | Proliferation |
| | | | TV2-016 | DR13, DR15, DR51, DR52, DQ6 | Proliferation |
| | | | TV2-017 | DR11, DR16, DR51, DR52, DQ5, DQ6 | Proliferation |
| | | | TV2-101 | | Proliferation |
| | | | TV2-102 | DR7, DR13, DR52, DR53, DQ2, DQ6 | Proliferation |
| | | | TV2-103 | DR15, DR17, DR51, DR52, DQ2, DQ6 | Proliferation |
| | | | TV2-104 | DR4, DR17, DR52, DR53, DQ2, DQ8 | Proliferation |
| | | | TV2-106 | | Proliferation |
| | | | TV2-107 | DR1, DQ5 | Proliferation |
| | | | TV2-113 | DR7, DR15, DR51, DR53, DQ2, DQ6 | Proliferation |
| | | | TV2-114 | DR1, DQ5 | Proliferation |
| 43.2 | LNSADLDCDPILPPSLQTSY | Peptide 43.2 | TV2-001 | DR15, DR51, DR103, DQ5, DQ6 | Proliferation |
| | | | TV2-007 | DR7, DR53, DQ2 | Proliferation |
| | | | TV2-014 | DR15, DR51, DQ6 | Proliferation |
| | | | TV2-015 | DR1, DR15, DR51, DQ5, DQ6 | Proliferation |
| | | | TV2-016 | DR13, DR15, DR51, DR52, DQ6 | Proliferation |
| | | | TV2-018 | DR7, DR8, DR53N, DQ4, DQ9 | Proliferation |
| | | | TV2-102 | DR7, DR13, DR52, DR53, DQ2, DQ6 | Proliferation |
| | | | TV2-103 | DR15, DR17, DR51, DR52, DQ2, DQ6 | Proliferation |
| | | | TV2-106 | | Proliferation |
| | | | TV2-113 | DR7, DR15, DR51, DR53, DQ2, DQ6 | Proliferation |
| | | | TV2-114 | DR1, DQ5 | Proliferation |
| | | | TV2-116 | DR11, DR17, DR52, DQ2, DQ7 | Proliferation |
| 44.2 | DPILPPSLQTSYVFLGIVLA | Peptide 44.2 | TV2-001 | DR15, DR51, DR103, DQ5, DQ6 | Proliferation |

TABLE 14-continued

| Class II Peptide ID | Peptide sequence | Peptide contained in pool: | Responding patient ID | Responding patient MHC type | Assay |
|---|---|---|---|---|---|
| | | | TV2-014 | DR15, DR51, DQ6 | Proliferation |
| | | | TV2-016 | DR13, DR15, DR51, DR52, DQ6 | Proliferation |
| | | | TV2-019 | DR4, DR15, DR51, DR53, DQ6, DQ7 | Proliferation |
| | | | TV2-103 | DR15, DR17, DR51, DR52, DQ2, DQ6 | Proliferation |
| | | | TV2-110 | DR9, DR12, DR52, DR53, DQ7, DQ9 | Proliferation |
| | | | TV2-114 | DR1, DQ5 | Proliferation |
| | | | TV2-116 | DR11, DR17, DR52, DQ2, DQ7 | Proliferation |
| | | | TV2-117 | DR1, DR17, DR52, DQ2, DQ5 | Proliferation |
| 45.2 | QTSYVFLGIVLALIGAIFLL | Peptide 45.2 | TV2-007 | DR7, DR53, DQ2 | Proliferation |
| | | | TV2-012 | DR4, DR15, DR51, DR53, DQ6, DQ7 | Proliferation |
| | | | TV2-019 | DR4, DR15, DR51, DR53, DQ6, DQ7 | Proliferation |
| | | | TV2-102 | DR7, DR13, DR52, DR53, DQ2, DQ6 | Proliferation |
| | | | TV2-103 | DR15, DR17, DR51, DR52, DQ2, DQ6 | Proliferation |
| | | | TV2-106 | | Proliferation |
| | | | TV2-107 | DR1, DQ5 | Proliferation |
| | | | TV2-112 | DR4, DR15, DR51, DR53, DQ6, DQ7 | Proliferation |
| | | | TV2-114 | DR1, DQ5 | Proliferation |
| 16.2-20.2 | AALNLSGSRLDEVRAGAFEH RLDEVRAGAFEHLPSLRQLD AFEHLPSLRQLDLSHNPLAD RQLDLSHNPLADLSPFAFSG PLADLSPFAFSGSNASVSAP | Pool 4.2 | TV2-002 | DR11, DR13, DR52, DQ6, DQ7 | Proliferation |
| | | | TV2-005 | DR17, DR52, DQ2 | Proliferation |
| | | | TV2-006 | DR1, DR17, DR52, DQ2, DQ5 | Proliferation |
| | | | TV2-007 | DR7, DR53, DQ2 | Proliferation |
| | | | TV2-010 | DR4, DR9, DR53, DQ7, DQ9 | Proliferation |
| | | | TV2-012 | DR4, DR15, DR51, DR53, DQ6, DQ7 | Proliferation |
| | | | TV2-013 | DR1, DR13, DR52, DQ5, DQ6 | Proliferation |
| | | | TV2-014 | DR15, DR51, DQ6 | Proliferation |
| | | | TV2-018 | DR7, DR8, DR53N, DQ4, DQ9 | Proliferation |
| | | | TV2-019 | DR4, DR15, DR51, DR53, DQ6, DQ7 | Proliferation |
| | | | TV2-104 | DR4, DR17, DR52, DR53, DQ2, DQ8 | Proliferation |
| | | | TV2-106 | | Proliferation |
| | | | TV2-107 | DR1, DQ5 | Proliferation |
| | | | TV2-113 | DR7, DR15, DR51, DR53, DQ2, DQ6 | Proliferation |
| | | | TV2-114 | DR1, DQ5 | Proliferation |
| | | | TV2-116 | DR11, DR17, DR52, DQ2, DQ7 | Proliferation |
| 21.2-25.2 | AFSGSNASVSAPSPLVELIL VSAPSPLVELILNHIVPPED ELILNHIVPPEDERQNRSFE PPEDERQNRSFEGMVVAALL RSFEGMVVAALLAGRALQGL | Pool 5.2 | TV2-002 | DR11, DR13, DR52, DQ6, DQ7 | Proliferation |
| | | | TV2-005 | DR17, DR52, DQ2 | Proliferation |
| | | | TV2-009 | DR1, DR7, DR53N, DQ5, DQ9 | Proliferation |
| | | | TV2-010 | DR4, DR9, DR53, DQ7, DQ9 | Proliferation |
| | | | TV2-016 | DR13, DR15, DR51, DR52, DQ6 | Proliferation |
| | | | TV2-101 | | Proliferation |
| | | | TV2-102 | DR7, DR13, DR52, DR53, DQ2, DQ6 | Proliferation |
| | | | TV2-103 | DR15, DR17, DR51, DR52, DQ2, DQ6 | Proliferation |
| | | | TV2-104 | DR4, DR17, DR52, DR53, DQ2, DQ8 | Proliferation |
| | | | TV2-105 | DR17, DR52, DQ2 | Proliferation |
| | | | TV2-106 | | Proliferation |
| | | | TV2-112 | DR4, DR15, DR51, | Proliferation |

TABLE 14-continued

| Class II Peptide ID | Peptide sequence | Peptide contained in pool: | Responding patient ID | Responding patient MHC type | Assay |
|---|---|---|---|---|---|
| | | | | DR53, DQ6, DQ7 | |
| | | | TV2-114 | DR1, DQ5 | Proliferation |
| | | | TV2-116 | DR11, DR17, DR52, DQ2, DQ7 | Proliferation |
| | | | TV2-117 | DR1, DR17, DR52, DQ2, DQ5 | Proliferation |
| 26.2-30.2 | AALLAGRALQGLRRLELASN LQGLRRLELASNHFLYLPRD LASNHFLYLPRDVLAQLPSL LPRDVLAQLPSLRHDLSNN LPSLRHDLSNNSLVSLTYV | Pool 6.2 | TV2-005 | DR17, DR52, DQ2 | Proliferation |
| | | | TV2-007 | DR7, DR53, DQ2 | Proliferation |
| | | | TV2-009 | DR1, DR7, DR53N, DQ5, DQ9 | Proliferation |
| | | | TV2-012 | DR4, DR15, DR51, DR53, DQ6, DQ7 | Proliferation |
| | | | TV2-013 | DR1, DR13, DR52, DQ5, DQ6 | Proliferation |
| | | | TV2-018 | DR7, DR8, DR53N, DQ4, DQ9 | Proliferation |
| | | | TV2-019 | DR4, DR15, DR51, DR53, DQ6, DQ7 | Proliferation |
| | | | TV2-102 | DR7, DR13, DR52, DR53, DQ2, DQ6 | Proliferation |
| | | | TV2-103 | DR15, DR17, DR51, DR52, DQ2, DQ6 | Proliferation |
| | | | TV2-107 | DR1, DQ5 | Proliferation |
| | | | TV2-108 | DR7, DR17, DR52, DR53, DQ2 | Proliferation |
| | | | TV2-109 | | Proliferation |
| | | | TV2-116 | DR11, DR17, DR52, DQ2, DQ7 | Proliferation |
| | | | TV2-117 | DR1, DR17, DR52, DQ2, DQ5 | Proliferation |
| 31.2-35.2 | LSNNSLVSLTYVSFRNLTHL LTYVSFRNLTHLESLHLEDN LTHLESLHLEDNALKVLHNG LEDNALKVLHNGTLAELQGL LHNGTLAELQGLPHIRVFLD | Pool 7.2 | TV2-003 | DR13, DR17, DR52, DQ2, DQ6 | Proliferation |
| | | | TV2-007 | DR7, DR53, DQ2 | Proliferation |
| | | | TV2-010 | DR4, DR9, DR53, DQ7, DQ9 | Proliferation |
| | | | TV2-012 | DR4, DR15, DR51, DR53, DQ6, DQ7 | Proliferation |
| | | | TV2-013 | DR1, DR13, DR52, DQ5, DQ6 | Proliferation |
| | | | TV2-014 | DR15, DR51, DQ6 | Proliferation |
| | | | TV2-015 | DR1, DR15, DR51, DQ5, DQ6 | Proliferation |
| | | | TV2-016 | DR13, DR15, DR51, DR52, DQ6 | Proliferation |
| | | | TV2-102 | DR7, DR13, DR52, DR53, DQ2, DQ6 | Proliferation |
| | | | TV2-103 | DR15, DR17, DR51, DR52, DQ2, DQ6 | Proliferation |
| | | | TV2-106 | | Proliferation |
| | | | TV2-107 | DR1, DQ5 | Proliferation |
| | | | TV2-114 | DR1, DQ5 | Proliferation |
| | | | TV2-116 | DR11, DR17, DR52, DQ2, DQ7 | Proliferation |
| 36.2-40.2 | LQGLPHIRVFLDNNPWVCDC VFLDNNPWVCDCHMADMVTW VCDCHMADMVTWLKETEVVQ MVTWLKETEVVQGKDRLTCA EVVQGKDRLTCAYPEKMRNR | Pool 8.2 | TV2-001 | DR15, DR51, DR103, DQ5, DQ6 | Proliferation |
| | | | TV2-005 | DR17, DR52, DQ2 | Proliferation |
| | | | TV2-007 | DR7, DR53, DQ2 | Proliferation |
| | | | TV2-009 | DR1, DR7, DR53N, DQ5, DQ9 | Proliferation |
| | | | TV2-012 | DR4, DR15, DR51, DR53, DQ6, DQ7 | Proliferation |
| | | | TV2-014 | DR15, DR51, DQ6 | Proliferation |
| | | | TV2-015 | DR1, DR15, DR51, DQ5, DQ6 | Proliferation |
| | | | TV2-016 | DR13, DR15, DR51, DR52, DQ6 | Proliferation |
| | | | TV2-018 | DR7, DR8, DR53N, DQ4, DQ9 | Proliferation |
| | | | TV2-102 | DR7, DR13, DR52, DR53, DQ2, DQ6 | Proliferation |

TABLE 14-continued

| Class II Peptide ID | Peptide sequence | Peptide contained in pool: | Responding patient ID | Responding patient MHC type | Assay |
|---|---|---|---|---|---|
| | | | TV2-103 | DR15, DR17, DR51, DR52, DQ2, DQ6 | Proliferation |
| | | | TV2-104 | DR4, DR17, DR52, DR53, DQ2, DQ8 | Proliferation |
| | | | TV2-106 | | Proliferation |
| | | | TV2-107 | DR1, DQ5 | Proliferation |
| | | | TV2-109 | | Proliferation |
| | | | TV2-110 | DR9, DR12, DR52, DR53, DQ7, DQ9 | Proliferation |
| | | | TV2-113 | DR7, DR15, DR51, DR53, DQ2, DQ6 | Proliferation |
| | | | TV2-114 | DR1, DQ5 | Proliferation |
| | | | TV2-116 | DR11, DR17, DR52, DQ2, DQ7 | Proliferation |
| | | | TV2-117 | DR1, DR17, DR52, DQ2, DQ5 | Proliferation |
| 41.2-45.2 | LTCAYPEKMRNRVLLELNSA MRNRVLLELNSADLDCDPIL LNSADLDCDPILPPSLQTSY DPILPPSLQTSYVFLGIVLA QTSYVFLGIVLALIGAIFLL | Pool 9.2 | TV2-007 | DR7, DR53, DQ2 | Proliferation |
| | | | TV2-012 | DR4, DR15, DR51, DR53, DQ6, DQ7 | Proliferation |
| | | | TV2-014 | DR15, DR51, DQ6 | Proliferation |
| | | | TV2-015 | DR1, DR15, DR51, DQ5, DQ6 | Proliferation |
| | | | TV2-016 | DR13, DR15, DR51, DR52, DQ6 | Proliferation |
| | | | TV2-018 | DR7, DR8, DR53N, DQ4, DQ9 | Proliferation |
| | | | TV2-101 | | Proliferation |
| | | | TV2-102 | DR7, DR13, DR52, DR53, DQ2, DQ6 | Proliferation |
| | | | TV2-103 | DR15, DR17, DR51, DR52, DQ2, DQ6 | Proliferation |
| | | | TV2-106 | | Proliferation |
| | | | TV2-109 | | Proliferation |
| | | | TV2-112 | DR4, DR15, DR51, DR53, DQ6, DQ7 | Proliferation |
| | | | TV2-113 | DR7, DR15, DR51, DR53, DQ2, DQ6 | Proliferation |
| | | | TV2-114 | DR1, DQ5 | Proliferation |
| | | | TV2-116 | DR11, DR17, DR52, DQ2, DQ7 | Proliferation |
| 46.2-51.2 | IVLALIGAIFLLVLYLNRKG IFLLVLYLNRKGIKKWMHNI NRKGIKKWMHNIRDACRDHM MHNIRDACRDHMEGYHYRYE RDHMEGYHYRYEINADPRLT YRYEINADPRLTNLSSNSDV | Pool 10.2 | TV2-002 | DR11, DR13, DR52, DQ6, DQ7 | Proliferation |
| | | | TV2-007 | DR7, DR53, DQ2 | Proliferation |
| | | | TV2-012 | DR4, DR15, DR51, DR53, DQ6, DQ7 | Proliferation |
| | | | TV2-014 | DR15, DR51, DQ6 | Proliferation |
| | | | TV2-015 | DR1, DR15, DR51, DQ5, DQ6 | Proliferation |
| | | | TV2-016 | DR13, DR15, DR51, DR52, DQ6 | Proliferation |
| | | | TV2-101 | | Proliferation |
| | | | TV2-102 | DR7, DR13, DR52, DR53, DQ2, DQ6 | Proliferation |
| | | | TV2-103 | DR15, DR17, DR51, DR52, DQ2, DQ6 | Proliferation |
| | | | TV2-104 | DR4, DR17, DR52, DR53, DQ2, DQ8 | Proliferation |
| | | | TV2-105 | DR17, DR52, DQ2 | Proliferation |
| | | | TV2-106 | | Proliferation |
| | | | TV2-107 | DR1, DQ5 | Proliferation |
| | | | TV2-112 | DR4, DR15, DR51, DR53, DQ6, DQ7 | Proliferation |
| | | | TV2-114 | DR1, DQ5 | Proliferation |
| | | | TV2-116 | DR11, DR17, DR52, DQ2, DQ7 | Proliferation |
| | | | TV2-117 | DR1, DR17, DR52, DQ2, DQ5 | Proliferation |

TABLE 15

HLA-type distribution

| Peptide | | | | | | | | | | | | | | | | | | | |
|---|---|---|---|---|---|---|---|---|---|---|---|---|---|---|---|---|---|---|---|
| | DQ2 | DR7 | DR53 | DQ5 | DQ6 | DQ7 | DQ9 | DR1 | DR15 | DR51 | DR52 | DR4 | DR9 | DR11 | DR13 | DR17 | DQ4 | DQ8 | DR8 |
| 36.2 | 3/7 | 3/7 | 3/7 | 2/7 | 2/7 | 2/7 | 2/7 | 2/7 | 2/7 | 2/7 | 2/7 | 1/7 | 1/7 | 1/7 | 1/7 | 1/7 | 0/7 | 0/7 | 0/7 |
| | DQ2 | DR52 | DR53 | DQ6 | DR17 | DQ5 | DR1 | DR7 | DR15 | DR51 | DQ7 | DR4 | DQ8 | DQ9 | DR9 | DR11 | DR13 | DQ4 | DR8 |
| 37.2 | 7/10 | 5/10 | 5/10 | 4/10 | 4/10 | 3/10 | 3/10 | 3/10 | 3/10 | 3/10 | 2/10 | 2/10 | 1/10 | 1/10 | 1/10 | 1/10 | 1/10 | 0/10 | 0/10 |
| | DQ2 | DQ6 | DR52 | DR15 | DR17 | DR51 | DQ5 | DR1 | DR53 | DQ7 | DR4 | DQ8 | DR7 | DR11 | DR13 | DQ4 | DQ9 | DR8 | DR9 |
| 38.2 | 5/10 | 5/10 | 5/10 | 4/10 | 4/10 | 4/10 | 3/10 | 3/10 | 3/10 | 2/10 | 2/10 | 1/10 | 1/10 | 1/10 | 1/10 | 0/10 | 0/10 | 0/10 | 0/10 |
| | DQ6 | DR51 | DR52 | DQ2 | DR15 | DQ5 | DR53 | DQ7 | DR1 | DR7 | DR11 | DR13 | DR17 | DR4 | DQ4 | DQ8 | DQ9 | DR8 | DR9 |
| 39.2 | 6/10 | 5/10 | 5/10 | 4/10 | 4/10 | 3/10 | 3/10 | 2/10 | 2/10 | 2/10 | 2/10 | 2/10 | 2/10 | 1/10 | 0/10 | 0/10 | 0/10 | 0/10 | 0/10 |
| | DQ6 | DR15 | DR51 | DR52 | DQ2 | DR53 | DQ7 | DR7 | DR13 | DR17 | DQ5 | DQ9 | DQ4 | DR1 | DR4 | DR8 | DR9 | DR11 | DQ8 |
| 40.2 | 8/12 | 6/12 | 6/12 | 6/12 | 5/12 | 4/12 | 3/12 | 3/12 | 3/12 | 3/12 | 2/12 | 2/12 | 1/12 | 1/12 | 1/12 | 1/12 | 1/12 | 1/12 | 0/12 |
| | DQ6 | DR51 | DR15 | DQ2 | DQ5 | DR52 | DR53 | DQ7 | DR1 | DR7 | DR11 | DR13 | DR17 | DR4 | DQ4 | DQ8 | DQ9 | DR8 | DR9 |
| 41.2 | 9/13 | 7/13 | 6/13 | 5/13 | 5/13 | 5/13 | 4/13 | 3/13 | 3/13 | 3/13 | 3/13 | 2/13 | 2/13 | 1/13 | 0/13 | 0/13 | 0/13 | 0/13 | 0/13 |
| | DQ6 | DR51 | DQ5 | DR15 | DR52 | DQ2 | DR1 | DR7 | DR53 | DR13 | DR17 | DQ8 | DQ9 | DR4 | DR11 | DQ4 | DQ7 | DR8 | DR9 |
| 42.2 | 8/12 | 7/12 | 6/12 | 6/12 | 5/12 | 4/12 | 4/12 | 3/12 | 3/12 | 2/12 | 2/12 | 1/12 | 1/12 | 1/12 | 1/12 | 0/12 | 0/12 | 0/12 | 0/12 |
| | DQ6 | DR15 | DR51 | DQ2 | DR7 | DR52 | DQ5 | DR53 | DR1 | DR13 | DR17 | DQ4 | DQ7 | DQ9 | DR8 | DR11 | DQ8 | DR4 | DR9 |
| 43.2 | 7/11 | 6/11 | 6/11 | 5/11 | 4/11 | 4/11 | 3/11 | 3/11 | 2/11 | 2/11 | 2/11 | 1/11 | 1/11 | 1/11 | 1/11 | 1/11 | 0/11 | 0/11 | 0/11 |
| | DQ6 | DR15 | DR51 | DR52 | DQ2 | DQ5 | DQ7 | DR17 | DR1 | DR53 | DQ9 | DR4 | DR9 | DR11 | DR13 | DQ4 | DQ8 | DR7 | DR8 |
| 44.2 | 5/9 | 5/9 | 5/9 | 5/9 | 3/9 | 3/9 | 3/9 | 3/9 | 2/9 | 2/9 | 1/9 | 1/9 | 1/9 | 1/9 | 1/9 | 0/9 | 0/9 | 0/9 | 0/9 |
| | DQ6 | DR53 | DR15 | DR51 | DQ2 | DQ7 | DR4 | DQ5 | DR1 | DR7 | DR52 | DR13 | DR17 | DQ4 | DQ8 | DQ9 | DR8 | DR9 | DR11 |
| 45.2 | 5/8 | 5/8 | 4/8 | 4/8 | 3/8 | 3/8 | 3/8 | 2/8 | 2/8 | 2/8 | 2/8 | 1/8 | 1/8 | 0/8 | 0/8 | 0/8 | 0/8 | 0/8 | 0/8 |
| | DQ2 | DQ6 | DR52 | DR53 | DQ7 | DQ5 | DR1 | DR4 | DR15 | DR17 | DR51 | DR7 | DQ9 | DR11 | DR13 | DQ4 | DQ8 | DR8 | DR9 |
| Pool 4.2 | 6/15 | 6/15 | 6/15 | 6/15 | 5/15 | 4/15 | 4/15 | 4/15 | 4/15 | 4/15 | 4/15 | 3/15 | 2/15 | 2/15 | 2/15 | 1/15 | 1/15 | 1/15 | 1/15 |
| | DR52 | DQ2 | DR17 | DQ6 | DQ7 | DR53 | DQ5 | DR1 | DR4 | DR13 | DR15 | DR51 | DQ9 | DR7 | DR11 | DQ8 | DR9 | DQ4 | DR8 |
| Pool 5.2 | 9/13 | 7/13 | 6/13 | 5/13 | 4/13 | 4/13 | 3/13 | 3/13 | 3/13 | 3/13 | 3/13 | 3/13 | 2/13 | 2/13 | 1/13 | 1/13 | 0/13 | 0/13 | 0/13 |
| | DQ2 | DR52 | DQ6 | DR7 | DR17 | DR53 | DQ5 | DR1 | DQ7 | DR15 | DR51 | DQ9 | DR4 | DR13 | DQ4 | DR8 | DR11 | DQ8 | DR9 |
| Pool 6.2 | 7/13 | 7/13 | 5/13 | 5/13 | 5/13 | 5/13 | 4/13 | 4/13 | 3/13 | 3/13 | 3/13 | 2/13 | 2/13 | 2/13 | 1/13 | 1/13 | 1/13 | 0/13 | 0/13 |
| | DQ6 | DR52 | DQ2 | DR15 | DR51 | DQ5 | DR1 | DR13 | DR53 | DQ7 | DR17 | DR4 | DR7 | DQ9 | DR9 | DR11 | DQ4 | DQ8 | DR8 |
| Pool 7.2 | 8/13 | 6/13 | 5/13 | 5/13 | 5/13 | 4/13 | 4/13 | 4/13 | 4/13 | 3/13 | 3/13 | 2/13 | 2/13 | 1/13 | 1/13 | 1/13 | 0/13 | 0/13 | 0/13 |
| | DQ2 | DQ6 | DR52 | DR15 | DR51 | DQ5 | DR53 | DR1 | DR7 | DR17 | DQ7 | DQ9 | DR4 | DR13 | DQ4 | DQ8 | DR8 | DR9 | DR11 |
| Pool 8.2 | 8/18 | 8/18 | 8/18 | 7/18 | 7/18 | 6/18 | 6/18 | 5/18 | 5/18 | 5/18 | 3/18 | 3/18 | 2/18 | 2/18 | 1/18 | 1/18 | 1/18 | 1/18 | 1/18 |
| | DQ6 | DR15 | DR51 | DQ2 | DR53 | DR7 | DR52 | DQ7 | DQ5 | DR1 | DR4 | DR13 | DR17 | DQ4 | DQ9 | DR8 | DR11 | DQ8 | DR9 |
| Pool 9.2 | 8/12 | 7/12 | 7/12 | 5/12 | 5/12 | 4/12 | 4/12 | 3/12 | 2/12 | 2/12 | 2/12 | 2/12 | 2/12 | 1/12 | 1/12 | 1/12 | 1/12 | 0/12 | 0/12 |
| | DQ6 | DR52 | DQ2 | DR15 | DR51 | DR17 | DR53 | DQ5 | DQ7 | DR1 | DR4 | DR13 | DR7 | DR11 | DQ8 | DQ4 | DQ9 | DR8 | DR9 |
| Pool 10.2 | 8/15 | 8/15 | 7/15 | 6/15 | 6/15 | 5/15 | 5/15 | 4/15 | 4/15 | 4/15 | 3/15 | 3/15 | 2/15 | 2/15 | 1/15 | 0/15 | 0/15 | 0/15 | 0/15 |

The invention claimed is:

1. An isolated peptide epitope of 5T4 consisting of the amino acid sequence as set out in SEQ ID NO: 125.

2. A composition comprising the peptide epitope of claim 1 and a carrier.

* * * * *